US012704517B2

(12) United States Patent
Goetz et al.

(10) Patent No.: US 12,704,517 B2
(45) Date of Patent: Aug. 11, 2026

(54) ANTI-SEVERE ACUTE RESPIRATORY SYNDROME CORONAVIRUS ANTIBODIES

(71) Applicant: BIO-TECHNE CORPORATION, Minneapolis, MN (US)

(72) Inventors: Christine Andrea Goetz, Blaine, MN (US); Jody Bonnevier, Chanhassen, MN (US); Christopher David Hammerbeck, Shoreview, MN (US); Ernesto Rubin Resnik, Minneapolis, MN (US); Cyrus B. Munshi, Blaine, MN (US); Enqing Tan, Lexington, MA (US)

(73) Assignee: Bio-Techne Corporation, Minneapolis, MN (US)

(*) Notice: Subject to any disclaimer, the term of this patent is extended or adjusted under 35 U.S.C. 154(b) by 590 days.

(21) Appl. No.: 18/037,591

(22) PCT Filed: Nov. 24, 2021

(86) PCT No.: PCT/US2021/060734

§ 371 (c)(1),
(2) Date: May 18, 2023

(87) PCT Pub. No.: WO2022/115538

PCT Pub. Date: Jun. 2, 2022

(65) Prior Publication Data

US 2023/0408517 A1 Dec. 21, 2023

Related U.S. Application Data

(60) Provisional application No. 63/194,501, filed on May 28, 2021, provisional application No. 63/117,960, filed on Nov. 24, 2020.

(51) Int. Cl.

| | |
|---|---|
| ***A61P 31/14*** | (2006.01) |
| ***A61K 39/00*** | (2006.01) |
| ***A61K 39/42*** | (2006.01) |
| ***C07K 16/10*** | (2026.01) |
| ***C07K 16/104*** | (2026.01) |
| ***G01N 33/543*** | (2006.01) |
| ***G01N 33/569*** | (2006.01) |
| ***G01N 33/573*** | (2006.01) |

(52) U.S. Cl.

CPC ..... *G01N 33/56983* (2013.01); *C07K 16/104* (2026.01); *G01N 33/54388* (2021.08); *G01N 33/573* (2013.01); *C07K 2317/24* (2013.01); *C07K 2317/33* (2013.01); *C07K 2317/76* (2013.01); *C07K 2317/92* (2013.01); *G01N 2333/948* (2013.01); *G01N 2469/10* (2013.01)

(58) Field of Classification Search

CPC . A61P 31/14; C07K 16/1003; C07K 2317/76; C07K 2317/565; C07K 16/1002

See application file for complete search history.

(56) References Cited

U.S. PATENT DOCUMENTS

| | | | |
|---|---|---|---|
| 4,741,900 | A | 5/1988 | Alvarez et al. |
| 5,223,409 | A | 6/1993 | Ladner et al. |
| 10,787,501 | B1 | 9/2020 | Babb et al. |

FOREIGN PATENT DOCUMENTS

| | | | |
|---|---|---|---|
| WO | WO-9117271 | A1 | 11/1991 |
| WO | WO-9201047 | A1 | 1/1992 |
| WO | WO-9209690 | A2 | 6/1992 |
| WO | WO-9218619 | A1 | 10/1992 |
| WO | WO-9220791 | A1 | 11/1992 |
| WO | WO-9301288 | A1 | 1/1993 |

OTHER PUBLICATIONS

Premkumar et al., "The receptor-binding domain of the viral spike protein is an immunodominant and highly specific target of antibodies in SARS-CoV-2 patients", Science Immunology, published Jun. 11, 2020, 5:1-9.*

Annavajhala M.K., et al., "A Novel and Expanding SARS-CoV-2 Variant, B.1.526, Identified in New York", medRxiv, 2021, 32 Pages.

Barton M.I., et al., "Effects of Common Mutations in the SARS-CoV-2 Spike RBD and its Ligand, the Human ACE2 Receptor on Binding Affinity and Kinetics", eLife, vol. 10, e70658, Aug. 26, 2021, pp. 1-19.

Bayarri-Olmos R., et al., "The SARS-CoV-2 Y453F Mink Variant Displays a Striking Increase in ACE-2 Affinity but Does Not Challenge Antibody Neutralization", bioRxiv, Jan. 29, 2021, 10 Pages.

Beigel J.H., et al., "Remdesivir for the Treatment of Covid-19—Final Report", The New England Journal of Medicine, vol. 383, No. 19, Nov. 5, 2020, pp. 1813-1826.

Biotechne: "SARS-CoV-2 Spike RBD Antibody", Monoclonal Mouse IgG2A Clone# 1035423, Catalog No. MAB105802, 2020, pp. 1-2.

Biotechne: "SARS-CoV-2 Spike RBD Antibody", Monoclonal Mouse $IgG_{2A}$ Clone# 1035419, Catalog No. MAB105801, 2020, pp. 1-2.

Biotechne: "SARS-CoV-2 Spike S1 Subunit Antibody", Monoclonal Mouse IgG1 Clone # 1035224, Catalog No. MAB105405, 2020, pp. 1-2.

Brouwer P.J.M., et al., "Potent Neutralizing Antibodies from COVID-19 Patients Define Multiple Targets of Vulnerability," Science, vol. 369, Aug. 7, 2020, pp. 643-650 (9 pages), DOI:10.1126/science.abc5902, XP055853089, [Retrieved on Oct. 20, 2021] Retrieved from URL: https://www.science.org/doi/10.1126/science.abc5902.

Cai Y., et al., "Distinct Conformational States of SARS-CoV-2 Spike Protein", Science, vol. 369, Jul. 21, 2020, pp. 1586-1592 (12 Pages).

(Continued)

*Primary Examiner* — Barry A Chestnut

(74) *Attorney, Agent, or Firm* — Mueting Raasch Group

(57) ABSTRACT

Anti-SARS-CoV-specific monoclonal antibodies, methods of making and characterizing those antibodies, and methods of using those antibodies are described herein. In some embodiments, the antibodies may bind to both SARS-CoV-1 and SARS-CoV-2. In some embodiments, the antibodies bind to $S_1$ of the spike protein of SARS-CoV-2 including, for example, to the receptor binding domain (RBD) of $S_1$. In some embodiments, the antibodies may block the binding of SARS-CoV-1 and/or SARS-CoV-2 to ACE-2. Such antibodies are useful as diagnostic and therapeutic agents.

25 Claims, 67 Drawing Sheets

Specification includes a Sequence Listing.

(56) References Cited

OTHER PUBLICATIONS

Cao Y., et al., "Potent Neutralizing Antibodies Against SARS-CoV-2 Identified by High-Throughput Single-Cell Sequencing of Convalescent Patients' B Cells," Cell, Elsevier, Amsterdam NL, Jul. 9, 2020, vol. 182, No. 1, pp. 73-84.e16 (28 Pages), DOI:10.1016/J.CELL.2020.05.025, ISSN: 0092-8674, XP086211425, (May 18, 2020).
Chen Y., et al., "Structure Analysis of the Receptor Binding of 2019-nCoV", Biochemical and Biophysical Research Communications, vol. 525, 2020, pp. 135-140.
Cherian S., et al., "Convergent Evolution of SARS-CoV-2 Spike Mutations, L452R, E484Q and P681R, in the Second Wave of COVID-19 in Maharashtra, India", BioRxiv, Apr. 24, 2021, 17 Pages, DOI: 10.1101/2021.04.22.440932.
Cucinotta D., et al., "WHO Declares COVID-19 a Pandemic", Acta Biomed, vol. 91, No. 1, 2020, pp. 157-160.
Davies N.G., et al., "Estimated Transmissibility and Impact of SARS-CoV-2 Lineage B.1.1.7 in England", Science, vol. 372, Apr. 9, 2021, 10 Pages.
De Wit E., et al., "Prophylactic and Therapeutic Remdesivir (GS-5734) Treatment in the Rhesus Macaque Model of MERS-CoV Infection", Proceedings of the National Academy of Sciences of the USA, vol. 117, No. 12, Mar. 24, 2020, pp. 6771-6776.
Deshpande A., et al., Epitope Classification and RBD Binding Properties of Neutralizing Antibodies Against SARS-COV-2 Variants of Concern, Frontiers in Immunology, vol. 12, No. 691715, Jun. 4, 2021, pp. 1-14.
Embregts C.W.E., et al., "Evaluation of a Multi-species SARS-CoV-2 Surrogate Virus Neutralization Test", One Health, vol. 13, No. 100313, 2021, 8 Pages.
Faria N.R., et al., "Genomics and Epidemiology of the p. 1 SARS-CoV-2 Lineage in Manaus, Brazil", Science, vol. 372, May 21, 2021, pp. 815-821.
"FDA's Approval of Veklury (remdesivir) for the Treatment of COVID-19—the Science of Safety and Effectiveness," Oct. 22, 2020, 3 pages.
FDA News Release: "Coronavirus (COVID-19) Update: FDA Authorizes Monoclonal Antibodies for Treatment of COVID-19", Nov. 21, 2020, 3 Pages, accessed on Apr. 14, 2025, at: https://www.fda.gov/news-events/press-announcements/coronavirus-covid-19-update-fda-authorizes-monoclonal-antibodies-treatment-covid-19.
FDA News Release: "Coronavirus (COVID-19) Update: FDA Authorizes Monoclonal Antibody for Treatment of COVID-19", Nov. 9, 2020, 3 pages, Accessed on Apr. 14, 2025, at: https://www.fda.gov/news-events/press-announcements/coronavirus-covid-19-update-fda-authorizes-monoclonal-antibody-treatment-covid-19.
FDA News Release: "Coronavirus (COVID-19) Update: FDA Revokes Emergency Use Authorization for Monoclonal Antibody Bamlanivimab", Apr. 16, 2021, 3 Pages, Accessed on Apr. 14, 2025, at: https://www.fda.gov/news-events/press-announcements/coronavirus-covid-19-update-fda-revokes-emergency-use-authorization-monoclonal-antibody-bamlanivimab#:~:text=Today%2C%20the%20U.S.%20Food%20and,adults%20and%20certain%20pediatric%20patients.
FDA News Release: FDA to Hold Advisory Committee Meeting to Discuss Merck and Ridgeback's EUA Application for COVID-19 Oral Treatment, Oct. 14, 2021, 2 Pages.
Fisman D.N., et al., "Progressive Increase in Virulence of Novel SARS-CoV-2 Variants in Ontario, Canada", medRxiv, 2021, 18 Pages, DOI: https://doi.org/10.1101/2021.07.05.21260050.
Fulford T.S., et al., "A Point-of-Care Lateral Flow Assay for Neutralising Antibodies Against SARS-CoV-2", medRxiv, 2021, 25 Pages, DOI: https://doi.org/10.1101/2021.04.12.21255368.
Gu H., et al., "Adaptation of SARS-CoV-2 in BALB/c Mice for Testing Vaccine Efficacy", Science, vol. 369, Sep. 25, 2020, pp. 1603-1607 (5 Pages).
Hansen J., et al., "Studies in Humanized Mice and Convalescent Humans Yield a SARS-CoV-2 Antibody Cocktail," Science, vol. 369, US, Aug. 21, 2020, pp. 1010-1014 (5 Pages) p. eabd0827, DOI: 10.1126/science.abd0827, ISSN 0036-8075, XP055707770.
Hansen J., et al., "Supplementary Materials for Studies in Humanized Mice and Convalescent Humans Yield a SARS-CoV-2 Antibody Cocktail", Science, U.S., Jun. 15, 2020, vol. 369, No. 6506, 30 Pages, DOI: 10.1126/science.abd0827, ISSN: 0036-8075, XP055780760.
Henderson R., et al., "Glycans on the SARS-CoV-2 Spike Control the Receptor Binding Domain Conformation", bioRxiv, 2020, 19 Pages.
Hoffmann M., et al., "SARS-CoV-2 Variants B.1.351 and B.1.1.248: Escape from Therapeutic Antibodies and Antibodies Induced by Infection and Vaccination", bioRxiv, 2021, 43 Pages, DOI: https://doi.org/10.1101/2021.02.11.430787.
Hoffmann M., et al., "SARS-CoV-2 Variants B.1.351 and p. 1 Escape from Neutralizing Antibodies", Cell, vol. 184, No. 9, Apr. 29, 2021, pp. 2384-2393 (23 Pages).
Holliger P., et al., "Diabodies": Small Bivalent and Bispecific Antibody Fragments, Proceedings of the National Academy of Sciences, USA, Jul. 1993, vol. 90, pp. 6444-6448.
Huang Y., et al., "Neutralizing antibodies against SARS-CoV-2: current understanding, challenge and perspective", Antibody Therapeutics, vol. 3, No. 4, 2020, pp. 285-299.
International Preliminary Report on Patentability for International Application No. PCT/US2021/060734, mailed Jun. 8, 2023, 14 Pages.
International Search Report and Written Opinion for International Application No. PCT/US2021/060734, mailed May 3, 2022, 21 Pages.
Jackson L.A., et al., "An mRNA Vaccine against SARS-CoV-2—Preliminary Report ", The New England Journal of Medicine, vol. 383, No. 20, 2020, pp. 1920-1931 (12 Pages).
Johnson M., et al., "Evaluation of a Novel Multiplexed Assay for Determining IgG levels and Functional Activity to SARS-CoV-2", Journal of Clinical Virology, 2020, vol. 130, No. 104572, 8 Pages.
Jones P.T., et al., "Replacing the Complementarily-Determining Regions in a Human Antibody with those from a Mouse," Nature, May 29, 1986, vol. 321, pp. 522-525.
Ju B., et al., "Human Neutralizing Antibodies Elicited by SARS-CoV-2 infection", Nature, vol. 584, No. 7819, May 26, 2020, pp. 115-119, XP037211705, 22 Pages, DOI: 10.1038/S41586-020-2380-Z [retrieved on May 26, 2020].
Ju B., et al., "Potent Human Neutralizing Antibodies Elicited by SARS-CoV-2 Infection", bioRxiv, Mar. 26, 2020, 42 Pages, DIO:10.1101/2020.03.21.990770, XP055737104, [Retrieved on Oct. 6, 2020] Retrieved from URL: https://www.biorxiv.org/content/10.1101/2020.03.21.990770v2.full.pdf.
Kalathiya U., et al., "Highly Conserved Homotrimer Cavity Formed by the SARS-CoV-2 Spike Glycoprotein: A Novel Binding Site", Journal of Clinical Medicine, May 14, 2020, vol. 9, No. 1473, pp. 1-18.
Karim S.S.A., et al., "New SARS-CoV-2 Variants-Clinical, Public Health, and Vaccine Implications", The New England Journal of Medicine, vol. 384, No. 19, May 13, 2021, pp. 1866-1868.
Khare S., et al., "Conformational Changes of the Receptor Binding Domain of SARS-CoV-2 Spike Protein and Prediction of a B-Cell Antigenic Epitope Using Structural Data", Frontiers in Artificial Intelligence, vol. 4, No. 630955, Mar. 25, 2021, pp. 1-12.
Kohler G., et al., "Derivation of Specific Antibody-producing Tissue Culture and Tumor Lines by Cell Fusion", European Journal of Immunology, vol. 6, 1976, pp. 511-519.
Kostelny S.A., et al., "Formation of a Bispecific Antibody by the Use of Leucine Zippers", The Journal of Immunology, Mar. 1, 1992, vol. 148, No. 5, pp. 1547-1553.
Lake D.F., et al., "Development of a Rapid Point-of-Care Test that measures Neutralizing Antibodies to SARS-CoV-2", Journal of Clinical Virology, vol. 145, No. 105024, 2021, pp. 1-7.
Lan J., et al., "Structure of the SARS-CoV-2 Spike Receptor-binding Domain Bound to the ACE2 Receptor", Nature, vol. 581, May 14, 2020, pp. 215-220 (16 Pages).
Lauring A.S., et al., "Variants of SARS-CoV-2", Journal of the American Medical Association, vol. 326, No. 9, Sep. 7, 2021, p. 880.

(56) References Cited

OTHER PUBLICATIONS

Letko M., et al., "Functional Assessment of Cell Entry and Receptor Usage for SARS-CoV-2 and other Lineage B Betacoronaviruses", Nature Microbiology, 2020, vol. 5, pp. 562-569 (17 Pages).
Li B., et al., "Viral Infection and Transmission in a Large, Well-traced Outbreak Caused by the SARS-CoV-2 Delta Variant", MedRxiv, 2021, 23 Pages, DOI: https://doi.org/10.1101/2021.07.07.21260122.
Li W., et al., "Angiotensin-Converting Enzyme 2 is a Functional Receptor for the SARS Coronavirus", Nature, vol. 426, Nov. 27, 2003, pp. 450-454.
Li Y., et al., "The MERS-CoV Receptor DPP4 as a Candidate Binding Target of the SARS-CoV-2 Spike", Integrated Science, vol. 23, No. 101160, Jun. 26, 2020, 17 pages.
Li Z., et al., "Development and Clinical Applications of a Rapid IgM-IgG Combined Antibody Test for SARS-CoV-2 Infection Diagnosis", Journal of Medical Virology, Feb. 26, 2020, pp. 1-7.
Lu R., et al., "Genomic Characterisation and Epidemiology of 2019 Novel Coronavirus: Implications for Virus Origins and Receptor Binding", 2020, vol. 395, Feb. 22, 2020, pp. 565-574.
Mlcochova P., et al., "SARS-CoV-2B.1.617.2 Delta Variant Replication and Immune Evasion", Nature, vol. 599, Nov. 4, 2021, pp. 114-119 (22 Pages).
Mulligan M.J., et al., "Phase I/II Study of COVID-19 RNA Vaccine BNT162b1 in Adults", Nature, vol. 586, Oct. 22, 2020, pp. 589-593 (13 Pages).
NCBI: "Surface Glycoprotein [Severe acute respiratory syndrome coronavirus 2]", Database Accession No. YP _009724390.1, 2020, pp. 1-3.
News Releases: "NIH Clinical Trial Evaluating Moderna COVID-19 Variant Vaccine Begins, Early-Stage Trial to Evaluate Safety and Immunogenicity", Mar. 31, 2021, 3 Pages, Accessed on Apr. 14, 2025, at: https://www.nih.gov/news-events/news-releases/nih-clinical-trial-evaluating-moderna-covid-19-variant-vaccine-begins.
Nie J., et al., "Three Epitope-Distinct Human Antibodies from RenMab Mice Neutralize SARS-CoV-2 and Cooperatively Minimize the Escape of Mutants", Cell Discovery, vol. 7, No. 53, 2021, pp. 1-11.
Orlandi R., et al., "Cloning Immunoglobulin Variable Domains for Expression by the Polymerase Chain Reaction", Proceedings of the National Academy of Sciences of the United States of America, vol. 86, May 1989, pp. 3833-3837.
Ou X., et al., "Characterization of Spike Glycoprotein of SARS-CoV-2 on Virus Entry and its Immune Cross-reactivity with SARS-CoV", Nature Communications, vol. 11, No. 1620, 2020, pp. 1-12.
Park E.J., et al., "The Spike Glycoprotein of SARS-CoV-2 Binds to Beta1 Integrins Expressed on the Surface of Lung Epithelial Cells", Viruses, vol. 13, No. 645, Apr. 9, 2021, pp. 1-11.
Pegu A., et al., "Durability of mRNA-1273 Vaccine-Induced Antibodies Against SARS-CoV-2 Variants", Science, vol. 373, Sep. 17, 2021, pp. 1372-1377 (5 Pages).
Pfizer: "Pfizer's Novel COVID-19 Oral Antiviral Treatment Candidate Reduced Risk of Hospitalization or Death by 89% in Interim Analysis of Phase 2/3 Epic-HR Study," Nov. 5, 2021, 6 Pages.
Pinto D., et al., "Cross-Neutralization of SARS-CoV-2 by a Human Monoclonal SARS-CoV Antibody," Nature, Nature Publishing Group, London, UK, May 18, 2020, vol. 583, No. 7815, pp. 290-295 (19 pages), DOI:10.1038/S41586-020-2349-Y, ISSN: 0028-0836, XP037289888.
Rambaut A., "Phylogenetic Analysis of nCoV-2019 Genomes", Phylodynamic Analysis, 176 genomes, Mar. 6, 2020, 9 Pages.
Santos J.C., et al., "The High Infectivity of SARS-CoV-2 B.1.1.7 is Associated with Increased Interaction Force Between Spike-ACE2 caused by the Viral N501Y Mutation", bioRxiv, 2021, 9 Pages, DOI: https://doi.org/10.1101/2020.12.29.424708.
Shang J., et al., "Cell Entry Mechanisms of SARS-CoV-2", Proceedings of the National Academy of Sciences, vol. 117, No. 21, May 26, 2020, pp. 11727-11734.
Singer I.I., et al., "Optimal Humanization of 1B4, an Anti-CD18 Murine Monoclonal Antibody, Is Achieved by Correct Choice of Human V-region Framework Sequences", Journal of Immunology, vol. 150, No. 7, Apr. 1, 1993, pp. 2844-2857.
Smith G.P., et al., "Phage Display", Chemical Reviews, vol. 97, No. 2, 1997, pp. 391-410.
Smith T.F., et al., "Comparison of Biosequences", Advances in Applied Mathematics, 1981, vol. 2, pp. 482-489.
Songsivilai S., et al., "Bispecific Antibody: A tool for Diagnosis and Treatment of Disease", Clinical and Experimental Immunology, 1990, vol. 79, pp. 315-321.
Starr T.N., et al., "Antibodies to the SARS-CoV-2 Receptor-binding Domain that Maximize Breadth and Resistance to Viral Escape", bioRxiv, 2021, 36 Pages, DOI: https://doi.org/10.1101/2021.04.06.438709.
Starr T.N., et al., "Complete Map of SARS-CoV-2 RBD Mutations that Escape the Monoclonal Antibody LY-CoV555 and its Cocktail with LY-CoV016", Cell Reports Medicine, vol. 2, No. 4, 100255, Apr. 20, 2021, pp. 1-12.
Starr T.N., et al., "Prospective Mapping of Viral Mutations that Escape Antibodies Used to Treat COVID-19", Science, vol. 371, Feb. 19, 2021, pp. 850-854 (5 pages).
Sullivan H.C., et al., "Convalescent Plasma: Therapeutic Hope or Hopeless Strategy in the SARS-CoV-2 Pandemic", Transfusion Medicine Reviews, vol. 34, 2020, pp. 145-150.
Supasa P., et al., "Reduced Neutralization of SARS-CoV-2 B.1.1.7 Variant by Convalescent and Vaccine Sera", Cell, vol. 184, Apr. 15, 2021, pp. 2201-2211.E1-E7 (18 pages).
Tai W., et al., "Characterization of the Receptor-binding Domain (RBD) of 2019 Novel Coronavirus: Implication for Development of RBD Protein as a Viral Attachment Inhibitor and Vaccine", Cellular & Molecular Immunology, vol. 17, 2020, pp. 613-620.
Takeda S., et al., "Construction of Chimaeric Processed Immunoglobulin Genes Containing Mouse Variable and Human Constant Region Sequences", Nature, vol. 314, 1985, pp. 452-454.
Tan C.W., et al., "A SARS-CoV-2 Surrogate Virus Neutralization Test Based on Antibody-Mediated Blockage of ACE2-Spike Protein-Protein Interaction", Nature Biotechnology, vol. 38, Sep. 2020, pp. 1073-1078 (17 Pages).
Tan E., et al., "Use of Lateral Flow Immunoassay to Characterize SARS-CoV-2 RBD-Specific Antibodies and Their Ability to React with the UK, SA and BR p. 1 Variant RBDs," Diagnostics, Jun. 30, 2021, vol. 11, No. 7, 1190, pp. 1-16, DOI: 10.3390/diagnostics11071190, XP055895105.
Tao K., et al., "The Biological and Clinical Significance of Emerging SARS-CoV-2 Variants", Nature Reviews Genetics, vol. 22, Dec. 2021, pp. 757-773.
Taylor S.C., et al., "A New SARS-CoV-2 Dual-Purpose Serology Test: Highly Accurate Infection Tracing and Neutralizing Antibody Response Detection", Journal of Clinical Microbiology, vol. 59, No. 4, Apr. 2021, pp. 1-13.
Thomson E.C., et al., "Circulating SARS-CoV-2 spike N439K Variants Maintain Fitness While Evading Antibody-Mediated Immunity", Cell, vol. 184, Mar. 4, 2021, pp. 1171-1187 (37 Pages).
Tortorici M.A, et al., "Ultrapotent Human Antibodies Protect Against SARS-CoV-2 Challenge via Multiple Mechanisms", Science, vol. 370, Nov. 20, 2020, pp. 950-957 (8 pages).
Traunecker A., et al., "Bispecific Single Chain Molecules (Janusins) Target Cytotoxic Lymphocytes on HIV Infected Cells", The EMBO Journal, 1991, vol. 10, pp. 3655-3659.
Traunecker A., et al., "Janusin: New Molecular Design for Bispecific Reagents", International Journal of Cancer Supplements, vol. 7, 1992, pp. 51-52 (3 pages).
UniProt: "PODTC2 Spike_SARS2", Database Accession No. PODTC2, 2020, 17 Pages.
Villoutreix B.O., et al., "In Silico Investigation of the New UK (B.1.1.7) and South African (501Y.V2) SARS-CoV-2 Variants with a Focus at the ACE2-Spike RBD Interface", International Journal of Molecular Sciences, vol. 22, No. 1695, Feb. 8, 2021, pp. 1-13.
Voloch C.M., et al., "Genomic Characterization of a Novel SARS-CoV-2 Lineage from Rio de Janeiro, Brazil", Journal of Virology, vol. 95, No. 10, May 2021, e00119-00121, pp. 1-5.
Volz E., et al., "Evaluating the Effects of SARS-CoV-2 Spike Mutation D614G on Transmissibility and Pathogenicity", Cell, vol. 184, Jan. 7, 2021, pp. 64-75 (23 Pages).

(56) References Cited

OTHER PUBLICATIONS

Walls A.C., et al., "Structure, Function, and Antigenicity of the SARS-CoV-2 Spike Glycoprotein", Cell, vol. 180, Apr. 16, 2020, pp. 281-292 (18 Pages).
Wang J.J., et al., "Rapid Lateral Flow Tests for the Detection of SARS-CoV-2 Neutralizing Antibodies", Expert Review of Molecular Diagnostics, 2021, pp. 1-8.
Wang L., et al., "Ultrapotent Antibodies Against Diverse and Highly Transmissible SARS-CoV-2 Variants", Science, vol. 373, Aug. 13, 2021, 15 Pages.
Wang Y., et al., "Enhanced Receptor Binding of SARS-CoV-2 Through Networks of Hydrogen-bonding and Hydrophobic Interactions", Proceedings of the National Academy of Sciences, USA, vol. 117, No. 25, Jun. 23, 2020, pp. 13967-13974.
Weisblum Y., et al., "Escape from Neutralizing Antibodies by SARS-CoV-2 Spike Protein Variants", Elife, vol. 9, e61312, Oct. 28, 2020, pp. 1-31.
Wen T., et al., "Development of a Lateral ?ow Immunoassay Strip for Rapid Detection of IgG Antibody Against SARS-CoV-2 Virus", he Royal Society of Chemistry, Analyst, vol. 145, 2020, pp. 5345-5352.
Wu F., et al., "A New Coronavirus Associated With Human Respiratory Disease in China," Nature, Feb. 3, 2020, vol. 579, No. 7798, 20 pages, DOI: 10.1038/S41586-020-2008-3, XP037060203.
Xie X., et al., "Neutralization of SARS-CoV-2 Spike 69/70 Deletion, E484K and N501Y Variants by BNT162b2 Vaccine-Elicited Sera", Nature Medicine, vol. 27, Apr. 2021, pp. 620-621 (6 pages).
Yang Y., et al., "Quantitative Interpretations of Energetic Features and Key Residues at SARS Coronavirus Spike Receptor-Binding Domain and ACE2 Receptor Interface", 2021, pp. 1-15, arXiv:2103.06578.
Yavuz S.S., et al., "An Update of Anti-viral Treatment of COVID-19", Turkish Journal of Medical Sciences, 2021, pp. 3372-3390.
Yuki K.,, et al., "COVID-19 Pathophysiology: A review", Clinical Immunology, vol. 215, No. 108427, 2020, pp. 1-7.
Zaki A.M., et al., "Isolation of a Novel Coronavirus from a Man with Pneumonia in Saudi Arabia", The New England Journal of Medicine, vol. 367, No. 19, Nov. 8, 2012, pp. 1814-1820.
Zhang W., et al., "Emergence of a Novel SARS-CoV-2 Variant in Southern California", Journal of the American Medical Association, vol. 325, No. 13, Apr. 6, 2021, pp. 1324-1326.
Zhou P., et al., "A Pneumonia Outbreak Associated with a New Coronavirus of Probable Bat Origin", Nature, vol. 579, Mar. 12, 2020, pp. 270-273 (20 Pages).
Zhu N., et al., "A Novel Coronavirus from Patients with Pneumonia in China, 2019", The New England Journal of Medicine, vol. 382, No. 8, Feb. 20, 2020, pp. 727-733.
Zost S.J., et al., "Potently Neutralizing Human Antibodies that Block SARS-CoV-2 Receptor Binding and Protect Animals," bioRxiv, May 22, 2020, 35 Pages, DOI:10.1101/2020.05.22.111005, XP055735422, Retrieved from URL: https://www.biorxiv.org/content/10.1101/2020.05.22.111005v1.full.pdf.
Zou X., et al., "Single-Cell RNA-seq Data Analysis on the Receptor ACE2 Expression Reveals the Potential Risk of Different Human Organs Vulnerable to 2019-nCoV Infection", Frontiers in Medicine, vol. 14, No. 2, 2020, pp. 185-192.
Zoufaly A., et al., "Human Recombinant Soluble ACE2 in Severe COVID-19", Lancet Respiratory Medicine, vol. 8, Nov. 2020, pp. 1154-1158.

* cited by examiner 1035419
2.5
2
1.5
1
0.5
0
OD
400 100 25 6.25 1.6 0
SARS-CoV2 Spike S1 protein (ng)

1035423
2.5
2
1.5
1
0.5
0
OD
400 100 25 6.25 1.6 0
SARS-CoV2 Spike S1 protein (ng)

1035433
2.5
2
1.5
1
0.5
0
OD
400 100 25 6.25 1.6 0
SARS-CoV2 Spike S1 protein (ng)

1035414
2.5
2
1.5
1
0.5
0
OD
400 100 25 6.25 1.6 0
SARS-CoV2 Spike S1 protein (ng)

FIG. 1E
1035709
2.5
2
1.5
1
0.5
0
OD
400 100 25 6.25 1.6 0
SARS-CoV2 Spike S1 protein (ng)
FIG. 1F
1035716
2.5
2
1.5
1
0.5
0
OD
400 100 25 6.25 1.6 0
SARS-CoV2 Spike S1 protein (ng)
FIG. 1G
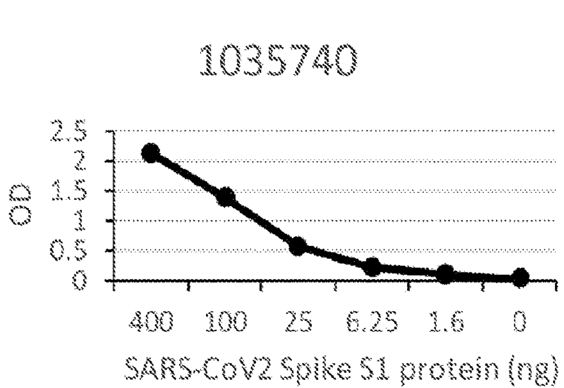
FIG. 1H
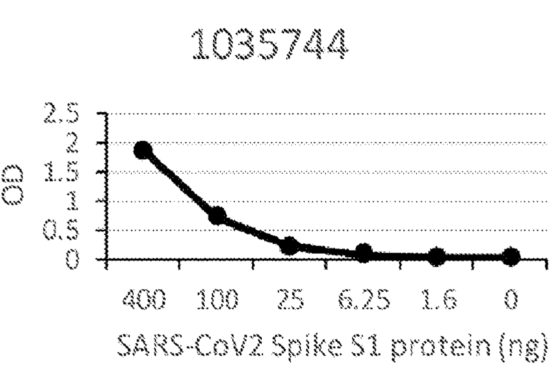

FIG. 1L anti-His / anti-Fc

SARS-Cov-2 S1/RBD

Host virus receptor:
SARS-COV1/2 = ACE-2
MERS-COV = CD26 hACE-2 HEK/eGFP Tfx
or
CD26 HEK/eGFP Tfx

Irrelevant antibody:
Antibody does not block interaction

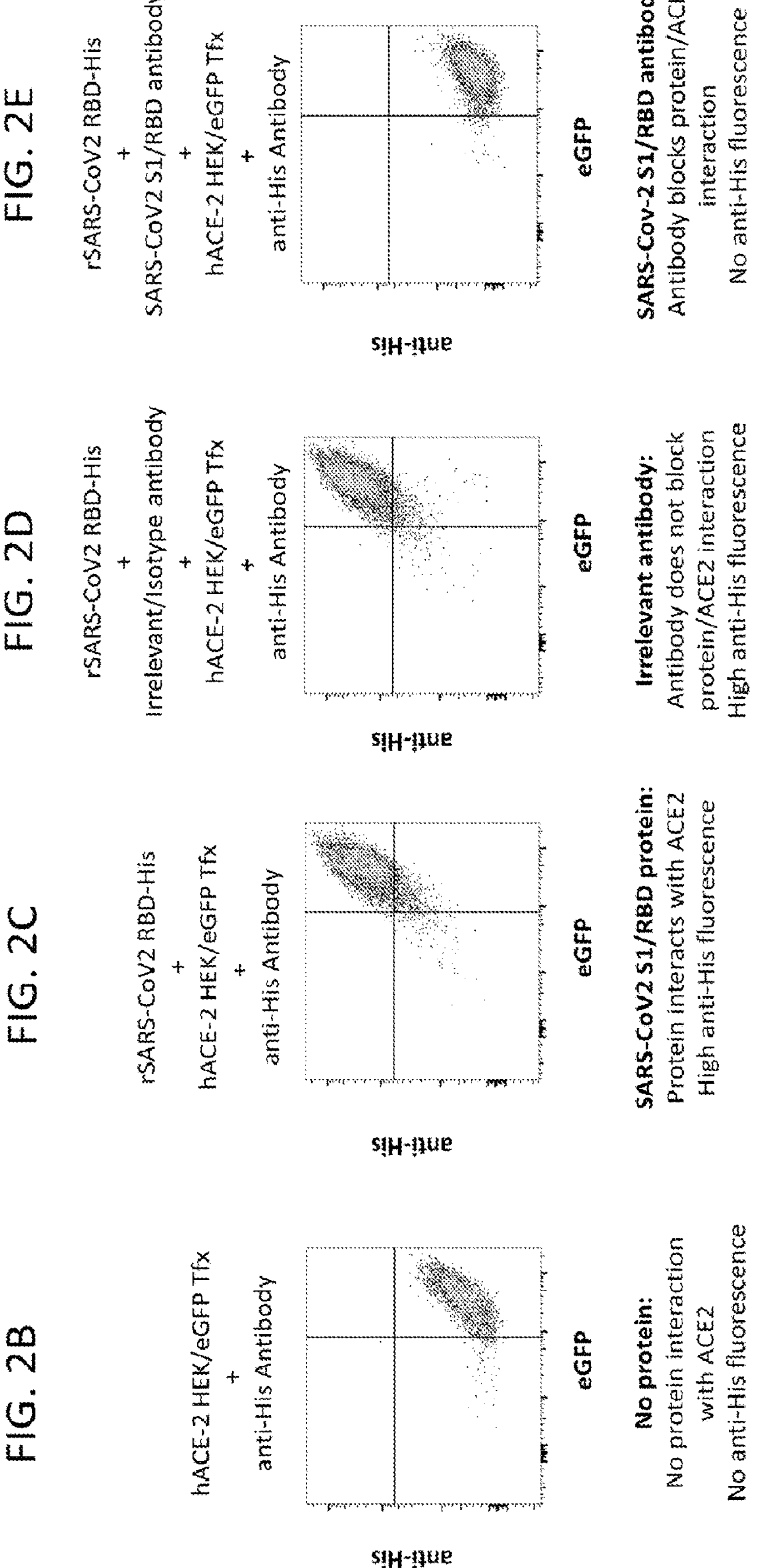
FIG. 2B
hACE-2 HEK/eGFP Tfx
+
anti-His Antibody
anti-His
eGFP
No protein:
No protein interaction
with ACE2
No anti-His fluorescence
FIG. 2C
rSARS-CoV2 RBD-His
+
hACE-2 HEK/eGFP Tfx
+
anti-His Antibody
anti-His
eGFP
SARS-CoV2 S1/RBD protein:
Protein interacts with ACE2
High anti-His fluorescence
FIG. 2D
rSARS-CoV2 RBD-His
+
Irrelevant/Isotype antibody
+
hACE-2 HEK/eGFP Tfx
+
anti-His Antibody
anti-His
eGFP
Irrelevant antibody:
Antibody does not block
protein/ACE2 interaction
High anti-His fluorescence
FIG. 2E
rSARS-CoV2 RBD-His
+
SARS-CoV2 S1/RBD antibody
+
hACE-2 HEK/eGFP Tfx
+
anti-His Antibody
anti-His
eGFP
SARS-Cov-2 S1/RBD antibody:
Antibody blocks protein/ACE2
interaction
No anti-His fluorescence rSARS-CoV2
RBD-His
Ms IgG1
Ms IgG2a
Ms IgG2b
anti-His
eGFP 1035709
1035716
1035740
1035744
1035752
1035753
1035755
1035762
anti-His
eGFP FIG. 7A
1035419
OD
2.5 2 1.5 1 0.5 0
400 100 25 6.25 1.6 0
SARS-CoV2 Spike S1 protein (ng)
FIG. 7B
1035423
OD
2.5 2 1.5 1 0.5 0
400 100 25 6.25 1.6 0
SARS-CoV2 Spike S1 protein (ng)
FIG. 7C
1035433
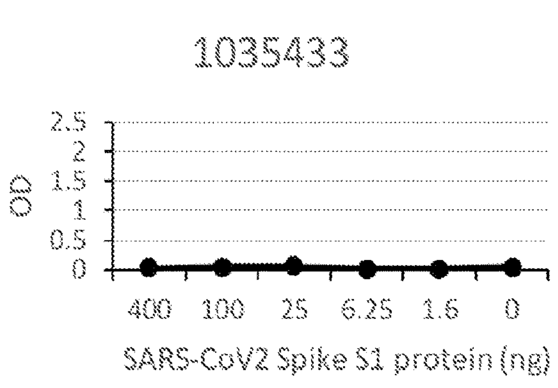
FIG. 7D
1035414
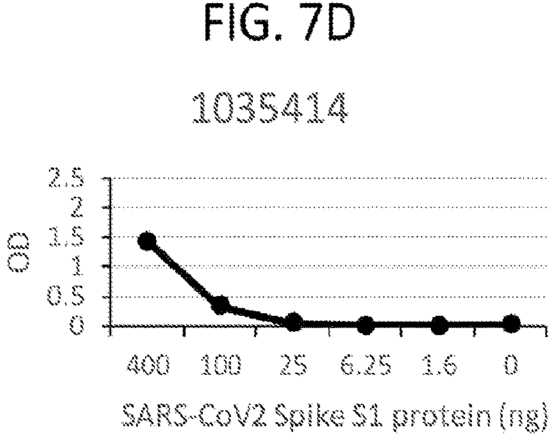

2.5
2
1.5
1
0.5
0
OD
400 100 25 6.25 1.6 0
SARS-CoV2 Spike S1 protein (ng)

1035753

2.5
2
1.5
1
0.5
0
OD
400 100 25 6.25 1.6 0
SARS-CoV2 Spike S1 protein (ng)

1035755

2.5
2
1.5
1
0.5
0
OD
400 100 25 6.25 1.6 0
SARS-CoV2 Spike S1 protein (ng)

FIG. 7M
1035211
OD 2.5 2 1.5 1 0.5 0
400 100 25 6.25 1.6 0
SARS-CoV2 Spike S1 protein (ng)
FIG. 7N
1035224
OD 2.5 2 1.5 1 0.5 0
400 100 25 6.25 1.6 0
SARS-CoV2 Spike S1 protein (ng)
FIG. 7O
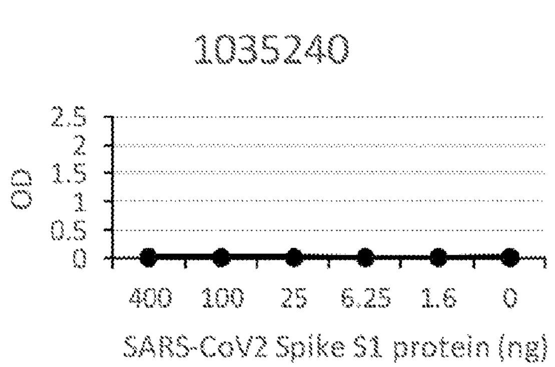
FIG. 7P
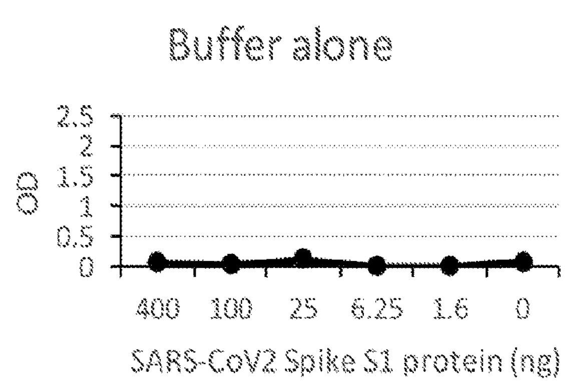

1035419
2.5
2
1.5
1
0.5
0
OD
400 100 25 6.25 1.6 0
SARS-CoV2 Spike S1 protein (ng)

1035423
2.5
2
1.5
1
0.5
0
OD
400 100 25 6.25 1.6 0
SARS-CoV2 Spike S1 protein (ng)

1035433
2.5
2
1.5
1
0.5
0
OD
400 100 25 6.25 1.6 0
SARS-CoV2 Spike S1 protein (ng)

1035414
2.5
2
1.5
1
0.5
0
OD
400 100 25 6.25 1.6 0
SARS-CoV2 Spike S1 protein (ng)

1035709
2.5
2
1.5
1
0.5
0
OD
400 100 25 6.25 1.6 0
SARS-CoV2 Spike S1 protein (ng)

1035716
2.5
2
1.5
1
0.5
0
OD
400 100 25 6.25 1.6 0
SARS-CoV2 Spike S1 protein (ng)

1035740
2.5
2
1.5
1
0.5
0
OD
400 100 25 6.25 1.6 0
SARS-CoV2 Spike S1 protein (ng)

1035744
2.5
2
1.5
1
0.5
0
OD
400 100 25 6.25 1.6 0
SARS-CoV2 Spike S1 protein (ng)

1035752
OD
2.5
2
1.5
1
0.5
0
400
100
25
6.25
1.6
0
SARS-CoV2 Spike S1 protein (ng)

1035753
OD
2.5
2
1.5
1
0.5
0
400
100
25
6.25
1.6
0
SARS-CoV2 Spike S1 protein (ng)

1035755
OD
2.5
2
1.5
1
0.5
0
400
100
25
6.25
1.6
0
SARS-CoV2 Spike S1 protein (ng)

1035762
OD
2.5
2
1.5
1
0.5
0
400
100
25
6.25
1.6
0
SARS-CoV2 Spike S1 protein (ng)

SARS-CoV2 Spike S1 protein (ng)

SARS-CoV2 Spike S1 protein (ng)

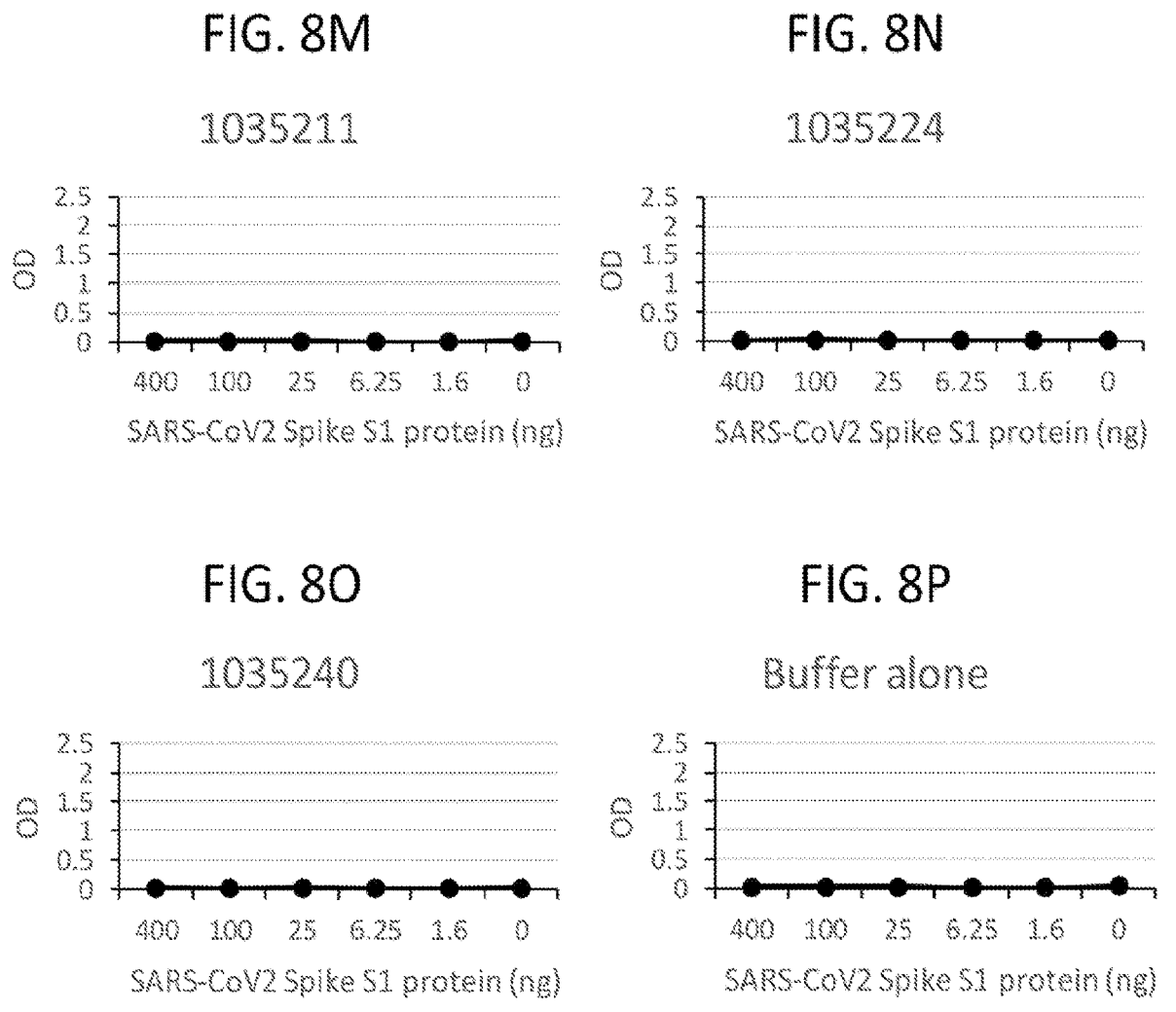

SARS-CoV2 Spike S1 protein (ng)

FIG. 8P

Buffer alone

OD 2.5 2 1.5 1 0.5 0

400 100 25 6.25 1.6 0

SARS-CoV2 Spike S1 protein (ng)

FIG. 9

```
1035744R_LC-1   DIkmTQSPsSmyaSlGERVTItCkASQdINSY----LsWFQQKPGkSPKtLIYrAnrMvd
1035744R_LC-2   DvqiTQSPsyLAaSpGEtITInCRvSkSIskY----LaWYQeKPGkTdKLLIYsgStLqS
1035716R_LC     DILLTQSPAiLSVSpGERVsfSCRASQSIgts----iHWYQQrtngSPrLLIkyASEsiS
1035740R_LC     DvLLTQSPAiLSVSpGERVsfSCRASQSIgts----LHWYQQrtngSPrLLIkyvSEsiS
1035419R_LC     nIVLTQSPASLAVSlGqRaTISCRASeSvDSYGaSFmHWcQQKPGqpPKLLIYlASnLeS
1035414R_LC     nIVLTQSPASLAVSlGqRaTISCRASeSvDSYGtSFmHWYQQKPGqpPKLLIYlASnLeS

1035744R_LC-1   GVPSRFSGSGSGqDysLTIsSlEyEDmgiYYClQydEfPyTFGGGTKLEIK
1035744R_LC-2   GIPSRFSGSGSGqDysLTIsSlEyEDmgiYYClQydEfPyTFGGGTKLEIK
1035716R_LC     GiPSRFSGSGSGTDyTLsInSVESEDiAdYYCQQSyswPTTFGaGTKLElK
1035740R_LC     GiPSRFSGSGSGTDFTLsInSVESEDiAdYYCQQSsswPTTFGaGTKLElK
1035419R_LC     GVPaRFSGSGSrTDFTLTIDpVEAdDAAtYYCQQNyEdPwTFGGGTKLEIK
1035414R_LC     GVPasFSGSGSrTDFTLTIDpVEAdDAAtYYCQQNnEdPwTFGGGTKLEIK

1035716R_HC     eVlLQQSGpELVKPGASVKIpCKASGYTFTDYnmdWVKQsHGksLEWIGdINPnNGgTiY
1035740R_HC     eVlLQQSGpELVKPGASVKIpCKASGYTFTDYnmdWVKQsHGksLEWIGdINPnNGfTiY
1035744R_HC     QVQLQQSdAELVKPGASVKlSCKASGYTFTDhaIHWVKQKpeQGLEWIGyISPGNGdikY
1035419R_HC     QVQLkQSGAELVrPGASVKlSCKtSGYiFTsYwIHWiKQRsGQGLEWIarIyPGtGsTyn
1035414R_HC     QVQLkQSGAELVrPGASVKlSCKtSGYiFTsYwIHWVKQRsGQGLEWIarIyPGtGnTyY

1035716R_HC     NqKFKGKATLTvDKSSSTAYMeLRSLTSEDtAVYyCAR---EgYgnyFDYWGQGTTlTVS
1035740R_HC     NqKFKGKATLTvDKSSSTAYMeLRSLTSEDtAVYyCAR---EgYgnyFDYWGQGTTlTVS
1035744R_HC     NEKFKGKATLTADKSSnTAYMQLnSLTSEDSAVYFCke--DDgfypwFVYWGQGTlVTVS
1035419R_HC     NEKFKGKATLTADKSSSTAYMQLsSLkSEDSAVYFCARGEDnlYfyamDYWGQGTSVTVS
1035414R_HC     NEKFKGKATLTADKSStTAYMQLsSLkSEDSAVYFCARGEDnlYyyamDYWGQGTSVTVS

1035716R_HC     S
1035740R_HC     S
1035744R_HC     a
1035419R_HC     S
1035414R_HC     S
```

FIG. 12A

```
1035423R_LC     DIVLTQSqkfmStSVGdRVSItCkASQn-v-----rtavaWYQQKPGQSPKaLIYlASNrh
1035752R_LC     DIVmTQSqkfmStSVGdRVSVtCkASQn-v-----gtnvaWYQQKPGQSPKaLIYsASyry
1035716R_LC     DILLTQSPAiLSvSpGERVSfSCRASQS-I-----gtsiHWYQQrtngSPrLLIkyASesi
1035740R_LC     DvLLTQSPAiLSvSpGERVSfSCRASQS-I-----gtsLHWYQQrtngSPrLLIkyvSesi
1035433R_LC     DIVmTQaapSvpAtpGEsVSISCRsSkSllhSnGNtYLYWFlQrPGQSPqLLIfrmSNLa
1035744R_LC     DIkmTQSPsSmyASLGERVtItCkASQd-I-----NSYLsWFQQKPGKSPKtLIYrAnrMv
1035744R_LC     DvqiTQSPsyLaASpGEtItInCRvSkS-I-----SkYLaWYQeKPGKtdKLLIYsgStLq
1035753R_LC     DIqmTQttsSLSASLGdRVtISCsASQg-I-----SnYLNWYQQKPdgtvKLLIYytSSLh
1035709R_LC     DIqmTQSPsSLSASLGERVSltCRASQe-I-----SgYLsWlQQKPdgtiKrLIYaAStLd
1035762R_LC     DIqmTQSPsSLSASLGERVSltCRASQe-I-----SgYLcWlQQKPdgtiKrLIYaAStLd
1035414R_LC     nIVLTQSPASLavSLGqRatISCRASeS-vDSYGTSFmHWYQQKPGQpPKLLIYlASNLe
1035419R_LC     nIVLTQSPASLavSLGqRatISCRASeS-vDSYGASFmHWcQQKPGQpPKLLIYlASNLe
1035755R_LC     qIVLTQSPAimSASpGEkVtISCsASsS-v------SYmYWYQQKPGsSPKpwIYrtSNLa

1035423R_LC     tGVPdRFtGSGSGTDFTLTISnVqSEDlADYfClQHwnYP--lTFGsGTKLElK
1035752R_LC     SGVPdRFtGSGSGTDFTLTInnVqSEDlAEYfCQQYnrYP--WTFGGGTKLEIK
1035716R_LC     SGiPSRFSGSGSGTDyTLsInSVESEDiADYYCQQsysWP--tTFGaGTKLElK
1035740R_LC     SGiPSRFSGSGSGTDFTLsInSVESEDiADYYCQQsssWP--tTFGaGTKLElK
1035433R_LC     SGVPdRFSGSGSGTaFTLrISrVEAEDvgvYYCmQHlEYP--yTFGGGTKLEIK
1035744R_LC1    dGVPSRFSGSGSGqDysLTISSlEyEDmgiYYClQYdEFP--yTFGGGTKLEIK
1035744R_LC2    SGiPSRFSGSGSGqDysLTISSlEyEDmgiYYClQYdEFP--yTFGGGTKLEIK
1035753R_LC     SGVPSRFSGSGSGTDysLTISnlEpEDiAtYYCQQYskLP--fTFGGGTnLEmK
1035709R_LC     SGVPkRFSGSrSGsDysLTISSlESEDfADYYClQYasYP--WTFGGGTKLEIK
1035762R_LC     SaVPkRFSGSrSGsDysLTISSlESEDfADfYClQYasYP--WTFGGGTKLEIK
1035414R_LC     SGVPAsFSGSGSrTDFTLTIdpVEAdDAAtYYCQQnnEdP--WTFGGGTKLEIK
1035419R_LC     SGVPARFSGSGSrTDFTLTIdpVEAdDAAtYYCQQnyEdP--WTFGGGTKLEIK
1035419R_LC     SGVPARFSGSGSrTDFTLTIdpVEAdDAAtYYCQQnyEdP--WTFGGGTKLEIK
1035755R_LC     SGVPARFSGSGSGTsysLTISSmEAEDAAtYYCQQYhsYPymyTFGGGTKLEIK
```

FIG. 13

| | Gly | Ala | Val | Leu | Ile | Met | Cys | Ser | Thr | Asn | Gln | Asp | Glu | Lys | Arg | His | Phe | Tyr | Trp | Pro |
|---|---|---|---|---|---|---|---|---|---|---|---|---|---|---|---|---|---|---|---|---|
| Gly | | | | | | | | | | | | | | | | | | | | |
| Ala | 58 | | | | | | | | | | | | | | | | | | | |
| Val | 10 | 37 | | | | | | | | | | | | | | | | | | |
| Leu | 2 | 10 | 30 | | | | | | | | | | | | | | | | | |
| Ile | | 7 | 66 | 25 | | | | | | | | | | | | | | | | |
| Met | 1 | 3 | 8 | 21 | 6 | | | | | | | | | | | | | | | |
| Cys | 1 | 3 | 3 | | 2 | | | | | | | | | | | | | | | |
| Ser | 45 | 77 | 4 | 3 | 2 | 2 | 12 | | | | | | | | | | | | | |
| Thr | 5 | 59 | 19 | 5 | 13 | 3 | 1 | 70 | | | | | | | | | | | | |
| Asn | 16 | 11 | 1 | 4 | 4 | | | 43 | 17 | | | | | | | | | | | |
| Gln | 3 | 9 | 3 | 8 | 1 | 2 | | 5 | 4 | 5 | | | | | | | | | | |
| Asp | 16 | 15 | 2 | | 1 | | | 10 | 6 | 53 | 8 | | | | | | | | | |
| Glu | 11 | 27 | 4 | 2 | 4 | 1 | | 9 | 3 | 9 | 42 | 83 | | | | | | | | |
| Lys | 6 | 6 | 2 | 4 | 4 | 9 | | 17 | 20 | 32 | 15 | | 10 | | | | | | | |
| Arg | 1 | 3 | 2 | 2 | 3 | 2 | 1 | 14 | 2 | 2 | 12 | 9 | | 48 | | | | | | |
| His | 1 | 2 | 3 | 4 | | | 1 | 3 | 1 | 23 | 24 | 4 | 2 | 2 | 10 | | | | | |
| Phe | 2 | 2 | 1 | 17 | 9 | 2 | | 4 | 1 | 1 | | | | | 1 | 2 | | | | |
| Tyr | | 2 | 2 | 2 | 1 | | 3 | 2 | 2 | 4 | | | 1 | 1 | | 4 | 26 | | | |
| Trp | | | | 1 | | | | 2 | | | | | | | 3 | | 1 | 1 | | |
| Pro | 5 | 35 | 5 | 4 | 1 | | 1 | 27 | 7 | 3 | 9 | 1 | 4 | 4 | 7 | 5 | 1 | | | |

FIG. 14

Neutralizing Ab (absent)

RBD

AuNP

ACE2

Neutralizing Ab (present)

RBD

AuNP

NAb

ACE2

100%
90%
80%
70%
60%
50%
40%
30%
20%
10%
0%
-10%
-20%
% Neutralization
0
2
4
6
8
10
CoV-2 RBD
SA RBD
BR P.1 RBD
UK RBD
Ab4 conc. (μg/mL)
Ab5 conc. (μg/mL)
Ab6 conc. (μg/mL)

SARS-CoV-2 RBD (Wildtype)

UK RBD (B.1.1.7) (Alpha variant)

SA RBD (B.1.351) (Beta variant)

BR P.1 RBD (B.1.1.28.1) (Gamma variant)

1. CoV-2 RBD
2. UK RBD
3. SA RBD
4. P.1 RBD
5. E484K RBD
6. K417E RBD
7. B.1.617.1 RBD
8. B.1.617.2 RBD
9. L452R RBD
10. T478K RBD
11. CoV RBD
12. anti-S2 Ab
13. BSA 1. CoV-2 RBD 2. UK RBD 3. SA RBD 4. P.1 RBD 5. E484K RBD
6. K417E RBD 7. B.1.617.1 RBD 8. B.1.617.2 RBD 9. L452R RBD 10. T478K RBD
11. CoV RBD 12. anti-S2 Ab 13. BSA

```
                              SEQUENCE LISTING


<160> NUMBER OF SEQ ID NOS: 104

<210> SEQ ID NO 1
<211> LENGTH: 107
<212> TYPE: PRT
<213> ORGANISM: Mus musculus

<400> SEQUENCE: 1

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Asn Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Phe
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105


<210> SEQ ID NO 2
<211> LENGTH: 108
<212> TYPE: PRT
<213> ORGANISM: Mus musculus

<400> SEQUENCE: 2

Gln Ile Val Leu Thr Gln Ser Pro Ala Ile Met Ser Ala Ser Pro Gly
1               5                   10                  15

Glu Lys Val Thr Ile Ser Cys Ser Ala Ser Ser Ser Val Ser Tyr Met
            20                  25                  30
```

```
Tyr Trp Tyr Gln Gln Lys Pro Gly Ser Ser Pro Lys Pro Trp Ile Tyr
        35                  40                  45

Arg Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Tyr His Ser Tyr Pro Tyr Met
                85                  90                  95

Tyr Thr Phe Gly Gly Gly Thr Lys Leu Glu Ile Lys
            100                 105


<210> SEQ ID NO 3
<211> LENGTH: 107
<212> TYPE: PRT
<213> ORGANISM: Mus musculus

<400> SEQUENCE: 3

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Asn Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105


<210> SEQ ID NO 4
<211> LENGTH: 111
<212> TYPE: PRT
<213> ORGANISM: Mus musculus

<400> SEQUENCE: 4

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Thr Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Ser Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Trp Thr Phe Gly Gly Gly Thr Lys Leu Glu Ile Lys
            100                 105                 110


<210> SEQ ID NO 5
<211> LENGTH: 111
<212> TYPE: PRT
<213> ORGANISM: Mus musculus
```

```
<400> SEQUENCE: 5

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Ala Ser Phe Met His Trp Cys Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Tyr
                85                  90                  95

Glu Asp Pro Trp Thr Phe Gly Gly Gly Thr Lys Leu Glu Ile Lys
            100                 105                 110


<210> SEQ ID NO 6
<211> LENGTH: 107
<212> TYPE: PRT
<213> ORGANISM: Mus musculus

<400> SEQUENCE: 6

Asp Ile Val Leu Thr Gln Ser Gln Lys Phe Met Ser Thr Ser Val Gly
1               5                   10                  15

Asp Arg Val Ser Ile Thr Cys Lys Ala Ser Gln Asn Val Arg Thr Ala
            20                  25                  30

Val Ala Trp Tyr Gln Gln Lys Pro Gly Gln Ser Pro Lys Ala Leu Ile
        35                  40                  45

Tyr Leu Ala Ser Asn Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Leu Gln His Trp Asn Tyr Pro Leu
                85                  90                  95

Thr Phe Gly Ser Gly Thr Lys Leu Glu Leu Lys
            100                 105


<210> SEQ ID NO 7
<211> LENGTH: 112
<212> TYPE: PRT
<213> ORGANISM: Mus musculus

<400> SEQUENCE: 7

Asp Ile Val Met Thr Gln Ala Ala Pro Ser Val Pro Ala Thr Pro Gly
1               5                   10                  15

Glu Ser Val Ser Ile Ser Cys Arg Ser Ser Lys Ser Leu Leu His Ser
            20                  25                  30

Asn Gly Asn Thr Tyr Leu Tyr Trp Phe Leu Gln Arg Pro Gly Gln Ser
        35                  40                  45

Pro Gln Leu Leu Ile Phe Arg Met Ser Asn Leu Ala Ser Gly Val Pro
    50                  55                  60

Asp Arg Phe Ser Gly Ser Gly Ser Gly Thr Ala Phe Thr Leu Arg Ile
65                  70                  75                  80

Ser Arg Val Glu Ala Glu Asp Val Gly Val Tyr Tyr Cys Met Gln His
                85                  90                  95
```

```
Leu Glu Tyr Pro Tyr Thr Phe Gly Gly Gly Thr Lys Leu Glu Ile Lys
            100                 105                 110


<210> SEQ ID NO 8
<211> LENGTH: 107
<212> TYPE: PRT
<213> ORGANISM: Mus musculus

<400> SEQUENCE: 8

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Trp
                85                  90                  95

Thr Phe Gly Gly Gly Thr Lys Leu Glu Ile Lys
            100                 105


<210> SEQ ID NO 9
<211> LENGTH: 107
<212> TYPE: PRT
<213> ORGANISM: Mus musculus

<400> SEQUENCE: 9

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Tyr Thr Leu Ser Ile Asn Ser Val Glu Ser
65                  70                  75                  80

Glu Asp Ile Ala Asp Tyr Tyr Cys Gln Gln Ser Tyr Ser Trp Pro Thr
                85                  90                  95

Thr Phe Gly Ala Gly Thr Lys Leu Glu Leu Lys
            100                 105


<210> SEQ ID NO 10
<211> LENGTH: 107
<212> TYPE: PRT
<213> ORGANISM: Mus musculus

<400> SEQUENCE: 10

Asp Val Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Leu His Trp Tyr Gln Gln Arg Thr Asn Gly Ser Pro Arg Leu Leu Ile
        35                  40                  45

Lys Tyr Val Ser Glu Ser Ile Ser Gly Ile Pro Ser Arg Phe Ser Gly
```

```
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Ser Ser Ser Trp Pro Thr
                85                  90                  95

Thr Phe Gly Ala Gly Thr Lys Leu Glu Leu Lys
            100                 105


<210> SEQ ID NO 11
<211> LENGTH: 107
<212> TYPE: PRT
<213> ORGANISM: Mus musculus

<400> SEQUENCE: 11

Asp Ile Lys Met Thr Gln Ser Pro Ser Ser Met Tyr Ala Ser Leu Gly
1               5                   10                  15

Glu Arg Val Thr Ile Thr Cys Lys Ala Ser Gln Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Met Val Asp Gly Val Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105


<210> SEQ ID NO 12
<211> LENGTH: 107
<212> TYPE: PRT
<213> ORGANISM: Mus musculus

<400> SEQUENCE: 12

Asp Val Gln Ile Thr Gln Ser Pro Ser Tyr Leu Ala Ala Ser Pro Gly
1               5                   10                  15

Glu Thr Ile Thr Ile Asn Cys Arg Val Ser Lys Ser Ile Ser Lys Tyr
            20                  25                  30

Leu Ala Trp Tyr Gln Glu Lys Pro Gly Lys Thr Asp Lys Leu Leu Ile
        35                  40                  45

Tyr Ser Gly Ser Thr Leu Gln Ser Gly Ile Pro Ser Arg Phe Ser Gly
    50                  55                  60

Ser Gly Ser Gly Gln Asp Tyr Ser Leu Thr Ile Ser Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Ile Lys
            100                 105


<210> SEQ ID NO 13
<211> LENGTH: 107
<212> TYPE: PRT
<213> ORGANISM: Mus musculus

<400> SEQUENCE: 13

Asp Ile Val Met Thr Gln Ser Gln Lys Phe Met Ser Thr Ser Val Gly
1               5                   10                  15
```

Asp Arg Val Ser Val Thr Cys Lys Ala Ser Gln Asn Val Gly Thr Asn
20 25 30

Val Ala Trp Tyr Gln Gln Lys Pro Gly Gln Ser Pro Lys Ala Leu Ile
35 40 45

Tyr Ser Ala Ser Tyr Arg Tyr Ser Gly Val Pro Asp Arg Phe Thr Gly
50 55 60

Ser Gly Ser Gly Thr Asp Phe Thr Leu Thr Ile Asn Asn Val Gln Ser
65 70 75 80

Glu Asp Leu Ala Glu Tyr Phe Cys Gln Gln Tyr Asn Arg Tyr Pro Trp
85 90 95

Thr Phe Gly Gly Gly Thr Lys Leu Glu Ile Lys
100 105

<210> SEQ ID NO 14
<211> LENGTH: 107
<212> TYPE: PRT
<213> ORGANISM: Mus musculus

<400> SEQUENCE: 14

Asp Ile Gln Met Thr Gln Thr Thr Ser Ser Leu Ser Ala Ser Leu Gly
1 5 10 15

Asp Arg Val Thr Ile Ser Cys Ser Ala Ser Gln Gly Ile Ser Asn Tyr
20 25 30

Leu Asn Trp Tyr Gln Gln Lys Pro Asp Gly Thr Val Lys Leu Leu Ile
35 40 45

Tyr Tyr Thr Ser Ser Leu His Ser Gly Val Pro Ser Arg Phe Ser Gly
50 55 60

Ser Gly Ser Gly Thr Asp Tyr Ser Leu Thr Ile Ser Asn Leu Glu Pro
65 70 75 80

Glu Asp Ile Ala Thr Tyr Tyr Cys Gln Gln Tyr Ser Lys Leu Pro Phe
85 90 95

Thr Phe Gly Gly Gly Thr Asn Leu Glu Met Lys
100 105

<210> SEQ ID NO 15
<211> LENGTH: 107
<212> TYPE: PRT
<213> ORGANISM: Mus musculus

<400> SEQUENCE: 15

Gln Ile Val Leu Thr Gln Ser Pro Ala Ile Met Ser Ala Ser Pro Gly
1 5 10 15

Glu Lys Val Thr Ile Ser Cys Ser Ala Ser Ser Ser Val Ser Tyr Met
20 25 30

Tyr Trp Tyr Gln Gln Lys Pro Gly Ser Ser Pro Lys Pro Trp Ile Tyr
35 40 45

Arg Thr Ser Asn Leu Ala Ser Val Pro Ala Arg Phe Ser Gly Ser Gly
50 55 60

Ser Gly Thr Ser Tyr Ser Leu Thr Ile Ser Ser Met Glu Ala Glu Asp
65 70 75 80

Ala Ala Thr Tyr Tyr Cys Gln Gln Tyr His Ser Tyr Pro Tyr Met Tyr
85 90 95

Thr Phe Gly Gly Gly Thr Lys Leu Glu Ile Lys
100 105

<210> SEQ ID NO 16

<211> LENGTH: 107
<212> TYPE: PRT
<213> ORGANISM: Mus musculus

<400> SEQUENCE: 16

```
Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Cys Trp Leu Gln Gln Lys Pro Asp Gly Thr Ile Lys Arg Leu Ile
        35                  40                  45

Tyr Ala Ala Ser Thr Leu Asp Ser Ala Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Phe Tyr Cys Leu Gln Tyr Ala Ser Tyr Pro Trp
                85                  90                  95

Thr Phe Gly Gly Gly Thr Lys Leu Glu Ile Lys
            100                 105
```

<210> SEQ ID NO 17
<211> LENGTH: 118
<212> TYPE: PRT
<213> ORGANISM: Mus musculus

<400> SEQUENCE: 17

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Asn Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Asn Tyr Asn Gln Lys Phe
    50                  55                  60

Lys Asp Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Asn Pro Leu Tyr Ala Met Asp Tyr Trp Gly Gln Gly Thr
            100                 105                 110

Ser Val Thr Val Ser Ser
        115
```

<210> SEQ ID NO 18
<211> LENGTH: 120
<212> TYPE: PRT
<213> ORGANISM: Mus musculus

<400> SEQUENCE: 18

```
Glu Val Gln Leu Gln Gln Ser Gly Ala Glu Phe Val Arg Pro Gly Ala
1               5                   10                  15

Leu Val Lys Leu Ser Cys Lys Ala Ser Gly Phe Asn Ile Lys Asp Asp
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asn Ser Ile Tyr Asp Pro Lys Phe
    50                  55                  60
```

```
Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Gly Glu Tyr Phe Gly Ser Gly Ser Phe Ala Tyr Trp Gly Gln
            100                 105                 110

Gly Thr Leu Val Thr Val Ser Ala
        115                 120


<210> SEQ ID NO 19
<211> LENGTH: 118
<212> TYPE: PRT
<213> ORGANISM: Mus musculus

<400> SEQUENCE: 19

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Thr Tyr
            20                  25                  30

Thr Met His Trp Val Lys Gln Arg Pro Gly Gln Gly Leu Glu Trp Ile
        35                  40                  45

Gly Tyr Ile Asn Pro Ser Ser Gly Tyr Thr Asn Tyr Asn Gln Lys Phe
    50                  55                  60

Lys Asp Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Asn Pro Leu Tyr Ala Met Asp Tyr Trp Gly Gln Gly Thr
            100                 105                 110

Ser Val Thr Val Ser Ser
        115


<210> SEQ ID NO 20
<211> LENGTH: 121
<212> TYPE: PRT
<213> ORGANISM: Mus musculus

<400> SEQUENCE: 20

Gln Val Gln Leu Lys Gln Ser Gly Ala Glu Leu Val Arg Pro Gly Ala
1               5                   10                  15

Ser Val Lys Leu Ser Cys Lys Thr Ser Gly Tyr Ile Phe Thr Ser Tyr
            20                  25                  30

Trp Ile His Trp Val Lys Gln Arg Ser Gly Gln Gly Leu Glu Trp Ile
        35                  40                  45

Ala Arg Ile Tyr Pro Gly Thr Gly Asn Thr Tyr Tyr Asn Glu Lys Phe
    50                  55                  60

Lys Gly Lys Ala Thr Leu Thr Ala Asp Lys Ser Ser Thr Thr Ala Tyr
65                  70                  75                  80

Met Gln Leu Ser Ser Leu Lys Ser Glu Asp Ser Ala Val Tyr Phe Cys
                85                  90                  95

Ala Arg Gly Glu Asp Asn Leu Tyr Tyr Tyr Ala Met Asp Tyr Trp Gly
            100                 105                 110

Gln Gly Thr Ser Val Thr Val Ser Ser
        115                 120


<210> SEQ ID NO 21
<211> LENGTH: 121
```

<212> TYPE: PRT
<213> ORGANISM: Mus musculus

<400> SEQUENCE: 21

```
Gln Val Gln Leu Lys Gln Ser Gly Ala Glu Leu Val Arg Pro Gly Ala
1               5                   10                  15

Ser Val Lys Leu Ser Cys Lys Thr Ser Gly Tyr Ile Phe Thr Ser Tyr
            20                  25                  30

Trp Ile His Trp Ile Lys Gln Arg Ser Gly Gln Gly Leu Glu Trp Ile
        35                  40                  45

Ala Arg Ile Tyr Pro Gly Thr Gly Ser Thr Tyr Asn Asn Glu Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Lys Ser Glu Asp Ser Ala Val Tyr Phe Cys
                85                  90                  95

Ala Arg Gly Glu Asp Asn Leu Tyr Phe Tyr Ala Met Asp Tyr Trp Gly
            100                 105                 110

Gln Gly Thr Ser Val Thr Val Ser Ser
        115                 120
```

<210> SEQ ID NO 22
<211> LENGTH: 119
<212> TYPE: PRT
<213> ORGANISM: Mus musculus

<400> SEQUENCE: 22

```
Glu Val Lys Leu Glu Glu Ser Gly Gly Gly Leu Val Gln Pro Gly Gly
1               5                   10                  15

Ser Met Lys Leu Ser Cys Thr Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Asn Lys Ala Asn Asn His Ala Thr Tyr Tyr Ala Glu
    50                  55                  60

Ser Val Lys Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Ile Leu Phe Ile Thr Tyr Ala Met Asp Tyr Trp Gly Gln Gly
            100                 105                 110

Thr Ser Val Thr Val Ser Ser
        115
```

<210> SEQ ID NO 23
<211> LENGTH: 117
<212> TYPE: PRT
<213> ORGANISM: Mus musculus

<400> SEQUENCE: 23

```
Gln Val Gln Leu Gln Gln Ser Gly Pro Gln Leu Val Arg Pro Gly Ala
1               5                   10                  15

Ser Val Lys Ile Ser Cys Lys Ala Ser Gly Tyr Ser Phe Thr Ile Tyr
            20                  25                  30

Trp Met His Trp Val Gln Gln Arg Pro Gly Gln Gly Leu Glu Trp Ile
        35                  40                  45

Gly Met Ile Asp Pro Ser Asp Ser Glu Thr Arg Leu Asn Gln Lys Phe
```

```
    50                  55                  60

Lys Asp Lys Ala Thr Leu Thr Val Asp Lys Ser Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Arg Arg Gly Asp Tyr Asn Phe Asp Tyr Trp Gly Gln Gly Thr Thr
            100                 105                 110

Leu Thr Val Ser Ser
        115


<210> SEQ ID NO 24
<211> LENGTH: 120
<212> TYPE: PRT
<213> ORGANISM: Mus musculus

<400> SEQUENCE: 24

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Asn Pro Asn Ile Val Asp Thr Gly Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Asp Gly Tyr Pro Leu Tyr Tyr Ala Met Asp Tyr Trp Gly Gln
            100                 105                 110

Gly Thr Ser Val Thr Val Ser Ser
        115                 120


<210> SEQ ID NO 25
<211> LENGTH: 118
<212> TYPE: PRT
<213> ORGANISM: Mus musculus

<400> SEQUENCE: 25

Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asp Ile Asn Pro Asn Asn Gly Gly Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Glu Gly Tyr Gly Asn Tyr Phe Asp Tyr Trp Gly Gln Gly Thr
            100                 105                 110

Thr Leu Thr Val Ser Ser
        115
```

<210> SEQ ID NO 26
<211> LENGTH: 118
<212> TYPE: PRT
<213> ORGANISM: Mus musculus

<400> SEQUENCE: 26

```
Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Asp Ile Asn Pro Asn Asn Gly Phe Thr Ile Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Glu Gly Tyr Gly Asn Tyr Phe Asp Tyr Trp Gly Gln Gly Thr
            100                 105                 110

Thr Leu Thr Val Ser Ser
        115
```

<210> SEQ ID NO 27
<211> LENGTH: 119
<212> TYPE: PRT
<213> ORGANISM: Mus musculus

<400> SEQUENCE: 27

```
Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Lys Pro Glu Gln Gly Leu Glu Trp Ile
        35                  40                  45

Gly Tyr Ile Ser Pro Gly Asn Gly Asp Ile Lys Tyr Asn Glu Lys Phe
    50                  55                  60

Lys Gly Lys Ala Thr Leu Thr Ala Asp Lys Ser Ser Asn Thr Ala Tyr
65                  70                  75                  80

Met Gln Leu Asn Ser Leu Thr Ser Glu Asp Ser Ala Val Tyr Phe Cys
                85                  90                  95

Lys Glu Asp Asp Gly Phe Tyr Pro Trp Phe Val Tyr Trp Gly Gln Gly
            100                 105                 110

Thr Leu Val Thr Val Ser Ala
        115
```

<210> SEQ ID NO 28
<211> LENGTH: 120
<212> TYPE: PRT
<213> ORGANISM: Mus musculus

<400> SEQUENCE: 28

```
Gln Val Gln Leu Gln Gln Pro Gly Ala Glu Leu Val Arg Pro Gly Ala
1               5                   10                  15

Ser Val Lys Met Ser Cys Lys Ala Ser Gly Tyr Thr Phe Thr Ser His
            20                  25                  30

Ser Ile His Trp Val Lys Gln Thr Pro Gly Gln Gly Leu Glu Trp Ile
        35                  40                  45
```

```
Gly Ala Val Tyr Pro Gly Asn Gly Asp Thr Ser Tyr Tyr Gln Lys Phe
    50                  55                  60

Lys Gly Lys Ala Thr Leu Thr Ala Asp Lys Ser Ser Ser Thr Ala Tyr
65                  70                  75                  80

Met His Leu Ser Ser Leu Thr Ser Glu Asp Ser Ala Val Tyr Tyr Cys
                85                  90                  95

Ala Arg Asp Gly Tyr Ser Asp Tyr Tyr Ala Met Asp Cys Trp Gly Gln
            100                 105                 110

Gly Thr Ser Val Thr Val Ser Ser
        115                 120


<210> SEQ ID NO 29
<211> LENGTH: 117
<212> TYPE: PRT
<213> ORGANISM: Mus musculus

<400> SEQUENCE: 29

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asn Thr Ile Tyr Asp Pro Lys Phe
    50                  55                  60

Leu Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Trp Tyr Tyr Tyr Ala Met Asp Ser Trp Gly Gln Gly Thr Ser
            100                 105                 110

Val Thr Val Ser Ser
        115


<210> SEQ ID NO 30
<211> LENGTH: 118
<212> TYPE: PRT
<213> ORGANISM: Mus musculus

<400> SEQUENCE: 30

Glu Val Gln Leu Gln Gln Ser Gly Ala Glu Leu Val Arg Pro Gly Ala
1               5                   10                  15

Leu Val Lys Leu Ser Cys Lys Ala Ser Gly Phe Asn Ile Lys Asp Tyr
            20                  25                  30

Tyr Met His Trp Val Lys Gln Arg Pro Glu Gln Gly Leu Glu Trp Ile
        35                  40                  45

Gly Trp Ile Asp Pro Glu Asn Gly Asn Ser Ile Tyr Asp Pro Lys Phe
    50                  55                  60

Gln Gly Lys Ala Ser Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Thr Pro Ser Ala Thr Ser Tyr Phe Asp Tyr Trp Gly Gln Gly Thr
            100                 105                 110

Thr Leu Thr Val Ser Ser
        115
```

<210> SEQ ID NO 31
<211> LENGTH: 120
<212> TYPE: PRT
<213> ORGANISM: Mus musculus

<400> SEQUENCE: 31

```
Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Val Lys Gln Ser His Gly Lys Ser Leu Glu Trp Ile
        35                  40                  45

Gly Gly Ile Asn Pro Asn Asn Gly Asp Thr Gly Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Phe Glu Asp Ser Ala Val Tyr Tyr Cys
                85                  90                  95

Ala Arg Asp Gly Tyr Pro Leu Tyr Tyr Ala Met Asp Tyr Trp Gly Gln
            100                 105                 110

Gly Thr Ser Val Thr Val Ser Ser
        115                 120
```

<210> SEQ ID NO 32
<211> LENGTH: 11
<212> TYPE: PRT
<213> ORGANISM: Mus musculus

<400> SEQUENCE: 32

```
Lys Ala Ser Gln Asp Ile Asn Ser Tyr Leu Asn
1               5                   10
```

<210> SEQ ID NO 33
<211> LENGTH: 7
<212> TYPE: PRT
<213> ORGANISM: Mus musculus

<400> SEQUENCE: 33

```
Arg Ala Asn Arg Leu Val Asp
1               5
```

<210> SEQ ID NO 34
<211> LENGTH: 9
<212> TYPE: PRT
<213> ORGANISM: Mus musculus

<400> SEQUENCE: 34

```
Leu Gln Tyr Asp Glu Phe Pro Tyr Thr
1               5
```

<210> SEQ ID NO 35
<211> LENGTH: 10
<212> TYPE: PRT
<213> ORGANISM: Mus musculus

<400> SEQUENCE: 35

```
Ser Ala Ser Ser Ser Val Ser Tyr Met Tyr
1               5                   10
```

<210> SEQ ID NO 36

<211> LENGTH: 7
<212> TYPE: PRT
<213> ORGANISM: Mus musculus

<400> SEQUENCE: 36

Arg Thr Ser Asn Leu Ala Ser
1               5

<210> SEQ ID NO 37
<211> LENGTH: 11
<212> TYPE: PRT
<213> ORGANISM: Mus musculus

<400> SEQUENCE: 37

Gln Gln Tyr His Ser Tyr Pro Tyr Met Tyr Thr
1               5                   10

<210> SEQ ID NO 38
<211> LENGTH: 15
<212> TYPE: PRT
<213> ORGANISM: Mus musculus

<400> SEQUENCE: 38

Arg Ala Ser Glu Ser Val Asp Ser Tyr Gly Ala Ser Phe Met His
1               5                   10                  15

<210> SEQ ID NO 39
<211> LENGTH: 7
<212> TYPE: PRT
<213> ORGANISM: Mus musculus

<400> SEQUENCE: 39

Leu Ala Ser Asn Leu Glu Ser
1               5

<210> SEQ ID NO 40
<211> LENGTH: 9
<212> TYPE: PRT
<213> ORGANISM: Mus musculus

<400> SEQUENCE: 40

Gln Gln Asn Tyr Glu Asp Pro Trp Thr
1               5

<210> SEQ ID NO 41
<211> LENGTH: 11
<212> TYPE: PRT
<213> ORGANISM: Mus musculus

<400> SEQUENCE: 41

Lys Ala Ser Gln Asn Val Arg Thr Ala Val Ala
1               5                   10

<210> SEQ ID NO 42
<211> LENGTH: 7
<212> TYPE: PRT
<213> ORGANISM: Mus musculus

<400> SEQUENCE: 42

Leu Ala Ser Asn Arg His Thr
1               5

<210> SEQ ID NO 43
<211> LENGTH: 9
<212> TYPE: PRT

<213> ORGANISM: Mus musculus

<400> SEQUENCE: 43

Leu Gln His Trp Asn Tyr Pro Leu Thr
1 5

<210> SEQ ID NO 44
<211> LENGTH: 16
<212> TYPE: PRT
<213> ORGANISM: Mus musculus

<400> SEQUENCE: 44

Arg Ser Ser Lys Ser Leu Leu His Ser Asn Gly Asn Thr Tyr Leu Tyr
1 5 10 15

<210> SEQ ID NO 45
<211> LENGTH: 7
<212> TYPE: PRT
<213> ORGANISM: Mus musculus

<400> SEQUENCE: 45

Arg Met Ser Asn Leu Ala Ser
1 5

<210> SEQ ID NO 46
<211> LENGTH: 9
<212> TYPE: PRT
<213> ORGANISM: Mus musculus

<400> SEQUENCE: 46

Met Gln His Leu Glu Tyr Pro Tyr Thr
1 5

<210> SEQ ID NO 47
<211> LENGTH: 15
<212> TYPE: PRT
<213> ORGANISM: Mus musculus

<400> SEQUENCE: 47

Arg Ala Ser Glu Ser Val Asp Ser Tyr Gly Thr Ser Phe Met His
1 5 10 15

<210> SEQ ID NO 48
<211> LENGTH: 9
<212> TYPE: PRT
<213> ORGANISM: Mus musculus

<400> SEQUENCE: 48

Gln Gln Asn Asn Glu Asp Pro Trp Thr
1 5

<210> SEQ ID NO 49
<211> LENGTH: 11
<212> TYPE: PRT
<213> ORGANISM: Mus musculus

<400> SEQUENCE: 49

Arg Ala Ser Gln Glu Ile Ser Gly Tyr Leu Ser
1 5 10

<210> SEQ ID NO 50
<211> LENGTH: 7
<212> TYPE: PRT
<213> ORGANISM: Mus musculus

<400> SEQUENCE: 50

```
Ala Ala Ser Thr Leu Asp Ser
1               5
```

<210> SEQ ID NO 51
<211> LENGTH: 9
<212> TYPE: PRT
<213> ORGANISM: Mus musculus

<400> SEQUENCE: 51

```
Leu Gln Tyr Ala Ser Tyr Pro Trp Thr
1               5
```

<210> SEQ ID NO 52
<211> LENGTH: 11
<212> TYPE: PRT
<213> ORGANISM: Mus musculus

<400> SEQUENCE: 52

```
Arg Ala Ser Gln Ser Ile Gly Thr Ser Ile His
1               5                   10
```

<210> SEQ ID NO 53
<211> LENGTH: 7
<212> TYPE: PRT
<213> ORGANISM: Mus musculus

<400> SEQUENCE: 53

```
Tyr Ala Ser Glu Ser Ile Ser
1               5
```

<210> SEQ ID NO 54
<211> LENGTH: 9
<212> TYPE: PRT
<213> ORGANISM: Mus musculus

<400> SEQUENCE: 54

```
Gln Gln Ser Tyr Ser Trp Pro Thr Thr
1               5
```

<210> SEQ ID NO 55
<211> LENGTH: 11
<212> TYPE: PRT
<213> ORGANISM: Mus musculus

<400> SEQUENCE: 55

```
Arg Ala Ser Gln Ser Ile Gly Thr Ser Leu His
1               5                   10
```

<210> SEQ ID NO 56
<211> LENGTH: 7
<212> TYPE: PRT
<213> ORGANISM: Mus musculus

<400> SEQUENCE: 56

```
Tyr Val Ser Glu Ser Ile Ser
1               5
```

<210> SEQ ID NO 57
<211> LENGTH: 9
<212> TYPE: PRT
<213> ORGANISM: Mus musculus

<400> SEQUENCE: 57

Gln Gln Ser Ser Ser Trp Pro Thr Thr
1               5

<210> SEQ ID NO 58
<211> LENGTH: 11
<212> TYPE: PRT
<213> ORGANISM: Mus musculus

<400> SEQUENCE: 58

Lys Ala Ser Gln Asp Ile Asn Ser Tyr Leu Ser
1               5                   10

<210> SEQ ID NO 59
<211> LENGTH: 7
<212> TYPE: PRT
<213> ORGANISM: Mus musculus

<400> SEQUENCE: 59

Arg Ala Asn Arg Met Val Asp
1               5

<210> SEQ ID NO 60
<211> LENGTH: 11
<212> TYPE: PRT
<213> ORGANISM: Mus musculus

<400> SEQUENCE: 60

Arg Val Ser Lys Ser Ile Ser Lys Tyr Leu Ala
1               5                   10

<210> SEQ ID NO 61
<211> LENGTH: 7
<212> TYPE: PRT
<213> ORGANISM: Mus musculus

<400> SEQUENCE: 61

Ser Gly Ser Thr Leu Gln Ser
1               5

<210> SEQ ID NO 62
<211> LENGTH: 11
<212> TYPE: PRT
<213> ORGANISM: Mus musculus

<400> SEQUENCE: 62

Lys Ala Ser Gln Asn Val Gly Thr Asn Val Ala
1               5                   10

<210> SEQ ID NO 63
<211> LENGTH: 7
<212> TYPE: PRT
<213> ORGANISM: Mus musculus

<400> SEQUENCE: 63

Ser Ala Ser Tyr Arg Tyr Ser
1               5

<210> SEQ ID NO 64
<211> LENGTH: 9
<212> TYPE: PRT
<213> ORGANISM: Mus musculus

<400> SEQUENCE: 64

Gln Gln Tyr Asn Arg Tyr Pro Trp Thr
1               5

<210> SEQ ID NO 65
<211> LENGTH: 11
<212> TYPE: PRT
<213> ORGANISM: Mus musculus

<400> SEQUENCE: 65

Ser Ala Ser Gln Gly Ile Ser Asn Tyr Leu Asn
1               5                   10

<210> SEQ ID NO 66
<211> LENGTH: 7
<212> TYPE: PRT
<213> ORGANISM: Mus musculus

<400> SEQUENCE: 66

Tyr Thr Ser Ser Leu His Ser
1               5

<210> SEQ ID NO 67
<211> LENGTH: 9
<212> TYPE: PRT
<213> ORGANISM: Mus musculus

<400> SEQUENCE: 67

Gln Gln Tyr Ser Lys Leu Pro Phe Thr
1               5

<210> SEQ ID NO 68
<211> LENGTH: 11
<212> TYPE: PRT
<213> ORGANISM: Mus musculus

<400> SEQUENCE: 68

Arg Ala Ser Gln Glu Ile Ser Gly Tyr Leu Cys
1               5                   10

<210> SEQ ID NO 69
<211> LENGTH: 5
<212> TYPE: PRT
<213> ORGANISM: Mus musculus

<400> SEQUENCE: 69

Asn Tyr Thr Met His
1               5

<210> SEQ ID NO 70
<211> LENGTH: 17
<212> TYPE: PRT
<213> ORGANISM: Mus musculus

<400> SEQUENCE: 70

Tyr Ile Asn Pro Ser Ser Gly Tyr Thr Asn Tyr Asn Gln Lys Phe Lys
1               5                   10                  15

Asp

<210> SEQ ID NO 71
<211> LENGTH: 9
<212> TYPE: PRT
<213> ORGANISM: Mus musculus

<400> SEQUENCE: 71

Arg Asn Pro Leu Tyr Ala Met Asp Tyr
1               5

<210> SEQ ID NO 72
<211> LENGTH: 5
<212> TYPE: PRT
<213> ORGANISM: Mus musculus

<400> SEQUENCE: 72

Asp Asp Tyr Met His
1 5

<210> SEQ ID NO 73
<211> LENGTH: 17
<212> TYPE: PRT
<213> ORGANISM: Mus musculus

<400> SEQUENCE: 73

Trp Ile Asp Pro Glu Asn Gly Asn Ser Ile Tyr Asp Pro Lys Phe Gln
1 5 10 15

Gly

<210> SEQ ID NO 74
<211> LENGTH: 11
<212> TYPE: PRT
<213> ORGANISM: Mus musculus

<400> SEQUENCE: 74

Gly Glu Tyr Phe Gly Ser Gly Ser Phe Ala Tyr
1 5 10

<210> SEQ ID NO 75
<211> LENGTH: 5
<212> TYPE: PRT
<213> ORGANISM: Mus musculus

<400> SEQUENCE: 75

Thr Tyr Thr Met His
1 5

<210> SEQ ID NO 76
<211> LENGTH: 5
<212> TYPE: PRT
<213> ORGANISM: Mus musculus

<400> SEQUENCE: 76

Ser Tyr Trp Ile His
1 5

<210> SEQ ID NO 77
<211> LENGTH: 17
<212> TYPE: PRT
<213> ORGANISM: Mus musculus

<400> SEQUENCE: 77

Arg Ile Tyr Pro Gly Thr Gly Ser Thr Tyr Asn Asn Glu Lys Phe Lys
1 5 10 15

Gly

<210> SEQ ID NO 78
<211> LENGTH: 12
<212> TYPE: PRT
<213> ORGANISM: Mus musculus

<400> SEQUENCE: 78

Gly Glu Asp Asn Leu Tyr Phe Tyr Ala Met Asp Tyr
1 5 10

<210> SEQ ID NO 79
<211> LENGTH: 5
<212> TYPE: PRT
<213> ORGANISM: Mus musculus

<400> SEQUENCE: 79

Asp Ala Trp Met Asp
1 5

<210> SEQ ID NO 80
<211> LENGTH: 19
<212> TYPE: PRT
<213> ORGANISM: Mus musculus

<400> SEQUENCE: 80

Glu Ile Arg Asn Lys Ala Asn Asn His Ala Thr Tyr Tyr Ala Glu Ser
1 5 10 15

Val Lys Gly

<210> SEQ ID NO 81
<211> LENGTH: 8
<212> TYPE: PRT
<213> ORGANISM: Mus musculus

<400> SEQUENCE: 81

Phe Ile Thr Tyr Ala Met Asp Tyr
1 5

<210> SEQ ID NO 82
<211> LENGTH: 5
<212> TYPE: PRT
<213> ORGANISM: Mus musculus

<400> SEQUENCE: 82

Ile Tyr Trp Met His
1 5

<210> SEQ ID NO 83
<211> LENGTH: 17
<212> TYPE: PRT
<213> ORGANISM: Mus musculus

<400> SEQUENCE: 83

Met Ile Asp Pro Ser Asp Ser Glu Thr Arg Leu Asn Gln Lys Phe Lys
1 5 10 15

Asp

<210> SEQ ID NO 84
<211> LENGTH: 8
<212> TYPE: PRT
<213> ORGANISM: Mus musculus

<400> SEQUENCE: 84

Arg Gly Asp Tyr Asn Phe Asp Tyr
1 5

<210> SEQ ID NO 85
<211> LENGTH: 17
<212> TYPE: PRT
<213> ORGANISM: Mus musculus

<400> SEQUENCE: 85

Arg Ile Tyr Pro Gly Thr Gly Asn Thr Tyr Tyr Asn Glu Lys Phe Lys
1 5 10 15

Gly

<210> SEQ ID NO 86
<211> LENGTH: 12
<212> TYPE: PRT
<213> ORGANISM: Mus musculus

<400> SEQUENCE: 86

Gly Glu Asp Asn Leu Tyr Tyr Tyr Ala Met Asp Tyr
1 5 10

<210> SEQ ID NO 87
<211> LENGTH: 5
<212> TYPE: PRT
<213> ORGANISM: Mus musculus

<400> SEQUENCE: 87

Glu Tyr Thr Met His
1 5

<210> SEQ ID NO 88
<211> LENGTH: 17
<212> TYPE: PRT
<213> ORGANISM: Mus musculus

<400> SEQUENCE: 88

Gly Ile Asn Pro Asn Ile Val Asp Thr Gly Tyr Asn Gln Lys Phe Lys
1 5 10 15

Gly

<210> SEQ ID NO 89
<211> LENGTH: 11
<212> TYPE: PRT
<213> ORGANISM: Mus musculus

<400> SEQUENCE: 89

Asp Gly Tyr Pro Leu Tyr Tyr Ala Met Asp Tyr
1 5 10

<210> SEQ ID NO 90
<211> LENGTH: 5
<212> TYPE: PRT
<213> ORGANISM: Mus musculus

<400> SEQUENCE: 90

Asp Tyr Asn Met Asp
1 5

<210> SEQ ID NO 91
<211> LENGTH: 17
<212> TYPE: PRT
<213> ORGANISM: Mus musculus

<400> SEQUENCE: 91

Asp Ile Asn Pro Asn Asn Gly Gly Thr Ile Tyr Asn Gln Lys Phe Lys
1 5 10 15

Gly

<210> SEQ ID NO 92

<211> LENGTH: 9
<212> TYPE: PRT
<213> ORGANISM: Mus musculus

<400> SEQUENCE: 92

Glu Gly Tyr Gly Asn Tyr Phe Asp Tyr
1               5

<210> SEQ ID NO 93
<211> LENGTH: 17
<212> TYPE: PRT
<213> ORGANISM: Mus musculus

<400> SEQUENCE: 93

Asp Ile Asn Pro Asn Asn Gly Phe Thr Ile Tyr Asn Gln Lys Phe Lys
1               5                   10                  15

Gly

<210> SEQ ID NO 94
<211> LENGTH: 5
<212> TYPE: PRT
<213> ORGANISM: Mus musculus

<400> SEQUENCE: 94

Asp His Ala Ile His
1               5

<210> SEQ ID NO 95
<211> LENGTH: 17
<212> TYPE: PRT
<213> ORGANISM: Mus musculus

<400> SEQUENCE: 95

Tyr Ile Ser Pro Gly Asn Gly Asp Ile Lys Tyr Asn Glu Lys Phe Lys
1               5                   10                  15

Gly

<210> SEQ ID NO 96
<211> LENGTH: 10
<212> TYPE: PRT
<213> ORGANISM: Mus musculus

<400> SEQUENCE: 96

Asp Asp Gly Phe Tyr Pro Trp Phe Val Tyr
1               5                   10

<210> SEQ ID NO 97
<211> LENGTH: 5
<212> TYPE: PRT
<213> ORGANISM: Mus musculus

<400> SEQUENCE: 97

Ser His Ser Ile His
1               5

<210> SEQ ID NO 98
<211> LENGTH: 17
<212> TYPE: PRT
<213> ORGANISM: Mus musculus

<400> SEQUENCE: 98

Ala Val Tyr Pro Gly Asn Gly Asp Thr Ser Tyr Tyr Gln Lys Phe Lys
1               5                   10                  15

Gly

<210> SEQ ID NO 99
<211> LENGTH: 11
<212> TYPE: PRT
<213> ORGANISM: Mus musculus

<400> SEQUENCE: 99

Asp Gly Tyr Ser Asp Tyr Tyr Ala Met Asp Cys
1 5 10

<210> SEQ ID NO 100
<211> LENGTH: 5
<212> TYPE: PRT
<213> ORGANISM: Mus musculus

<400> SEQUENCE: 100

Asp Tyr Tyr Met His
1 5

<210> SEQ ID NO 101
<211> LENGTH: 17
<212> TYPE: PRT
<213> ORGANISM: Mus musculus

<400> SEQUENCE: 101

Trp Ile Asp Pro Glu Asn Gly Asn Thr Ile Tyr Asp Pro Lys Phe Leu
1 5 10 15

Gly

<210> SEQ ID NO 102
<211> LENGTH: 8
<212> TYPE: PRT
<213> ORGANISM: Mus musculus

<400> SEQUENCE: 102

Trp Tyr Tyr Tyr Ala Met Asp Ser
1 5

<210> SEQ ID NO 103
<211> LENGTH: 9
<212> TYPE: PRT
<213> ORGANISM: Mus musculus

<400> SEQUENCE: 103

Pro Ser Ala Thr Ser Tyr Phe Asp Tyr
1 5

<210> SEQ ID NO 104
<211> LENGTH: 17
<212> TYPE: PRT
<213> ORGANISM: Mus musculus

<400> SEQUENCE: 104

Gly Ile Asn Pro Asn Asn Gly Asp Thr Gly Tyr Asn Gln Lys Phe Lys
1 5 10 15

Gly

ANTI-SEVERE ACUTE RESPIRATORY SYNDROME CORONAVIRUS ANTIBODIES

CONTINUING APPLICATION DATA

This application is the § 371 U.S. National Stage of International Application No. PCT/US2021/060734, filed Nov. 24, 2021, which claims the benefit of U.S. Provisional Application No. 63/194,501, filed May 28, 2021, and U.S. Provisional Application No. 63/117,960, filed Nov. 24, 2020, each of which is incorporated by reference herein in its entirety.

SEQUENCE LISTING

This application contains a Sequence Listing electronically submitted to the United States Patent and Trademark Office via EFS-Web as an ASCII text file entitled "0541-000015WO01_ST25.txt" having a size of 44 kilobytes and created on Jun. 16, 2023. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein.

BACKGROUND

Severe acute respiratory syndrome coronaviruses (SARS-CoV) including SARS-CoV-1 and SARS-CoV-2 are RNA viruses that are members of the coronaviridae family. SARS-CoV-1 and SARS-CoV-2 are the etiological agents of severe acute respiratory syndrome (SARS) and COVID-19, respectively. Both SARS-CoV-1 and SARS-CoV-2 primarily infect pulmonary epithelial cells (Parks et al., *Viruses* 13, 645 (2021) of the human respiratory system by binding to the angiotensin converting enzyme 2 (ACE-2) via the virus's homotrimeric spike protein (Kalathiya et al. *J Clin Med* 9, 1473 (2020)). The SARS-coronavirus spike protein is composed of two subunits: $S_1$ and $S_2$, with the $S_1$ being primarily responsible for binding to the host cell receptor (ACE-2) via a highly conserved receptor binding domain (RBD).

Highly characterized antibodies that are capable of binding to and blocking the binding of SARS-coronavirus spike protein to human ACE-2 are useful for elucidating SARS-coronavirus/host interactions, for identifying target epitopes on the SARS-coronavirus spike protein, for prevention of a SARS-coronavirus infection, for development of assays to detect the presence of SARS-coronavirus in clinical specimens, and for therapeutic treatment of COVID-19.

SUMMARY OF THE INVENTION

The present disclosure includes an anti-SARS-CoV antibody, wherein the anti-SARS-CoV antibody comprises an antibody or antigen binding fragment thereof that binds to the same epitope as an antibody produced a clone selected from 1035211.11, 1035224.11, 1035240.11, 1035414.11, 1035419.11, 1035423.11, 1035433.11, 1035709.11, 1035716.11, 1035740.11, 1035744.11, 1035752.11, 1035753.11, 1035755.11, and 1035762.11.

The present disclosure includes an anti-SARS-CoV antibody, wherein the anti-SARS-CoV antibody comprises: a heavy chain variable region ($V_H$) of an antibody selected from 1035211, 1035224, 1035240, 1035414, 1035419, 1035423, 1035433, 1035709, 1035716, 1035740, 1035744, 1035752, 1035753, 1035755, and 1035762; or a light chain variable region ($V_L$) of an antibody selected from 1035211, 1035224, 1035240, 1035414, 1035419, 1035423, 1035433, 1035709, 1035716, 1035740, 1035744, 1035752, 1035753, 1035755, and 1035762; or both.

The present disclosure includes an anti-SARS-CoV antibody, wherein the anti-SARS-CoV antibody comprises: a heavy chain variable region ($V_H$) comprising one or more complementary determining regions (CDRs) of Table 9; or a light chain variable region ($V_L$) comprising one or more CDRs of Table 8; or both.

The present disclosure includes an anti-SARS-CoV antibody, wherein the anti-SARS-CoV antibody comprises: each of the complementary determining regions (CDRs) of a heavy chain variable region of a monoclonal antibody produced by one of the clones of Table 1; or each of the CDRs of a light chain variable region of a monoclonal antibody produced by one of the clones of Table 1; or each of the CDRs of a heavy chain variable region of a monoclonal antibody produced by one of the clones of Table 1 and each of the CDRs of a light chain variable region of a monoclonal antibody produced by one of the clones of Table 1; or each of the CDRs of a heavy chain variable region of a monoclonal antibody produced by one of the clones of Table 1, and each of the CDRs of a light chain variable region of a monoclonal antibody produced by the same clone. In some embodiments, the CDRs of the heavy chain variable region have an amino acid sequence set forth in Table 9; or wherein the CDRs of the light chain variable region have an amino acid sequence set forth in Table 8; or both.

The present disclosure includes an anti-SARS-CoV antibody, wherein the anti-SARS-CoV antibody comprises an amino acid sequence having: at least 75%, at least 80%, at least 85%, at least 90%, at least 95%, at least 96%, at least 97%, at least 98%, or at least 99% sequence identity to the heavy chain variable region of a monoclonal antibody produced by a clone of Table 1; or at least 75%, at least 80%, at least 85%, at least 90%, at least 95%, at least 96%, at least 97%, at least 98%, or at least 99% sequence identity to the light chain variable region of a monoclonal antibody produced by a clone of Table 1; or at least 75%, at least 80%, at least 85%, at least 90%, at least 95%, at least 96%, at least 97%, at least 98%, or at least 99% sequence identity to the heavy chain variable region of a monoclonal antibody produced by a clone of Table 1, and at least 75%, at least 80%, at least 85%, at least 90%, at least 95%, at least 96%, at least 97%, at least 98%, or at least 99% sequence identity to the light chain variable region of a monoclonal antibody produced by a clone of Table 1.

The present disclosure includes an anti-SARS-CoV antibody, wherein the anti-SARS-CoV antibody comprises an antibody produced by a clone selected from 1035211.11, 1035224.11, 1035240.11, 1035414.11, 1035419.11, 1035423.11, 1035433.11, 1035709.11, 1035716.11, 1035740.11, 1035744.11, 1035752.11, 1035753.11, 1035755.11, and 1035762.11.

The present disclosure includes an anti-SARS-CoV antibody, wherein the anti-SARS-CoV antibody comprises the 1035211, 1035224, 1035240, 1035414, 1035419, 1035423, 1035433, 1035709, 1035716, 1035740, 1035744, 1035752, 1035753, 1035755, or 1035762 antibody.

In some embodiments, an anti-SARS-CoV antibody as disclosed herein specifically binds to the receptor binding domain (RBD) of the SARS-CoV spike (S) protein.

In some embodiments, an anti-SARS-CoV antibody as disclosed herein decreases binding of SARS-CoV-1 or SARS-CoV-2 or both SARS-CoV-1 and SARS-CoV-2 to ACE-2 by at least 10 percent (%), at least 15%, at least 20%, at least 25%, at least 30%, at least 40%, at least 50%, at least 60%, at least 70%, at least 80%, at least 90%, at least 95%, or at least 98%.

In some embodiments, an anti-SARS-CoV antibody as disclosed herein comprises an anti-SARS-CoV-2 antibody.

In some embodiments, an anti-SARS-CoV antibody as disclosed herein comprises an anti-SARS-CoV-1 antibody.

In some embodiments, an anti-SARS-CoV antibody as disclosed herein specifically binds to a SARS-CoV-2 variant selected from: the alpha variant (the United Kingdom variant (UK), B.1.1.7 lineage, RBD with N501Y); the beta variant (South African variant (SA), B.1.3512 lineage, RBD with K417N, E484K, and N501Y); the gamma variant (Brazilian variant P.1 (BR P.1), B.1.1.28.1 lineage, RBD with K417T, E484K, and N501Y); the delta variant (Indian variant 2 (IN v2), B.1.617.2 lineage, RBD with L452R and T478K); the epsilon variant (California variant (CA), B.1.427/9 lineage, RBD with L452R); the kappa variant (Indian variant 1 (IN v1), B.1.617.1 lineage, RBD with L452R and E484Q); the zeta variant (Brazilian variant P.2 (BR P.2), B.1.1.28.2 lineage, RBD with E484K); the K417E RBD (R319-F541 with K417E); the T478K RBD (R319-F541 with T478K); the iota variant (New York variant (NY), B.1.526 lineage, RBD with a single mutation E484K); the eta variant (Nigeria variant, B.1.525 lineage); the lambda variant (Peru variant, C.37 lineage, RBD with L452Q and F490S); the theta variant (Philippine variant, P.3 lineage, RBD with E484K and N501Y); and/or the Denmark mink variant (B.1.1.298 lineage, DM, RBD with Y453).

In some embodiments, for an anti-SARS-CoV antibody as disclosed herein binding specificity is characterized by a lateral flow immunoassay.

In some embodiments, an anti-SARS-CoV antibody as disclosed herein has an $NC_{50}$ of about 0.3 μg/μl to about 1.5 μg/μl.

In some embodiments, an anti-SARS-CoV antibody as disclosed herein binds to a bin A RBD epitope, a bin B RBD epitope, or a bin C RBD epitope.

In some embodiments, an anti-SARS-CoV antibody as disclosed herein comprises a humanized antibody.

In some embodiments, an anti-SARS-CoV antibody as disclosed herein is labeled with one or more detectable markers.

In some embodiments, an anti-SARS-CoV antibody as disclosed herein is for use as a reference control solution.

The present disclosure includes a composition comprising an anti-SARS-CoV antibody as disclosed herein.

In some embodiments, a composition as disclosed herein further comprises one or more additional anti-SARS-CoV antibodies. In some embodiments, one anti-SARS-CoV antibody binds to a bin A epitope of RBD and one anti-SARS-CoV antibody binds to a bin B epitope of RBD.

In some embodiments, a composition as disclosed herein comprises two or more anti-SARS-CoV antibodies as disclosed herein. In some embodiments, one anti-SARS-CoV antibody binds to a bin A epitope of RBD and one anti-SARS-CoV antibody binds to a bin B epitope of RBD. In some embodiments, the anti-SARS-CoV antibody that binds to a bin A epitope of RBD is selected from: an antibody that binds to the same epitope as an antibody produced by clone 1035709.11; an antibody produced by clone 1035709.11; an antibody comprising a heavy chain variable region ($V_H$) of the antibody 1035709; an antibody comprising a light chain variable region ($V_L$) of the antibody 1035709; an antibody comprising a heavy chain $V_H$ and a light chain $V_L$ of the antibody 1035709; an antibody comprising a heavy chain $V_H$ comprising one or more of the heavy chain complementary determining regions (CDRs) of antibody 1035709; an antibody comprising a light chain $V_L$ comprising one or more of the light chain CDRs of the antibody 1035709; an antibody comprising a heavy chain $V_H$ comprising one or more of the heavy chain CDRs and a light chain $V_L$ comprising one or more of the light chain CDRs of the antibody 1035709; an antibody comprising the three heavy chain CDRs of the antibody 1035709; an antibody comprising the three light chain CDRs the antibody 1035709; an antibody comprising the three heavy chain CDRs and the three light chain CDRs of the antibody 1035709; an antibody comprising a heavy chain $V_H$ with at least 75%, at least 80%, at least 85%, at least 90%, at least 95%, at least 96%, at least 97%, at least 98%, or at least 99% sequence identity to a heavy chain $V_H$ of the antibody 1035709; an antibody comprising a light chain $V_L$ with at least 75%, at least 80%, at least 85%, at least 90%, at least 95%, at least 96%, at least 97%, at least 98%, or at least 99% sequence identity to the light chain variable region of the antibody 1035709; and an antibody comprising a heavy chain $V_H$ with at least 75%, at least 80%, at least 85%, at least 90%, at least 95%, at least 96%, at least 97%, at least 98%, or at least 99% sequence identity to a heavy chain $V_H$ of the antibody 1035709 and a light chain $V_L$ with at least 75%, at least 80%, at least 85%, at least 90%, at least 95%, at least 96%, at least 97%, at least 98%, or at least 99% sequence identity to the light chain variable region of the antibody 1035709; and the anti-SARS-CoV antibody binds to the bin B epitope of RBD is selected from an antibody that binds to the same epitope as an antibody produced by clone 1035740.11; an antibody produced by clone 135740.11; an antibody comprising a heavy chain variable region ($V_H$) of the antibody 135740; an antibody comprising a light chain variable region ($V_L$) of the antibody 135740; an antibody comprising a heavy chain $V_H$ and a light chain $V_L$ of the antibody 135740; an antibody comprising a heavy chain $V_H$ comprising one or more of the heavy chain complementary determining regions (CDRs) of antibody 135740; an antibody comprising a light chain $V_L$ comprising one or more of the light chain CDRs of the antibody 135740; an antibody comprising a heavy chain $V_H$ comprising one or more of the heavy chain CDRs and a light chain $V_L$ comprising one or more of the light chain CDRs of the antibody 135740; an antibody comprising the three heavy chain CDRs of the antibody 135740; an antibody comprising the three light chain CDRs the antibody 135740; an antibody comprising the three heavy chain CDRs and the three light chain CDRs of the antibody 135740; an antibody comprising a heavy chain $V_H$ with at least 75%, at least 80%, at least 85%, at least 90%, at least 95%, at least 96%, at least 97%, at least 98%, or at least 99% sequence identity to a heavy chain $V_H$ of the antibody 135740; an antibody comprising a light chain $V_L$ with at least 75%, at least 80%, at least 85%, at least 90%, at least 95%, at least 96%, at least 97%, at least 98%, or at least 99% sequence identity to the light chain variable region of the antibody 135740; an antibody comprising a heavy chain $V_H$ with at least 75%, at least 80%, at least 85%, at least 90%, at least 95%, at least 96%, at least 97%, at least 98%, or at least 99% sequence identity to a heavy chain $V_H$ of the antibody 1035709 and a light chain $V_L$ with at least 75%, at least 80%, at least 85%, at least 90%, at least 95%, at least 96%, at least 97%, at least 98%, or at least 99% sequence identity to the light chain variable region of the antibody 135740.

In some embodiments, a composition as disclosed herein further comprises a pharmaceutically acceptable carrier.

In some embodiments, a composition as disclosed herein is for use as a reference control solution.

The present disclosure includes a method comprising administering an anti-SARS-CoV antibody as disclosed herein or a composition thereof as disclosed herein to a subject. In some embodiments, the subject is suspected of having SARS-CoV-1 or SARS-CoV-2 or has been diagnosed with SARS-CoV-1 or SARS-CoV-2. In some embodiments, wherein the method comprises administering multiple doses of the anti-SARS-CoV antibody or composition thereof. In some embodiments, the subject has been exposed to SARS-CoV-1 or SARS-CoV-2.

In some embodiments, the subject is suspected of having, has been diagnosed with, or has been exposed to a SARS-CoV-2 variant selected from: the alpha variant (the United Kingdom variant (UK), B.1.1.7 lineage, RBD with N501Y); the beta variant (South African variant (SA), B.1.3512 lineage, RBD with K417N, E484K, and N501Y); the gamma variant (Brazilian variant P.1 (BR P.1), B.1.1.28.1 lineage, RBD with K417T, E484K, and N501Y); the delta variant (Indian variant 2 (IN v2), B.1.617.2 lineage, RBD with L452R and T478K); the epsilon variant (California variant (CA), B.1.427/9 lineage, RBD with L452R); the kappa variant (Indian variant 1 (IN v1), B.1.617.1 lineage, RBD with L452R and E484Q); the zeta variant (Brazilian variant P.2 (BR P.2), B.1.1.28.2 lineage, RBD with E484K); the K417E RBD (R319-F541 with K417E); the T478K RBD (R319-F541 with T478K); the iota variant (New York variant (NY), B.1.526 lineage, RBD with a single mutation E484K); the eta variant (Nigeria variant, B.1.525 lineage); the lambda variant (Peru variant, C.37 lineage, RBD with L452Q and F490S); the theta variant (Philippine variant, P.3 lineage, RBD with E484K and N501Y); and/or the Denmark mink variant (B.1.1.298 lineage, DM, RBD with Y453). In some embodiments, the subject is a human.

In some embodiments, the method comprises administering about 1 g to about 12 g of the anti-SARS-CoV antibody.

In some embodiments, the method further comprises administering a small molecule antiviral therapeutic agent to the subject. In some embodiments, the small molecule antiviral therapeutic agent is selected from remdesivir, molnupiravir, paxlovid, or a combination thereof.

The present disclosure includes an immunoassay device comprising one or more of an anti-SARS-CoV antibody as disclosed herein. In some embodiments, the immunoassay device further comprises an anti-SARS-CoV nucleocapsid protein (NP) antibody.

The present disclosure includes a lateral flow immunoassay device comprising one or more of an anti-SARS-CoV antibody as disclosed herein. In some embodiments, the lateral flow immunoassay device further comprises an anti-SARS-CoV nucleocapsid protein (NP) antibody.

The present disclosure includes a method comprising using an anti-SARS-CoV antibody as disclosed herein or a composition as disclosed herein to diagnose a subject with SARS-CoV-1 or SARS-CoV-2. In some embodiments, the method comprises contacting a biosample from the subject with an anti-SARS-CoV antibody as disclosed.

The present disclosure includes a method of identifying a SARS-CoV-2 receptor binding domain (RBD) variant in a sample, the method comprising contacting the biosample with an anti-SARS-CoV antibody as disclosed. In some embodiments, the method comprises contacting the biosample with more than one anti-SARS-CoV antibody as disclosed. In some embodiments, multiple SARS-CoV-2 receptor binding domain (RBD) variants are identified simultaneously.

The term "antibody" as used herein refers to a molecule that contains at least one antigen binding site that immunospecifically binds to a particular antigen target of interest. The term "antibody" thus includes but is not limited to a full-length antibody and/or its variants, a fragment thereof, peptibodies and variants thereof, monoclonal antibodies (including full-length monoclonal antibodies), polyclonal antibodies, multispecific antibodies (for example, bispecific antibodies) formed from at least two intact antibodies, human antibodies, humanized antibodies, and antibody mimetics that mimic the structure and/or function of an antibody or a specified fragment or portion thereof, including single chain antibodies and fragments thereof. Binding of an antibody to a target can cause a variety of effects, such as but not limited to where such binding modulates, decreases, increases, antagonizes, agonizes, mitigates, alleviates, blocks, inhibits, abrogates and/or interferes with at least one target activity or binding, or with receptor activity or binding, in vitro, in situ, and/or in vivo. An antibody of the present disclosure thus encompasses antibody fragments capable of binding to a biological molecule (such as an antigen or receptor) or portions thereof, including but not limited to Fab, Fab' and F(ab')2, pFc', Fd, a single domain antibody (sdAb), a variable fragment (Fv), a single-chain variable fragment (scFv) or a disulfide-linked Fv (sdFv); a diabody or a bivalent diabody; a linear antibody; a single-chain antibody molecule; and a multispecific antibody formed from antibody fragments. The antibody may be of any type, any class, or any subclass. When the antibody is a human or mouse antibody, the type may include, for example, IgG, IgE, IgM, IgD, IgA and IgY, and the class may include, for example, IgG1, IgG2, IgG3, IgG4, IgA1 and IgA2.

The term "monoclonal antibody" as used herein refers to an antibody obtained from a population of substantially homogeneous antibodies, that is, the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which typically include different antibodies directed against different determinants (epitopes), each monoclonal antibody is directed against a single determinant on the antigen. The monoclonal antibodies may be synthesized by hybridoma cells uncontaminated by other immunoglobulin producing cells. Alternatively, the monoclonal antibody may be produced recombinantly including, for example, by cells stably or transiently transfected with the heavy and light chain genes encoding the monoclonal antibody.

The modifier "monoclonal" indicates the character of an antibody, as defined above, as being obtained from a substantially homogeneous population of antibodies and is not to be construed as requiring engineering of the antibody by any particular method. In some embodiments, the term "monoclonal" is used herein to refers to an antibody that is derived from a clonal population of cells, including any eukaryotic, prokaryotic, or phage clone, and not the method by which the antibody was engineered.

As used herein, "isolated" refers to material removed from its original environment (for example, the natural environment if it is naturally occurring), and thus is altered "by the hand of man" from its natural state.

As used herein, "room temperature" is about 16° C. to about 26° C. or, more preferably, about 18° C. to about 24° C. In some embodiments, "room temperature" is about 20° C. to about 22° C.

As used herein "sequence identity" between two polypeptides is determined by comparing the amino acid sequence of one polypeptide to the sequence of a second polypeptide. When discussed herein, whether any particular polypeptide is at least 40 percent (%), at least 45%, at least 50%, at least 55%, at least 60%, at least 65%, at least 70%, at least 75%, at least 80%, at least 85%, at least 90%, at least 95%, at least 96%, at least 97%, at least 98%, or at least 99% identical to another polypeptide may be determined using methods and computer programs/software known in the art such as, but not limited to, the BESTFIT program (Wisconsin Sequence Analysis Package, Version 8 for Unix, Genetics Computer Group, University Research Park, 575 Science Drive, Madison, Wis. 53711). BESTFIT uses the local homology algorithm of Smith and Waterman (1981) *Advances in Applied Mathematics* 2:482-489, to find the best segment of homology between two sequences. When using BESTFIT or any other sequence alignment program to determine whether a particular sequence is, for example, 95% identical to a reference sequence according to the present disclosure, the parameters are set such that the percentage of identity is calculated over the full-length of the reference polypeptide sequence and that gaps in homology of up to 5% of the total number of amino acids in the reference sequence are allowed.

"Binding affinity" or "affinity binding" refers to the strength of the sum total of noncovalent interactions between a single binding site of a molecule (for example, an antibody) and its binding partner (for example, an antigen or antigenic epitope). The affinity of a molecule X for its partner Y is represented by the dissociation constant ($K_D$), which can generally be determined by using methods known in the art, for example, using the BIACORE biosensor, commercially available from BIACORE (GE Healthcare Worldwide, Chicago, IL). In some embodiments, antibodies of the present disclosure may be described in terms of their binding affinity for SARS-CoV. In some embodiments, antibodies of the present disclosure include antibodies that interact with an antigen wherein the dissociation constant ($K_D$) is less than or equal to $5\times10^{-6}$ M, less than or equal to $1\times10^{-6}$ M, less than or equal to $5\times10^{-7}$ M, less than or equal to $1\times10^{-7}$ M, less than or equal to $5\times10^{-8}$ M, less than or equal to $1\times10^{-8}$ M, less than or equal to $5\times10^{-9}$ M, less than or equal to $1\times10^{-9}$ M, less than or equal to $5\times10^{-10}$ M, less than or equal to $1\times10^{-10}$ M, less than or equal to $5\times10^{-11}$ M, less than or equal to $1\times10^{-11}$ M, less than or equal to $5\times10^{-12}$ M, less than or equal to $1\times10^{-12}$ M, less than or equal to $5\times10^{-13}$ M, less than or equal to $1\times10^{-13}$ M, less than or equal to $5\times10^{-14}$ M, less than or equal to $1\times10^{-14}$ M, less than or equal to $5\times10^{-15}$ M, or less than or equal to $1\times10^{-15}$ M.

As used herein, the term "subject" includes, but is not limited to, humans and non-human vertebrates. In some embodiments, a subject is a mammal, particularly a human. A subject may be an individual. A subject may be an "individual," "patient," or "host." Non-human vertebrates include livestock animals, companion animals, and laboratory animals. Non-human subjects also include non-human primates as well as rodents, such as, but not limited to, a rat or a mouse. Non-human subjects also include, without limitation, chickens, horses, cows, pigs, goats, dogs, cats, guinea pigs, hamsters, mink, and rabbits.

As used herein "in vitro" is in cell culture and "in vivo" is within the body of a subject.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the invention.

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements.

By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

Unless otherwise specified, "a," "an," "the," and "at least one" are used interchangeably and mean one or more than one.

As used herein, the term "or" is generally employed in its usual sense including "and/or" unless the content clearly dictates otherwise.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

Herein, "up to" a number (for example, up to 50) includes the number (for example, 50).

The term "in the range" or "within a range" (and similar statements) includes the endpoints of the stated range.

For any method disclosed herein that includes discrete steps, the steps may be conducted in any feasible order. And, as appropriate, any combination of two or more steps may be conducted simultaneously.

All headings are for the convenience of the reader and should not be used to limit the meaning of the text that follows the heading, unless so specified.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

Unless otherwise indicated, all numbers expressing quantities of components, molecular weights, and so forth used in the specification and claims are to be understood as being modified in all instances by the term "about." As used herein in connection with a measured quantity, the term "about" refers to that variation in the measured quantity as would be expected by the skilled artisan making the measurement and exercising a level of care commensurate with the objective of the measurement and the precision of the measuring equipment used. Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 2A-FIG. 2E. FIG. 2A shows a schematic of SARS-CoV-2 viral antibody blocking cell model. An antibody and a recombinant SARS-CoV-2 $S_1$ RBD-His protein are exposed to one another, allowing a complex to form between the antibody (for example, an anti-SARS-CoV-2 antibody) and the SARS-CoV-2 $S_1$ RBD-His protein if the antibody can bind to the SARS-CoV-2 $S_1$ RBD-His protein. This mixture (including, if one formed, an antibody-SARS-CoV-2 $S_1$ RBD-His protein complex) is added to a GFP-labeled HEK transfectant cell stably over-expressing human ACE-2 (hACE-2 HEK/eGFP Tfx). Binding between the SARS-CoV-2 $S_1$ RBD-His protein and the human ACE-2 is detected using an anti-His antibody. Exemplary results are shown in FIG. 2B-FIG. 2E. In the absence of a SARS-CoV-2 protein, no anti-His fluorescence is detected by flow cytometry (FIG. 2B); however, when a SARS-CoV-2 $S_1$ RBD protein is added to hACE-2 HEK/eGFP cells, a high level of anti-His fluorescence is detected (FIG. 2C). In the presence of irrelevant or isotype control antibodies SARS-CoV-2 $S_1$/RBD proteins bind to ACE-2, and fluorescence remains high (FIG. 2D). In contrast, when anti-SARS-CoV-2 $S_1$ RBD antibodies are added, the antibodies form a complex with SARS-CoV-2 $S_1$/RBD proteins, preventing the viral proteins from binding ACE-2, resulting in decreased anti-His fluorescence (FIG. 2E).

FIG. 9 shows a sequence alignment of the amino acid sequences of the light chains of antibody candidates 1035419 (SEQ ID NO: 5), 1035414 (SEQ ID NO: 4), 1035716 (SEQ ID NO: 9), 1035740 (SEQ ID NO: 10), 1036744-1 (SEQ ID NO: 11), and 1036744-1 (SEQ ID NO: 12) and the heavy chains of antibody candidates 1035419 (SEQ ID NO: 21), 1035414 (SEQ ID NO: 20), 1035716 (SEQ ID NO: 25), 1035740 (SEQ ID NO: 26), and 1036744 (SEQ ID NO: 27). Bold letters indicate CDRs.

FIG. 12A-FIG. 12B shows sequence alignments of full antibody panel. FIG. 12A shows light chain variable region sequences and FIG. 12B show heavy chain variable region sequences.

In FIG. 12A, 1035423R_LC is SEQ ID NO: 6; 1035752R_LC is SEQ ID NO: 13; 1035716R_LC is SEQ ID NO: 9; 1035740R_LC is SEQ ID NO: 10; 1035433R_LC is SEQ ID NO: 7; 1035744R_LC1 is SEQ ID NO: 11; 1035744R_LC2 is SEQ ID NO: 12; 1035753R_LC is SEQ ID NO: 14; 1035709R_LC is SEQ ID NO: 8; 1035762R_LC is SEQ ID NO: 16; 1035414R_LC is SEQ ID NO: 4; 1035419R_LC is SEQ ID NO: 5; and 1035755R_LC is SEQ ID NO: 15.

In FIG. 12 B, 1035423R_HC is SEQ ID NO: 22; 1035753R_HC is SEQ ID NO: 29; 1035755R_HC is SEQ ID NO: 30; 1035433R_HC is SEQ ID NO:23; 1035744R_HC is SEQ ID NO: 27; 1035716R_HC is SEQ ID NO: 25; 1035740R_HC is SEQ ID NO: 26; 1035709R_HC is SEQ ID NO: 24; 1035762R_HC is SEQ ID NO: 31; 1035752R_HC is SEQ ID NO: 28; 1035414R_HC is SEQ ID NO: 20; and 1035419R_HC is SEQ ID NO: 21.

FIG. 13 shows a representative table of frequency with which one amino acid is replaced by another residue of the same protein across different species. A larger number indicates higher probability of substitution. For example, Glu and Asp can substitute each other at a higher frequency (score 83) than Glu and Met which has a score of 1.

FIG. 14 shows mutations in the spike RBD protein of currently circulating SARS-CoV-2 variants. The top panel shows variants included in this analysis. The bottom panel shows variants not addressed in this analysis.

1035740, Ab3 is clone No. 1035753, Ab4 is clone No. 1035762, Ab5 is clone No. 1035419, Ab6 is clone No. 1035224, and Ab7 is clone No. 1035240.

Figure 17A:
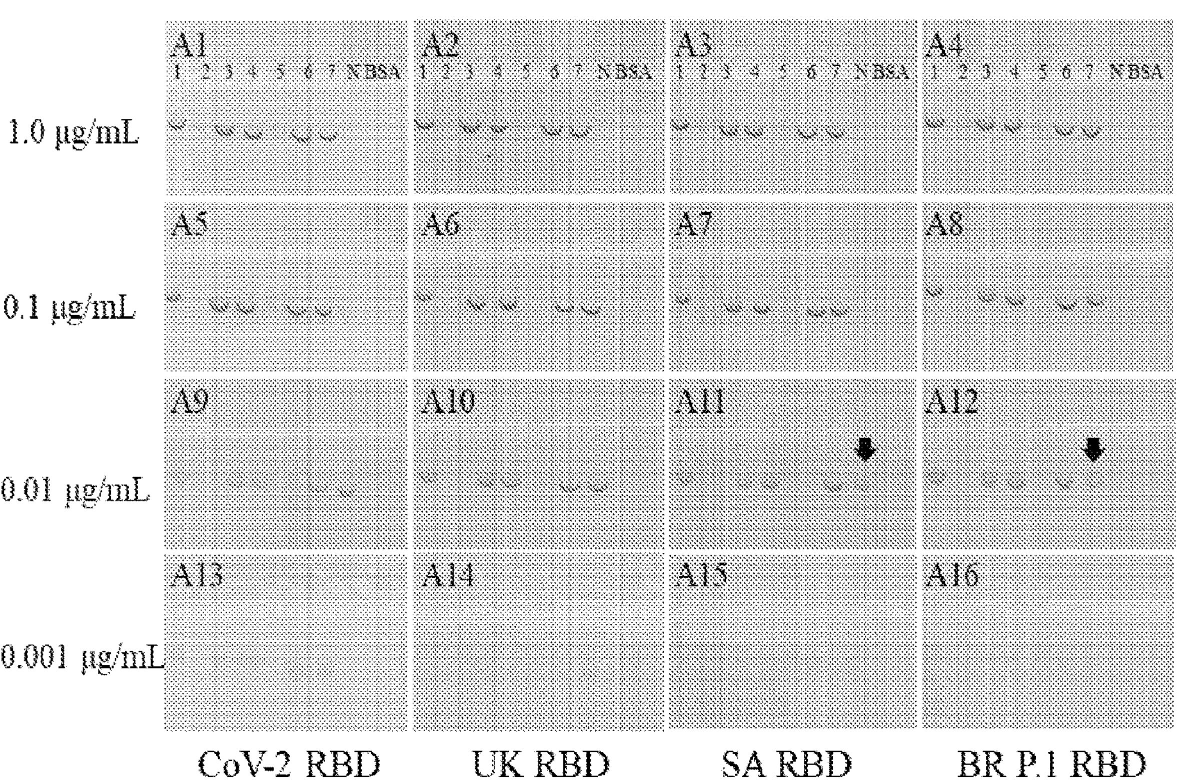
Figure 17B:
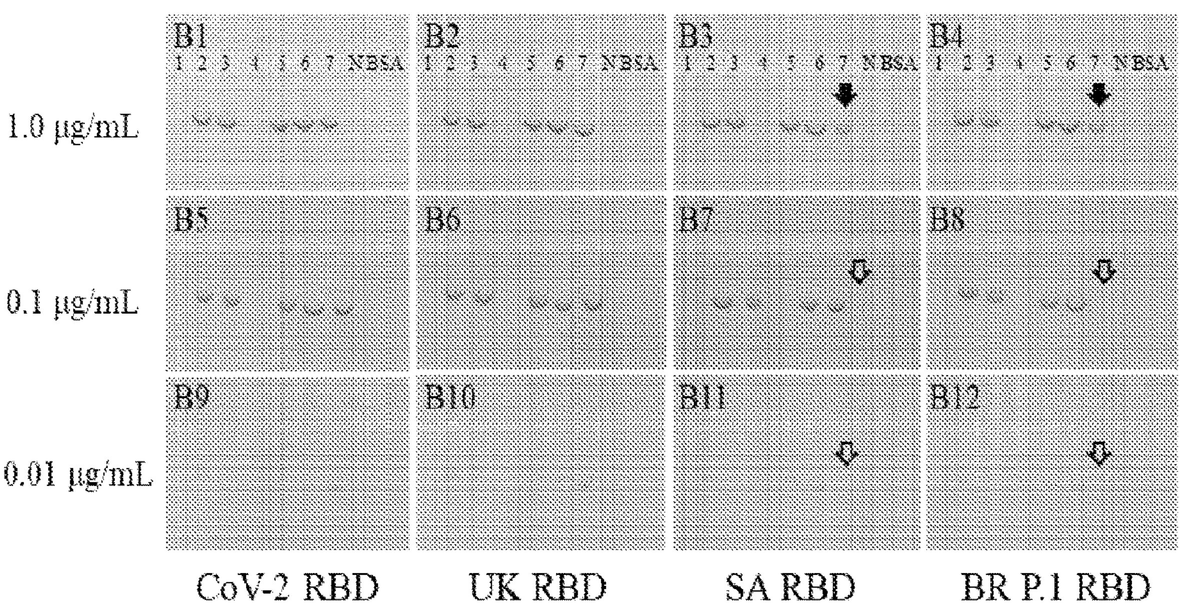

FIG. 17A-FIG. 17B show comparative binding characteristics to four RBDs using Ab4 and Ab5 as detectors and the Ab1, Ab2, Ab3, Ab4, Ab5, Ab6, Ab7 antibodies as captures in sandwich immunoassay. FIG. 17A shows binding behavior of Ab5-AuNP conjugate to four RBDs. FIG. 17B shows binding behavior of Ab4-AuNP conjugate to four RBDs. Solid arrow in dipsticks (A11, A12, B3, B4) indicates similar level of spot signal intensity. Open arrow in dipsticks (B7, B8, B11 and B12) indicates very faint or invisible Ab7 spot.

Figure 18A:
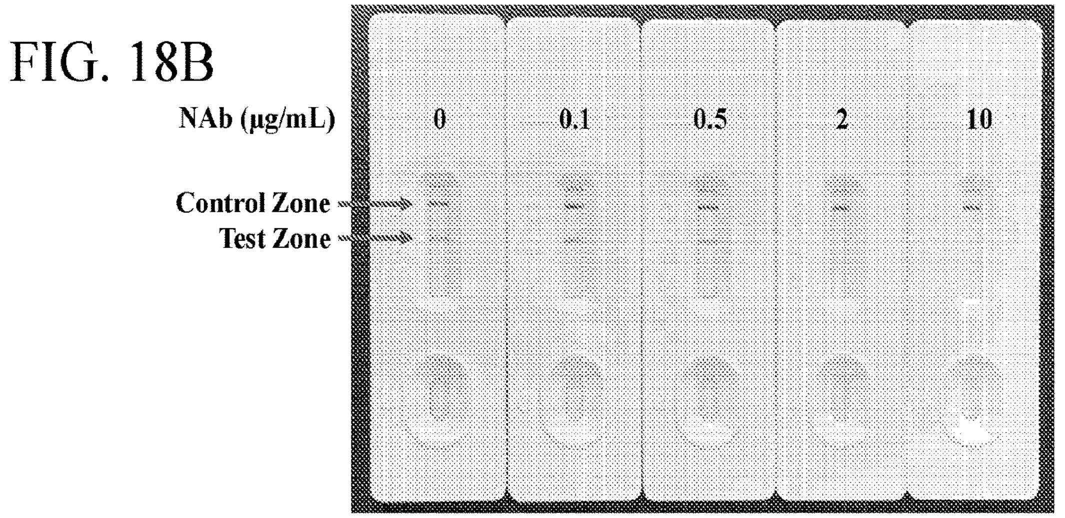

FIG. 18A-FIG. 18B show the neutralizing antibody test principle and images of representative test devices. FIG. 18A shows the lateral flow cassette neutralization assay principle. FIG. 18B is a photograph of a representative set of lateral flow neutralization test devices. (Units=neutralizing antibody concentration in μg/mL).

Figures 19A, 19B, 19C:
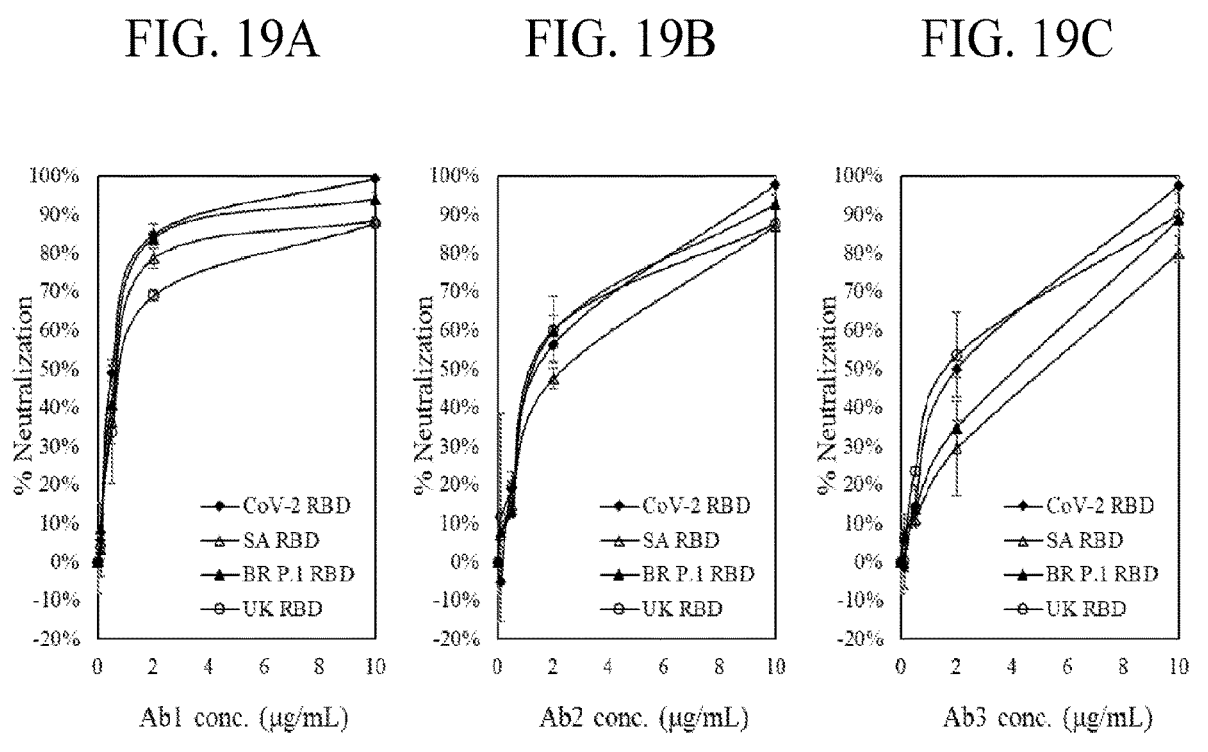
Figures 19D, 19E, 19F:
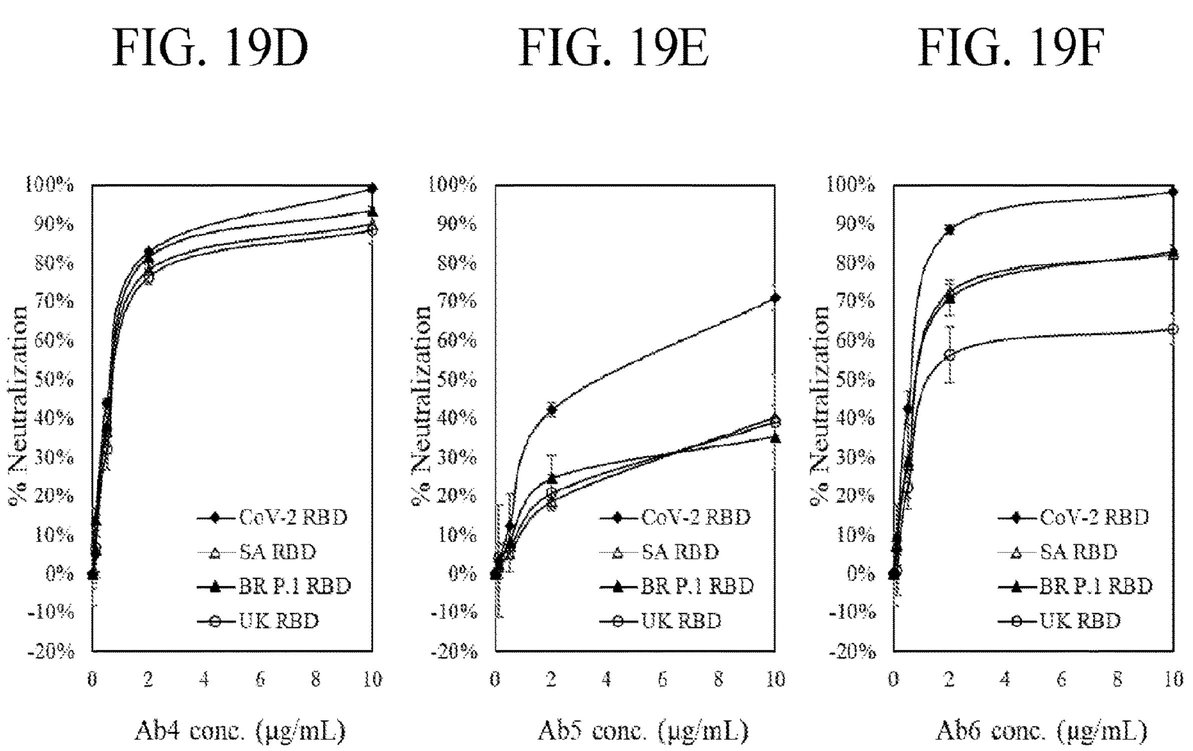
Figure 19G:
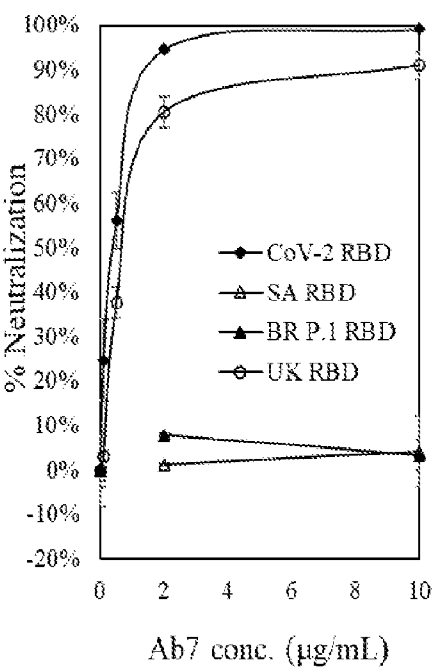
Figure 19H:
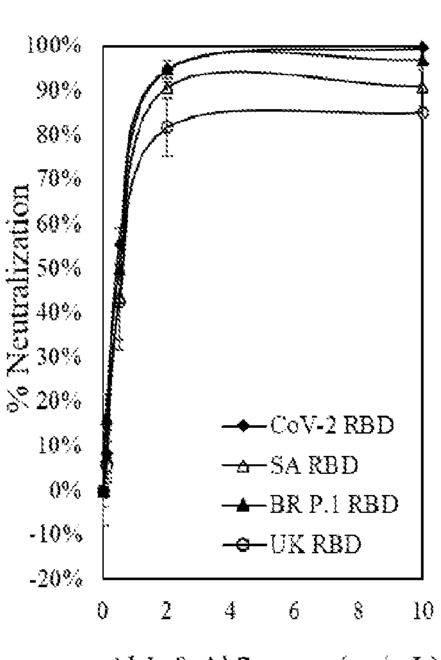

FIG. 19A-FIG. 19H show the neutralization kinetics by lateral flow cassette neutralization assays. FIG. 19A-FIG. 19G are kinetic curves for individual antibodies against the four RBDs. FIG. 19H is the kinetic curve for the combined two antibodies against the four RBDs. Ab1 is clone No. 1035709, Ab2 is clone No. 1035740, Ab3 is clone No. 1035753, Ab4 is clone No. 1035762, Ab5 is clone No. 1035419, Ab6 is clone No. 1035224, and Ab7 is clone No. 1035240.

Figure 20A:
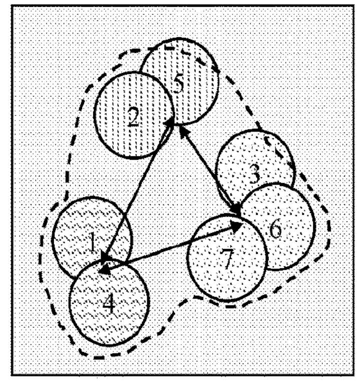
Figure 20B:
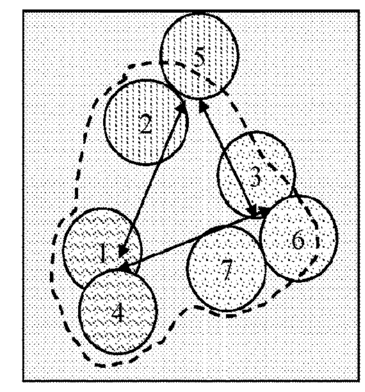
Figure 20C:
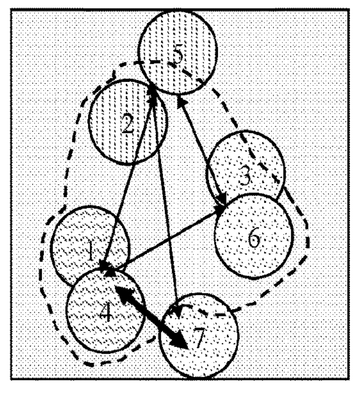
Figure 20D:
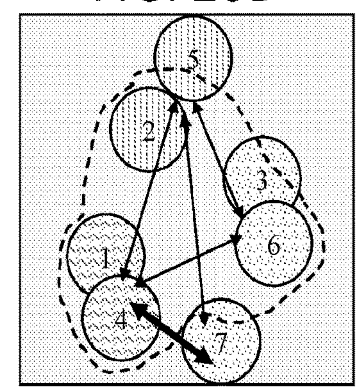

FIG. 20A-FIG. 20D show the functional arrangement of the antibody pairing capability and neutralizing activity for the SARS-CoV-2 RBD (FIG. 20A), the UK RBD (FIG. 20B), the SA RBD (FIG. 20C), and the BR P.1 RBD (FIG. 20D). Bin A epitope antibodies include Ab1 (1) and Ab4 (4). Bin B epitope antibodies include Ab2 (2) and Ab5 (5). Bin C epitope antibodies include Ab3 (3), Ab6 (6), and Ab7 (7). Double-headed arrow indicates antibody pairing with strong detection capability; bold double-headed arrow indicates antibody pairing with weakened detection capability. Dotted line indicates the neutralization functionality—if inside the dotted line, strong neutralization activity; if on or outside the dotted line, weak or no neutralization activity.

Figures 21A, 21B:
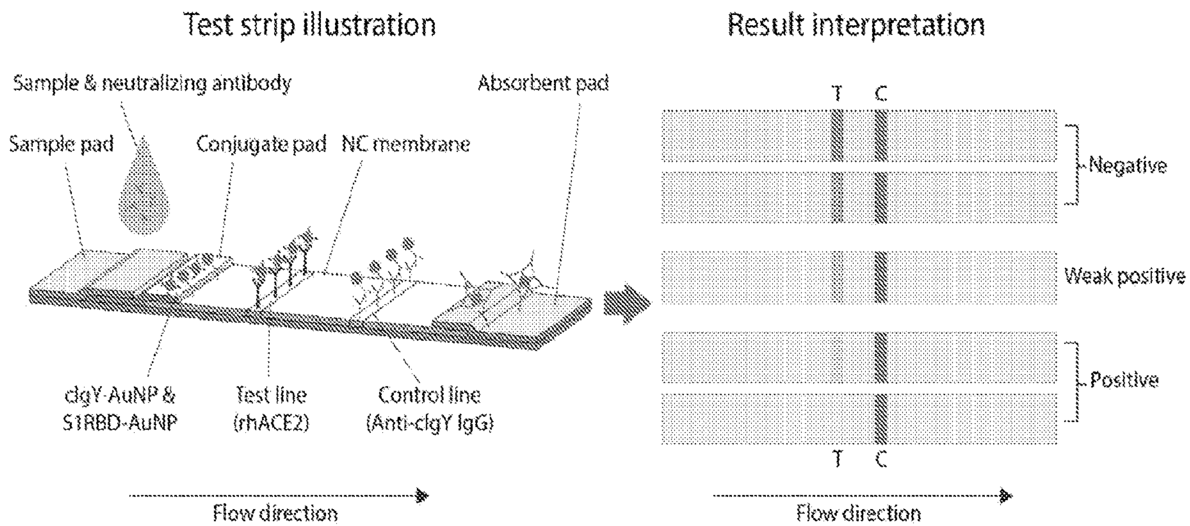

FIG. 21A-FIG. 21B show the lateral flow neutralizing antibody test strip design and assay principle. As shown in FIG. 21A, each strip consists of aplastic backed nitrocellulose membrane with sample pad, conjugate pad, and wick pad attached. The conjugate pad contains dried RBD-AuNP and cIgY-AuNP conjugates as the detectors of the test line and the control line, respectively. On the nitrocellulose membrane, recombinant ACE2 and goat anti-cIgY antibody were stripped at the test line and control line as the capture agents, respectively. Upon the addition of sample solution, cIgY-AuNP will flow forward and binds to immobilized anti-cIgY antibody, forming red colored control line. Similarly, in the absence of neutralizing antibody, the RBD-AuNP will flow and bind to ACE2, forming a colored test line; in the presence of neutralizing antibodies, the neutralizing antibody will bind to RBD-AuNP, thus preventing it from binding to ACE2, no colored line is formed.). FIG. 21B shows visual result interpretation reference. The colored control line (C) must be present for a test to be valid. The neutralizing activity of a sample is inversely correlated with the red color intensity of the test line. The absence or a faint colored test (T) line indicates that the sample has strong neutralizing activity; a light-colored test line indicates a moderate neutralizing activity; and a dark colored test (T) line indicates that the sample has weak or no neutralizing activity. The test cassette can also be read using a cassette reader for quantitative evaluation of color intensity.

Figure 22A:
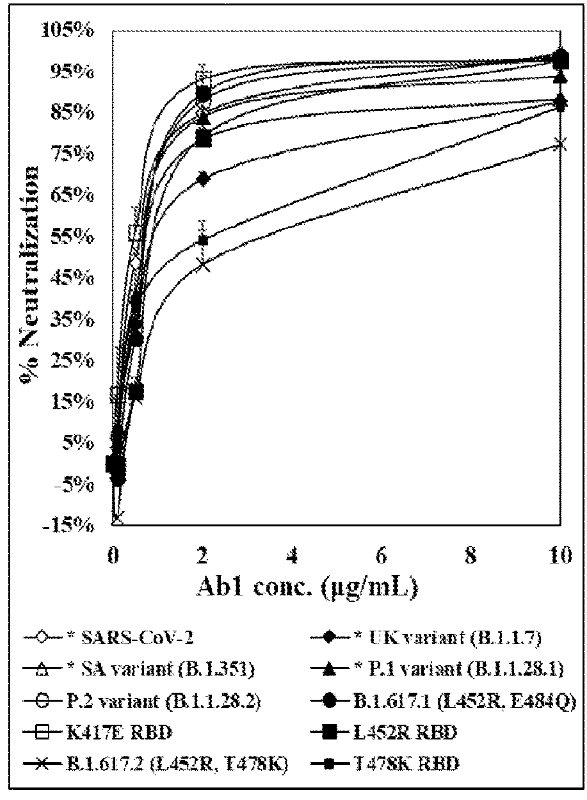
Figure 22B:
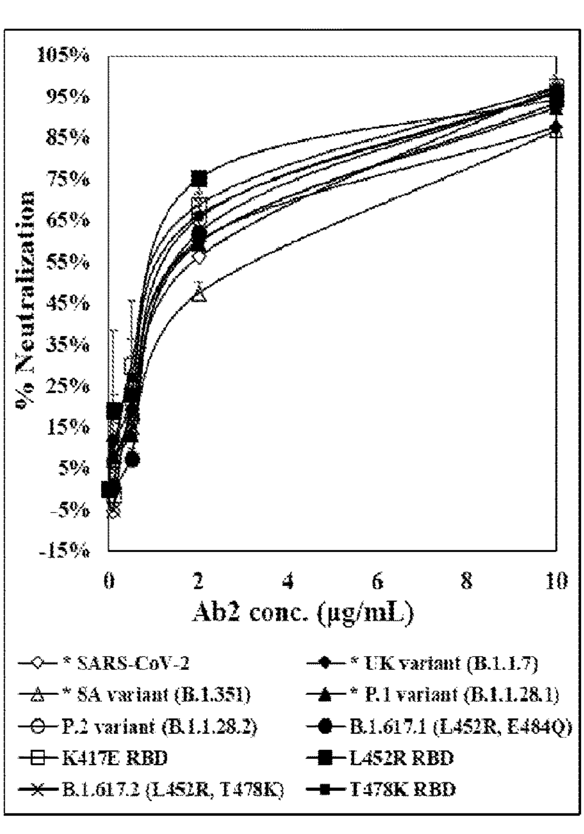
Figure 22C:
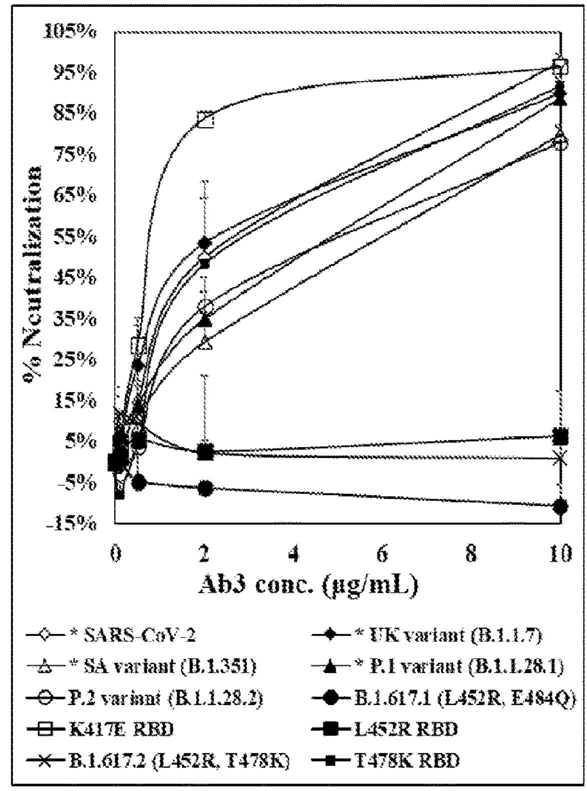
Figure 22D:
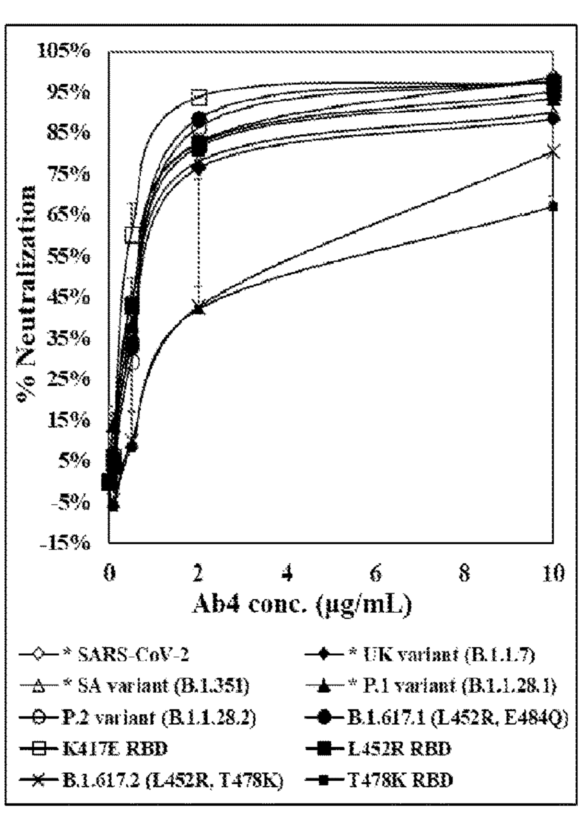
Figure 22E:
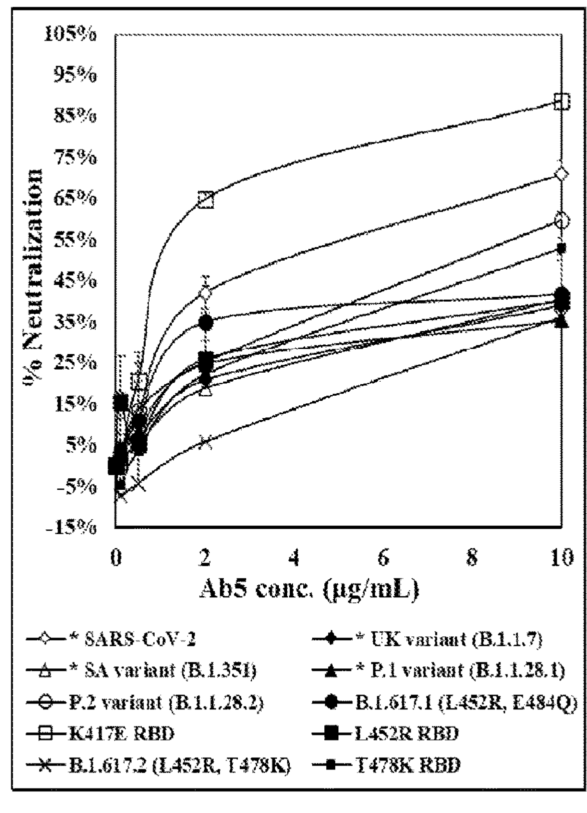
Figure 22F:
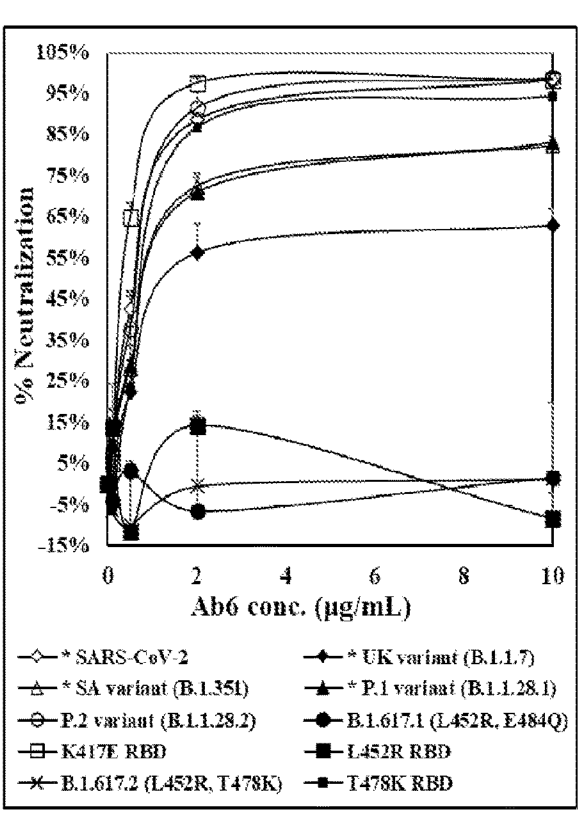
Figure 22G:
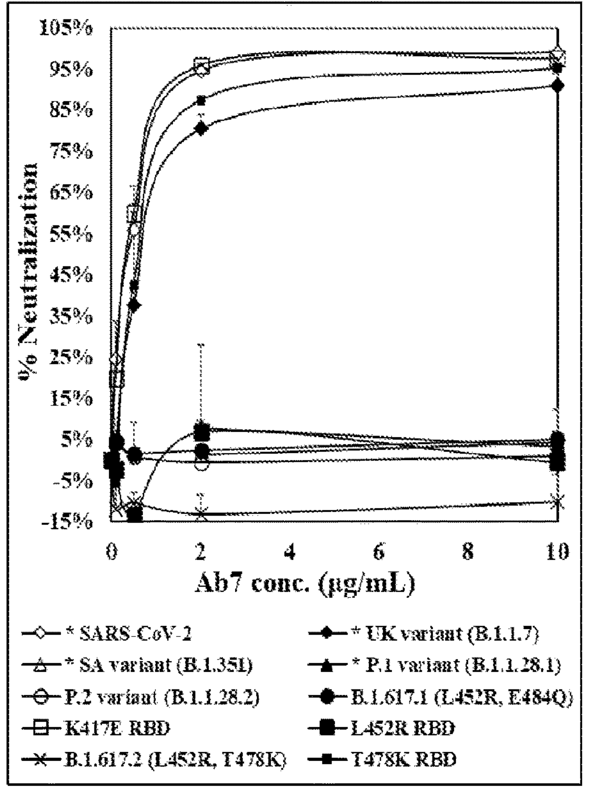
Figure 22H:
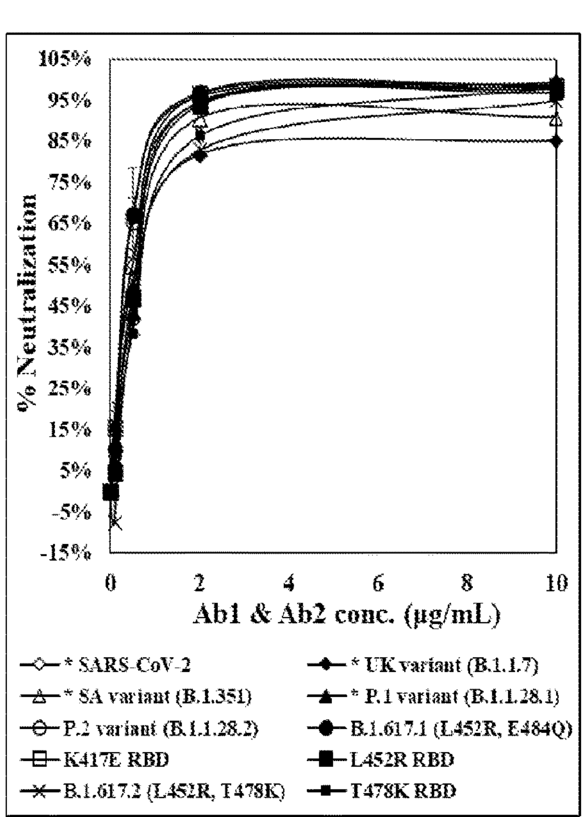
Figure 22I:
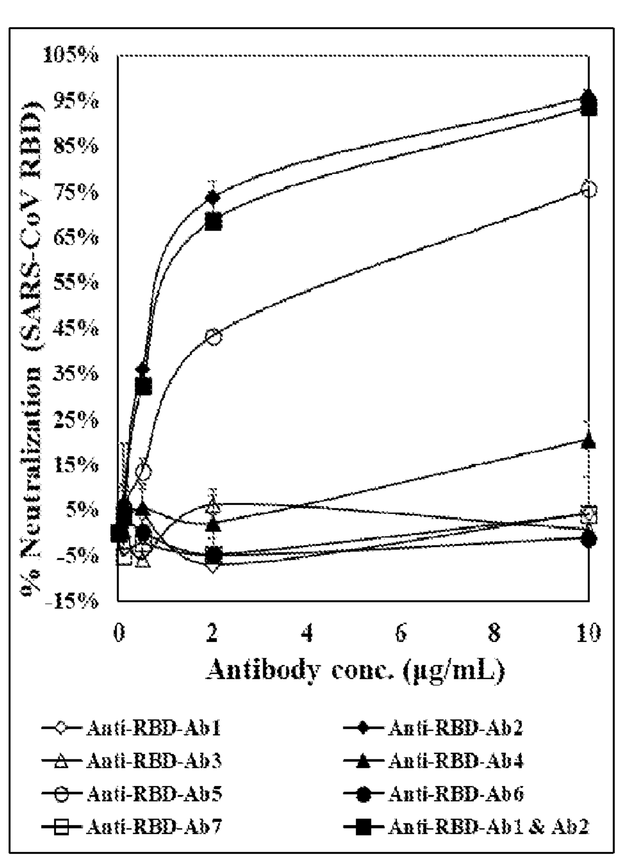

FIG. 22A-22I show neutralization kinetics by lateral flow cassette neutralization assays. FIG. 22A-22G are kinetic curves for individual antibodies against the ten SARS-CoV-2 RBDs. FIG. 22H is a kinetic curve for the two combined antibodies against the ten SARS-CoV-2 RBDs. FIG. 22I is a kinetic curve for seven individual antibodies and the two-antibody combination against the SARS-CoV RBD. For side-by-side comparison purposes, the neutralization kinetics data of the seven monoclonal antibodies and the two-antibody combo for CoV-2, UK, SA, and BR P.1 variant RBDs as reported in Example 3 were included and combined with the data newly generated for six additional SARS-CoV-2 RBDs.

Figure 23:
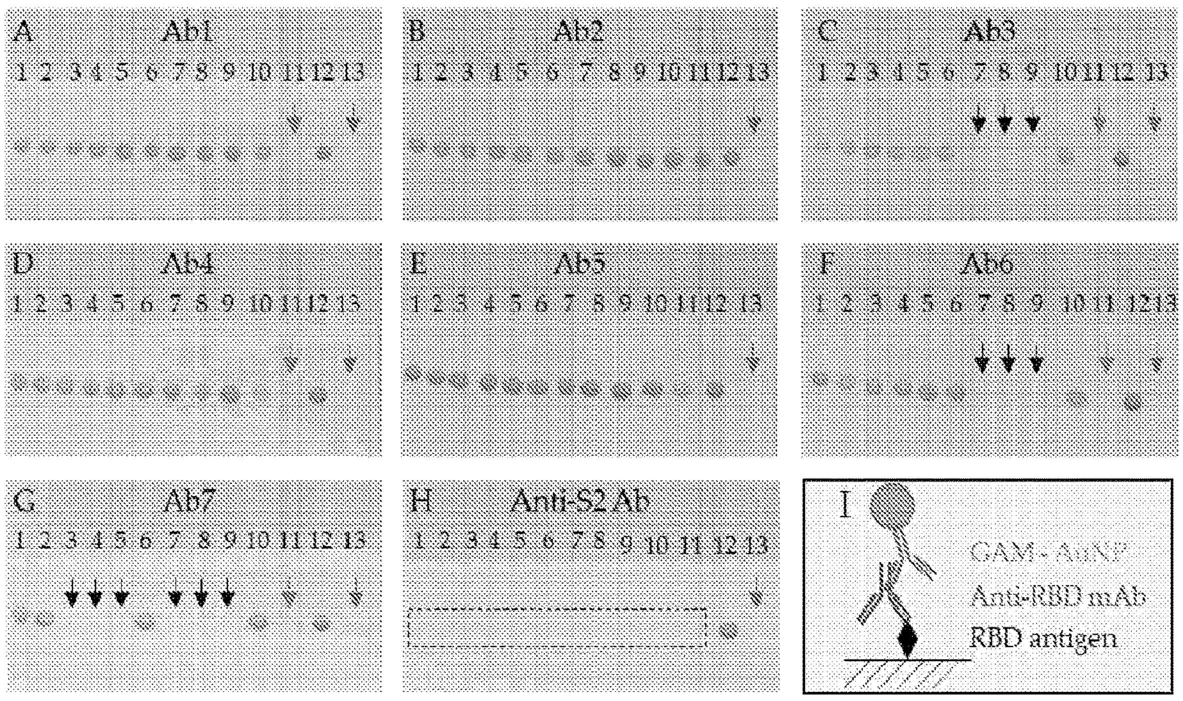

FIG. 23 shows antibody binding activities to various RBD proteins adsorbed on lateral flow nitrocellulose membrane. Panels are photographs of a representative set of lateral flow dipstick assays using anti-RBD antibodies (Ab1, Ab2, Ab3, Ab4, Ab5, Ab6 and Ab7) and anti-SARS-CoV-2 spike S2 antibody as primary detector for the detection of all immobilized RBDs. Each dipstick has 13 spots: 10 spots for various SARS-CoV-2 RBD proteins, 1 spot for SARS-CoV RBD (#11) and 1 spot for mIgG (anti-SARS-CoV-2 spike subunit 2, #12) as the GAM-AuNP detector positive control, and 1 spot for BSA (#13) as negative control. From left to right, the ten SARS-CoV-2 RBD proteins sequentially are wild-type RBD, UK variant RBD, SA variant RBD, BR P.1 RBD, E484K RBD, K417E RBD, IN v1 (B.1.617.v1) RBD, IN v2 (B.1.617.v2) RBD, L452R RBD, and T478N RBD. The lower right panel is a schematic of the immunoassay principle. Anti-RBD mAbs first bind to adsorbed RBD, and then detected by GAM-AuNP. All primary detector antibodies were used at 10 μg/mL concentration and the secondary detector were 1:10 diluted GAM-AuNP in Brij-35 assay buffer. For negative control antibody, anti-SARS-CoV-2 spike subunit 2 was spotted onto the nitrocellulose membrane as a capture negative control, as well as used as primary antibody negative control.

Figure 24:
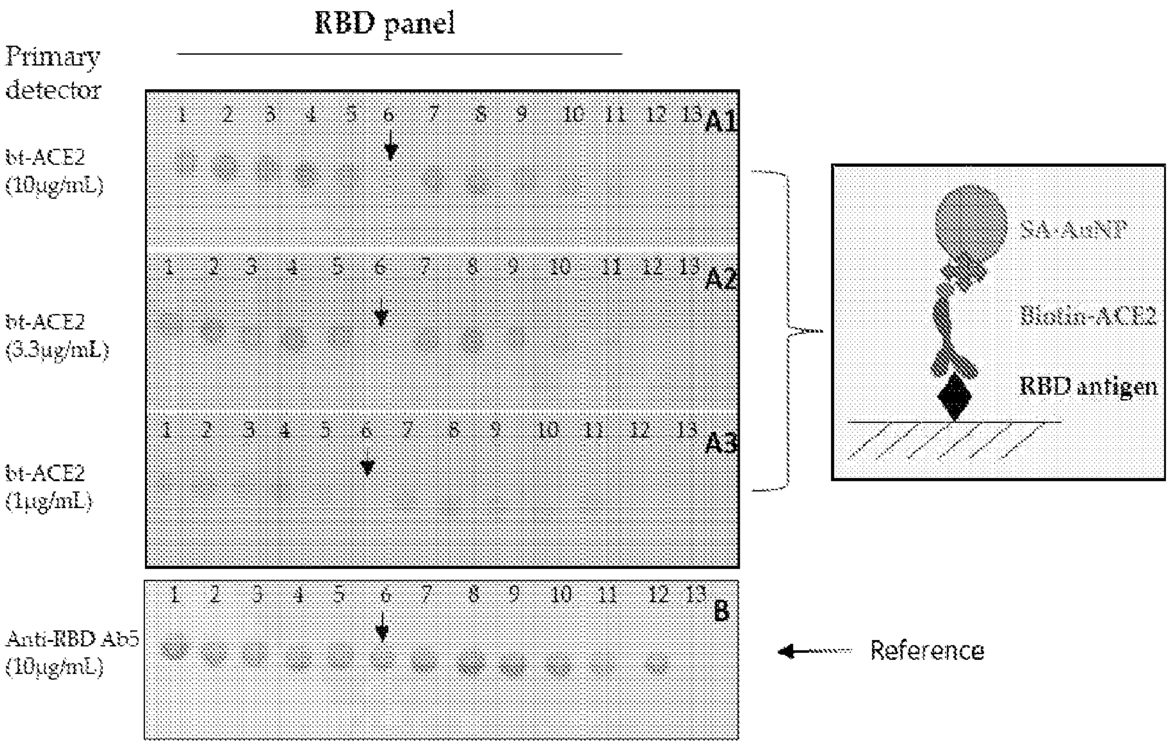

FIG. 24 shows binding activity of biotinylated ACE2 to RBD proteins adsorbed onto lateral flow nitrocellulose mem-brane. On the right are photographs of a representative set of lateral flow dipstick assays. Panels A1-A3 show the detection of adsorbed RBDs were performed using 10 μg/mL, 3.3 μg/mL, and 1 μg/mL biotinylated ACE2, as the primary detector, respectively. Panel B shows the detection of adsorbed RBDs were achieved by anti-RBD antibody Ab5 as control. On the left is a schematic of the assay principle for ACE2 detection of adsorbed RBDs. The black solid arrow indicates the K417E-RBD, which was weakly detected by bio-tin-ACE2, but strongly detected by the anti-RBD antibody Ab5.

Figure 25A:
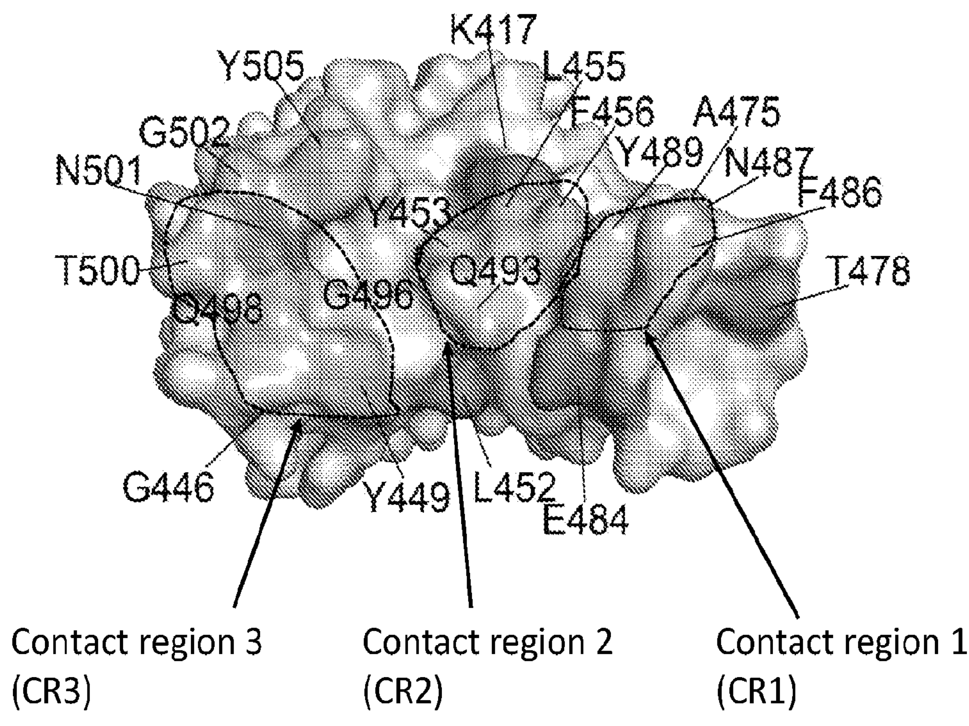
Figure 25B:
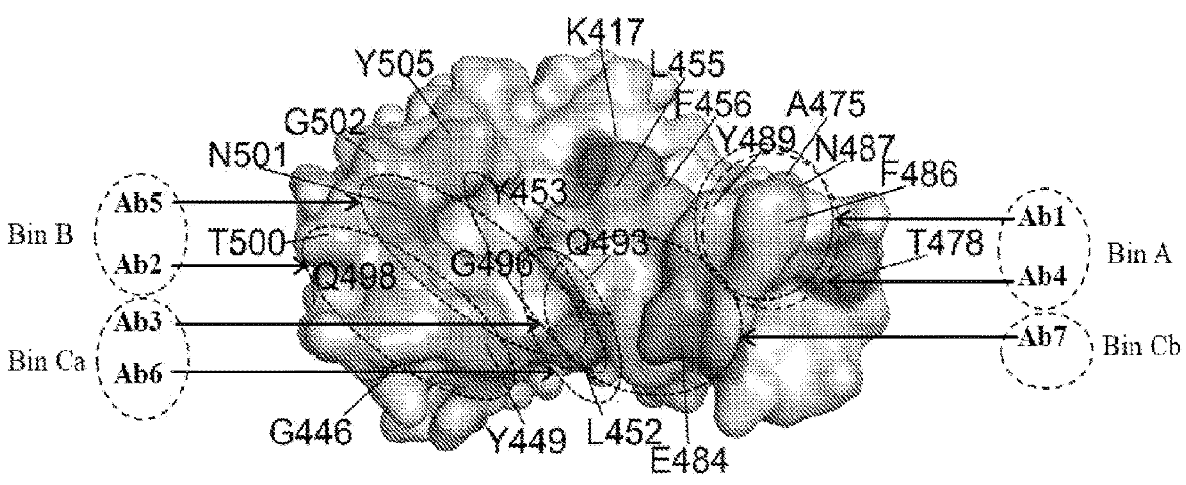
Figure 25C:
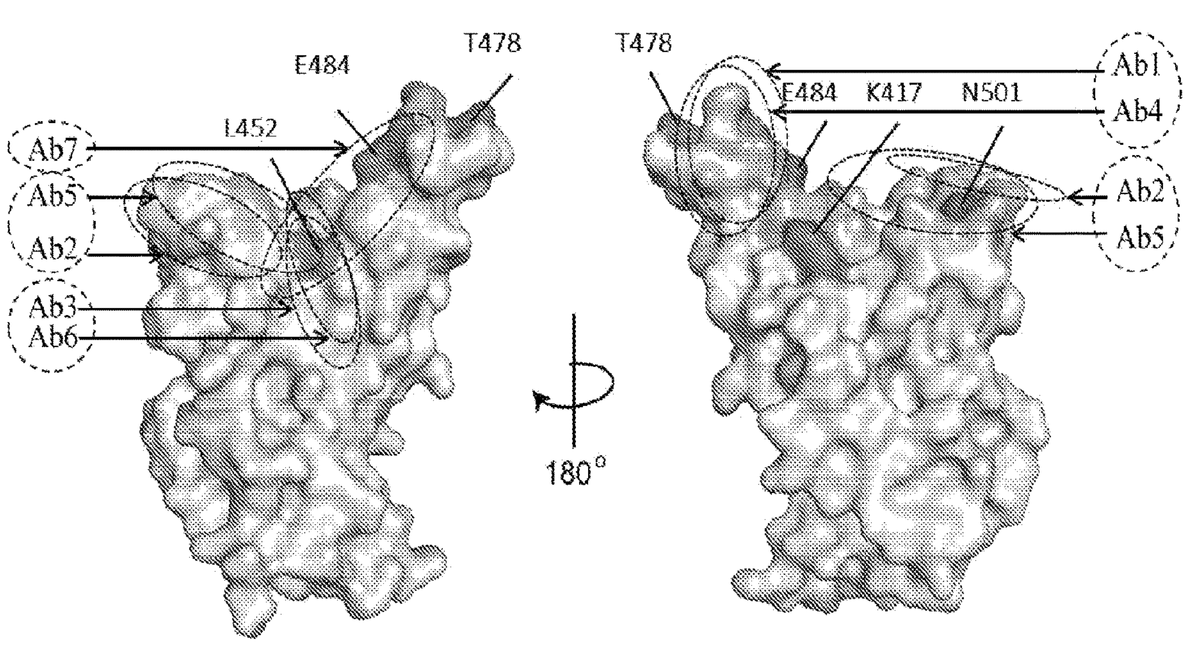

FIG. 25A-FIG. 25C show surface presentation map of SARS-CoV-2 spike RBD with the corresponding epitope regions of the seven mAbs. FIG. 25A shows a top surface view of the RBD protein that interfaces with ACE2, with three contact regions designated as irregular shaped circle (xx). FIG. 25B shows a top surface view of the RBD protein that interfaces with ACE2, with the predicted epitopes. FIG. 25C show two side surface views of the RBD protein with the predicted epitope. The predicted epitope regions for the seven anti-RBD monoclonal antibodies are identified in circles.

Figure 26A:
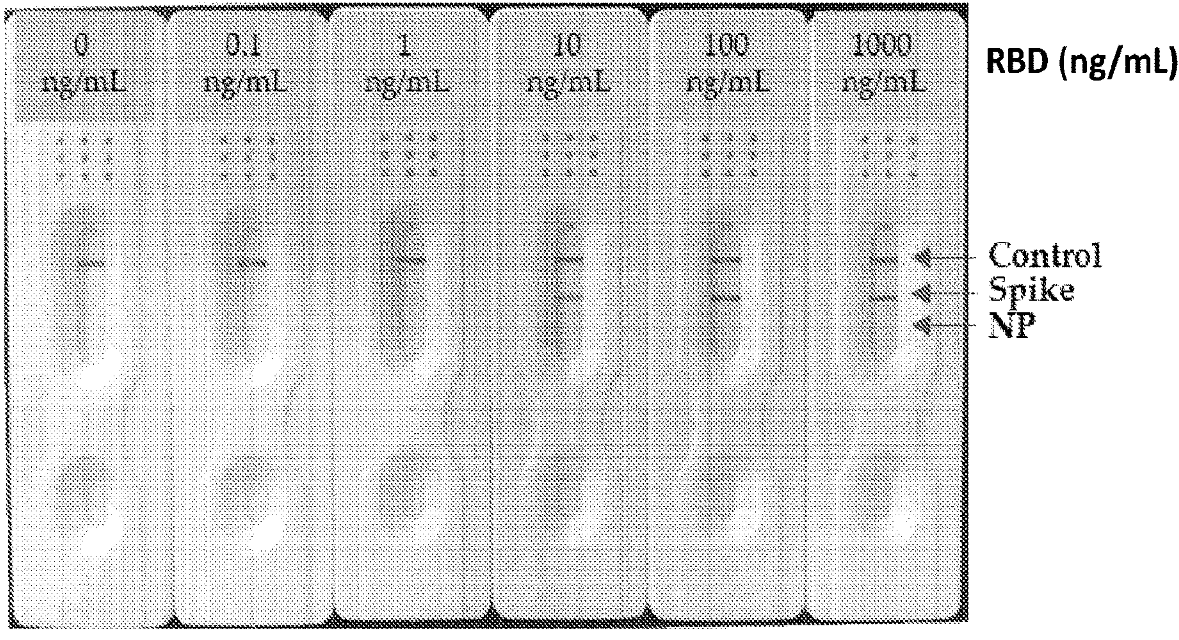
Figure 26B:
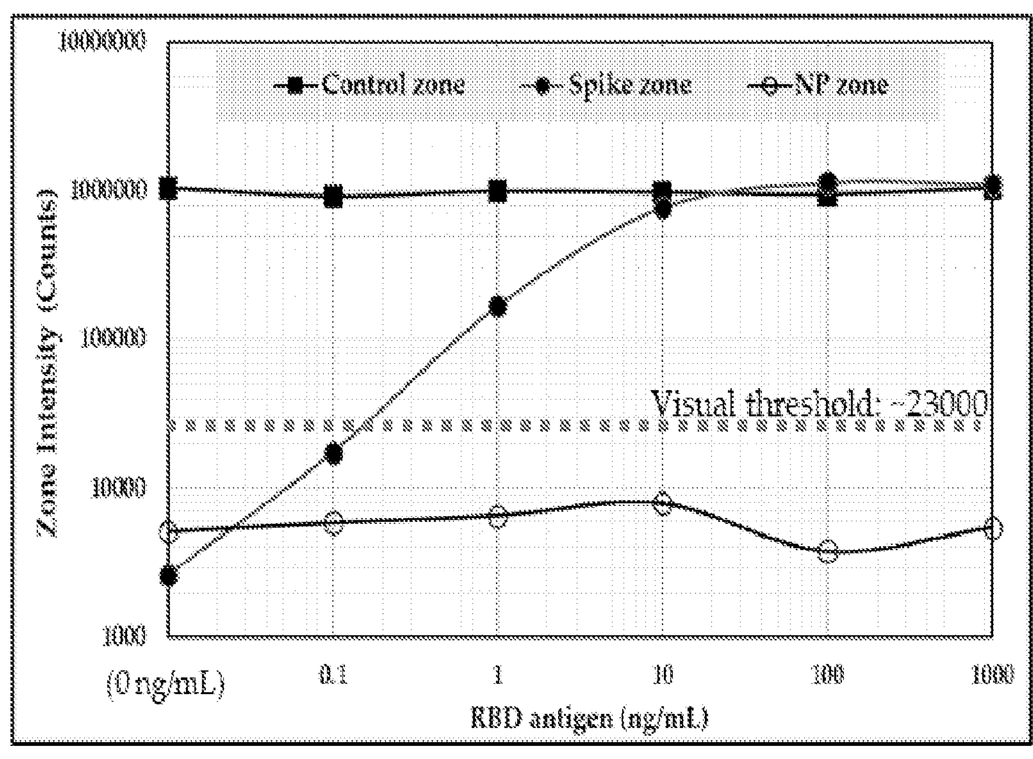

FIG. 26A-FIG. 26B show performance of the S/N (spike and nucleocapsid) dual antigen test strip for assaying RBD antigen in buffer system using the anti-RBD antibody of interest. FIG. 26A shows a representative set of photo images of the assay devices. The photo was taken within minutes after the assay was completed, while the strips is still in wet condition. FIG. 26B shows corresponding assay signal of the control zone, the spike zone, and the NP (nucleocapsid) zone, recorded using an RDS-2500 reader. For these 40-nm size AuNP and the RDS reader, a visual line corresponds to approximately 23,000 counts of the signal intensity.

Figure 27A:
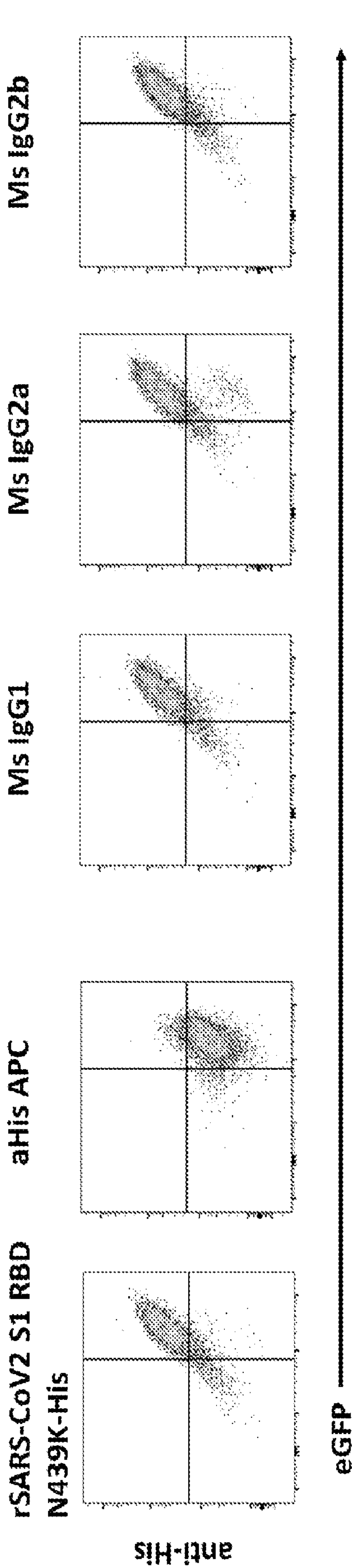
Figure 27B:
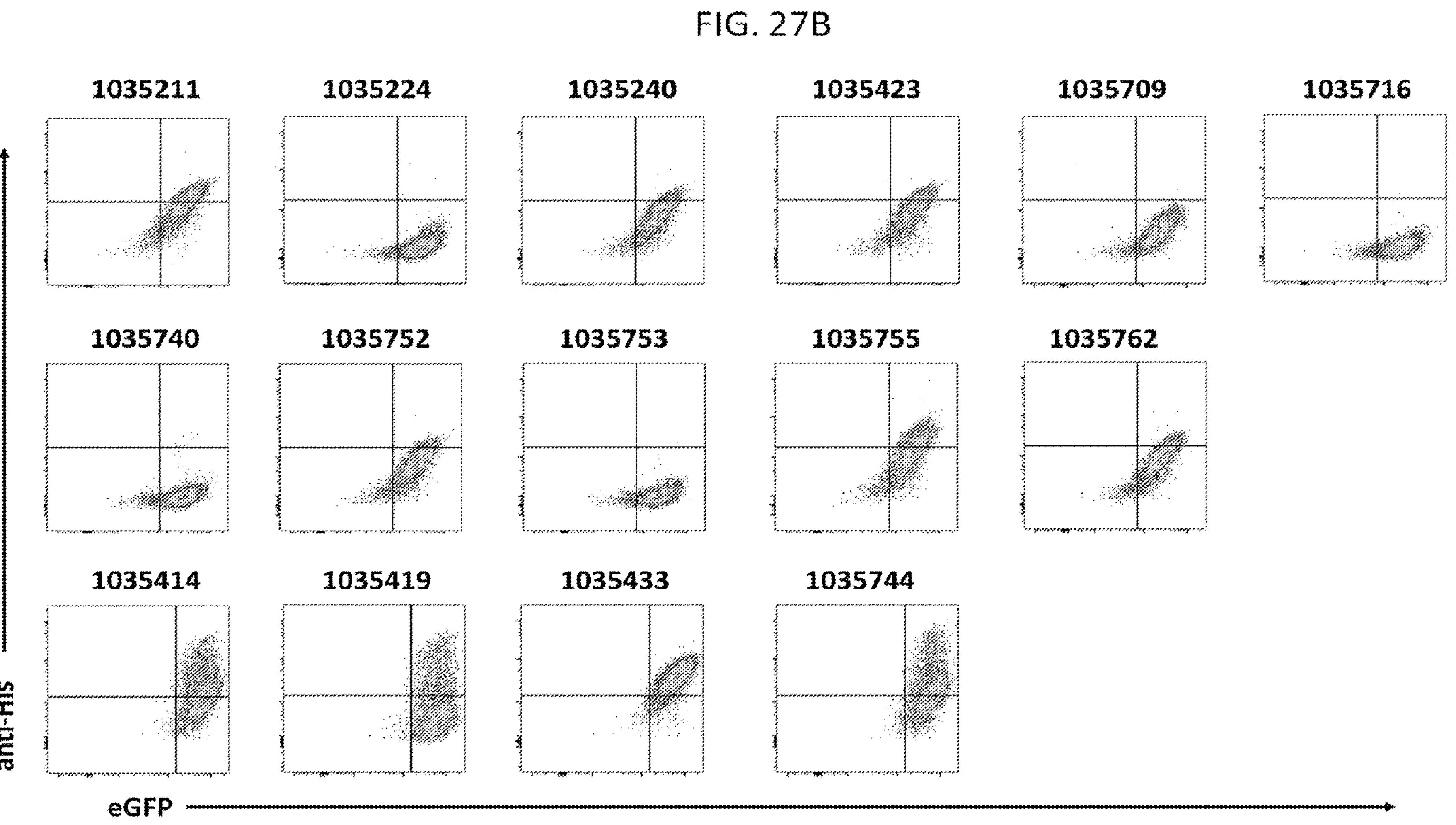

FIG. 27A-FIG. 27B show select anti-SARS-CoV-2 antibodies block binding of the SARS-CoV-2 $S_1$ RBD N439K variant to ACE-2. rSARS2 RBD aa319-541 N439K protein was mixed and then incubated with flow cytometry staining buffer, Mouse IgG1, IgG2a or IgG2b isotype control antibodies (FIG. 27A); or with anti-SARS-CoV-2 monoclonal antibodies from panels 10352XX, 10354XX, or 10357XX (FIG. 27B) to allow a complex to form. After incubation, the mixture was added to a single cell suspension of hACE-2 HEK/eGFP Tfx, followed by addition of a secondary anti-His antibody to assess viral antibody blocking. Flow cytometry gates were set on anti-His fluorescence of hACE-2 HEK/eGFP Tfx cells without SARS-CoV-2 $S_1$ RBD N439K variant protein.

Figure 28A:
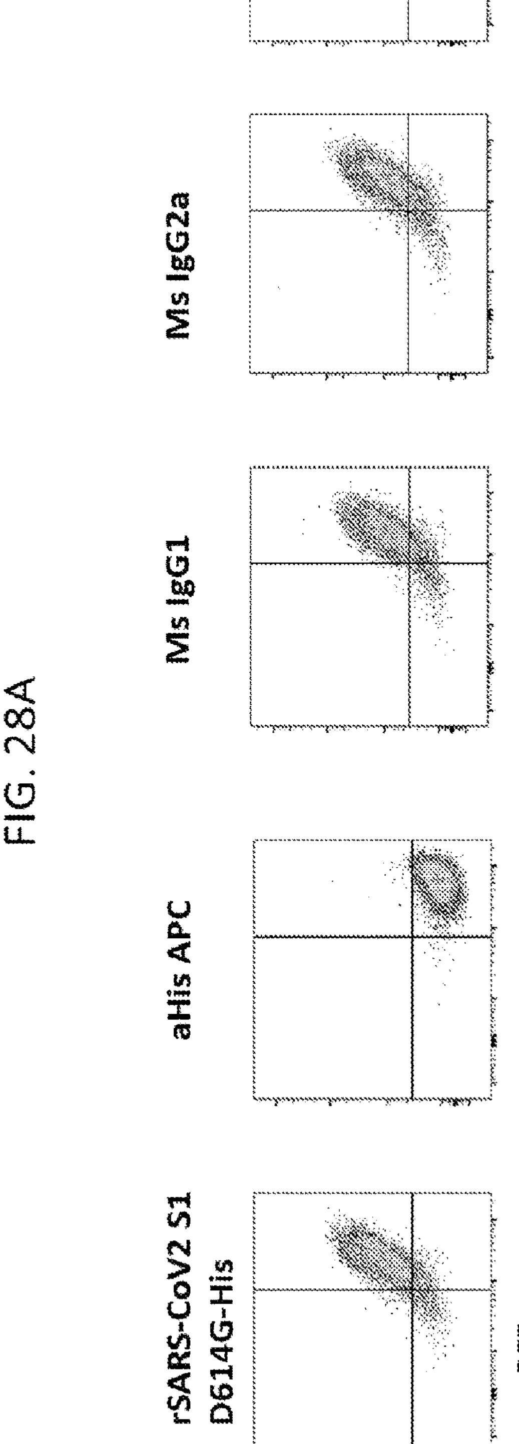
Figure 28B:
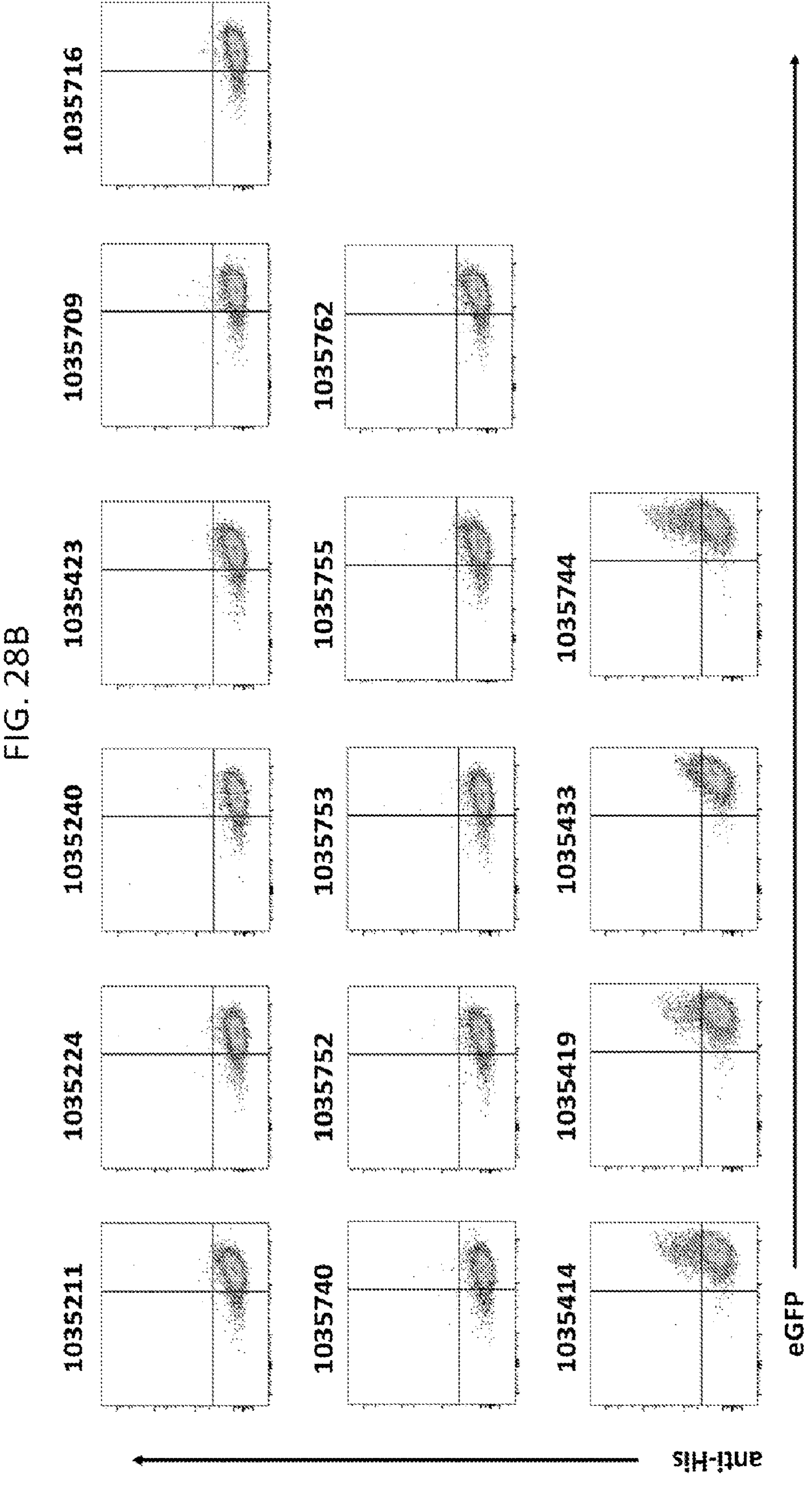

FIG. 28A-FIG. 28B show anti-SARS-CoV-2 antibodies block binding of the SARS-CoV-2 $S_1$ D614G variant to ACE-2. rSARS2-S1 aa16-681 D614G protein was mixed and then incubated with flow cytometry staining buffer, Mouse IgG1, IgG2a or IgG2b isotype control antibodies (FIG. 28A); or with anti-SARS-CoV-2 monoclonal antibodies from panels 10352XX, 10354XX, or 10357XX (FIG. 28B) to allow a complex to form. After incubation, the mixture was added to a single cell suspension of hACE-2 HEK/eGFP Tfx, followed by addition of a secondary anti-His antibody to assess viral antibody blocking. Flow cytometry gates were set on anti-His fluorescence of hACE-2 HEK/eGFP Tfx cells without SARS-CoV-2 $S_1$ D614G variant protein.

Figure 29A:
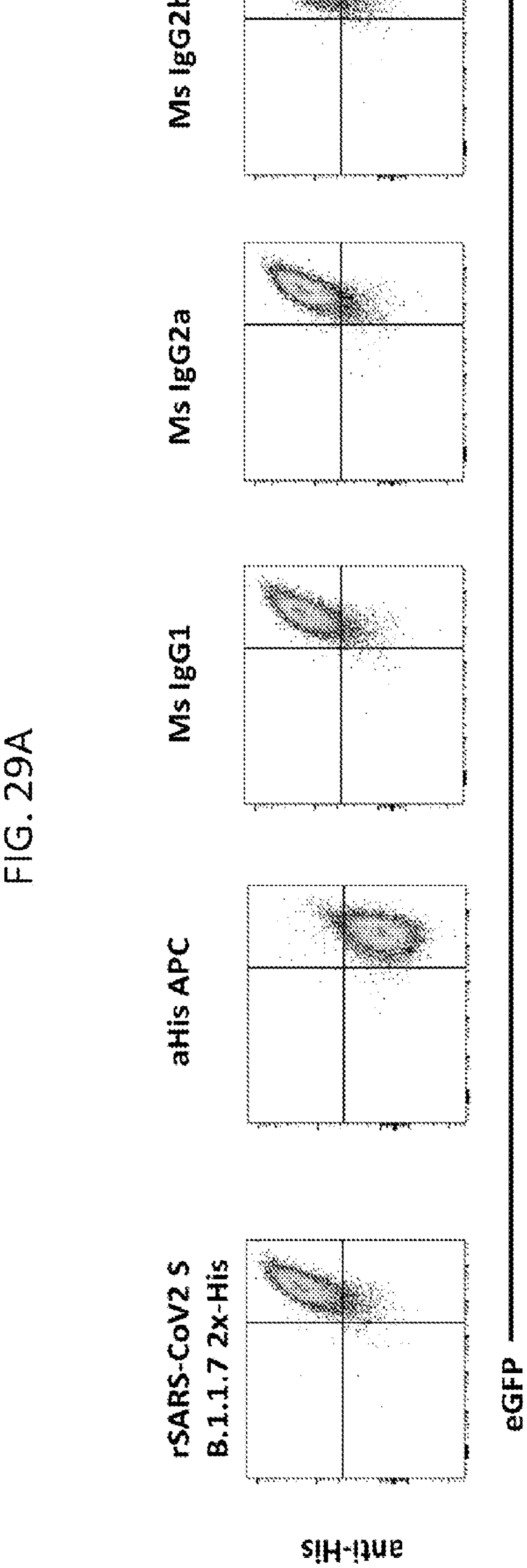
Figure 29B:
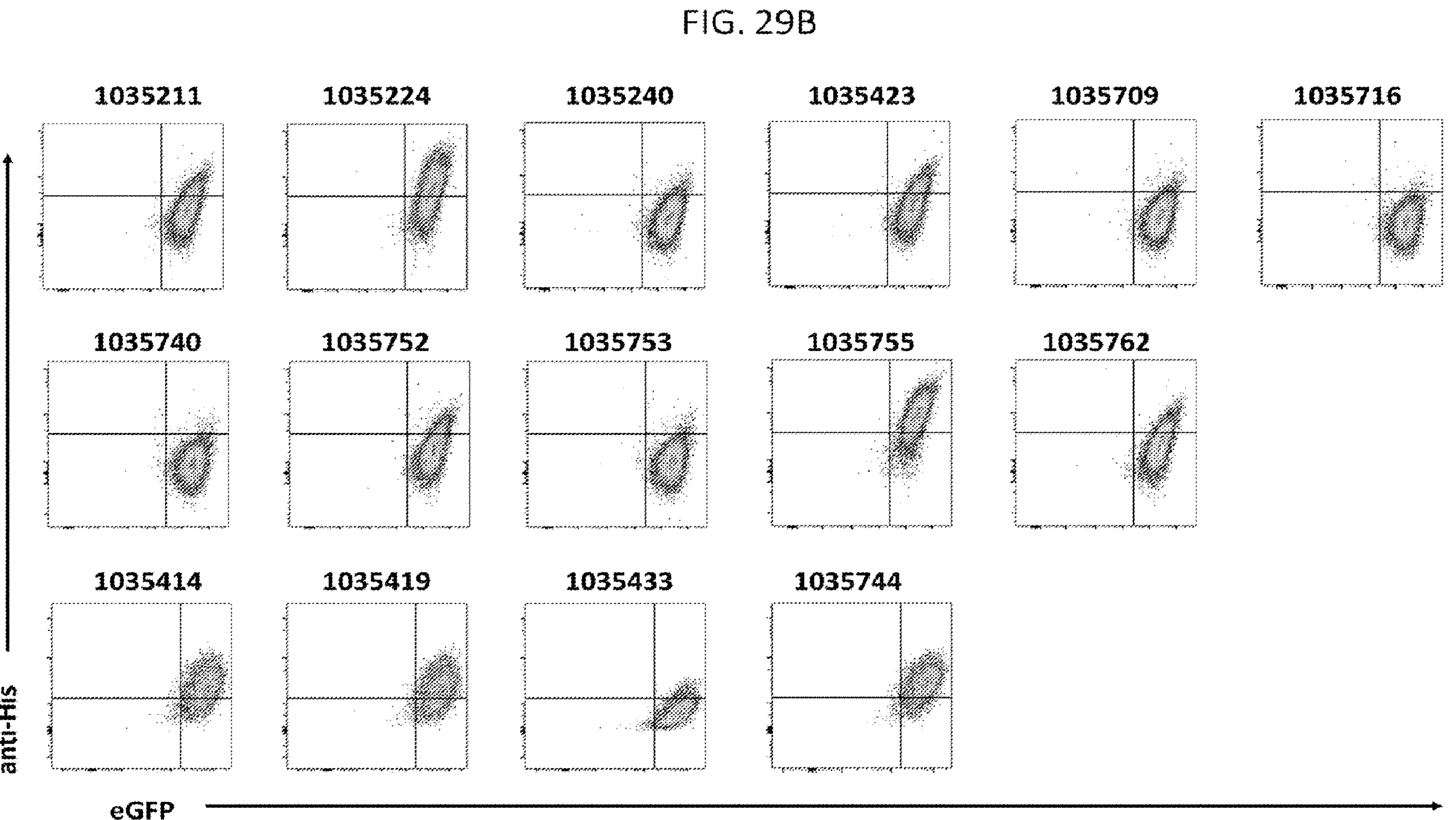

FIG. 29A-FIG. 29B show select anti-SARS-CoV-2 antibodies block binding of the SARS-CoV-2 S B.1.1.7 2× variant to ACE-2. rSARS2-B.1.1.7 S aa16-1211 2×aa mut. protein was mixed and then incubated with flow cytometry staining buffer, Mouse IgG1, IgG2a or IgG2b isotype control antibodies (FIG. 29A); or with anti-SARS-CoV-2 monoclonal antibodies from panels 10352XX, 10354XX, or 10357XX (FIG. 29B) to allow a complex to form. After incubation, the mixture was added to a single cell suspension of hACE-2 HEK/eGFP Tfx, followed by addition of a secondary anti-His antibody to assess viral antibody blocking. Flow cytometry gates were set on anti-His fluorescence of hACE-2 HEK/eGFP Tfx cells without SARS-CoV-2 S B.1.1.7 2× variant protein.

Figure 30A:
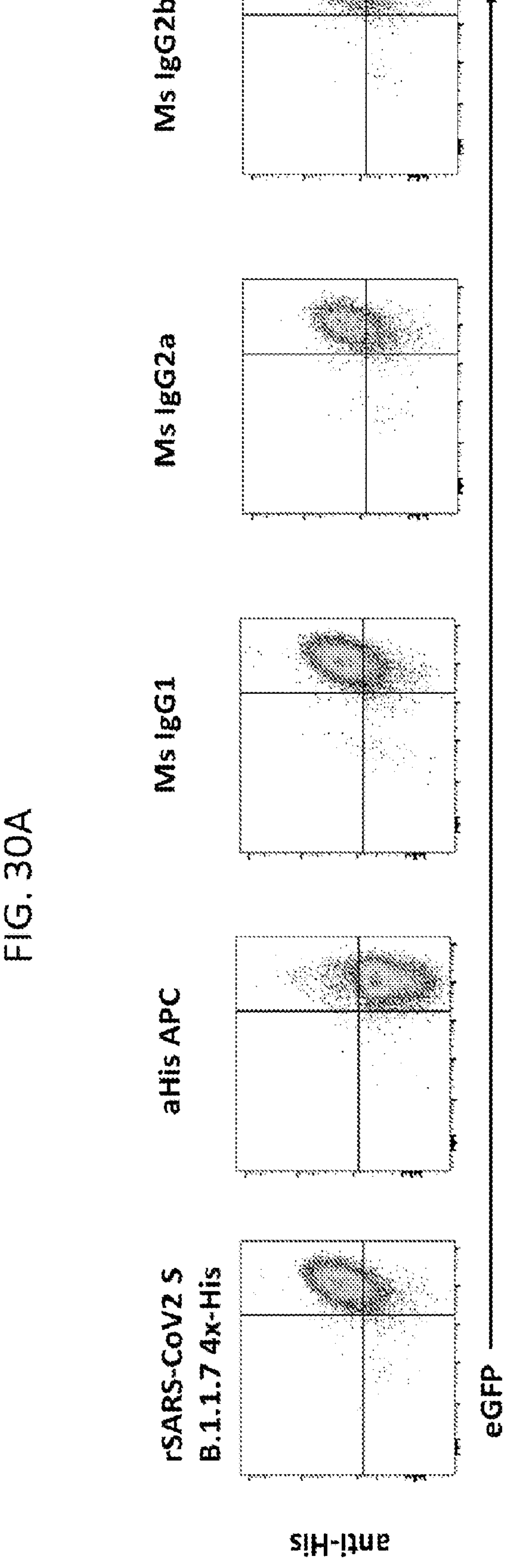
Figure 30B:
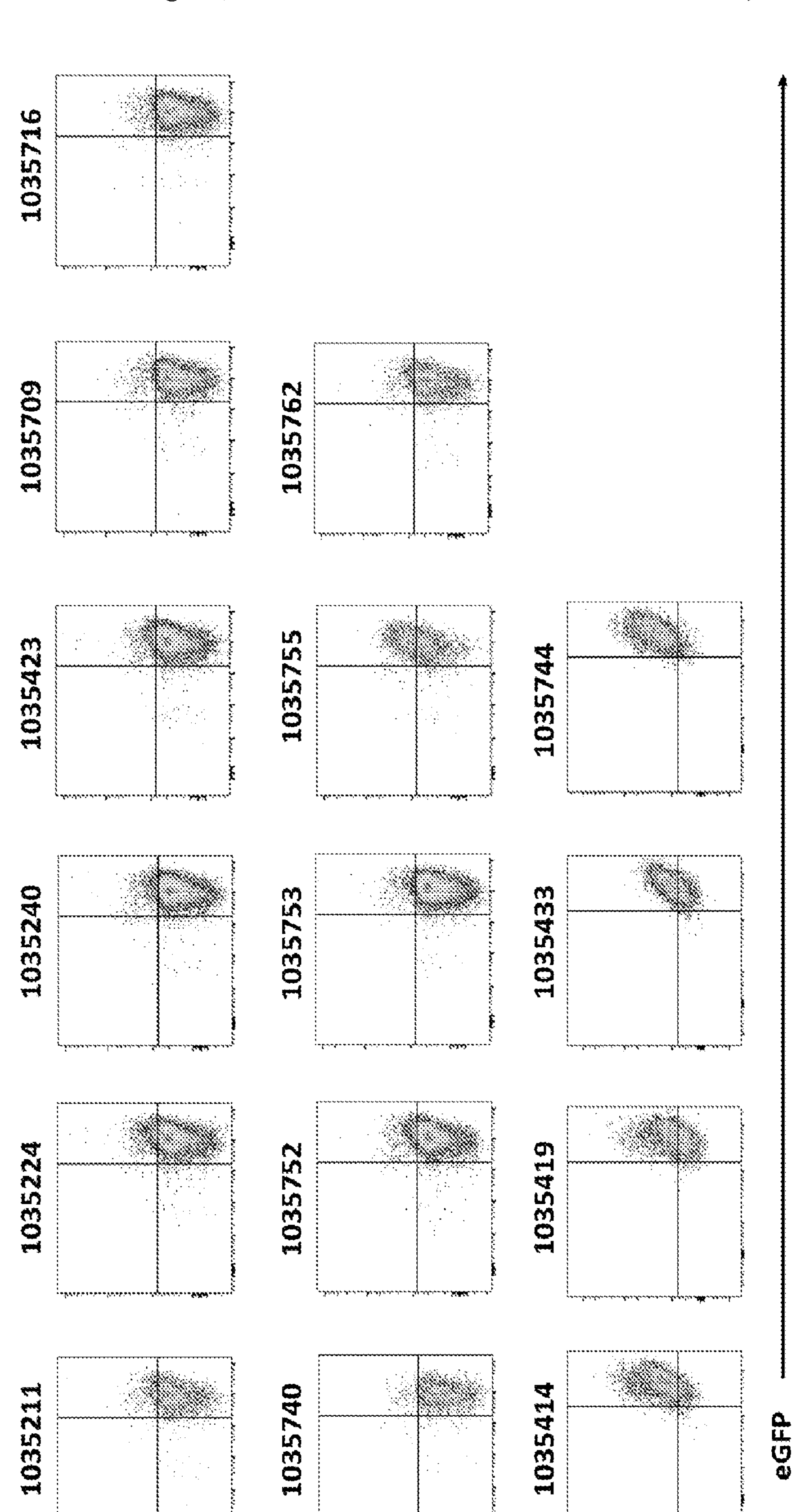

FIG. 30A-FIG. 30B show select anti-SARS-CoV-2 antibodies block binding of the SARS-CoV-2 S B.1.1.7 4× variant to ACE-2. rSARS2-B.1.1.7 S aa16-1211 4×aa mut. protein was mixed and then incubated with flow cytometry staining buffer, Mouse IgG1, IgG2a or IgG2b isotype control antibodies (FIG. 30A); or with anti-SARS-CoV-2 monoclonal antibodies from panels 10352XX, 10354XX, or 10357XX (FIG. 30B) to allow a complex to form. After incubation, the mixture was added to a single cell suspension of hACE-2 HEK/eGFP Tfx, followed by addition of a secondary anti-His antibody to assess viral antibody blocking. Flow cytometry gates were set on anti-His fluorescence of hACE-2 HEK/eGFP Tfx cells without SARS-CoV-2 S B.1.1.7 4× variant protein.

Figure 31A:
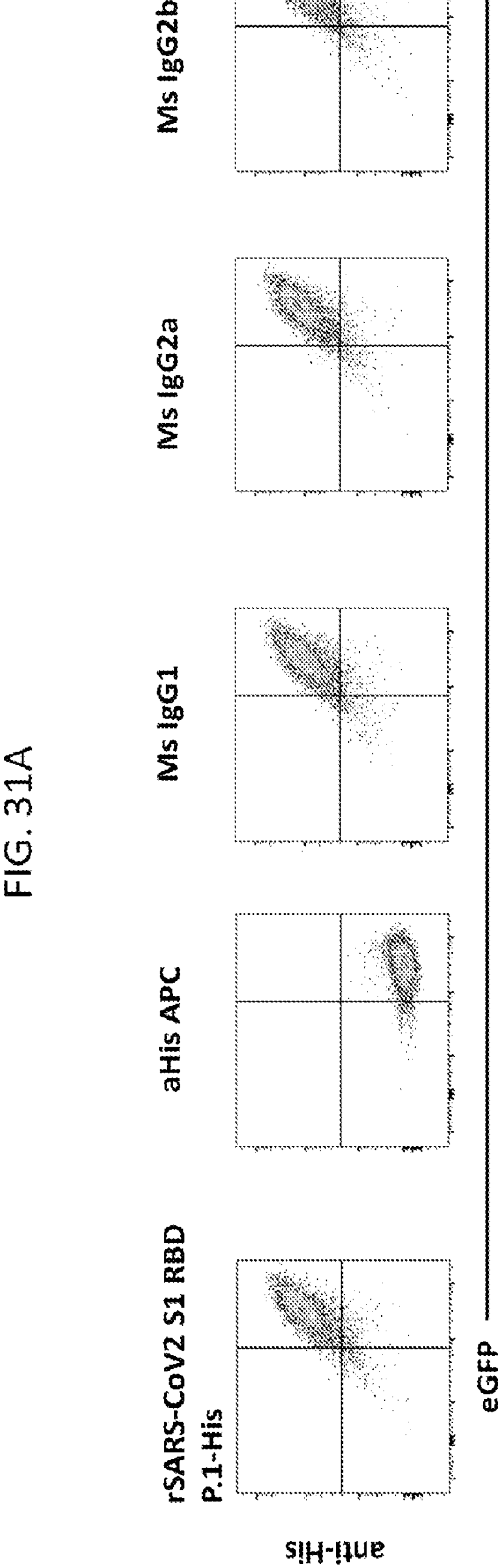
Figure 31B:
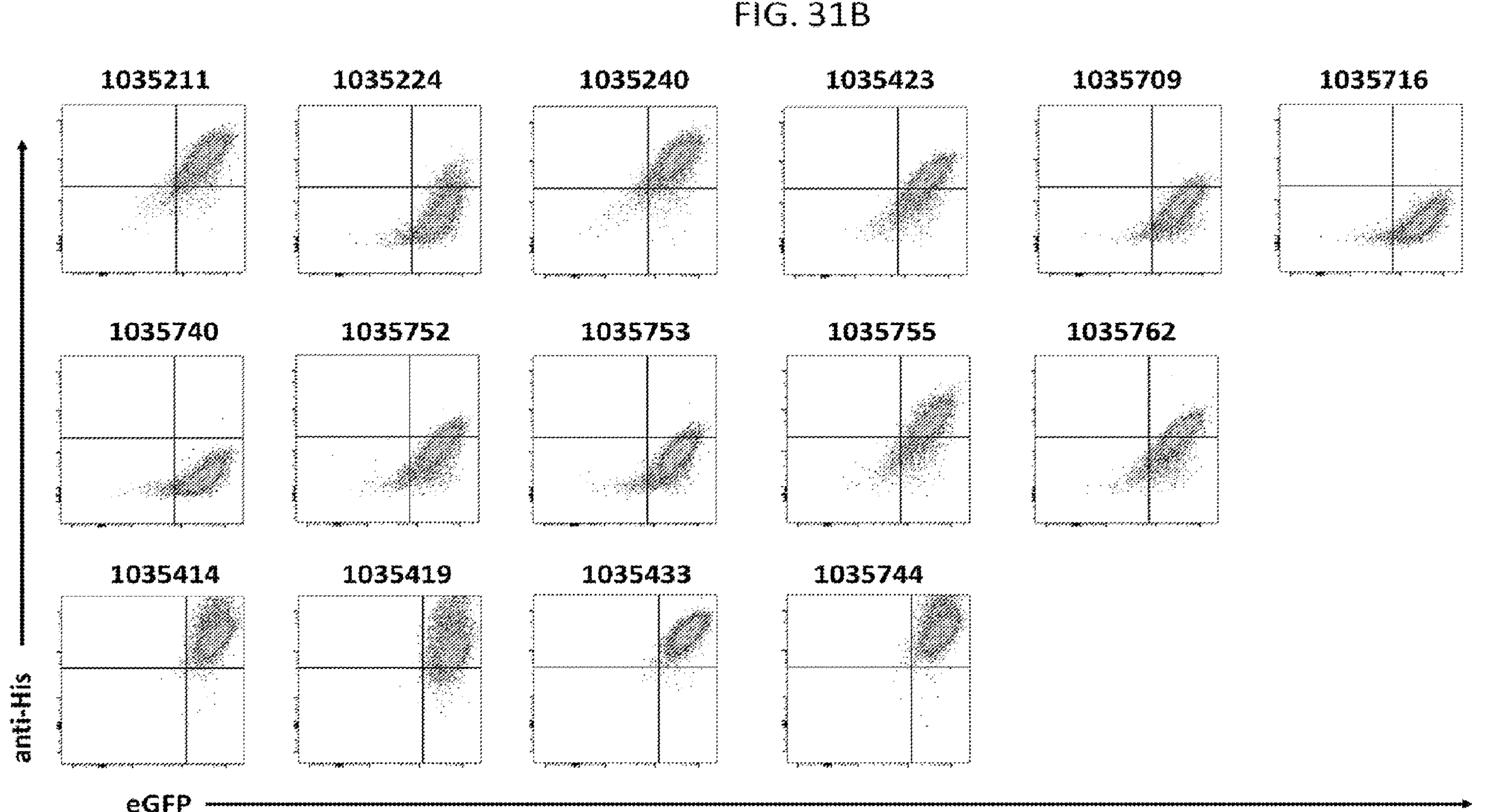

FIG. 31A-FIG. 31B show select anti-SARS-CoV-2 antibodies block binding of the SARS-CoV-2 $S_1$ RBD P.1 variant to ACE-2. rSARS2-P.1 RBD aa319-541 3×aa mut. protein was mixed and then incubated with flow cytometry staining buffer, Mouse IgG1, IgG2a or IgG2b isotype control antibodies (FIG. 31A); or with anti-SARS-CoV-2 monoclonal antibodies from panels 10352XX, 10354XX, or 10357XX (FIG. 31B) to allow a complex to form. After incubation, the mixture was added to a single cell suspension of hACE-2 HEK/eGFP Tfx, followed by addition of a secondary anti-His antibody to assess viral antibody blocking. Flow cytometry gates were set on anti-His fluorescence of hACE-2 HEK/eGFP Tfx cells without SARS-CoV-2 $S_1$ RBD P.1 variant protein.

Figure 32A:
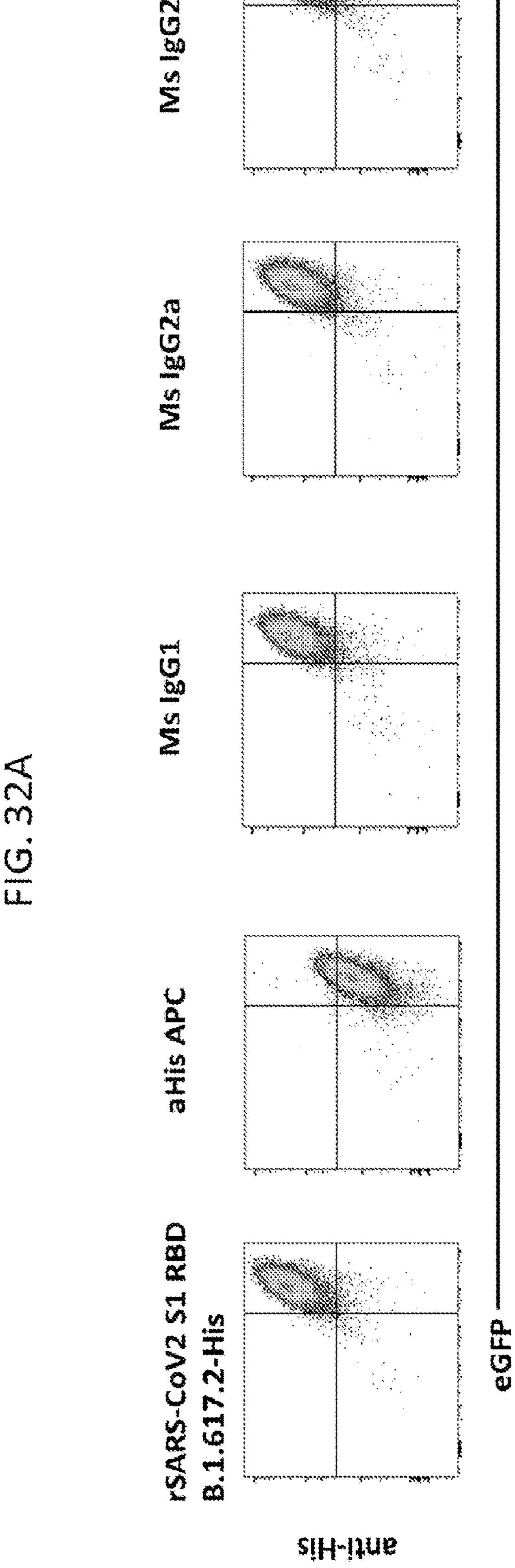
Figure 32B:
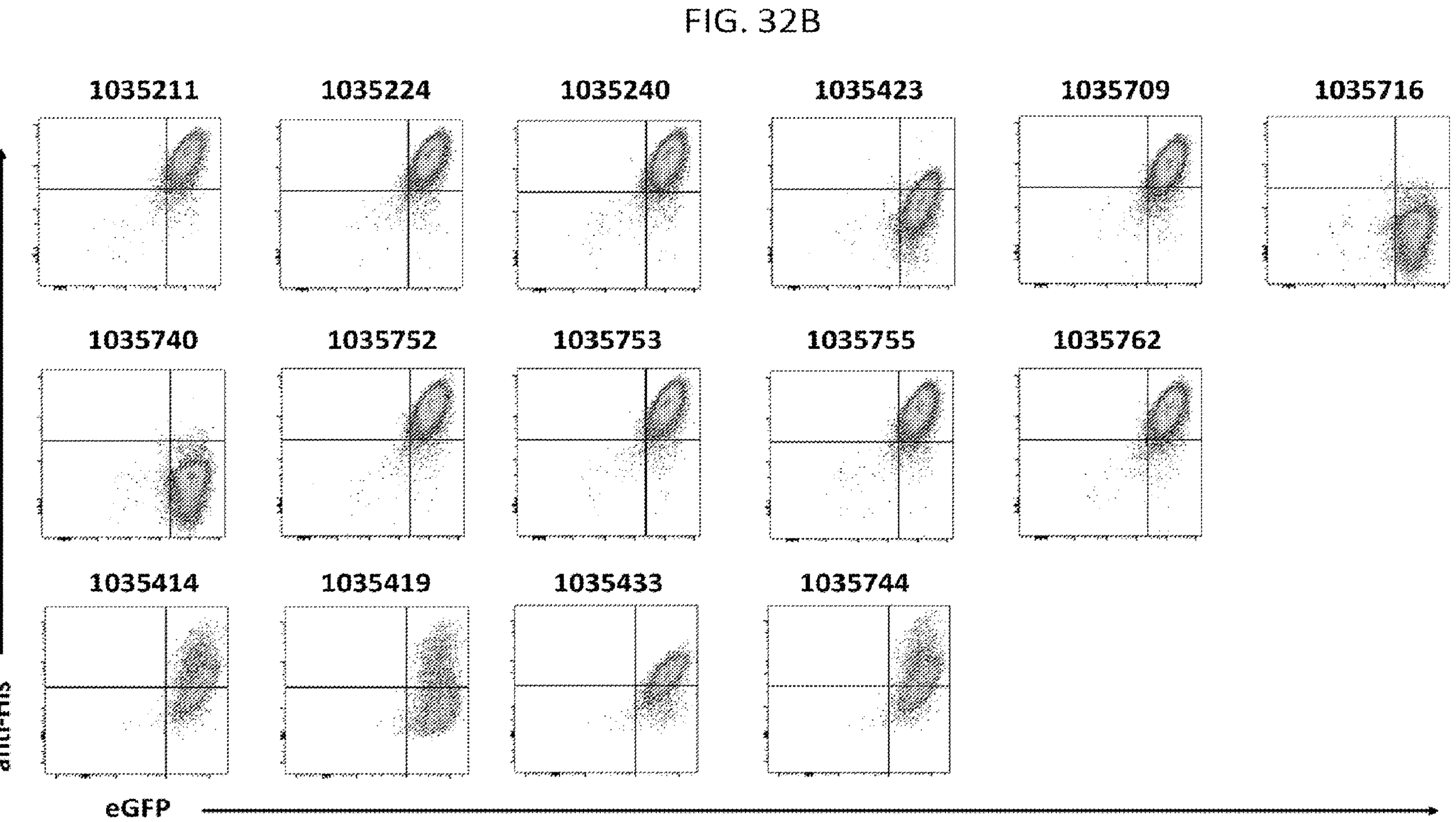

FIG. 32A-FIG. 32B show select anti-SARS-CoV-2 antibodies block binding of the SARS-CoV-2 $S_1$ RBD B.1.617.2 variant to ACE-2. rSARS2-B.1.617.2 RBD aa319-541 L452R T478K protein was mixed and then incubated with flow cytometry staining buffer, Mouse IgG1, IgG2a or IgG2b isotype control antibodies (FIG. 32A); or with anti-SARS-CoV-2 monoclonal antibodies from panels 10352XX, 10354XX, or 10357XX (FIG. 32B) to allow a complex to form. After incubation, the mixture was added to a single cell suspension of hACE-2 HEK/eGFP Tfx, followed by addition of a secondary anti-His antibody to assess viral antibody blocking. Flow cytometry gates were set on anti-His fluorescence of hACE-2 HEK/eGFP Tfx cells without SARS-CoV-2 $S_1$ RBD B.1.617.2 variant protein.

Figure 33A:
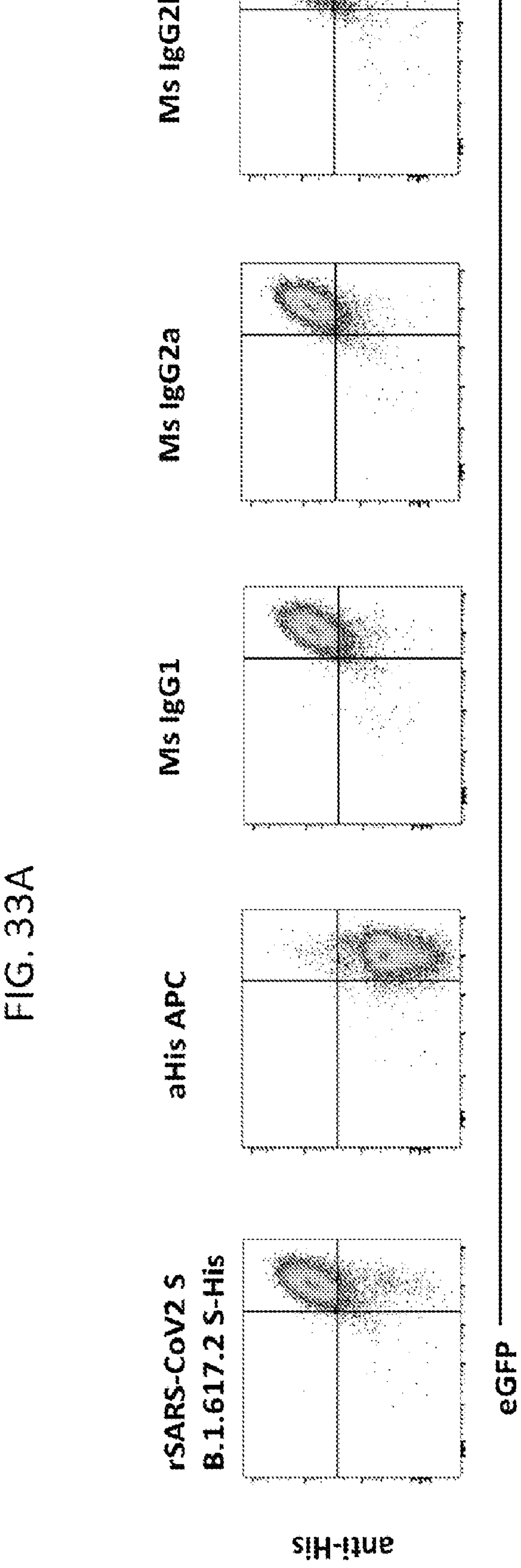
Figure 33B:
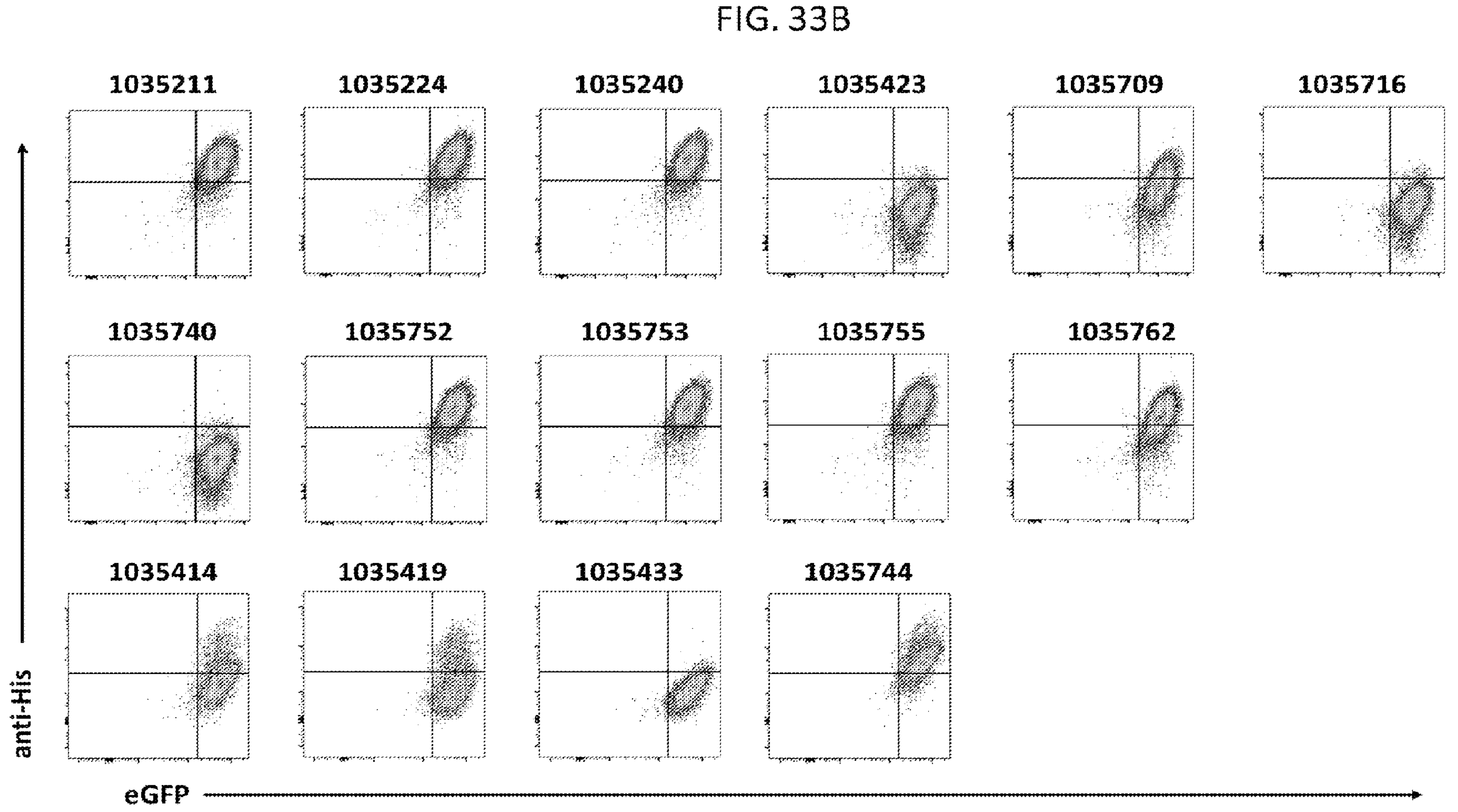

FIG. 33A-FIG. 33B show select anti-SARS-CoV-2 antibodies block binding of the SARS-CoV-2 S B.1.617.2 variant to ACE-2. rSARS2-B.1.617.2 S aa16-1211 10+4×aa mut. protein was mixed and then incubated with flow cytometry staining buffer, Mouse IgG1, IgG2a or IgG2b isotype control antibodies (FIG. 33A); or with anti-SARS-CoV-2 monoclonal antibodies from panels 10352XX, 10354XX, or 10357XX (FIG. 33B) to allow a complex to form. After incubation, the mixture was added to a single cell suspension of hACE-2 HEK/eGFP Tfx, followed by addition of a secondary anti-His antibody to assess viral antibody blocking. Flow cytometry gates were set on anti-His fluorescence of hACE-2 HEK/eGFP Tfx cells without SARS-CoV-2 S B.1.617.2 variant protein.

DETAILED DESCRIPTION OF ILLUSTRATIVE EMBODIMENTS

This disclosure describes anti-SARS-CoV-specific monoclonal antibodies, methods of making and characterizing those antibodies, and methods of using those antibodies in both diagnostic and therapeutic applications. In some embodiments, the antibodies may bind to both SARS-CoV-1 and SARS-CoV-2. In some embodiments, the antibodies bind to $S_1$ of the spike protein of SARS-CoV-2 including, for example, to the receptor binding domain (RBD) of $S_1$. In some embodiments, the antibodies may block the binding of SARS-CoV-1 and/or SARS-CoV-2 to ACE-2.

SARS-CoV-1 and SARS-CoV-2

Severe acute respiratory syndrome-coronavirus 2 (SARS-CoV-2) virus is a positive stranded RNA virus that is a member of the coronaviridae family, and is the causative agent of the COVID-19 pandemic (Lu et al. *Lancet* 395, 565-574 (2020); Wu et al. *Nature* 579, 265-269 (2020); Zhou et al. *Nature* 579, 270-273 (2020); Zhu et al. *N Engl J Med* 382, 727-733 (2020)). Coronaviruses include four structural proteins: a spike protein (S), a membrane protein (M), an envelope protein (E), and a nucleocapsid protein (N). The spike protein is composed of two subunits: $S_1$ which is responsible for binding to the host cell receptor via a highly conserved receptor binding domain (RBD) (Lan et al. *Nature* 581, 215-220 (2020)), and $S_2$ which facilitates fusion of the virus to a target cell membrane.

Like the related severe acute respiratory syndrome (SARS) virus, SARS-CoV-1, the causative agent of the 2002 SARS pandemic, SARS-CoV-2 primarily infects cells of a host's respiratory system by binding to the angiotensin converting enzyme 2 (ACE-2) (Chen et al. *Biochem Biophys Res Commun*, (2020); Letko et al. *Nat Microbiol* 5, 562-569 (2020); Li et al. *Nature* 426, 450-454 (2003); Walls et al. *Cell* 181, 281-292 e286 (2020)) which is highly expressed in lung epithelial cell vascular endothelia. Other organ systems are also involved, however, due to the high level expression of ACE-2 on cells in cardiovascular tissue, kidney, and bladder tissue, and on the epithelia of the small intestine and testes (Zou et al. *Front Med* 14, 185-192 (2020)). The resulting inflammation and tissue damage caused either by direct viral infection by lung epithelial cells, or indirectly by host immune responses to infection and subsequent cytokine storm, can, in cases of severe, result in severe respiratory failure with multiple organ failure and death (Yuki et al. *Clin Immunol* 215, 108427 (2020)).

Phylogenetically, SARS-CoV-2 and SARS-CoV-1 belong to the Betacoronavirus genus which can be found in human and many animal species (Lu et al. *Lancet* 395, 565-574 (2020); Wu et al. *Nature* 579, 265-269 (2020); Zhou et al. *Nature* 579, 270-273 (2020); Zhu et al. *N Engl J Med* 382, 727-733 (2020)). Although both viruses have been responsible for independent severe acute respiratory syndromes in humans, SARS-CoV-2 is more closely related to bat coronavirus RaTG13, sharing more than 93% homology in the spike gene, than SARS-CoV-1 (Zhou et al. *Nature* 579, 270-273 (2020)). Sequence analysis of the S gene of SARS-CoV-2 and SARS-CoV-1 reveals that spike proteins of the two viruses are highly divergent, sharing about 76% homology while the receptor binding protein shares less than 75% homology (Zhou et al. *Nature* 579, 270-273 (2020); Ou et al. *Nat Commun* 11, 1620 (2020)); still, the portion of the receptor binding domains for both viruses that is critical for binding to ACE-2 is nearly identical (Lan et al. *Nature* 581, 215-220 (2020)) suggesting that antibodies that block the correct portion of the receptor binding domain of SARS-CoV-2 may also block the receptor binding domain of SARS-CoV-1.

A third member of the Betacoronavirus genus, Middle East respiratory syndrome coronavirus (MERS-CoV), was identified as the causative agent of a human severe respiratory syndrome in 2012 in Saudi Arabia (Zaki et al. *N Engl J Med* 367, 1814-1820 (2012)), known as Middle East respiratory syndrome (HERS). Whereas SARS-CoV-1 and SARS-CoV-2 use human ACE-2 as their main receptor, MERS-CoV uses transmembrane dipeptidylpeptidase 4 (DPP4), also known as CD26, as its primary receptor. The homology between the receptor binding domains (RBDs) of SARS-CoV-2 spike protein and MERS-CoV spike protein is low, only 19.1%; however, both SARS-CoV-2 and MERS-CoV can bind DPP4 by virtue of identical amino acids at their respective DPP4 binding residues (Li et al. *iScience* 23, 101160 (2020)).

The SARS-CoV-2 virus infects mammalian cells by attaching transmembrane spike proteins (S protein) to angiotensin-converting enzyme 2 receptors (ACE-2) found on the surface of human target cells (Ou et al. *Nature Communications* 11, 1620 (2020); Shang et al. *Proceedings of the National Academy of Sciences* 117, 11727-11734 (2020)). Hence, inhibiting the binding of SARS-CoV-2 spike protein to ACE-2 has been the primary strategy behind most SARS-CoV-2 vaccines (Jackson et al. *N Engl J Med* 383, 1920-1931 (2020); Mulligan et al. *Nature* 590, E26-E26 (2021)), therapeutic antibodies (Food and Drug Administration. Letter to Regeneron Pharmaceuticals, Inc. (21 Nov. 2020)) (Food and Drug Administration. Letter to Eli Lilly and Company. (10 Nov. 2020)), and therapeutic soluble ACE-2 molecules (Zoufaly et al. *Lancet Respir Med* 8, 1154-1158 (2020)).

The receptor binding domain (RBD) of the viral spike protein plays a critical role in the binding of SARS-CoV-2 to ACE-2. The SARS-CoV-2 RBD is a 220-amino acid fragment (Arg319-Phe541) in the 51 subunit of SARS-CoV-2 spike protein. The spike protein has two conformational states—the pre-fusion state (closed conformation) and the post-fusion state (open conformation) (Cai et al. *Science* 369, 1586-1592 (2020)), and the RBD portion fluctuates between the "up" and "down" conformations (Khare et al. *Front Artif Intell* 4, 630955 (2021)). The RBD consists of a twisted five-stranded antiparallel β sheet core with disulfide bonds and short connecting helices and loops outside as well as a looped-out extension from the β4 and β7 strands of the core (Lan et al. *Nature* 581, 215-220 (2020)). The looped-out extension, e.g., the receptor binding motif (RBM), forms the boat-shaped bowl structure that interacts with and holds the contacting arm of ACE2. Seventeen amino acid resides of the RBD contact their partners in ACE2. These contacting resides of the RBD include one residue from the non-RBM portion (K417) and 16 residues from the RBM portion (i.e., G446, Y449, Y453, L455, F456, A475, F486, N487, Y489, Q493, G496, Q498, T500, N501, G502, and Y505) (Lan et al. Nature 581, 215-220 (2020)). Five amino acid residues of the RBD are often mutated in currently dominant variants, including two ACE2 contacting residues (K417 and N501) and three residues near the ACE2 contacting residues (L452, T478, E484). These mutations have been shown to increase ACE2-RBD affinity, induce escape from monoclonal antibody or convalescent sera, and cause severe disease (Tao et al. *Nat Rev Genet,* 22, 757-773 (2021); Xie et al. *Nat Med* 27, 620-621 (2021)).

The spike protein is highly antigenic glycosylated protein (Henderson et al. *bioRxiv*, (2020)). Numerous anti-spike antibodies, isolated from the sera post-infection patients, are able to neutralize the SARS-CoV-2 adhesion and reduces viral infection, alleviating the disease status (Huang et al. *Antib Ther* 3, 285-299 (2020); Zost et al. *Nature* 584, 443-449 (2020)). Most of these neutralizing antibodies belong to anti-RBD antibodies. Therefore, the identification of potent neutralizing antibodies has significant implication for the development of therapeutic antibodies and better understanding the humoral immune response to SARS-CoV-2 variants. In fact, all three FDA approved anti-SARS-CoV-2 monoclonal antibody products with Emergency Use Authorizations (EUAs) designation are anti-RBD antibodies. For example, the bamlanivimab (LY-CoV555) plus etesevimab (LY-CoV016) cocktail targets two partially non-overlapping epitopes on the RBD and the casirivimab (REGN10933) plus imdevimab (REGN10987) cocktail targets two nonoverlapping epitopes on the RBD. The third antibody product, sotrovimab, targets an epitope on the RBD that is conserved between SARS-CoV and SARS-CoV-2 (NIH website—Anti-SARS-CoV-2 Monoclonal Antibodies).

Anti-SARS-CoV Antibodies

In one aspect, this disclosure describes an antibody that binds to SARS-CoV (that is, an anti-SARS CoV antibody). An antibody that binds to SARS-CoV includes an antibody that binds to SARS-CoV-1 and/or SARS-CoV-2. In some embodiments, an antibody that binds to SARS-CoV may bind to both SARS-CoV-1 and SARS-CoV-2. In some embodiments, an antibody that binds to SARS-CoV may bind to SARS-CoV-1 but not SARS-CoV-2 or to SARS-CoV-2 but not SARS-CoV-1. In some embodiments an anti-SARS-CoV antibody preferably binds to SARS-CoV-2 and may optionally bind to SARS-CoV-1.

In some embodiments, an antibody that binds to SARS-CoV preferably binds to SARS-CoV-2 $S_1$ or SARS-CoV-2 $S_1$. For example, as described in Example 1 and shown in FIG. 1, antibodies 1035419 (FIG. 1A), 1035423 (FIG. 1B), 1035433 (FIG. 1C), 1035414 (FIG. 1D), 1035709 (FIG. 1E), 1035716 (FIG. 1F), 1035740 (FIG. 1G), 1035744 (FIG. 1H), 1035752 (FIG. 1I), 1035753 (FIG. 1J), 1035755 (FIG. 1K), 1035762 (FIG. 1L), 1035211 (FIG. 1M), 1035224 (FIG. 1N), and 1035240 bind to recombinant SARS-CoV-2 $S_1$ RBD.

In some embodiments, an antibody that binds to SARS-CoV may inhibit the binding of SARS-CoV-2 $S_1$ to ACE-2 and/or may inhibit the binding of SARS-CoV-2 $S_1$ RBD to ACE-2. For example, as described in Example 1 and shown in Table 2, antibodies 1035211, 1035224, 1035240, 1035414, 1035419, 1035423, 1035433, 1035709, 1035716, 1035740, 1035744, 1035752, 1035753, 1035755, and 1035762 reduced the binding of SARS-CoV-2 $S_1$ RBD to ACE-2 expressing cells (by at least 50%), and monoclonal antibodies 1035211, 1035224, 1035240, 1035419, 1035709, 1035716, 1035740, 1035744, 1035752, 1035753, 1035755, and 1035762 reduced of the binding of SARS-CoV-2 $S_1$ to ACE-2 expressing cells (by at least 85%).

In some embodiments, an antibody binds to the receptor binding domain (RBD) of the viral spike (S) protein.

In some embodiments, an antibody that binds to SARS-CoV-2 may also inhibit the binding of SARS-CoV-1 $S_1$ to ACE-2 or may inhibit the binding of SARS-CoV-1 $S_1$ RBD to ACE-2. For example, as described in Example 1 and shown in Table 4, antibodies 1035419, 1035716, and 1035740 inhibited SARS-CoV-1 $S_1$ and SARS-CoV-1 $S_1$ RBD binding to ACE-2 as well as SARS-CoV-2 $S_1$ and SARS-CoV-2 $S_1$ RBD binding to ACE-2.

In some embodiments, the antibody may decrease the binding of SARS-CoV (including SARS-CoV-1, SARS-CoV-2, SARS-CoV-1 spike protein, SARS-CoV-1 $S_1$, SARS-CoV-1 $S_1$ RBD, SARS-CoV-2 spike protein, SARS-CoV-2 $S_1$, and/or SARS-CoV-2 $S_1$ RBD) to a SARS-CoV ligand (including, for example, ACE-2) by at least 10 percent (%), at least 15%, at least 20%, at least 25%, at least 30%, at least 40%, at least 50%, at least 60%, at least 70%, at least 80%, at least 90%, at least 95%, or at least 98%. In some embodiments, the antibody may decrease the binding of SARS-CoV to a SARS-CoV ligand (including, for example, ACE-2) by up to 99% or up to 99.5%. For example, the antibody may decrease the binding of SARS-CoV to a SARS-CoV ligand by 50% to 99.5% or by 80% to 99.5%. In some embodiments, the binding of SARS-CoV to a SARS-CoV ligand may be measured using an antibody-blocking assay as described in the Examples.

In some embodiments, the antibody may bind to one or more variants of the RBD of SARS-CoV-2 $S_1$. In some embodiments, an antibody that binds to one or more variants of the RBD may also inhibit and/or neutralize the binding of SARS-CoV-2 $S_1$ to ACE-2. The continued emergence of SARS-CoV-2 variants has raised concerns and challenges for the control, prevention, and management of the coronavirus disease (COVID-19) (Abdool Karim et al. *N Engl J Med* 384, 1866-1868 (2021)). After over 18 months since the World Health Organization (WHO) declared COVID-19 a pandemic on Mar. 11, 2020 (Cucinotta et al. *Acta Biomed* 91, 157-160 (2020)), the spread of constantly emerging SARS-CoV-2 variants remains a global threat to the world-wide health and economy. As of Oct. 1, 2021, the WHO classifies four variants (alpha, beta, gamma, and delta) as VOC (variants of concern), two variants (lambda and mu) as VOI (variants of interest), and eleven variants as VUM (variants under monitoring) (WHO website—Tracking SARS-CoV-2 variants). Each variant carries a specific set of mutations in their respective viral genome, particularly in the spike protein that is key to the virus adhesion to target cells. Since the RBD plays a central role in the binding of the spike protein and the viral particle to the ACE2 receptor, mutations in the RBD that result in changes of the epitope structure or conformations on the RBD, at the location where the neutralizing antibodies bind, will cause subsequent evasion of post-infection and/or post vaccination induced immune protection (Tao et al. *Nat Rev Genet,* 22, 757-773 (2021); Xie et al. *Nat Med* 27, 620-621 (2021)).

Figure 14:
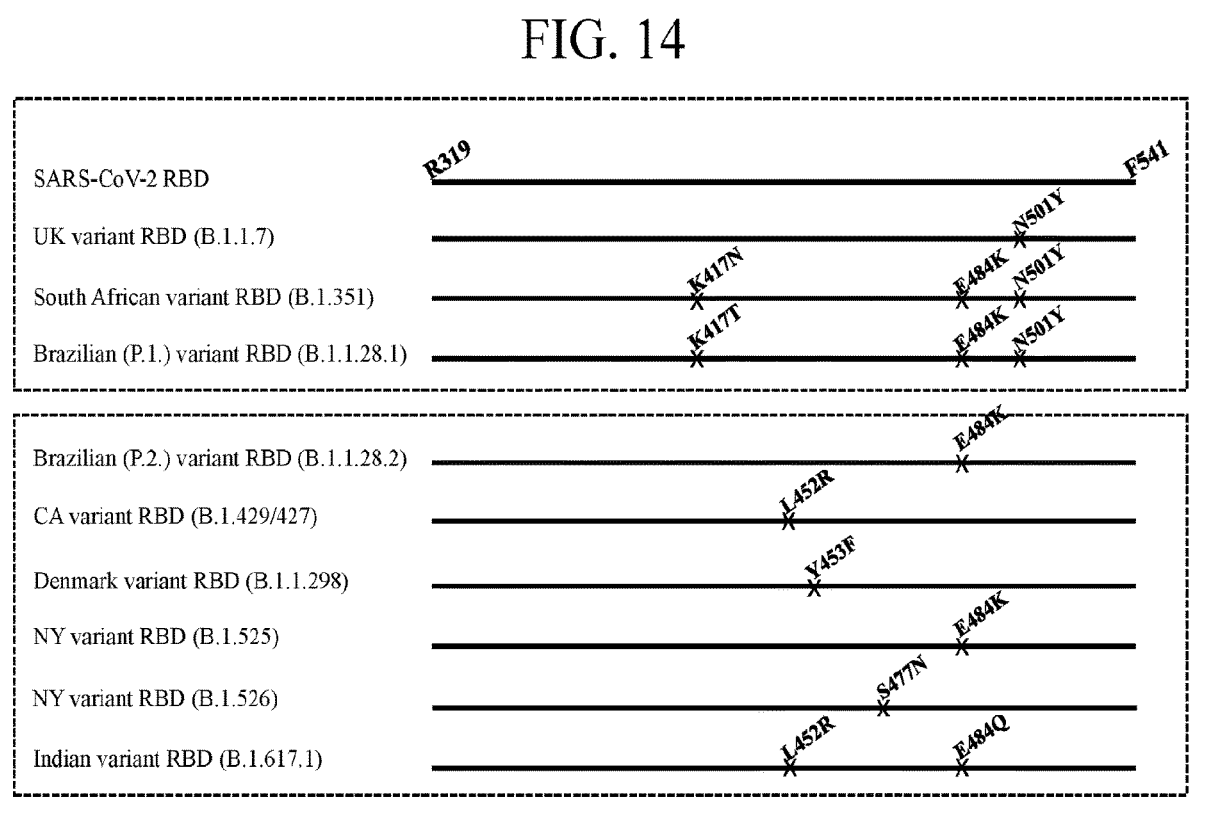

In some embodiments, the antibody may bind to one or more the RBD variants as described in more detail in Examples 3 and 4, including one or more of those shown in FIG. 14 and Tables 11 and 12. RBD variants can include, but are not limited to, the United Kingdom variant ((B.1.1.7 lineage, UK, alpha, RBD with N501Y) (Santos et al. *bioRxiv,* 2020.2012.2029.424708 (2021); and Rambaut et al. nCoV-2019 *Genomic Epidemiology—Virological*, (2020))), the South African variant ((B.1.351 lineage, SA, beta, RBD with K417N, E484K, and N510Y) (Villoutreix et al. *International Journal of Molecular Sciences* 22, 1695 (2021))), the Brazilian variant P.1 ((B.1.1.28.1 lineage, BR P.1, gamma, RBD with K417T, E484K, and N510Y) (Faria et al. *Science* 372, 815-821 (2021))), the Indian variant 2 (B.1.617.2 lineage, IN v2, delta, RBD with L452R, T478K), the California variants ((B.1.429/427 lineage, CA, epsilon, RBD with L452R) (Zhang et al. *JAMA* 325, 1324-1326 (2021))), the New York variants ((B.1.526/525 lineage, NY, eta and iota, with E484K) (Annavajhala et al, *medRxiv,* 2021.2002.2023.21252259 (2021))), the Indian variant 1 ((B.1.617.1 lineage, IN v1, kappa, RBD with L452R, E484Q) (Cherian et al. *bioRxiv,* 2021.2004.2022.440932 (2021))), the Brazilian variant P.2 ((B.1.1.28.2 lineage, BR P.2, zeta, RBD with E484K) (Voloch et al. *Journal of Virology* 95, e00119-00121 (2021))), the K417E RBD (R319-F541 with K417E), and the T478K RBD (R319-F541 with T478K). Additional variants include the Denmark mink variant ((B.1.1.298 lineage, DM, RBD with Y453F) (Bayarri-Olmos et al. *bioRxiv,* 2021.2001.2029.428834 (2021))), the Peru variant (C.37 lineage, lambda, RBD with L452Q and F490S), and the Philippine variant (P.3 lineage or theta, RBD with E484K and N501Y) (Tao et al., *Nat Rev Genet* 22, 757-773 (2021)).

In some embodiments, an antibody that binds to one or more of these variants of these RBDs may also inhibit and/or neutralize the binding of SARS-CoV-2 S1 to ACE-2.

In some embodiments, an antibody may bind to the delta variant of the RBD. In some embodiments, an antibody that binds to the delta variant of the RBD may inhibit and/or neutralize the binding of a delta variant of SARS-CoV-2 to ACE-2 and/or may inhibit the binding of the delta variant SARS-CoV-2 $S_1$ RBD to ACE-2. The delta variant (B.1.617.2) includes mutations in the gene encoding the SARS-CoV-2 spike protein causing the substitutions T478K, P681R and L452R (Starr et al., *Cell Reports Medicine.* 2 (4): 100255.doi:10.1016/j.xcrm.2021.100255. PMC 8020059. PMID 33842902), which are known to affect transmissibility of the virus as well as whether it can be neutralized by antibodies for previously circulating variants of the COVID- 19 virus ("SARS-CoV-2 variants of concern as of 24 May 2021," European Centre for Disease Prevention and Control. Retrieved 6 Aug. 2021).

In some embodiments, an antibody may block, inhibit, and/or neutralize the binding of a SARS-CoV-2 RBD polypeptide to ACE-2. Neutralization activity of an antibody may be strong, moderate, or weak. In some embodiments, strong neutralization activity is a $NC_{50}$ value of less than about 1.5 μg/μl, moderate neutralization activity is a $NC_{50}$ value between greater than or equal to about 1.5 μg/μl and less than or equal to about 15 μg/μl, and weak neutralization activity is a $NC_{50}$ value of greater than about 15 μg/μl, all as measured by the lateral flow immunoassay described in more detail in Examples 3 and 4. In some embodiments, an antibody as described may have a $NC_{50}$ of about 0.3 μg/μl to about 1.5 μg/μl, as measured by the lateral flow immunoassay described in more detail in Examples 3 and 4.

In some embodiments, an antibody may bind to a RBD bin A epitope, a RBD bin B epitope, or RBD bin C epitope, as described in more detail in Examples 3 and 4. As shown in Table 11, RBD epitope bin A includes the epitope of the RBD polypeptide recognized by the 1035709 and 1035762 antibodies, RBD epitope bin B includes the epitope of the RBD polypeptide recognized by the 1035740 and 1035419 antibodies, and RBD epitope bin C includes the epitope of the RBD polypeptide recognized by the 1035753, 1035224, and 1035240 antibodies. RBD epitope bin C epitope may be further classified bin Ca (1035753 and 1035224) and bin Cb (1035240). FIG. 25A-FIG. 25C show surface presentation map of SARS-CoV-2 spike RBD with the corresponding epitope regions of these seven mAbs. The RBD interface may be classified into three regions—N-terminal contact region 1 (CR1) covering key residues E484, F486, E471, T478 etc., the middle contact region 2 (CR2) covering key residues R403, L452, S494, Q493, K417 etc. and the distal contact region 3 covering key resides N501 and Q498. (Wang et al. Proceedings of the National Academy of Sciences 117, 13967-13974 (2020)). RBD epitope bin A is near the T478 residue and overlaps the RBD interface contact region 1 (CR1). RBD epitope bin B is near N501 and L452 residues and overlaps with the RBD interface contact region 2 and region 3 (CR2 and CR3). RBD epitope bin C is at E484 and L452 and overlaps with the RBD interface contact region 1 and 2 (CR1 and CR2).

In some embodiments, the antibody may be an isolated antibody. In some embodiments, the antibodies may be isolated or purified by conventional immunoglobulin purification procedures, such as protein A- or G-Sepharose, hydroxylapatite chromatography, gel electrophoresis, dialysis, or affinity chromatography.

In some embodiments, an antibody that binds to SARS-CoV may include a derivative of an antibody that is modified or conjugated by the covalent attachment of any type of molecule to the antibody. Such antibody derivatives include, for example, antibodies that have been modified by glycosylation, acetylation, pegylation, phosphorylation, amidation, derivatization by known protecting/blocking groups, proteolytic cleavage, toxins, or linkage to a cellular ligand or other protein. Any of numerous chemical modifications may be carried out by known techniques, including, but not limited to, specific chemical cleavage, acetylation, formylation, and metabolic synthesis of tunicamycin. Additionally, the derivatives may contain one or more non-classical amino acids.

An antibody that binds to SARS-CoV may be coupled directly or indirectly to a detectable marker by techniques well known in the art. A detectable marker is an agent detectable, for example, by spectroscopic, photochemical, biochemical, immunochemical, or chemical means. Useful detectable markers include, but are not limited to, fluorescent dyes, chemiluminescent compounds, radioisotopes, electron-dense reagents, enzymes, coenzymes, colored particles, biotin, or digoxigenin. A detectable marker often generates a measurable signal, such as radioactivity, fluorescent light, color, or enzyme activity. Antibodies conjugated to detectable agents may be used for diagnostic or therapeutic purposes. Examples of detectable agents include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody or indirectly, through an intermediate such as, for example, a linker known in the art, using techniques known in the art. See, for example, U.S. Pat. No. 4,741,900, describing the conjugation of metal ions to antibodies for diagnostic use. Examples of suitable enzymes include horseradish peroxidase, alkaline phosphatase, beta-galactosidase, and acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride and phycoerythrin; an example of a luminescent material includes luminol; examples of bioluminescent materials include luciferin, and aequorin; and examples of suitable radioactive material include iodine ($^{121}I$, $^{123}I$, $^{125}I$, $^{131}I$) carbon ($^{14}C$), sulfur ($^{35}S$), tritium ($^{3}H$), indium ($^{111}In$, $^{112}In$, $^{113}mIn$, $^{115}mIn$), technetium ($^{99}Tc$, $^{99}mTc$), thallium ($^{201}Ti$), gallium ($^{68}Ga$, $^{67}Ga$), palladium ($^{103}Pd$), molybdenum ($^{99}Mo$), xenon ($^{133}Xe$), fluorine ($^{18}F$), $^{153}Sm$, $^{177}Lu$, $^{159}Gd$, $^{149}Pm$, $^{140}La$, $^{175}Yb$, $^{166}Ho$, $^{90}Y$, $^{47}Sc$, $^{186}Re$, $^{188}Re$, $^{142}Pr$, $^{105}Rh$, and $^{97}Ru$. Techniques for conjugating such therapeutic moieties to antibodies are well-known.

The antibody may be an antibody from any suitable species. For example, the antibody may be a human antibody, a mouse antibody, a rat antibody, a rabbit antibody, a goat antibody, a shark antibody, or a camelid antibody, such as a llama antibody, etc.

The antibody may be of any type, any class, or any subclass. When the antibody is a human or mouse antibody, for example, the type may include, for example, IgG, IgE, IgM, IgD, IgA and IgY; and/or the class may include, for example, IgG1, IgG2, IgG3, IgG4, IgA1 and IgA2.

In some embodiments, the antibody is an IgG antibody. In some embodiments, the IgG antibody may be a human antibody of any one of the IgG subclasses including, for example, IgG1, IgG2, IgG3 or IgG4. In some embodiments, the antibody may be a mouse IgG of one of the following sub-classes: IgG1, IgG2A, IgG2B, IgG2C and IgG3. In some embodiments, the antibody may be a rat IgG of one of the following sub-classes: IgG1, IgG2A, IgG2B, or IgG2C.

In some embodiments, the antibody may include a kappa light chain. In some embodiments, the antibody may include a lambda light chain.

In some embodiments, the antibody includes an antibody fragment capable of binding to a biological molecule (such as an antigen or receptor) or portions thereof, including but not limited to Fab, Fab' and $F(ab')_2$, pFc', Fd, a single domain antibody (sdAb), a variable fragment (Fv), a single-chain variable fragment (scFv) or a disulfide-linked Fv (sdFv); a diabody or a bivalent diabody; a linear antibody;

a single-chain antibody molecule; and a multispecific antibody formed from antibody fragments.

In some embodiments, the antibody may be a humanized antibody. An antibody that binds to SARS-CoV may be humanized by any suitable method. Techniques for producing humanized monoclonal antibodies may be found, for example, in Jones et al. (Jones et al. *Nature* 321, 522-525 (1986)) and Singer et al. (Singer et al. *J Immunol* 150, 2844-2857 (1993)). For example, humanization of the antibody may include changes to the antibody to reduce the immunogenicity of the antibody when used in humans. In some embodiments, a humanized antibody that binds to SARS-CoV may include at least a portion of an immunoglobulin constant region (Fc) of a human immunoglobulin. A humanized antibody that binds to SARS-CoV-2 may include, in some embodiments, a human immunoglobulin (recipient antibody) in which residues from one or more complementary determining regions (CDRs) of the recipient antibody are replaced by residues from one or more CDRs of a non-human species antibody (donor antibody), such as mouse, rat, or rabbit antibody, that binds to SARS-CoV. In some embodiments, Fv framework residues (FR) of a human immunoglobulin may be replaced by corresponding non-human residues from an antibody that binds to SARS-CoV.

In some embodiments, one or more of the variable regions of Table 6 or Table 7 and/or CDR regions of Table 8 or Table 9 may be included in an antibody sequence (e.g., a constant region) of any suitable species (e.g., rat, rabbit, goat, shark, or a camelid species, such as, for example, a llama, etc.).

In some embodiments, a monoclonal antibody includes a chimeric antibody, that is, an antibody in which different portions are derived from different animal species. A chimeric antibody may be obtained by, for example, splicing the genes from a mouse antibody molecule with appropriate antigen specificity together with genes from a human antibody molecule of appropriate biological specificity. See, for example, Takeda et al. (Takeda et al. *Nature* 314, 452-454 (1985)). Additional chimeric antibodies including genes from different species may be envisioned.

In some embodiments, an antibody includes a bispecific or a bifunctional antibody. A bispecific or bifunctional antibody is an artificial hybrid antibody having two different heavy/light chain pairs and two different binding sites. A bispecific antibody may be produced by a variety of methods including fusion of hybridomas or linking of F(ab') fragments. See, for example, Songsivilai et al. and Kostelny et al. (Kostelny et al. *J Immunol* 148, 1547-1553 (1992); Songsivilai et al. *Clin Exp Immunol* 79, 315-321 (1990)). In addition, bispecific antibodies may be formed as "diabodies" (Holliger et al. *Proc Natl Acad Sci USA* 90, 6444-6448 (1993)) or "Janusins" (Traunecker et al. *EMBO J* 10, 3655-3659 (1991); Traunecker et al *Int J Cancer Suppl* 7, 51-52 (1992)).

In some embodiments, an antibody includes a multispecific antibody that includes more than one variable region, wherein each variable region binds to a different site of a single target molecule or more than one target molecule.

In some embodiments, the antibody may be produced by an animal (including, but not limited to, human, mouse, rat, rabbit, hamster, goat, horse, chicken, turkey, or camelid species, such as, for example, a llama), produced by a cell from an animal, chemically synthesized, or recombinantly expressed. The antibody may be purified by any method known in the art for purification of an immunoglobulin molecule, for example, by chromatography (for example, ion exchange, affinity, and sizing column chromatography), centrifugation, differential solubility, or by any other standard technique for the purification of proteins. In addition, an antibody may be fused to a heterologous polypeptide sequence, as described herein or otherwise known in the art, including, for example, to facilitate purification.

In some embodiments, an antibody that binds to SARS-CoV may be made by immunizing an animal with a SARS-CoV protein or fragment thereof (including, for example, SARS-CoV-1 spike protein, SARS-CoV-1 $S_1$, SARS-CoV-1 $S_1$ RBD, SARS-CoV-2 spike protein, SARS-CoV-2 $S_1$, and/or SARS-CoV-2 $S_1$ RBD). In some embodiments, an antibody that binds to SARS-CoV may be made by immunizing an animal with at least a portion of SARS-CoV-2 $S_1$ (UniProt PODTC2). In some embodiments, the animal may be a mammal. For example, the animal may be a rabbit, a mouse, a goat, a sheet, a rat, or a camelid species, including, for example, a llama. In some embodiments, the animal may be a chicken.

For example, as described in Example 1, mice were immunized with amino acids 1-666 of SARS-CoV-2 $S_1$, amino acids 319-541 of SARS-CoV-2 $S_1$, or amino acids 1-681 of SARS-CoV-2 $S_1$.

A monoclonal antibody may be assayed for immunospecific binding by the methods described herein and by any suitable method known in the art. The immunoassay that may be used includes but is not limited to a competitive and/or a non-competitive assay system using a technique such as BIACORE analysis, fluorescence activated cell sorter (FACS) analysis, immunofluorescence, immunocytochemistry, Western blot, radio-immunoassay, enzyme linked immunosorbent assay (ELISA), "sandwich" immunoassay, immunoprecipitation assay, precipitin reaction, gel diffusion precipitin reaction, immunodiffusion assay, agglutination assay, complement-fixation assay, immunoradiometric assay, fluorescent immunoassay, and protein A immunoassay. Such assays are routine and well known in the art (see for example, Ausubel et al., eds, Current Protocols in Molecular Biology, Vol. 1, John Wiley & Sons, Inc., N.Y. (1994)).

In some embodiments, the anti-SARS CoV antibody is preferably a monoclonal antibody.

The anti-SARS CoV monoclonal antibody may be produced by progeny or derivatives of a hybridoma cell line described herein, a monoclonal antibody produced by equivalent or similar hybridoma cell line, and/or a recombinant derivative made therefrom. In some embodiments, an antibody that binds to SARS-CoV includes a recombinantly derived monoclonal antibody including, for example, a rabbit B cell derived monoclonal antibody or a mouse B-cell derived monoclonal antibody.

An intact antibody molecule has two heavy (H) chain variable regions (abbreviated herein as $V_H$) and two light (L) chain variable regions (abbreviated herein as $V_L$). The $V_H$ and $V_L$ regions can be further subdivided into regions of hypervariability, termed "complementarity determining regions" ("CDRs"), interspersed with regions that are more conserved, termed "framework regions" ("FRs"). The extent of the FRs and CDRs has been precisely defined (see, Kabat et al. (1991) Sequences of Proteins of Immunological Interest, Fifth Edition, U.S. Department of Health and Human Services, NIH Publication No. 91-3242, and (Chothia et al. *J Mol Biol* 196, 901-917 (1987))). Each $V_H$ and $V_L$ is composed of three CDRs and four FRs, arranged from amino-terminus to carboxy-terminus in the following order: FR1, CDR1, FR2, CDR2, FR3, CDR3, FR4.

A monoclonal antibody may be obtained by any suitable technique. In some embodiments, an antibody that binds to SARS-CoV may be made by recombinant DNA methods, produced by phage display, and/or produced by combinatorial methods. DNA encoding an antibody that binds to SARS-CoV may be readily isolated and sequenced using conventional procedures. In some embodiments, a hybridoma cell described herein may serve as a source of such DNA. Once isolated, the DNA may be transfected into a host cell (including, for example, simian COS cells, Chinese hamster ovary (CHO) cells, human embryonic kidney cells (HEK), or myeloma cells that do not otherwise produce immunoglobulin protein) or introduced into a host cell by genome editing (for example, using a CRISPR-Cas system) to obtain the synthesis of monoclonal antibodies in recombinant host cells. The DNA encoding an antibody that binds to SARS-CoV may be modified to, for example, humanize the antibody.

In some embodiments, an antibody includes the same light chain sequence as a monoclonal antibody produced by at least one of the clones of Table 1: 1035211.11, 1035224.11, 1035240.11, 1035414.11, 1035419.11, 1035423.11, 1035433.11, 1035709.11, 1035716.11, 1035740.11, 1035744.11, 1035752.11, 1035753.11, 1035755.11, and 1035762.11 (which produce monoclonal antibodies 1035211, 1035224, 1035240, 1035414, 1035419, 1035423, 1035433, 1035709, 1035716, 1035740, 1035744, 1035752, 1035753, 1035755, and 1035762, respectively). In some embodiments, an antibody includes the same heavy chain sequence as a monoclonal antibody produced by at least one of the clones of Table 1. In some embodiments, an antibody includes the same heavy chain sequence and the same light chain sequence as a monoclonal antibody produced by at least one of the clones of Table 1. In some embodiments, a monoclonal antibody can contain one, two, three, four, five, six, or more amino acid substitutions in the heavy and/or the light chain sequences identified above wherein the amino acid substitutions do not substantially affect binding of the antibody to SARS-CoV, and, in some embodiments, preferably do not substantially affect binding of the antibody to SARS-CoV-2.

In some embodiments, an antibody includes a light chain variable region ($V_L$) sequence of Table 6 (that is, one of SEQ ID NO:1 to SEQ ID NO:16). In some embodiments, an antibody includes a heavy chain variable region ($V_H$) sequence of Table 7 (that is, one of SEQ ID NO:17 to SEQ ID NO:31). In some embodiments, an antibody includes a $V_L$ sequence of Table 6 and a $V_H$ sequence of Table 7. In some embodiments, an antibody includes a $V_L$ sequence of Table 6 and a corresponding $V_H$ sequence of Table 7. For example, if the antibody includes the $V_L$ of antibody 1035419 in Table 6 (e.g., SEQ ID NO:5), the antibody includes a corresponding $V_H$ sequence if the antibody also includes the $V_H$ sequence of antibody 1035419 in Table 7 (SEQ ID NO:21). In some embodiments, an antibody can contain one, two, three, four, five, six, or more amino acid substitutions in the heavy and/or the light chain variable regions identified above wherein the amino acid substitutions do not substantially affect binding of the antibody to SARS-CoV, and, in some embodiments, preferably do not substantially affect binding of the antibody to SARS-CoV-2.

In some embodiments, an antibody includes at least one CDR of the $V_L$ domain of an antibody produced by at least one of the clones of Table 1; those CDR sequences are provided in Table 8. In some embodiments, an antibody includes at least two CDRs of the $V_L$ domain of an antibody produced by at least one of the clones of Table 1. In some embodiments, an antibody includes all three CDRs of the $V_L$ domain of an antibody produced by at least one of the clones of Table 1.

In some embodiments, an antibody includes at least one CDR of the $V_H$ domain of an antibody produced by at least one of the clones of Table 1; those CDR sequences are provided in Table 9. In some embodiments, an antibody includes at least two CDRs of the $V_H$ domain of an antibody produced by at least one of the clones of Table 1. In some embodiments, an antibody includes all three CDRs of the $V_H$ domain of an antibody produced by at least one of the clones of Table 1.

In some embodiments, an antibody may preferably include all three CDRs of the $V_L$ domain of an antibody produced by one of clones of Table 1 and all three CDRs of the $V_H$ domain of an antibody produced by a different clone of Table 1.

In some embodiments, an antibody may preferably include all three CDRs of the $V_L$ domain of an antibody produced by one of clones of Table 1 and all three CDRs of the $V_H$ domain of an antibody produced by the same clone of Table 1. For example, in an exemplary embodiment, an antibody may include all three CDRs of the $V_L$ domain of antibody 1035419: RASESVDSYGASFMH (SEQ ID NO: 38), LASNLES (SEQ ID NO: 39), and QQNYEDPWT (SEQ ID NO: 40); and all three CDRs of the $V_H$ domain of antibody 1035419: SYWIH (SEQ ID NO:76), RIYPGTGSTYNNEKFKG (SEQ ID NO:77), and GEDNLYFYAMDY (SEQ ID NO:78).

In some embodiments, an antibody can contain one, two, three, four, five, six, or more amino acid substitutions in one or more CDRs identified above which do not substantially affect binding of the antibody to SARS-CoV, and, in some embodiments, preferably do not substantially affect binding of the antibody to SARS-CoV-2. In some embodiments, the substitutions in one or more CDRs may be substitutions with conserved amino acids. FIG. 13 depicts exemplary frequencies of conserved amino acid substitution at a specific location in the variable regions of the antibodies.

In some embodiments, an antibody can contain one, two, three, four, five, six, or more amino acid substitutions in one or more framework regions (FRs). In some embodiments, the substitutions, or substitutions in the framework regions (FRs) do not substantially affect binding of the antibody to SARS-CoV, and, in some embodiments, preferably do not substantially affect binding of the antibody to SARS-CoV-2. In some embodiments, the substitutions in one or more FRs may be substitutions with conserved amino acids.

In some embodiments, an antibody can contain one, two, three, four, five, six, or more amino acid substitutions relative to an antibody produced by one of the clones of Table 1, wherein the substitutions do not substantially affect binding of the antibody to SARS-CoV, and, in some embodiments, preferably do not substantially affect binding of the antibody to SARS-CoV-2. In some embodiments, the substitutions may be substitutions with conserved amino acids.

In some embodiments, the antibody includes an amino acid sequence that is at least 70%, at least 80%, at least 85%, at least 90%, at least 95%, at least 96%, at least 97%, at least 98%, or at least 99% identical to an amino acid sequence of at least one $V_L$ domain of an antibody produced by one of the clones of Table 1 (see Table 6).

In some embodiments, the antibody includes an amino acid sequence that is at least 70%, at least 80%, at least 85%, at least 90%, at least 95%, at least 96%, at least 97%, at least 98%, or at least 99% identical to an amino acid sequence of at least one $V_H$ domain of an antibody produced by one of the clones of Table 1 (see Table 7).

In some embodiments, an anti-SARS-CoV antibody includes an antibody that binds to the same SARS-CoV epitope as an antibody produced by one of the clones of Table 1.

In another aspect, this disclosure describes an isolated polynucleotide molecule. In some embodiments, the isolated polynucleotide molecule includes a nucleotide sequence encoding an antibody. In some embodiments, the isolated polynucleotide molecule includes a nucleotide sequence that has at least 75%, at least 80%, at least 85%, at least 90%, at least 95%, at least 96%, at least 97%, at least 98%, or at least 99% sequence identity to nucleotide sequence encoding an antibody described herein. In some embodiments, the isolated polynucleotide molecule includes polynucleotides that hybridize under high stringency to a nucleotide sequence encoding an antibody or a complement thereof. As used herein "stringent conditions" refer to the ability of a first polynucleotide molecule to hybridize, and remain bound to, a second, filter-bound polynucleotide molecule in 0.5 M $NaHPO_4$, 7% sodium dodecyl sulfate (SDS), and 1 mM EDTA at 65° C., followed by washing in 0.2×SSC/0.1% SDS at 42° C. (see Ausubel et al. (eds.), Current Protocols in Molecular Biology, Vol. 1, Green Publishing Associates, Inc., and John Wiley & Sons, Inc., N.Y. (1989), at p. 2.10.3). In some embodiments, the isolated polynucleotide molecule includes polynucleotides that encode one or more of the CDRs or the heavy and/or light chains of a monoclonal antibody of the present disclosure. General techniques for cloning and sequencing immunoglobulin variable domains and constant regions are well known. See, for example, Orlandi et al. (Orlandi et al. *Proc Natl Acad Sci USA* 86, 3833-3837 (1989)).

In another aspect, this disclosure describes recombinant vectors including an isolated polynucleotide of the present disclosure. The vector may be, for example, in the form of a plasmid, a viral particle, or a phage. The appropriate DNA sequence may be inserted into a vector by a variety of procedures. In general, the DNA sequence is inserted into an appropriate restriction endonuclease site(s) in a vector by procedures known in the art. Such procedures are deemed to be within the scope of those skilled in the art. Large numbers of suitable vectors and promoters are known to those of skill in the art and are commercially available. The following vectors are provided by way of example. Bacterial vectors include, for example, pQE70, pQE60, pQE-9, pBS, pD10, phagescript, psiX174, pbluescript SK, pbsks, pNH8A, pNH16a, pNH18A, pNH46A, ptrc99a, pKK223-3, pKK233-3, pDR540, and pRIT5. Eukaryotic vectors include, for example, pWLNEO, pSV2CAT, pOG44, pXT1, pSG, pSVK3, pBPV, pMSG, and pSVL. However, any other plasmid or vector may be used.

In a further aspect, this disclosure also includes a host cell containing at least one of the above-described vectors. The host cell may be a higher eukaryotic cell, such as a mammalian or insect cell, or a lower eukaryotic cell, such as a yeast cell. Or, the host cell may be a prokaryotic cell, such as a bacterial cell, or a plant cell. Introduction of a vector construct into the host cell may be affected by any suitable techniques, such as, for example, calcium phosphate transfection, DEAE-Dextran mediated transfection, electroporation, or nucleofection.

Antibodies of the present disclosure may be expressed in mammalian cells, yeast, bacteria, or other cells under the control of appropriate promoters. Cell-free translation systems may also be employed to produce such proteins using RNAs derived from the DNA constructs of the present disclosure. Appropriate cloning and expression vectors for use with prokaryotic and eukaryotic hosts are described by, for example, Sambrook et al., Molecular Cloning: A Laboratory Manual, Second Edition, Cold Spring Harbor, N.Y. (1989).

Also included in the present disclosure are phage display libraries expressing one or more hypervariable regions from an antibody of the present disclosure, and clones obtained from such a phage display library. A phage display library is used to produce antibody derived molecules. Gene segments encoding the antigen-binding variable domains of antibodies are fused to genes encoding the coat protein of a bacteriophage. Bacteriophage containing such gene fusions are used to infect bacteria, and the resulting phage particles have coats that express the antibody-fusion protein, with the antigen-binding domain displayed on the outside of the bacteriophage. Phage display libraries may be prepared, for example, using the PH.D.-7 Phage Display Peptide Library Kit (Catalog #E8100S) or the PH.D.-12 Phage Display Peptide Library Kit (Catalog #E8110S), available from New England Biolabs Inc., Ipswich, MA. See, for example, Smith and Petrenko (Smith et al. *Chem Rev* 97, 391-410 (1997)).

Hybridoma Cell Lines

This disclosure further describes hybridoma cell lines (also referred to herein as "clones" or "antibody clones") expressing monoclonal antibodies including, for example, the hybridoma cell lines of Table 1. In some embodiments, a monoclonal antibody produced by a hybridoma cell line binds to SARS-CoV. In some embodiments, a monoclonal antibody produced by a hybridoma cell line abrogates binding of SARS-CoV to ACE-2.

Hybridoma cell lines may be obtained by various techniques familiar to those skilled in the art. For example, cells from an animal immunized with a desired antigen are immortalized, commonly by fusion with a myeloma cell (see, for example, Kohler and Milstein (Kohler et al. *Eur J Immunol* 6, 511-519 (1976)); J. Goding in "Monoclonal Antibodies: Principles and Practice," Academic Press, pp 59-103 (1986); and Harlow et al., Antibodies: A Laboratory Manual, page 726 (Cold Spring Harbor Pub. 1988). In some embodiments, the immunized animal is preferably a mammal. In some embodiments, the immunized animal is a rat including, for example, a Wistar rat, or a mouse including, for example, a BALB/C mouse. In some embodiments, the cells from the animal are spleen cells. In some embodiments, the cells from the animal are preferably lymphocytes. In some embodiments, the myeloma cell includes a P3X63Ag8.653 cell.

Other known methods of producing transformed B cell lines that produce monoclonal antibodies may also be used.

Exemplary hybridoma cell lines include 1035211.11, 1035224.11, 1035240.11, 1035414.11, 1035419.11, 1035423.11, 1035433.11, 1035709.11, 1035716.11, 1035740.11, 1035744.11, 1035752.11, 1035753.11, 1035755.11, and 1035762.11 which produce antibodies 1035211, 1035224, 1035240, 1035414, 1035419, 1035423, 1035433, 1035709, 1035716, 1035740, 1035744, 1035752, 1035753, 1035755, and 1035762, respectively.

Recombinant Antibodies

This disclosure further describes recombinantly derived monoclonal antibodies. Recombinantly derived monoclonal antibodies may include, for example, rabbit B cell derived monoclonal antibodies or mouse B cell derived antibodies. Monoclonal antibodies of the present disclosure may be produced by any suitable recombinant technique including, for example, by phage display or by combinatorial methods. See, for example, U.S. Pat. No. 5,223,409; WO 92/18619; WO 91/17271; WO 92/20791; WO 92/15679; WO 93/01288; WO 92/01047; WO 92/09690; or WO 90/02809. Such methods may be used to generate human monoclonal antibodies.

Uses for the Anti-SARS-CoV Antibodies

An antibody that binds to SARS-CoV, as described herein, may be used for any suitable application. For example, a monoclonal antibody may be used in both in vitro and in vivo diagnostic and therapeutic methods.

In some embodiments, an antibody may be used to determine a level of expression of SARS-CoV protein in vitro or in vivo. In some embodiments, an antibody may be used to label a cell in vivo or in vitro. In some embodiments, an antibody may be used to determine a level of expression of SARS-CoV protein in a patient sample.

In some embodiments, an antibody may be used to identify the presence or absence of SARS-CoV protein in a sample from a subject. In some embodiments, identifying the presence of SARS-CoV may include identifying an amount of SARS-CoV in a sample from a subject.

In some embodiments, an antibody may be used to identify a SARS-CoV-2 receptor binding domain (RBD) variant in a sample from a subject.

The sample from the subject may include any suitable or useful samples. Exemplary samples include saliva, sputum, blood, urine, feces, nasal swabs, and bronchial brush or bronchoalveolar lavage (BAL) fluid.

In some embodiments, the antibody may be labeled. The antibodies may be labeled with one or more detectable markers, as described herein. For example, a labeled antibody may be used to label a cell, and the labeled cell may be directly or indirectly imaged via secondary methods. In some embodiments, the cell may be a mammalian cell.

In some embodiments, the antibody may be used to modulate the interaction of SARS-CoV and a ligand of SARS-CoV including, for example, ACE-2. In some embodiments, modulation of the interaction of SARS-CoV and ACE-2 can include inhibiting the interaction of SARS-CoV and ACE-2. Such inhibition may produce immunotherapeutic effects including, for example, the prevention of infection of a cell expressing ACE-2 by SARS-CoV, delaying the onset of SARS or COVID-19, and/or delaying the progression of SARS or COVID-19.

In some embodiments, an antibody as described herein may be administered as a therapeutic agent to prevent the binding of SARS-CoV-2 to the host ACE-2 enzyme.

This disclosure further describes a kit including an antibody. For example, a kit may include a composition that includes an anti-SARS-CoV monoclonal antibody. The antibodies in the kit may be labeled with one or more detectable markers, as described herein. A kit may include one or more containers filled with one or more of the monoclonal antibodies of the disclosure. Additionally, the kit may include other reagents such as buffers and solutions needed to practice the disclosure are also included. Optionally associated with such container(s) may be a notice or printed instructions. As used herein, the phrase "packaging material" refers to one or more physical structures used to house the contents of the kit. The packaging material is constructed by well-known methods, preferably to provide a sterile, contaminant-free environment. As used herein, the term "package" refers to a solid matrix or material such as glass, plastic, paper, foil, and the like, capable of holding within fixed limits a polypeptide.

This disclosure further describes a lateral flow immunoassay device including one or more of the antibodies described herein. The antibodies may be labeled with one or more detectable markers, as described herein. In some embodiments, the lateral flow immunoassay may also include an antibody with a specificity other than a SARS-CoV, such as, for example, an anti-nucleocapsid protein (NP) antibody. Such a lateral flow immunoassay device may be provided in a package that may include other reagents such as buffers and solutions needed to practice the disclosure are also included. Optionally the package may also include a notice or printed instructions. As used herein, the phrase "packaging material" refers to one or more physical structures used to house the contents of the immunoassay device. The packaging material is constructed by well-known methods, preferably to provide a sterile, contaminant-free environment. As used herein, the term "package" refers to a solid matrix or material such as glass, plastic, paper, foil, and the like, capable of holding within fixed limits a polypeptide.

Compositions Including Antibodies

In some embodiments, this disclosure describes a composition including at least one of the antibodies described herein.

In some embodiments, the composition may also include, for example, buffering agents to help to maintain the pH in an acceptable range or preservatives to retard microbial growth. A composition may also include, for example, carriers, excipients, stabilizers, chelators, salts, or antimicrobial agents. Acceptable carriers, excipients, stabilizers, chelators, salts, preservatives, buffering agents, or antimicrobial agents, include, but are not limited to, buffers such as phosphate, citrate, and other organic acids; antioxidants including ascorbic acid and methionine; preservatives, such as sodium azide, octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol; polypeptides; proteins, such as serum albumin, gelatin, or non-specific immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (for example, Zinc (Zn)-protein complexes); and/or non-ionic surfactants such as TWEEN, PLURONICS, or polyethylene glycol (PEG).

In some embodiments, the composition is a pharmaceutical composition and includes the monoclonal antibody and a pharmaceutically acceptable carrier, diluent, or excipient. In the preparation of the pharmaceutical compositions comprising the antibodies described in the teachings herein, a variety of vehicles and excipients may be used, as will be apparent to the skilled artisan.

The pharmaceutical compositions will generally comprise a pharmaceutically acceptable carrier and a pharmacologically effective amount of an antibody, or mixture of antibodies.

The pharmaceutical composition may be formulated as a powder, a granule, a solution, a suspension, an aerosol, a solid, a pill, a tablet, a capsule, a gel, a topical cream, a suppository, a transdermal patch, and/or another formulation known in the art.

For the purposes described herein, pharmaceutically acceptable salts of an antibody are intended to include any art-recognized pharmaceutically acceptable salts including organic and inorganic acids and/or bases. Examples of salts include but are not limited to sodium, potassium, lithium, ammonium, calcium, as well as primary, secondary, and tertiary amines, esters of lower hydrocarbons, such as methyl, ethyl, and propyl. Other salts include but are not limited to organic acids, such as acetic acid, propionic acid, pyruvic acid, maleic acid, succinic acid, tartaric acid, citric acid, benzoic acid, cinnamic acid, salicylic acid, etc.

As used herein, "pharmaceutically acceptable carrier" comprises any standard pharmaceutically accepted carriers known to those of ordinary skill in the art in formulating pharmaceutical compositions. For example, the antibody may be prepared as a formulation in a pharmaceutically acceptable diluent, including for example, saline, phosphate buffer saline (PBS), aqueous ethanol, or solutions of glucose, mannitol, dextran, propylene glycol, oils (for example, vegetable oils, animal oils, synthetic oils, etc.), microcrystalline cellulose, carboxymethyl cellulose, hydroxylpropyl methyl cellulose, magnesium stearate, calcium phosphate, gelatin, polysorbate 80 or as a solid formulation in an appropriate excipient.

A pharmaceutical composition will often further comprise one or more buffers (for example, neutral buffered saline or phosphate buffered saline), carbohydrates (for example, glucose, sucrose or dextrans), mannitol, proteins, polypeptides or amino acids such as glycine, antioxidants (for example, ascorbic acid, sodium metabisulfite, butylated hydroxytoluene, butylated hydroxyanisole, etc.), bacteriostats, chelating agents such as EDTA or glutathione, adjuvants (for example, aluminium hydroxide), solutes that render the formulation isotonic, hypotonic or weakly hypertonic with the blood of a recipient, suspending agents, thickening agents and/or preservatives. Alternatively, compositions of the present disclosure may be formulated as a lyophilizate.

Any suitable carrier known to those of ordinary skill in the art may be employed in a composition including at least one of the antibodies describes herein. Antibody compositions may be formulated for any appropriate manner of administration, including for example, oral, nasal, mucosal, intravenous, intraperitoneal, intradermal, subcutaneous, and intramuscular administration.

In some embodiments a composition may include at least one of the anti-SARS-CoV antibodies described herein and one or more additional anti-SARS-CoV antibodies. Such an additional therapeutic agent may be an anti-SARS-CoV antibody, including a polyclonal antibody, such as convalescent serum, or one or more monoclonal antibodies that bind to the SARS-CoV-1 or the SARS-CoV-2 virus. Such a monoclonal antibody may bind to one of the structural proteins of the SARS-CoV virus, such as the spike protein (S), membrane protein (M), envelope protein (E), or nucleocapsid protein (N). Such a monoclonal antibody may bind to the RBD of the S protein. Such a monoclonal antibody may bind to the RBD of the S protein of the SARS-CoV-1 or the SARS-CoV-2 virus. Such a monoclonal antibody may include one of the FDA approved anti-SARS-CoV-2 monoclonal antibody products with Emergency Use Authorizations (EUAs) designation, including the anti-RBD antibodies bamlanivimab (LY-CoV555), etesevimab (LY-CoV016), casirivimab (REGN10933), imdevimab (REGN10987), and sotrovimab.

The neutralization activity of the cocktail may be additive or more than additive compared to the neutralization of the antibodies individually. In some embodiments, neutralization activity may be determined by the lateral flow immunoassay described in more detail in Examples 3 and 4.

In some embodiments a composition may include a cocktail of two or more anti-RBD antibodies, each anti-RBD antibody binding to a different epitope of RBD.

For example, a cocktail of antibodies binding to RBD epitope bin A, RBD epitope bin B, and/or RBD epitope bin C, as described in more detail in Examples 3 and 4.

In some embodiments, includes the cocktail includes an antibody binding to RBD epitope bin A and an antibody binding to RBD epitope bin B, an antibody binding to RBD epitope bin A and an antibody binding to RBD epitope bin C, or an antibody binding to RBD epitope bin B and an antibody binding to RBD epitope bin C.

One embodiment includes a cocktail of at least two antibodies, wherein one antibody is an anti-SARS-CoV antibody that binds to a bin A epitope of RBD is selected from:

- an antibody that binds to the same epitope as an antibody produced by clone 1035709.11;
- an antibody produced by clone 1035709.11;
- an antibody comprising a heavy chain variable region ($V_H$) of the antibody 1035709 (SEQ ID NO: 24);
- an antibody comprising a light chain variable region ($V_L$) of the antibody 1035709 (SEQ ID NO:8);
- an antibody comprising a heavy chain $V_H$ and a light chain $V_L$ of the antibody 1035709;
- an antibody comprising a heavy chain $V_H$ comprising one or more of the heavy chain complementary determining regions (CDRs) of antibody 1035709;
- an antibody comprising a light chain $V_L$ comprising one or more of the light chain CDRs of the antibody 1035709;
- an antibody comprising a heavy chain $V_H$ comprising one or more of the heavy chain CDRs and a light chain $V_L$ comprising one or more of the light chain CDRs of the antibody 1035709;
- an antibody comprising the three heavy chain CDRs of the antibody 1035709 (SEQ ID NO: 87, SEQ ID NO: 88, and SEQ ID NO: 89);
- an antibody comprising the three light chain CDRs the antibody 1035709 (SEQ ID NO: 49, SEQ ID NO:50, and SEQ ID NO: 51);
- an antibody comprising the three heavy chain CDRs and the three light chain CDRs of the antibody 1035709;
- an antibody comprising a heavy chain $V_H$ with at least 75%, at least 80%, at least 85%, at least 90%, at least 95%, at least 96%, at least 97%, at least 98%, or at least 99% sequence identity to a heavy chain $V_H$ of the antibody 1035709 (SEQ ID NO: 24);
- an antibody comprising a light chain $V_L$ with at least 75%, at least 80%, at least 85%, at least 90%, at least 95%, at least 96%, at least 97%, at least 98%, or at least 99% sequence identity to the light chain variable region of the antibody 1035709 (SEQ ID NO: 8); or
- an antibody comprising a heavy chain $V_H$ with at least 75%, at least 80%, at least 85%, at least 90%, at least 95%, at least 96%, at least 97%, at least 98%, or at least 99% sequence identity to a heavy chain $V_H$ of the antibody 1035709 and a light chain $V_L$ with at least 75%, at least 80%, at least 85%, at least 90%, at least 95%, at least 96%, at least 97%, at least 98%, or at least 99% sequence identity to the light chain variable region of the antibody 1035709;

and wherein a second antibody is an anti-SARS-CoV antibody that binds to a bin B epitope of RBD selected from:

- an antibody that binds to the same epitope as an antibody produced by clone 1035740.11;
- an antibody produced by clone 135740.11;

an antibody comprising a heavy chain variable region ($V_H$) of the antibody 135740 (SEQ ID NO: 26);

an antibody comprising a light chain variable region ($V_L$) of the antibody 135740 (SEQ ID NO: 10);

an antibody comprising a heavy chain $V_H$ and a light chain $V_L$ of the antibody 135740;

an antibody comprising a heavy chain $V_H$ comprising one or more of the heavy chain complementary determining regions (CDRs) of antibody 135740;

an antibody comprising a light chain $V_L$ comprising one or more of the light chain CDRs of the antibody 135740;

an antibody comprising a heavy chain $V_H$ comprising one or more of the heavy chain CDRs and a light chain $V_L$ comprising one or more of the light chain CDRs of the antibody 135740;

an antibody comprising the three heavy chain CDRs of the antibody 135740 (SEQ ID NO: 90, SEQ ID NO: 93, and SEQ ID NO: 92);

an antibody comprising the three light chain CDRs the antibody 135740 (SEQ ID NO: 55, SEQ ID NO: 56, and SEQ ID NO: 57);

an antibody comprising the three heavy chain CDRs and the three light chain CDRs of the antibody 135740;

an antibody comprising a heavy chain $V_H$ with at least 75%, at least 80%, at least 85%, at least 90%, at least 95%, at least 96%, at least 97%, at least 98%, or at least 99% sequence identity to a heavy chain $V_H$ of the antibody 135740 (SEQ ID NO: 26);

an antibody comprising a light chain $V_L$ with at least 75%, at least 80%, at least 85%, at least 90%, at least 95%, at least 96%, at least 97%, at least 98%, or at least 99% sequence identity to the light chain variable region of the antibody 135740 (SEQ ID NO: 10); or an antibody comprising a heavy chain $V_H$ with at least 75%, at least 80%, at least 85%, at least 90%, at least 95%, at least 96%, at least 97%, at least 98%, or at least 99% sequence identity to a heavy chain $V_H$ of the antibody 1035709 and a light chain $V_L$ with at least 75%, at least 80%, at least 85%, at least 90%, at least 95%, at least 96%, at least 97%, at least 98%, or at least 99% sequence identity to the light chain variable region of the antibody 135740.

A composition including an anti-SARS-CoV antibody may be formulated in pharmaceutical preparations in a variety of forms adapted to the chosen route of administration. One of skill will understand that the composition will vary depending on mode of administration and dosage unit. For example, for parenteral administration, isotonic saline may be used. For topical administration a cream, including a carrier such as dimethylsulfoxide (DMSO), or other agents typically found in topical creams that do not block or inhibit activity of the peptide, may be used. Other suitable carriers include, but are not limited to alcohol, phosphate buffered saline, and other balanced salt solutions. The compounds of this disclosure may be administered in a variety of ways, including, but not limited to, intravenous, topical, oral, subcutaneous, intraperitoneal, and intramuscular delivery. In some embodiments, the compounds of the present disclosure may be formulated for controlled or sustained release. In some embodiments, a formulation for controlled or sustained release is suitable for subcutaneous implantation. In some embodiments, a formulation for controlled or sustained release includes a patch.

Administration may be as a single dose or in multiple doses. In some embodiments, the dose is an effective amount as determined by the standard methods, including, but not limited to, those described herein. Those skilled in the art of clinical trials will be able to optimize dosages of particular compounds through standard studies. Additionally, proper dosages of the compositions may be determined without undue experimentation using standard dose-response protocols. Administration includes, but is not limited to, any of the dosages and dosing schedules, dosing intervals, and/or dosing patterns described in the examples included herewith.

The composition including an antibody according to the present disclosure may be administered by any suitable means including, but not limited to, for example, oral, rectal, nasal, topical (including transdermal, aerosol, buccal and/or sublingual), vaginal, parenteral (including subcutaneous, intramuscular, and/or intravenous), intradermal, intravesical, intra joint, intra-arteriole, intraventricular, intracranial, intraperitoneal, intranasal, by inhalation, or intralesional (for example, by injection into or around a tumor).

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, and intraperitoneal administration. In this connection, sterile aqueous media that may be employed will be known to those of skill in the art. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA. Such preparations may be pyrogen-free.

Many suitable formulations are known, including polymeric or protein microparticles encapsulating drug to be released, ointments, gels, or solutions which may be used topically or locally to administer drug, and even patches, which provide controlled release over a prolonged period of time. These may also take the form of implants. Such an implant may be implanted within the tumor.

The compounds of the present disclosure may also be provided in a lyophilized form. Such compositions may include a buffer, for example, bicarbonate, for reconstitution prior to administration, or the buffer may be included in the lyophilized composition for reconstitution with, for example, water. The lyophilized composition may further comprise a suitable vasoconstrictor, for example, epinephrine. The lyophilized composition may be provided in a syringe, optionally packaged in combination with the buffer for reconstitution, such that the reconstituted composition may be immediately administered to a patient.

As used herein "treating" or "treatment" may include therapeutic and/or prophylactic treatments. "Treating a disorder," as used herein, is not intended to be an absolute term. Treatment may lead to an improved prognosis or a reduction in the frequency or severity of symptoms. A "therapeutically effective" concentration or amount as used herein is an amount that provides some improvement or benefit to the subject. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. Likewise, the term "preventing," as used herein, is not intended as an absolute term. Instead, prevention refers to delay of onset, reduced frequency of symptoms, or reduced severity of symptoms associated with a disorder. Prevention therefore refers to a broad range of prophylactic measures that will be understood by those in the art. In some circumstances, the frequency and severity of symptoms is reduced to non-pathological levels. In some circumstances, the symptoms of an individual receiving the compositions of the disclosure are only 90%, 80%, 70%, 60%, 50%, 40%, 30%, 20%, 10%, 5%, or 1% as frequent or severe as symptoms experienced by an untreated individual with the disorder.

In some embodiments, the compounds of the present disclosure may be used for the presymptomatic treatment of individuals, with the administration of an anti-SARS-CoV antibody as described herein beginning after the determination or diagnosis of SARS or COVID-19, prior to the onset of symptoms. The diagnosis of SARS or COVID-19 may be made by any suitable method including, for example, antibody testing, PCR testing, etc.

Therapeutically effective concentrations and amounts may be determined for each application herein empirically by testing the compounds in known in vitro and in vivo systems, such as those described herein, dosages for humans or other animals may then be extrapolated therefrom.

It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

Toxicity and therapeutic efficacy of the compositions may be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it may be expressed as the ratio between $LD_{50}$ and $ED_{50}$. Compositions that exhibit high therapeutic indices may be preferred. The data obtained from cell culture assays and animal studies may be used in formulating a range of dosage for use in humans. The dosage of such compositions may preferably lie within a range of circulating concentrations that include the $ED_{50}$ with little or no toxicity. The dosage may vary within this range depending upon the dosage form employed and the route of administration utilized. The exact formulation, route of administration and dosage may be chosen by the individual physician in view of the patient's condition.

The dosage of such compositions may include similar doses as other antibody cocktails. Exemplary doses of antibody cocktails include, for example, antibody in a range of 25 mg/kg to 200 mg/kg including for example, 50 mg/kg of antibody or 150 mg/kg of antibody. If multiple antibodies are administered together, the dose may include 25 mg/kg to 75 mg/kg of each antibody, or, for example, 50 mg/kg of each antibody or 150 mg/kg of antibody. Exemplary doses for a human (having an average weight of 62 kg) may include a dose in a range of 1 g to 12 g of antibody, in a range of 1 g to 6 g of antibody, or in a range of 6 g to 12 g of antibody.

A composition as described herein may be administered at once or may be divided into a number of smaller doses to be administered at intervals of time. For example, compositions may be administered repeatedly, for example, at least 2, 3, 4, 5, 6, 7, 8, or more times, or may be administered by continuous infusion. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

In some therapeutic embodiments, an "effective amount" of an agent is an amount that results in a reduction of at least one pathological parameter. Thus, for example, in some aspects of the present disclosure, an effective amount is an amount that is effective to achieve a reduction of at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95% compared to the expected reduction in the parameter in an individual not treated with the agent.

In some aspects of the methods of the present disclosure, a method further includes the administration of one or more additional therapeutic agents. One or more additional therapeutic agents may be administered before, after, and/or coincident to the administration of a monoclonal antibody as described herein. An additional therapeutic agent may include, for example, chemotherapy, radiation therapy, etc. Additional therapeutic agents may be administered separately or as part of a mixture or cocktail. In some aspects of the present disclosure, the administration of an antibody may allow for the effectiveness of a lower dosage of other therapeutic modalities when compared to the administration of the other therapeutic modalities alone, providing relief from the toxicity observed with the administration of higher doses of the other modalities.

An additional therapeutic agent may be an anti-SARS-CoV antibody, including a polyclonal antibody, such as convalescent serum, and one or more known monoclonal antibodies that bind to the SARS-CoV-1 or SARS-CoV-2 virus. Such a monoclonal antibody may bind to one of the structural proteins of the SARS-CoV virus, such as the spike protein (S), membrane protein (M), envelope protein (E), or nucleocapsid protein (N). Such a monoclonal antibody may bind to the RBD of the S protein. Such a monoclonal antibody may include one of the FDA approved anti-SARS-CoV-2 monoclonal antibody products with Emergency Use Authorizations (EUAs) designation, including the anti-RBD antibodies bamlanivimab (LY-CoV555), etesevimab (LY-CoV016), casirivimab (REGN10933), imdevimab (REGN10987), and sotrovimab.

An additional therapeutic agent include small molecule antiviral agents, including, but not limited to a small molecule anti-COVID-19 agent. COVID-19 antiviral small molecules may be classified based on their mechanism of action and/or target. Example classes of COVID-19 small molecule inhibitors include, but are not limited to, TMPRRS2 inhibitors, androgen antagonists, endosomal entry inhibitors, protease inhibitors, inhibitors of viral RNA and/or viral RNA synthesis, inhibitors of host proteins that support viral RNA or viral protein synthesis (Şimşek-Yavuz et al. *Turk J Med Sci*, (2021)), Many small molecule based COVID-19 treatments have entered clinical trials including AT-527, a viral RNA synthesis inhibitor, and plitidepsin, an inhibitor of proteins supporting viral protein synthesis. Additionally, remdesivir (VEKLURY, N4-hydroxycytidine), an inhibitor of viral RNA synthesis, has received FDA emergency use authorization (U.S. Food & Drug Administration. FDA's approval of Veklury (remdesivir) for the treatment of COVID-19—the science of safety and effectiveness. 2020 Oct. 22). The FDA is also considering emergency use authorization of MOLNUPIRAVIR (N4-hydroxycytidine), an inhibitor of viral RNA synthesis (U.S. Food & Drug Administration. FDA to Hold Advisory Committee Meeting to Discuss Merck and Ridgeback's EUA Application for COVID-19 Oral Treatment, 2021 Oct. 14.). Furthermore, Pfizer has recently disclosed promising data regarding PAXLOVID™ (PF-07321332, ritonavir combination), a small molecule protease inhibitor (Pfizer, "Pfizer's Novel COVID-19 Oral Antiviral Treatment Candidate Reduced Risk of Hospitalization or Death by 89% in Interim Analysis of Phase 2/3 Epic-HR Study," 2021 Nov. 5).

In some embodiments, the composition including at least one antibody as described herein, also includes an FDA approved, or an FDA issued notice of emergency use authorization, COVID-19 antiviral small molecule. In some embodiments, the COVID-19 antiviral small molecule is a protease inhibitor. In some embodiments the protease inhibitor is PAXLOVID™ (PF-07321332, ritonavir combination). In some embodiments, the COVID-19 antiviral small molecule is an inhibitor of viral RNA synthesis. In some embodiments, the inhibitor of viral RNA synthesis is MOLNUPIRAVIR and/or remdesivir.

In some aspects of the methods of the present disclosure, the administration of a composition as described herein and the at least one additional therapeutic agent demonstrate therapeutic synergy. In some aspects of the methods of the present disclosure, a measurement of response to treatment observed after administering both an antibody as described herein and the additional therapeutic agent is improved over the same measurement of response to treatment observed after administering either the antibody or the additional therapeutic agent alone. In some aspects of the methods of the present disclosure, a measurement of response to treatment observed after administering both an antibody as described herein and the additional therapeutic agent is improved over the combined measurements of the response to treatment observed after administering either the antibody or the additional therapeutic agent alone.

The invention is defined in the claims. However, below there is provided a non-exhaustive listing of non-limiting exemplary aspects. Any one or more of the features of these aspects may be combined with any one or more features of another example, embodiment, or aspect described herein.

Exemplary Antibody Aspects

A1. An anti-SARS-CoV antibody, wherein the anti-SARS-CoV antibody comprises an antibody or antigen binding fragment thereof that binds to the same epitope as an antibody produced a clone selected from 1035211.11, 1035224.11, 1035240.11, 1035414.11, 1035419.11, 1035423.11, 1035433.11, 1035709.11, 1035716.11, 1035740.11, 1035744.11, 1035752.11, 1035753.11, 1035755.11, and 1035762.11.

A2. An anti-SARS-CoV antibody, wherein the anti-SARS-CoV antibody comprises:
- a heavy chain variable region ($V_H$) of an antibody selected from 1035211, 1035224, 1035240, 1035414, 1035419, 1035423, 1035433, 1035709, 1035716, 1035740, 1035744, 1035752, 1035753, 1035755, and 1035762; or
- a light chain variable region ($V_L$) of an antibody selected from 1035211, 1035224, 1035240, 1035414, 1035419, 1035423, 1035433, 1035709, 1035716, 1035740, 1035744, 1035752, 1035753, 1035755, and 1035762; or
- both.

A3. An anti-SARS-CoV antibody, wherein the anti-SARS-CoV antibody comprises:
- a heavy chain variable region ($V_H$) comprising one or more complementary determining regions (CDRs) of Table 9; or
- a light chain variable region ($V_L$) comprising one or more CDRs of Table 8; or
- both.

A4. An anti-SARS-CoV antibody, wherein the anti-SARS-CoV antibody comprises:
- each of the complementary determining regions (CDRs) of a heavy chain variable region of a monoclonal antibody produced by one of the clones of Table 1; or
- each of the CDRs of a light chain variable region of a monoclonal antibody produced by one of the clones of Table 1;
- each of the CDRs of a heavy chain variable region of a monoclonal antibody produced by one of the clones of Table 1 and each of the CDRs of a light chain variable region of a monoclonal antibody produced by one of the clones of Table 1; or
- each of the CDRs of a heavy chain variable region of a monoclonal antibody produced by one of the clones of Table 1, and each of the CDRs of a light chain variable region of a monoclonal antibody produced by the same clone.

A5. The anti-SARS-CoV antibody of Aspect A4,
- wherein the CDRs of the heavy chain variable region have an amino acid sequence set forth in Table 9; or
- wherein the CDRs of the light chain variable region have an amino acid sequence set forth in Table 8; or
- both.

A6. An anti-SARS-CoV antibody, wherein the anti-SARS-CoV antibody comprises an amino acid sequence having
- at least 75%, at least 80%, at least 85%, at least 90%, at least 95%, at least 96%, at least 97%, at least 98%, or at least 99% sequence identity to the heavy chain variable region of a monoclonal antibody produced by a clone of Table 1; or
- at least 75%, at least 80%, at least 85%, at least 90%, at least 95%, at least 96%, at least 97%, at least 98%, or at least 99% sequence identity to the light chain variable region of a monoclonal antibody produced by a clone of Table 1; or at least 75%, at least 80%, at least 85%, at least 90%, at least 95%, at least 96%, at least 97%, at least 98%, or at least 99% sequence identity to the heavy chain variable region of a monoclonal antibody produced by a clone of Table 1, and at least 75%, at least 80%, at least 85%, at least 90%, at least 95%, at least 96%, at least 97%, at least 98%, or at least 99% sequence identity to the light chain variable region of a monoclonal antibody produced by a clone of Table 1.

A7. The anti-SARS-CoV antibody of any one of Aspects A1 to A6, wherein the anti-SARS-CoV antibody comprises an antibody produced by a clone selected from 1035211.11, 1035224.11, 1035240.11, 1035414.11, 1035419.11, 1035423.11, 1035433.11, 1035709.11, 1035716.11, 1035740.11, 1035744.11, 1035752.11, 1035753.11, 1035755.11, and 1035762.11.

A8. The anti-SARS-CoV antibody of any one of Aspects A1 to A7, wherein the anti-SARS-CoV antibody specifically binds to the receptor binding domain (RBD) of the SARS-CoV spike (S) protein.

A8. The anti-SARS-CoV antibody of any one of Aspects A1 to A7, wherein the anti-SARS-CoV antibody decreases binding of SARS-CoV-1 or SARS-CoV-2 or both SARS-CoV-1 and SARS-CoV-2 to ACE-2 by at least 10 percent (%), at least 15%, at least 20%, at least 25%, at least 30%, at least 40%, at least 50%, at least 60%, at least 70%, at least 80%, at least 90%, at least 95%, or at least 98%.

A9. The anti-SARS-CoV antibody of any one of Aspects A1 to A8, wherein the anti-SARS-CoV antibody comprises an anti-SARS-CoV-2 antibody.

A10. The anti-SARS-CoV antibody of any one of Aspects A1 to A9, wherein the anti-SARS-CoV antibody comprises an anti-SARS-CoV-1 antibody.

A11. The anti-SARS-CoV antibody of any one of Aspects A1 to A10, wherein the anti-SARS-CoV antibody specifically binds to a SARS-CoV-2 variant selected from:
- the alpha variant (the United Kingdom variant (UK), B.1.1.7 lineage, RBD with N501Y);
- the beta variant (South African variant (SA), B.1.3512 lineage, RBD with K417N, E484K, and N501Y);
- the gamma variant (Brazilian variant P.1 (BR P.1), B.1.1.28.1 lineage, RBD with K417T, E484K, and N501Y);
- the delta variant (Indian variant 2 (IN v2), B.1.617.2 lineage, RBD with L452R and T478K);
- the epsilon variant (California variant (CA), B.1.427/9 lineage, RBD with L452R);
- the kappa variant (Indian variant 1 (IN v1), B.1.617.1 lineage, RBD with L452R and E484Q);
- the zeta variant (Brazilian variant P.2 (BR P.2), B.1.1.28.2 lineage, RBD with E484K);
- the K417E RBD (R319-F541 with K417E);
- the T478K RBD (R319-F541 with T478K);
- the iota variant (New York variant (NY), B.1.526 lineage, RBD with a single mutation E484K);
- the eta variant (Nigeria variant, B.1.525 lineage);
- the lambda variant (Peru variant, C.37 lineage, RBD with L452Q and F490S);
- the theta variant (Philippine variant, P.3 lineage, RBD with E484K and N501Y), and/or
- the Denmark mink variant (B.1.1.298 lineage, DM, RBD with Y453).

A12. The anti-SARS-CoV antibody of any one Aspects A1 to A11, wherein binding specificity is characterized by a lateral flow immunoassay.

A13. The anti-SARS-CoV antibody of any one of Aspects A1 to A12, wherein the anti-SARS-CoV antibody has an $NC_{50}$ of about 0.3 μg/μl to about 1.5 μg/μl.

A14. The anti-SARS-CoV antibody of any one of Aspects A1 to A13, wherein the anti-SARS-CoV antibody binds to a bin A RBD epitope, a bin B RBD epitope, or a bin C RBD epitope.

A15. The anti-SARS-CoV antibody of any one Aspects A1 to A14, wherein the anti-SARS-CoV antibody comprises a humanized antibody.

A16. The anti-SARS-CoV antibody of any one of Aspects A1 to A15, wherein the anti-SARS-CoV antibody is labeled with one or more detectable markers.

A17. The anti-SARS-CoV antibody of any one of Aspects A1 to A16 for use as a reference control solution.

Exemplary Composition Aspects

B1. A composition comprising the anti-SARS-CoV antibody of any one of Aspects A1 to A17.

B2. The composition of Aspect B1 further comprising one or more additional anti-SARS-CoV antibodies.

B3. A composition comprising two or more anti-SARS-CoV antibodies of any one of Aspects A1 to A17.

B4 The composition of Aspect B2 or B3, wherein one anti-SARS-CoV antibody binds to a bin A epitope of RBD and one anti-SARS-CoV antibody binds to a bin B epitope of RBD.

B5. The composition of Aspect B4, wherein the anti-SARS-CoV antibody that binds to a bin A epitope of RBD is selected from:
- an antibody that binds to the same epitope as an antibody produced by clone 1035709.11;
- an antibody produced by clone 1035709.11;
- an antibody comprising a heavy chain variable region ($V_H$) of the antibody 1035709;
- an antibody comprising a light chain variable region ($V_L$) of the antibody 1035709;
- an antibody comprising a heavy chain $V_H$ and a light chain $V_L$ of the antibody 1035709;
- an antibody comprising a heavy chain $V_H$ comprising one or more of the heavy chain complementary determining regions (CDRs) of antibody 1035709;
- an antibody comprising a light chain $V_L$ comprising one or more of the light chain CDRs of the antibody 1035709;
- an antibody comprising a heavy chain $V_H$ comprising one or more of the heavy chain CDRs and a light chain $V_L$ comprising one or more of the light chain CDRs of the antibody 1035709;
- an antibody comprising the three heavy chain CDRs of the antibody 1035709;
- an antibody comprising the three light chain CDRs the antibody 1035709;
- an antibody comprising the three heavy chain CDRs and the three light chain CDRs of the antibody 1035709;
- an antibody comprising a heavy chain $V_H$ with at least 75%, at least 80%, at least 85%, at least 90%, at least 95%, at least 96%, at least 97%, at least 98%, or at least 99% sequence identity to a heavy chain $V_H$ of the antibody 1035709;
- an antibody comprising a light chain $V_L$ with at least 75%, at least 80%, at least 85%, at least 90%, at least 95%, at least 96%, at least 97%, at least 98%, or at least 99% sequence identity to the light chain variable region of the antibody 1035709; and an antibody comprising a heavy chain $V_H$ with at least 75%, at least 80%, at least 85%, at least 90%, at least 95%, at least 96%, at least 97%, at least 98%, or at least 99% sequence identity to a heavy chain $V_H$ of the antibody 1035709 and a light chain $V_L$ with at least 75%, at least 80%, at least 85%, at least 90%, at least 95%, at least 96%, at least 97%, at least 98%, or at least 99% sequence identity to the light chain variable region of the antibody 1035709; and wherein the anti-SARS-CoV antibody binds to the bin B epitope of RBD is selected from
- an antibody that binds to the same epitope as an antibody produced by clone 1035740.11;
- an antibody produced by clone 135740.11;

- an antibody comprising a heavy chain variable region ($V_H$) of the antibody 135740;
- an antibody comprising a light chain variable region ($V_L$) of the antibody 135740;
- an antibody comprising a heavy chain $V_H$ and a light chain $V_L$ of the antibody 135740;
- an antibody comprising a heavy chain $V_H$ comprising one or more of the heavy chain complementary determining regions (CDRs) of antibody 135740;
- an antibody comprising a light chain $V_L$ comprising one or more of the light chain CDRs of the antibody 135740;
- an antibody comprising a heavy chain $V_H$ comprising one or more of the heavy chain CDRs and a light chain $V_L$ comprising one or more of the light chain CDRs of the antibody 135740;
- an antibody comprising the three heavy chain CDRs of the antibody 135740;
- an antibody comprising the three light chain CDRs the antibody 135740;
- an antibody comprising the three heavy chain CDRs and the three light chain CDRs of the antibody 135740;
- an antibody comprising a heavy chain $V_H$ with at least 75%, at least 80%, at least 85%, at least 90%, at least 95%, at least 96%, at least 97%, at least 98%, or at least 99% sequence identity to a heavy chain $V_H$ of the antibody 135740;
- an antibody comprising a light chain $V_L$ with at least 75%, at least 80%, at least 85%, at least 90%, at least 95%, at least 96%, at least 97%, at least 98%, or at least 99% sequence identity to the light chain variable region of the antibody 135740;
- an antibody comprising a heavy chain $V_H$ with at least 75%, at least 80%, at least 85%, at least 90%, at least 95%, at least 96%, at least 97%, at least 98%, or at least 99% sequence identity to a heavy chain $V_H$ of the antibody 1035709 and a light chain $V_L$ with at least 75%, at least 80%, at least 85%, at least 90%, at least 95%, at least 96%, at least 97%, at least 98%, or at least 99% sequence identity to the light chain variable region of the antibody 135740.

B6 The composition of any one of Aspects B1 to B5, wherein the composition further comprises a pharmaceutically acceptable carrier.

B7. The composition of any one of Aspects B1 to B6 for use as a reference control solution.

Exemplary Administration Method Aspects

C1. A method comprising administering the anti-SARS-CoV antibody of any one Aspects A1 to A17 or the composition of any one of Aspects B1 to B7 to a subject.

C2. The method of Aspect C1, wherein the subject is suspected of having SARS-CoV-1 or SARS-CoV-2 or has been diagnosed with SARS-CoV-1 or SARS-CoV-2.

C3. The method of Aspect C1, wherein the subject has been exposed to SARS-CoV-1 or SARS-CoV-2.

C4. The method of any one of Aspects C1 to C3, wherein the subject is suspected of having, has been diagnosed with, or has been exposed to a SARS-CoV-2 variant selected from:

- the alpha variant (the United Kingdom variant (UK), B.1.1.7 lineage, RBD with N501Y);
- the beta variant (South African variant (SA), B.1.3512 lineage, RBD with K417N, E484K, and N501Y);
- the gamma variant (Brazilian variant P.1 (BR P.1), B.1.1.28.1 lineage, RBD with K417T, E484K, and N501Y);
- the delta variant (Indian variant 2 (IN v2), B.1.617.2 lineage, RBD with L452R and T478K);
- the epsilon variant (California variant (CA), B.1.427/9 lineage, RBD with L452R);
- the kappa variant (Indian variant 1 (IN v1), B.1.617.1 lineage, RBD with L452R and E484Q);
- the zeta variant (Brazilian variant P.2 (BR P.2), B.1.1.28.2 lineage, RBD with E484K);
- the K417E RBD (R319-F541 with K417E);
- the T478K RBD (R319-F541 with T478K);
- the iota variant (New York variant (NY), B.1.526 lineage, RBD with a single mutation E484K);
- the eta variant (Nigeria variant, B.1.525 lineage);
- the lambda variant (Peru variant, C.37 lineage, RBD with L452Q and F490S);
- the theta variant (Philippine variant, P.3 lineage, RBD with E484K and N501Y); and/or
- the Denmark mink variant (B.1.1.298 lineage, DM, RBD with Y453).

C5. The method of any one of Aspects C1 to C4, wherein the subject is a human.

C6. The method of any one of Aspects C1 to C5, wherein the method comprises administering about 1 g to about 12 g of the anti-SARS-CoV antibody.

C7. The method of any one of Aspects C1 to C6, wherein the method comprises administering multiple doses of the anti-SARS-CoV antibody or composition thereof.

C8. The method of any one of Aspects C1 to C7, the method further comprising administering a small molecule antiviral therapeutic agent to the subject.

C9. The method of Aspect C8, wherein the small molecule antiviral therapeutic agent is selected from remdesivir, molnupiravir, paxlovid, or a combination thereof.

Exemplary Immunoassay Devices

D1. An immunoassay device comprising one or more of the anti-SARS-CoV antibodies of any one of Aspects A1 to A17.

D2. A lateral flow immunoassay device comprising one or more of the anti-SARS-CoV antibodies of any one of Aspects A1 to A17.

D3. The immunoassay device of Aspect D1 or the lateral flow immunoassay device of Aspect D2 further comprising an anti-SARS-CoV nucleocapsid protein (NP) antibody.

Exemplary Diagnosis Method Aspects

E1. A method comprising using the anti-SARS-CoV antibody of any one of Aspects A1 to A17 or the composition of any one of Aspects B1 to B7 to diagnose a subject with SARS-CoV-1 or SARS-CoV-2.

E2. A method of diagnosing a subject with SARS-CoV-1 or SARS-CoV-2, the method comprising contacting a biosample from the subject with an antibody of any one of Aspects A1 to A17 or a composition of any one of Aspects B1 to B.

E3. A method of identifying a SARS-CoV-2 receptor binding domain (RBD) variant in a sample, the method comprising contacting the biosample with an antibody of any one of Aspects A1 to A17 or a composition of any one of Aspects B1 to B.

E4. The method of any one of Aspects E1 to E2, the method comprising contacting the biosample with more than one antibody of any one of Aspects A1 to A17.

E5. The method of Aspect E4, wherein multiple SARS-CoV-2 receptor binding domain (RBD) variants are identified simultaneously.

The present invention is illustrated by the following examples. It is to be understood that the particular examples, materials, amounts, and procedures are to be interpreted broadly in accordance with the scope and spirit of the invention as set forth herein.

EXAMPLES

All reagents, starting materials, and solvents used in the following examples were purchased from commercial suppliers (such as Sigma Aldrich, St. Louis, MO) and were used without further purification unless otherwise indicated.

Example 1

This Example describes the development and characterization of anti-SARS specific monoclonal antibodies that can bind to both SARS-CoV-2 and SARS-CoV. Antigen-down ELISA was used to demonstrate that the specificity of the antibodies. Flow cytometry was used to demonstrate the ability of these antibodies to block the binding of both SARS-CoV-2 and SARS-CoV-1 to human ACE-2.

Materials and Methods

Immunization and Hybridoma Strategy for Production of SARS-CoV-2 Antibodies:

Hybridoma cell lines were obtained by immunizing Balb/c mice with the antigens described in Table 1. Mice were immunized with 20 μg total antigen per animal, administered in the footpad of the mouse in 5 boosts (4 ug per boost) twice per week (Mondays and Fridays). Three to four days after the final dose, lymphocytes were harvested from lymph nodes and immortalized, by fusion with a P3X63Ag8.653 myeloma cell.

TABLE 1

| Clone Name | Antibody | Antigen |
|---|---|---|
| 1035211.11 | 1035211 | recombinant SARS-CoV-2 |
| 1035224.11 | 1035224 | Spike protein $S_1$ (aa1-666)* |
| 1035240.11 | 1035240 | |
| 1035414.11 | 1035414 | recombinant SARS-CoV-2 |
| 1035419.11 | 1035419 | Spike protein $S_1$ RBD (aa319-541) |
| 1035423.11 | 1035423 | |
| 1035433.11 | 1035433 | |
| 1035709.11 | 1035709 | recombinant SARS-CoV-2 |
| 1035716.11 | 1035716 | Spike protein $S_1$ (aa1-681)* |
| 1035740.11 | 1035740 | |
| 1035744.11 | 1035744 | |
| 1035752.11 | 1035752 | |
| 1035753.11 | 1035753 | |
| 1035755.11 | 1035755 | |
| 1035762.11 | 1035762 | |

*All amino acid ranges are with reference to UniProt P0DTC2.

Antigen-Down ELISA:

The specificity of antibodies for monomeric SARS-CoV-2 $S_1$ RBD protein was tested using an antigen-down ELISA.

Briefly, SARS-CoV-2 $S_1$ was titrated in 1×TBS and coated on 96-well plates at the following concentrations: 400 ng/mL, 100 ng/mL, 25 ng/mL, 6.25 ng/mL, and 1.56 ng/mL. Control wells were coated in 1×TBS Buffer alone. Purified mouse anti-SARS-CoV mAb candidates were added at 1 ug/ml in Capture Buffer (5× Tris Buffered Saline (TBS), 50 mg/mL BSA and 10% TWEEN). 3,3',5,5'-tetramethylbenzidine (TMB) buffer alone was added to some wells as a second negative control. Goat anti-mouse/HRP-conjugated polyclonal antibody (Cat. No. HAF007, Bio-Techne, Minneapolis, MN) was used as secondary antibody in capture buffer. ELISA reactions were carried out in TMB buffer for 10 minutes.

Construction of hACE-2 HEK/eGFP and hCD26 HEK/eGFP Transfectants:

HEK-293 wild-type cells were transfected with expression plasmids containing a hACE-2 (amino acids 1-708; Accession No. Q9BYF1) cDNA insert and eGFP cDNA insert (amino acids 1-239; Accession No. U57607) downstream of a CMV promoter or a hCD26 (amino acids 1-766; Accession No. Q53TN1) cDNA insert and eGFP cDNA insert (amino acids 1-239; Accession No. U57607) downstream of a CMV promoter. Stable clones expressing hACE-2/eGFP or hCD26/eGFP were used in all assays.

The resulting GFP-labeled HEK transfectant cells stably over-expressing human ACE-2 ("hACE-2 HEK/eGFP Tfx") and GFP-labeled HEK transfectant cells stably over-expressing human CD26 ("hCD26 HEK/eGFP Tfx") were grown in IMDM complete selection media (5% FBS, 1× Pen/Strep, and 1 μg/mL puromycin).

hACE-2 HEK/eGFP Tfx were screened periodically with anti-hACE-2 antibody (MAB9332, Bio-Techne, Minneapolis, MN) to ensure continued high expression of hACE-2.

Figure 2A:
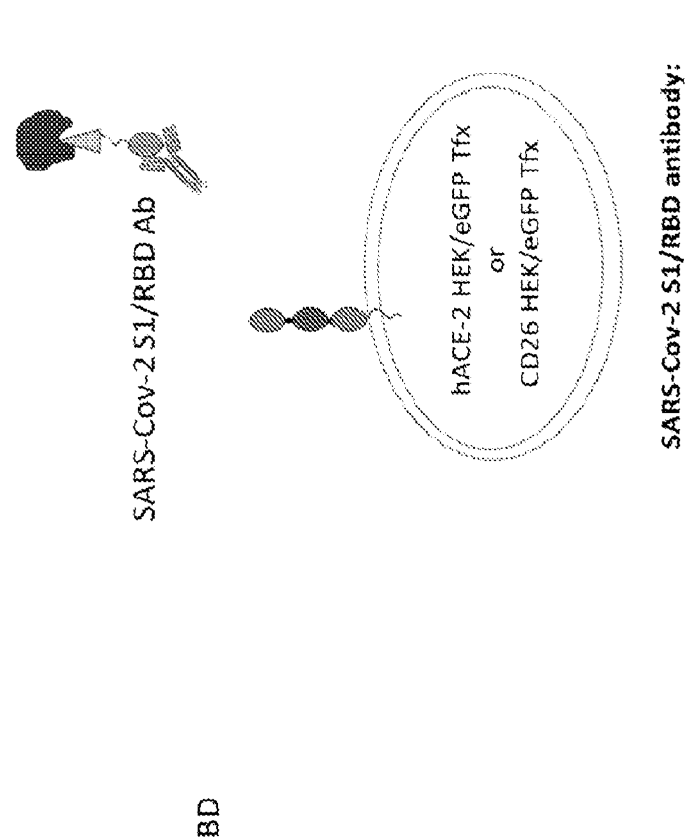

SARS-CoV-2 Antibody Blocking Assay with rSARS-CoV-2 Proteins, TSARS-CoV-1 Proteins, and rMERS Proteins:

A schematic description of the SARS-CoV-2 antibody blocking assay is shown in FIG. 2A (using a hACE-2 HEK/eGFP Tfx and rSARS-CoV-2 $S_1$ RBD protein for illustrative purposes).

The blocking assays described herein used hACE-2 HEK/eGFP Tfx or hCD26 HEK/eGFP Tfx for the cell model; rSARS-CoV-2, rSARS-CoV-1, or MERS proteins as the protein; and an antibody including, for example, the antibodies produced by the anti-SARS-CoV-2 antibody panels 10352XX, 10354XX, and 10357XX. Each monoclonal antibody tested was added at a final concentration of 25 μg/mL. Proteins were added at a final concentration ranging from 50 ng/mL to 1 μg/mL.

Viral proteins/antibodies were co-incubated to form a complex and then added to hACE-2 HEK/eGFP Tfx or hCD26 HEK/eGFP Tfx.

Anti-His APC or anti-Fc APC was added to the antibody/protein/Tfx samples for detection. The samples were then washed, a live/dead stain was added to exclude dead cells, and analysis was carried out on a BD LSRFortessa™.

Negative controls included hACE-2 HEK/eGFP Tfx or hCD26 HEK/eGFP Tfx alone; anti-His APC+(hACE-2 HEK/eGFP Tfx or hCD26 HEK/eGFP Tfx) (FIG. 2B); and isotype controls (Ms IgG1, Ms IgG2a, or Ms IgG2b)+protein+(hACE-2 HEK/eGFP Tfx or hCD26 HEK/eGFP Tfx)+anti-His APC (FIG. 2D).

rSARS-CoV-2 $S_1$, rSARS-CoV-2 $S_1$ RBD, rSARS-CoV-2 active trimer, rSARS-CoV-1 $S_1$, or rSARS-CoV-1 $S_1$ RBD+(hACE-2 HEK/eGFP Tfx or hCD26 HEK/eGFP Tfx)+anti-His APC served as a protein binding control for rSARS-CoV-1 and rSARS-CoV-2 (FIG. 2C).

rMERS $S_1$+(hACE-2 HEK/eGFP Tfx or hCD26 HEK/eGFP Tfx)+anti-Fc APC, or rMERS $S_1$ RBD+(hACE-2 HEK/eGFP Tfx or hCD26 HEK/eGFP Tfx)+anti-His APC served as the protein binding controls for rMERS.

Anti-viral antibodies+viral proteins+(hACE-2 HEK/eGFP Tfx or hCD26 HEK/eGFP Tfx)+(anti-His APC or anti-Fc APC) were used to assess viral antibody blocking of hACE-2 vs. SARS-CoV-2 or SARS-CoV-1 proteins, or antibody blocking of hCD26 vs. MERS proteins (FIG. 2E).

Results

SARS-CoV-2 Monoclonal Antibody Specificity

To determine the specificity of the anti-SARS-CoV-2 monoclonal antibodies in panels 10352XX, 10354XX, and 10357XX, candidate antibodies were screened against varying concentrations of recombinant SARS-CoV-2 $S_1$ RBD in an antigen-down ELISA.

Figures 1A, 1B, 1C, 1D:
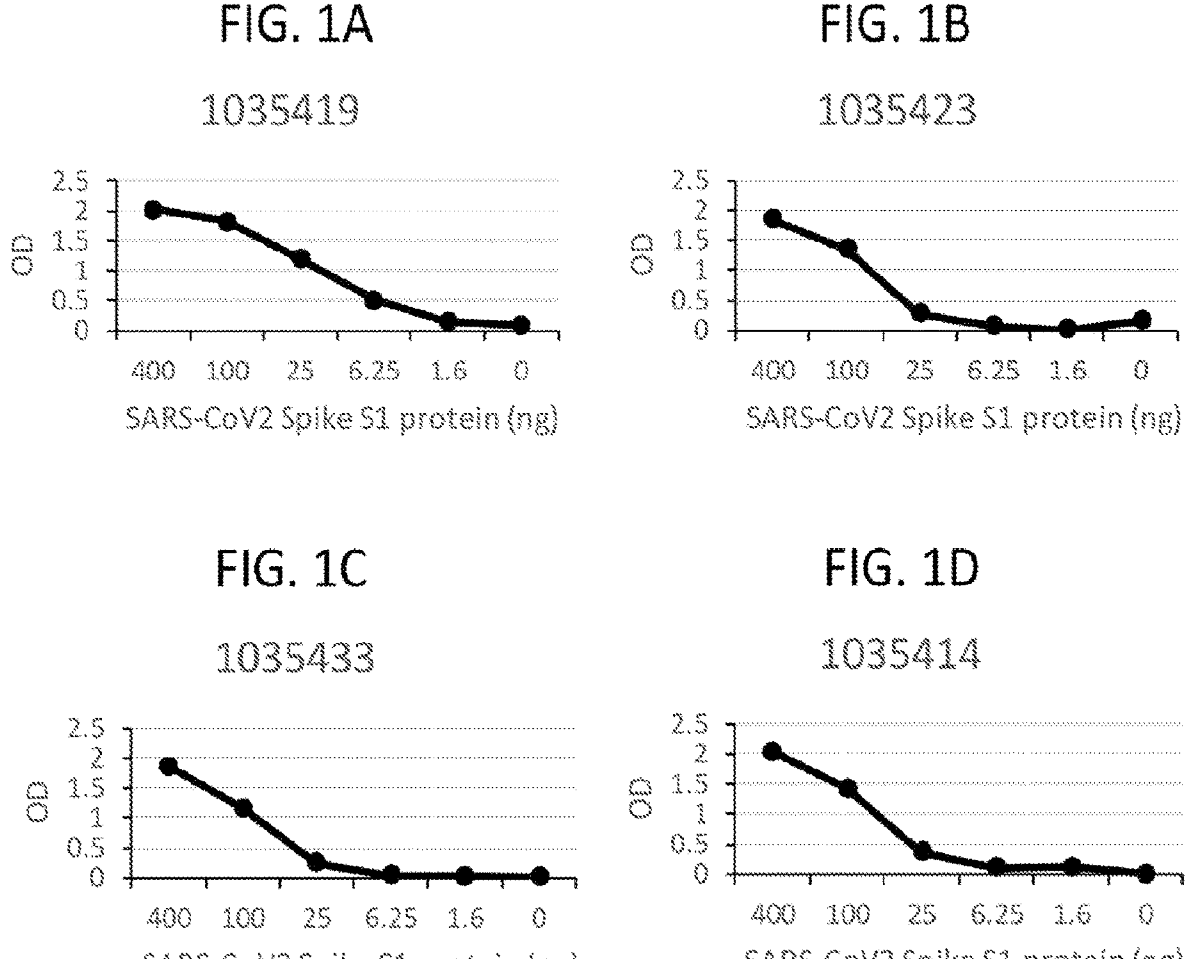
FIG. 1A-FIG. 1Q show antibody binding of monomeric SARS-CoV-2 $S_1$ RBD with controls for comparison. Wells of a 96-well microtiter plate were coated with recombinant monomeric SARS-CoV-2 $S_1$ RBD diluted to 400 ng/mL, 100 ng/mL, 25 ng/mL, 6.25 ng/mL, and 1.56 ng/mL in 1×TBS Buffer. Control wells were coated in 1×TBS Buffer alone. Purified mouse anti-SARS-CoV-2 monoclonal antibodies 1035419 (FIG. 1A), 1035423 (FIG. 1B), 1035433 (FIG. 1C), 1035414 (FIG. 1D), 1035709 (FIG. 1E), 1035716 (FIG. 1F), 1035740 (FIG. 1G), 1035744 (FIG. 1H), 1035752 (FIG. 1I), 1035753 (FIG. 1J), 1035755 (FIG. 1K), 1035762 (FIG. 1L), 1035211 (FIG. 1M), 1035224 (FIG. 1N), or 1035240 (FIG. 1O) (each at 1 μg/mL in Capture Buffer) were added to wells coated with RBD protein and incubated for either 30 minutes on a shaker table or for 1 hour without shaking. An antibody produced by a mouse immunized with recombinant SARS-CoV-2 Spike protein $S_1$ (aa1-681) that did not exhibit any binding to SARS-CoV-2 $S_1$ RBD, antibody 1035729, is shown in FIG. 1P. 3,3',5,5'-tetramethylbenzidine TMB buffer alone (with no antibody) is shown in FIG. 1Q. Detection was performed by the addition of a goat anti-mouse/HRP-conjugated polyclonal secondary detection antibody in capture buffer followed by allowing a chromogenic reaction to proceed in TMB for 10 minutes.
Figures 1I, 1J, 1K, 1L:
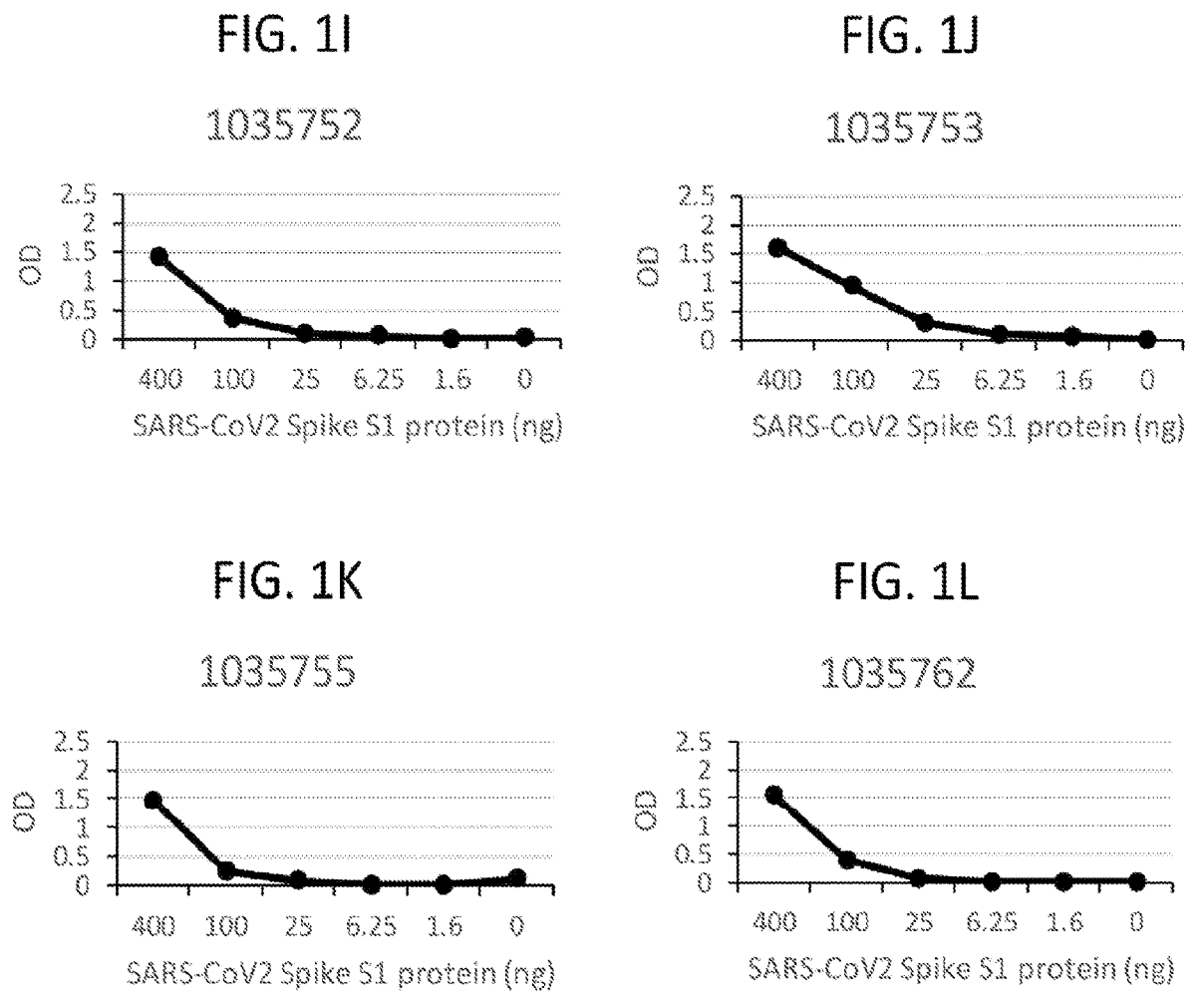
Figures 1M, 1N, 1O, 1P, 1Q:
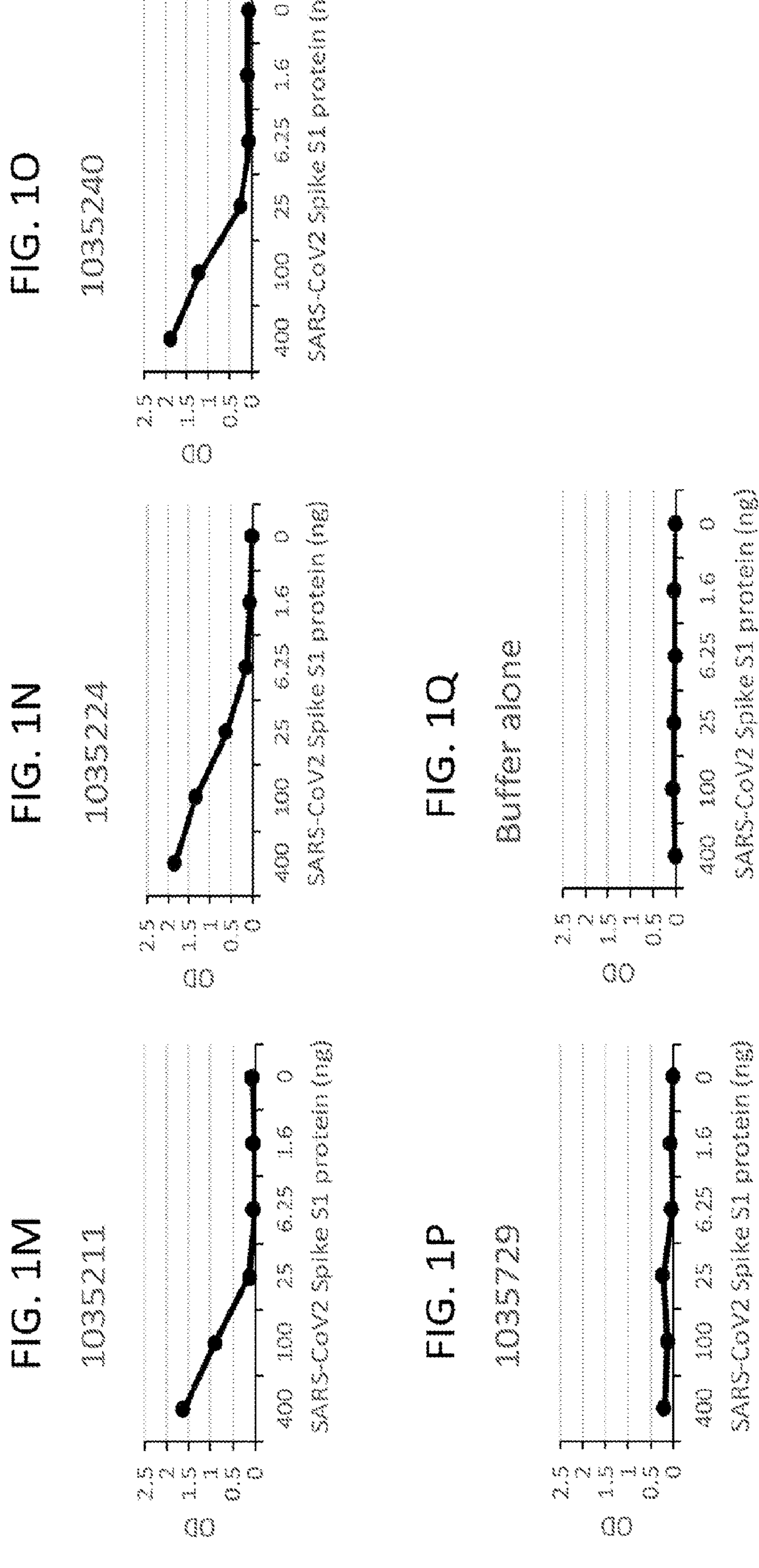

As shown in FIG. 1, antibody candidates 1035419 (FIG. 1A), 1035423 (FIG. 1B), 1035433 (FIG. 1C), 1035414 (FIG. 1D), 1035709 (FIG. 1E), 1035716 (FIG. 1F), 1035740 (FIG. 1G), 1035744 (FIG. 1H), 1035752 (FIG. 1I), 1035753 (FIG. 1J), 1035755 (FIG. 1K), 1035762 (FIG. 1L), 1035211 (FIG. 1M), 1035224 (FIG. 1N), and 1035240 (FIG. 1O) elicited strong binding to the highest concentration of recombinant SARS-CoV-2 $S_1$ RBD and showed decreased binding as protein concentration diminished.

By comparison, antibody 1035729 (FIG. 1P), as well as other antibodies obtained following immunization (not shown) failed to bind recombinant SARS-CoV-2 $S_1$ RBD at any concentration and resembled the buffer alone control well (FIG. 1Q).

Antibody candidates were not screened against full-length recombinant SARS-CoV-2 $S_1$ protein by antigen-down ELISA as the full-length protein already contains the RBD motif and would be redundant.

These results demonstrate that antibodies 1035414, 1035419, 1035423, 1035433, 1035709, 1035716, 1035740, 1035744, 1035752, 1035753, 1035755, 1035762, 1035211, 1035224, and 1035240 are specific for SARS-CoV-2 $S_1$ RBD.

Flow Cytometry Antibody/Protein Blocking Assay

To evaluate whether the anti-SARS-CoV-2 $S_1$ RBD monoclonal antibodies identified in FIG. 1 would be able to block the binding of recombinant SARS-CoV-2 $S_1$ and $S_1$ RBD proteins to cells over-expressing human ACE-2, a flow cytometry blocking assay was used. A schematic of the assay is shown in FIG. 2A.

Candidate antibodies, or mouse isotype-control antibodies, were pre-incubated with a pre-determined amount of his-tagged SARS-CoV-2 $S_1$ or his-tagged SARS-CoV-2 $S_1$ RBD to form an antibody/SARS-CoV-2 protein complex. The antibody/SARS-CoV-2 protein complex was then added to GFP-labeled HEK transfectant cells stably over-expressing human ACE-2 (hACE-2 HEK/eGFP Tfx). Protein binding was determined by staining the hACE-2 HEK/eGFP Tfx cells with a fluorescent anti-His antibody and analyzing the cells for fluorescence by flow cytometry.

In the absence of viral proteins, no anti-His fluorescence may be detected on hACE-2 HEK/eGFP Tfx cells (FIG. 2B); however, when SARS-CoV-2 $S_1$ or SARS-CoV-2 $S_1$ RBD is added, the proteins bind to the ACE-2 expressed by the hACE-2 HEK/eGFP Tfx cells and anti-His fluorescence can be detected (FIG. 2C). Irrelevant or isotype control antibodies failed to block SARS-CoV-2 protein binding to ACE-2, and anti-His fluorescence remains high (FIG. 2D). In contrast, SARS-CoV-2-specific antibodies form a complex with SARS-CoV-2 proteins, preventing the proteins from binding ACE-2, resulting in reduced anti-His fluorescence (FIG. 2E).

Figure 3A:
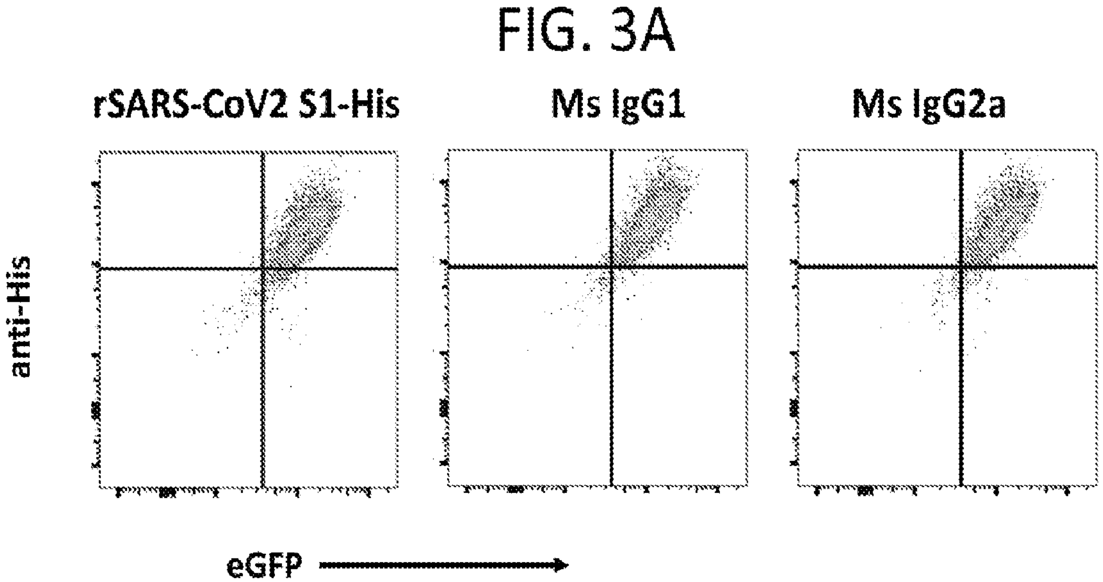
FIG. 3A-FIG. 3D show anti-SARS-CoV-2 antibody (panel 10352XX) blocking of SARS-CoV-2 $S_1$ binding to ACE-2. Recombinant monomeric SARS-CoV-2 $S_1$ protein was mixed and then incubated with staining buffer, mouse IgG1 or IgG2a isotype control antibodies (FIG. 3A) or anti-SARS-CoV-2 $S_1$ monoclonal antibodies from panel 10352XX (FIG. 3B) to allow a complex to form. rSARS-CoV-2 $S_1$ RBD was mixed and then incubated with staining buffer, mouse IgG2a isotype control antibodies (FIG. 3C) or anti-SARS-CoV-2 $S_1$ monoclonal antibodies from panel 10352XX (FIG. 3D) to allow a complex to form. After incubation, the mixture was added to a single cell suspension of hACE-2 HEK/eGFP Tfx, followed by a secondary anti-His antibody to assess viral antibody blocking. Flow cytometry gates were set on anti-His fluorescence of hACE-2 HEK/eGFP Tfx cells in the absence of any SARS-CoV-2 protein.
Figure 3B:
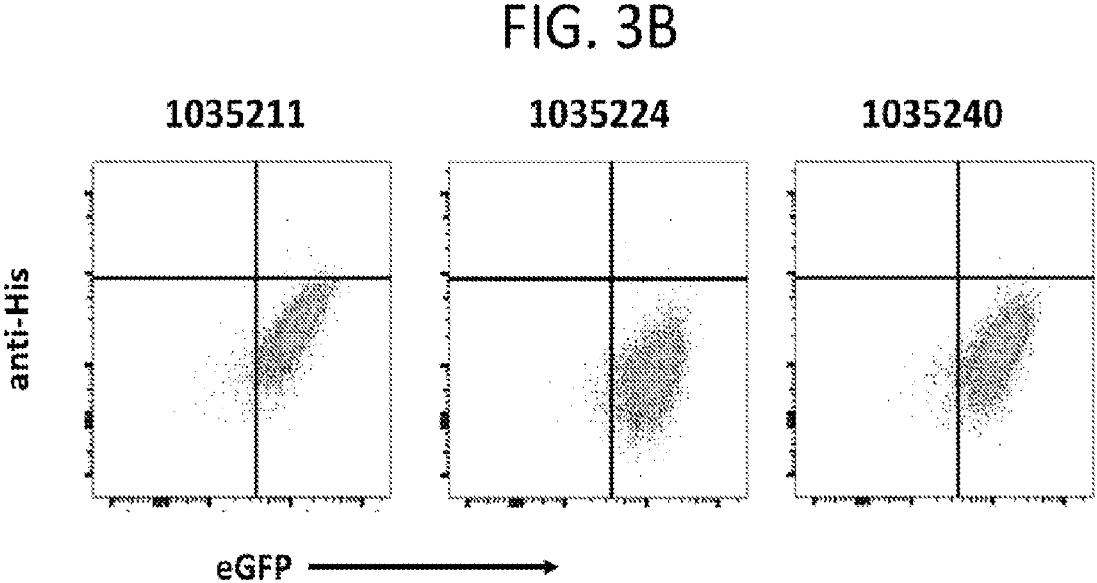
Figure 3C:
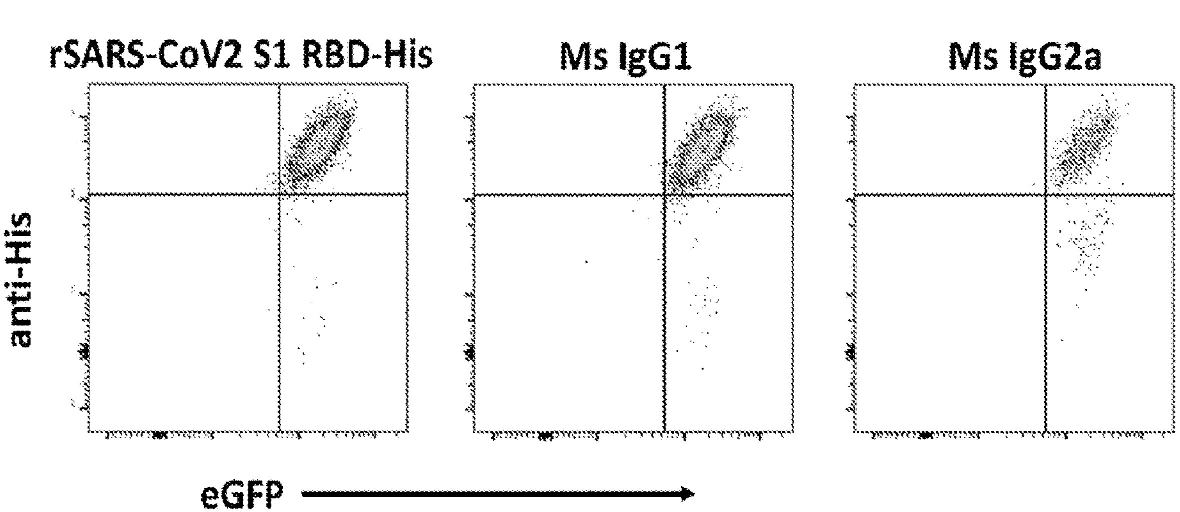
Figure 3D:
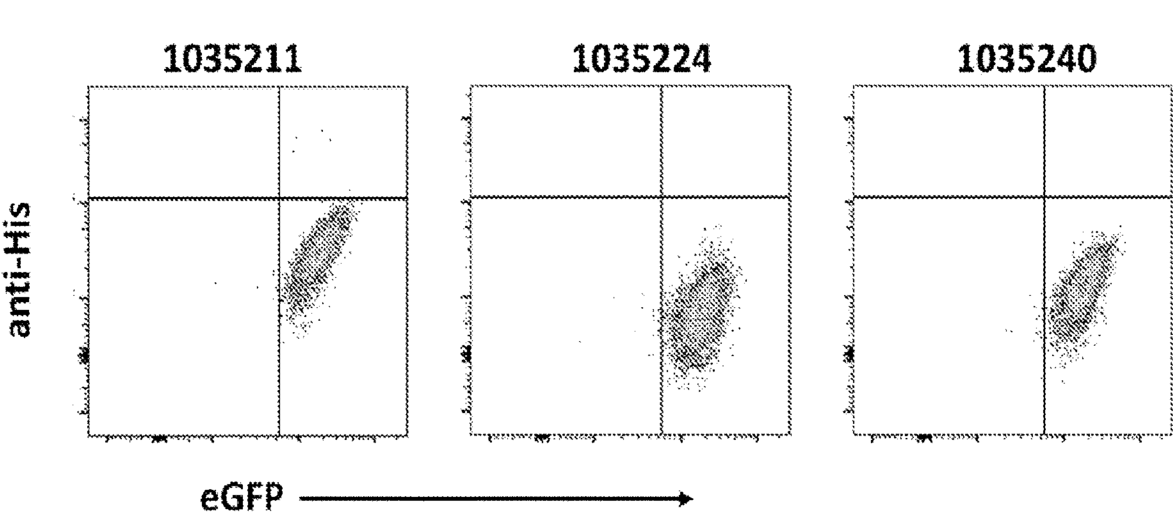

SARS-CoV-2 Monomeric $S_1$ and SARS-CoV-2 $S_1$ RBD Protein Blocking by Anti-SARS-CoV-2 Monoclonal Antibodies As shown in FIG. 3A, when SARS-CoV-2 $S_1$ protein was added to hACE-2 HEK/eGFP Tfx cells in the absence of antibody (FIG. 3A, left panel), or when irrelevant mouse isotype control antibodies were added (FIG. 3A, center and right panels), high levels of protein binding were detected, as indicated by the high level of anti-His fluorescence. In contrast, in the presence of the monoclonal antibodies from fusion panel 10352XX (specifically candidates 1035211, 1035224, and 1035240), the level of anti-His fluorescence was reduced (FIG. 3B) compared to mouse isotype control antibodies (FIG. 3A) to levels similar to that of the background fluorescence of hACE-2 HEK/eGFP Tfx cells alone. These results suggest antibodies 1035211, 1035224 and 1035240 blocked the binding of SARS-CoV-2 $S_1$ protein to ACE-2.

Figures 4A, 4B:
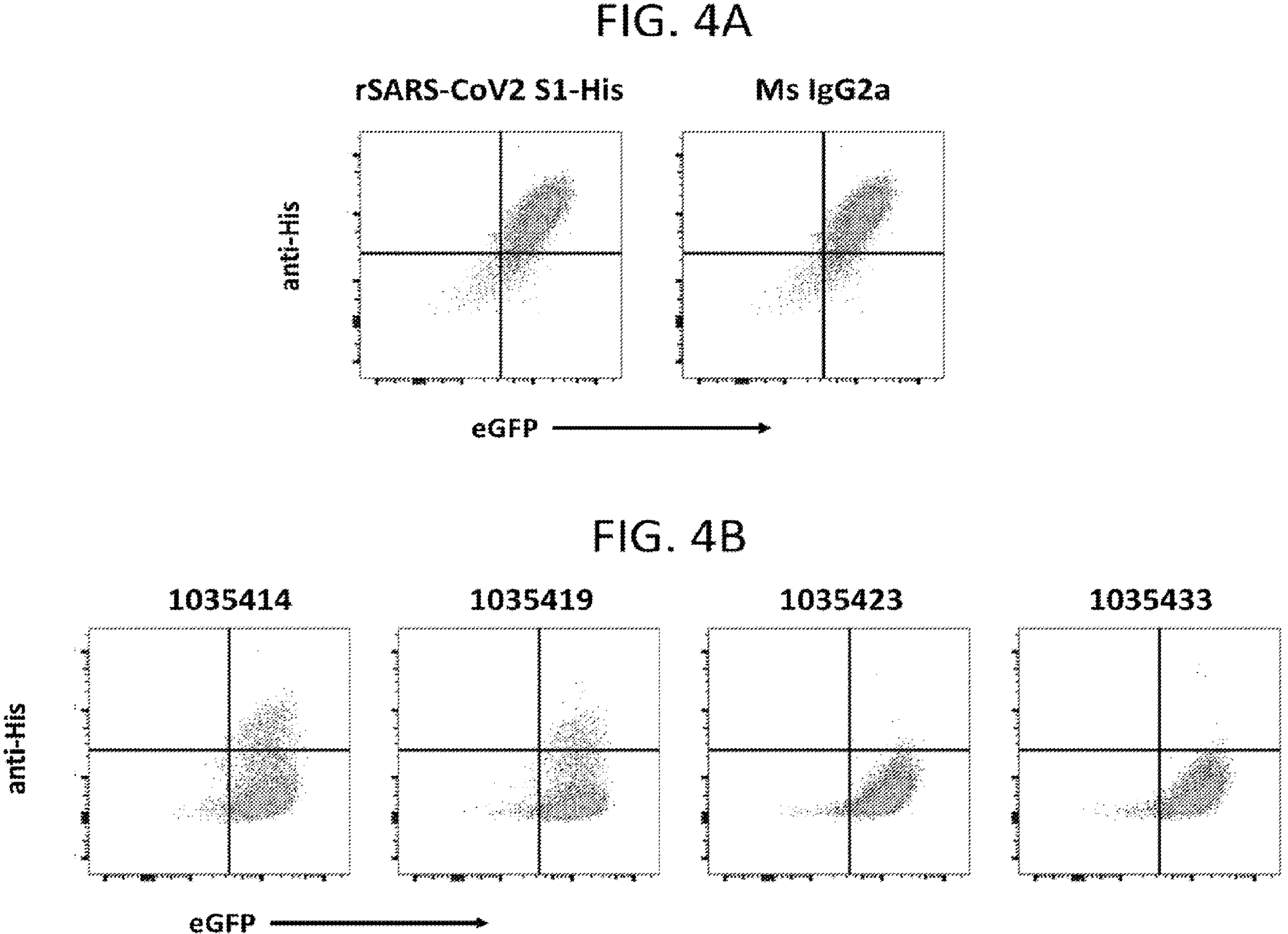
FIG. 4A-FIG. 4D show anti-SARS-CoV-2 antibody (panel 10354XX) blocking of SARS-CoV-2 $S_1$ binding to ACE-2. Recombinant monomeric SARS-CoV-2 $S_1$ protein was mixed and then incubated with staining buffer, mouse IgG2a isotype control antibodies (FIG. 4A) or anti-SARS-CoV-2 $S_1$ monoclonal antibodies from panel 10354XX (FIG. 4B) to allow a complex to form. rSARS-CoV-2 $S_1$ RBD was mixed and then incubated with staining buffer, mouse IgG2a isotype control antibodies (FIG. 4C) or anti-SARS-CoV-2 $S_1$ monoclonal antibodies from panel 10354XX (FIG. 4D) to allow a complex to form. After incubation, the mixture was added to a single cell suspension of hACE-2 HEK/eGFP Tfx, followed by a secondary anti-His antibody to assess viral antibody blocking. Flow cytometry gates were set on anti-His fluorescence of hACE-2 HEK/eGFP Tfx cells in the absence of any SARS-CoV-2 protein.
Figures 4C, 4D:
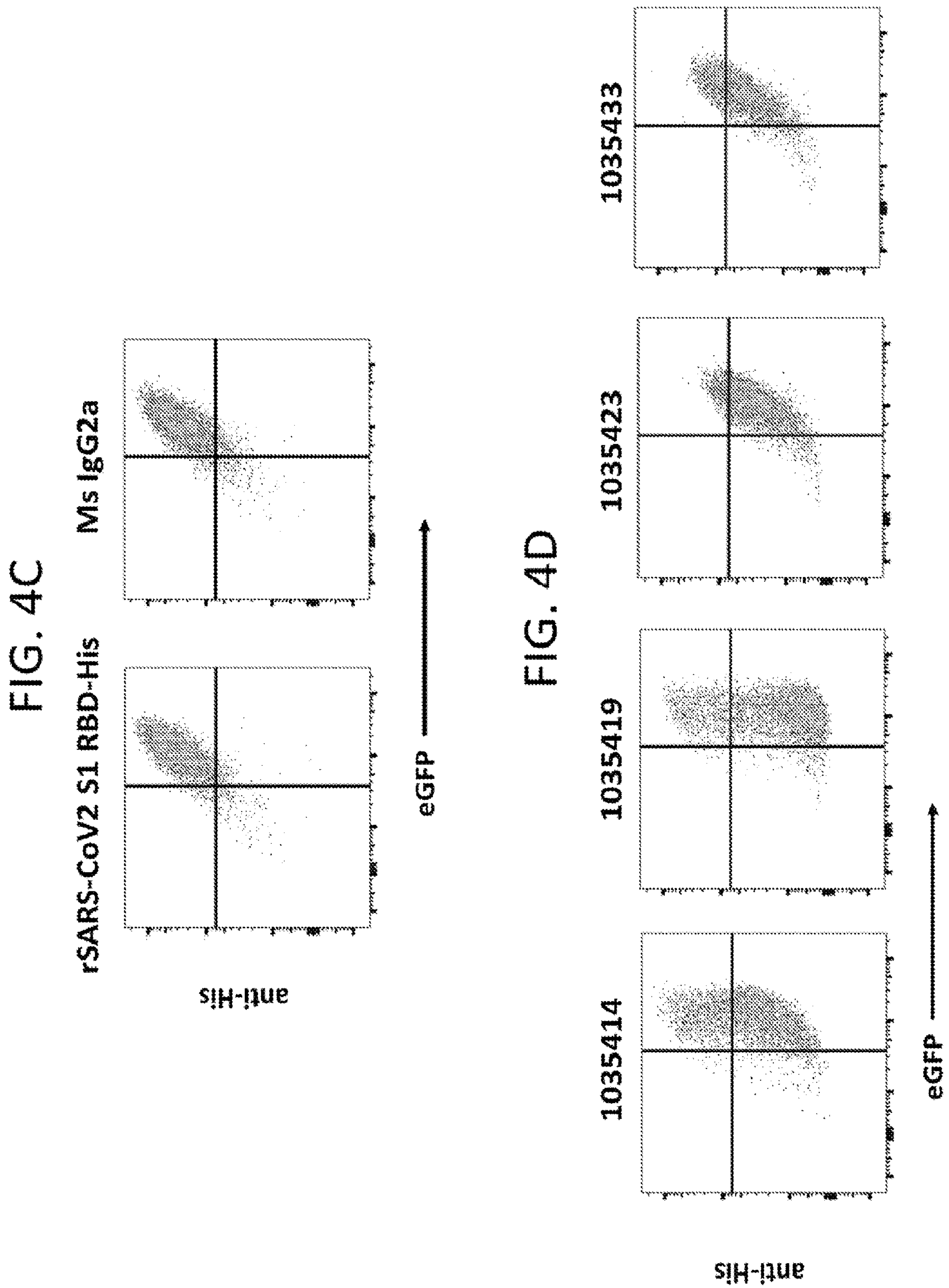
Figures 5A, 5B:
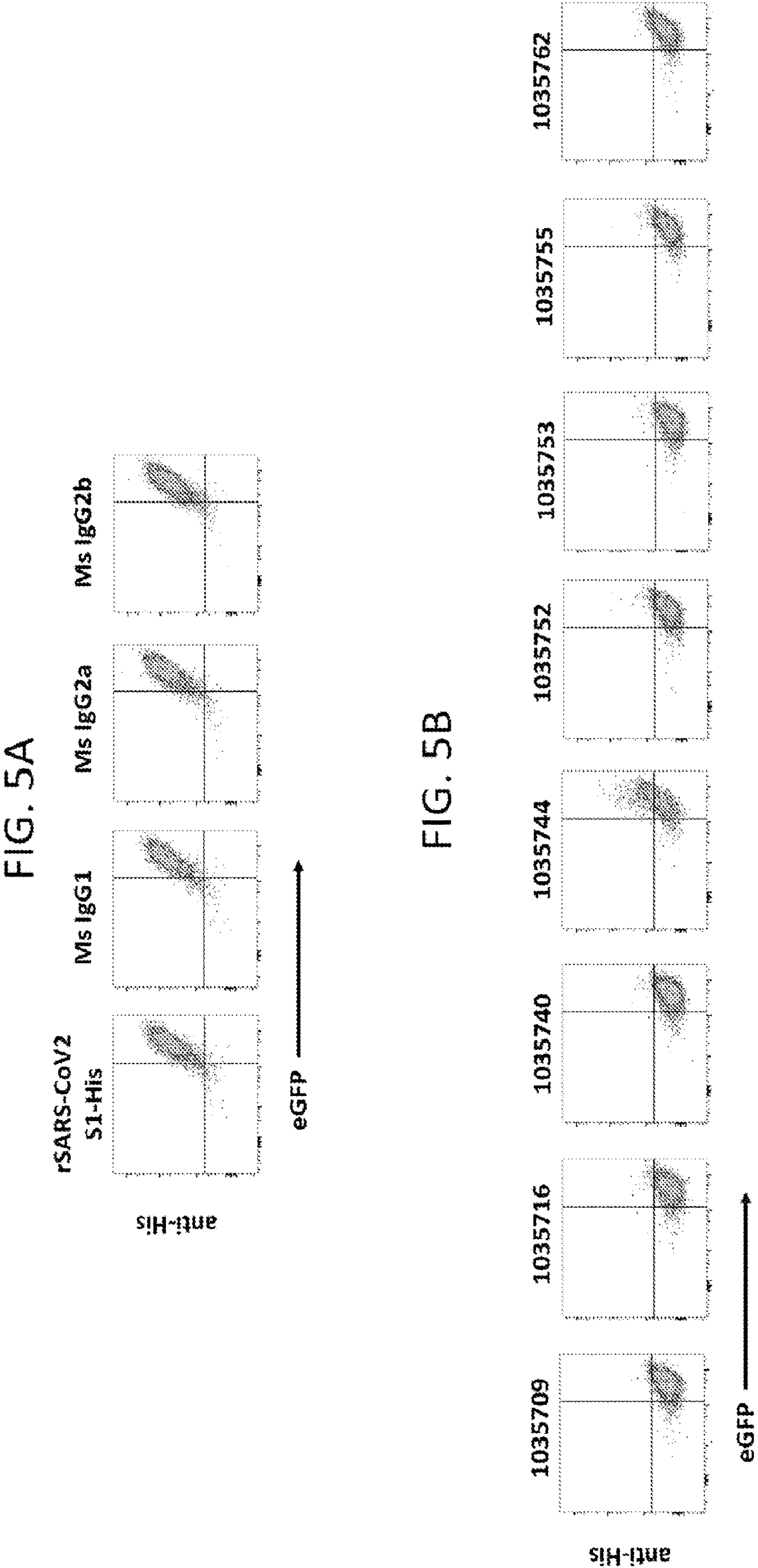
FIG. 5A-FIG. 5D show anti-SARS-CoV-2 antibody (panel 10357XX) blocking of SARS-CoV-2 $S_1$ binding to ACE-2. Recombinant monomeric SARS-CoV-2 $S_1$ protein was mixed and then incubated with staining buffer, mouse IgG2a isotype control antibodies (FIG. 5A) or anti-SARS-CoV-2 $S_1$ monoclonal antibodies from panel 10357XX (FIG. 5B) to allow a complex to form. rSARS-CoV-2 $S_1$ RBD was mixed and then incubated with staining buffer, mouse IgG2a isotype control antibodies (FIG. 5C) or anti-SARS-CoV-2 $S_1$ monoclonal antibodies from panel 10357XX (FIG. 5D) to allow a complex to form. After incubation, the mixture was added to a single cell suspension of hACE-2 HEK/eGFP Tfx, followed by a secondary anti-His antibody to assess viral antibody blocking. Flow cytometry gates were set on anti-His of hACE-2 HEK/eGFP Tfx cells in the absence of any SARS-CoV-2 protein.
Figures 5C, 5D:
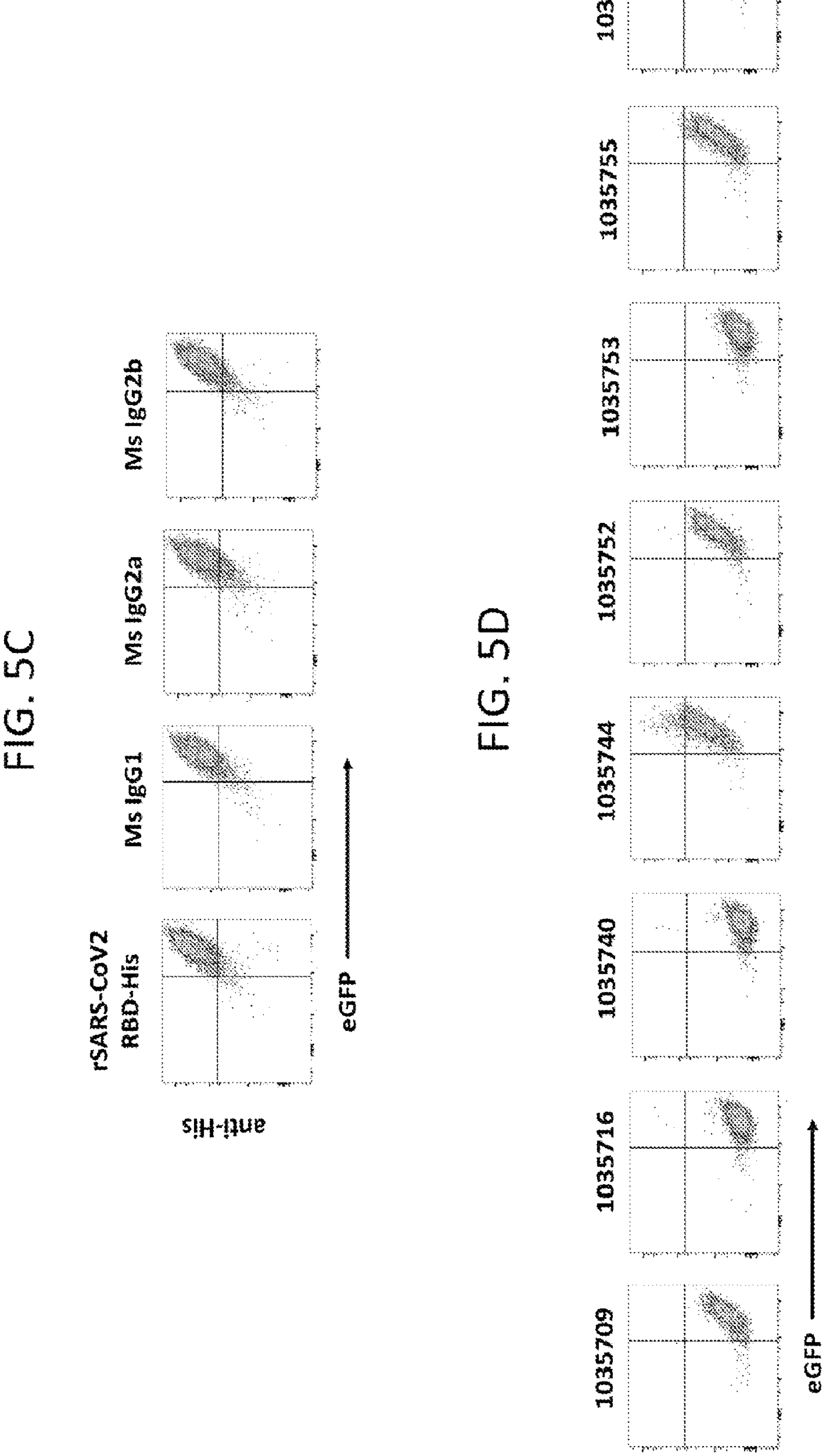

Similarly, in the presence of the monoclonal antibodies from fusion panel 10354XX, candidate 1035419 (FIG. 4B) or the monoclonal antibodies from fusion panel 10357XX, candidates 1035709, 1035716, 1035740, 1035744, 1035752, 1035753, 1035755, and 1035762 (FIG. 5B) the level of SARS-CoV-2 $S_1$ protein binding was also significantly reduced (for example, 85-95% reduced) compared to the level of protein binding seen in the presence of mouse isotype control antibodies (FIG. 4A and FIG. 5A).

Antibodies from panels 10352XX, 10354XX, and 10357XX also demonstrated the ability to complex with SARS-CoV-2 $S_1$ RBD and the ability to block the binding of the RBD with SARS-CoV-2 $S_1$ to ACE-2 (FIG. 3C-FIG. 3D, FIG. 4C-FIG. 4D, and FIG. 5C-FIG. 5D). The level of SARS-CoV-2 $S_1$ protein binding was again significantly reduced (for example, 85-99% reduced) compared to the level of protein binding seen in the presence of mouse isotype control antibodies (Table 2). These data suggest that most of the antibodies from panels 10352XX, 10354XX, and 10357XX bind to, or adjacent to, the RBD portion of SARS-CoV-2 $S_1$ but do so in such a way that antibody binding of $S_1$ sterically interferes with an RBD-ACE-2 interaction.

Interestingly, monoclonal antibodies 1035414, 1035423, and 1035433 showed a reduced ability to block the binding of full-length $S_1$ protein to ACE-2 suggesting that these antibodies uniquely interfere with the RBD of the $S_1$ protein.

These results demonstrate that monoclonal antibodies 1035211, 1035224, 1035240, 1035414, 1035419, 1035423, 1035433, 1035709, 1035716, 1035740, 1035744, 1035752, 1035753, 1035755, and 1035762 exhibit at least 50% reduction of the binding of SARS-CoV-2 $S_1$ RBD to ACE-2 expressing cells.

These results also demonstrate that monoclonal antibodies 1035211, 1035224, 1035240, 1035419, 1035709, 1035716, 1035740, 1035744, 1035752, 1035753, 1035755, and 1035762 exhibit at least 85% reduction of the binding of SARS-CoV-2 $S_1$ to ACE-2 expressing cells, with many of the antibodies exhibiting more than 90% reduction, as shown in Table 2.

TABLE 2

Antibody blocking of a recombinant monomeric SARS-CoV-2 $S_1$-ACE-2 interaction and a recombinant monomeric SARS-CoV-2 $S_1$ RBD-ACE-2 interaction.

| Target | Antibody clone | Host | S1 blocking | RBD blocking |
|---|---|---|---|---|
| S1 | 1035211 | Mouse | 88.7% | 98.7% |
| S1 | 1035224 | Mouse | 86.6% | 99.1% |
| S1 | 1035240 | Mouse | 56.5% | 99.1% |
| RBD | 1035414 | Mouse | 25.9% | 85.2% |
| RBD | 1035419 | Mouse | 70.1% | 90.2% |
| RBD | 1035423 | Mouse | 19.% | 94.1% |
| RBD | 1035433 | Mouse | 9.3% | 93.7% |
| S1 | 1035709 | Mouse | 93.6% | 94.7% |

TABLE 2-continued

Antibody blocking of a recombinant monomeric SARS-CoV-2 $S_1$-ACE-2 interaction and a recombinant monomeric SARS-CoV-2 $S_1$ RBD-ACE-2 interaction.

| Target | Antibody clone | Host | S1 blocking | RBD blocking |
|---|---|---|---|---|
| S1 | 1035716 | Mouse | 93.8% | 94.6% |
| S1 | 1035740 | Mouse | 93.4% | 94.6% |
| S1 | 1035744 | Mouse | 84.2% | 85.4% |
| S1 | 1035752 | Mouse | 93.3% | 94.5% |
| S1 | 1035753 | Mouse | 94.0% | 94.7% |
| S1 | 1035755 | Mouse | 93.3% | 94.1% |
| S1 | 1035762 | Mouse | 93.2% | 94.1% |

Percent Blocking was calculated by subtracting the percent of anti-His positive cells in the presence of each monoclonal antibody from the percent of anti-His positive cells incubated with either $S_1$ or $S_1$ RBD. 100% Blocking would indicate an antibody that completely prevented the binding of SARS-CoV-2 $S_1$ or SARS-CoV-2 $S_1$ RBD to ACE-2.

SARS-CoV-2 Homotrimeric Protein Blocking by SARS-CoV-2 Monoclonal Antibodies

Figure 6A:
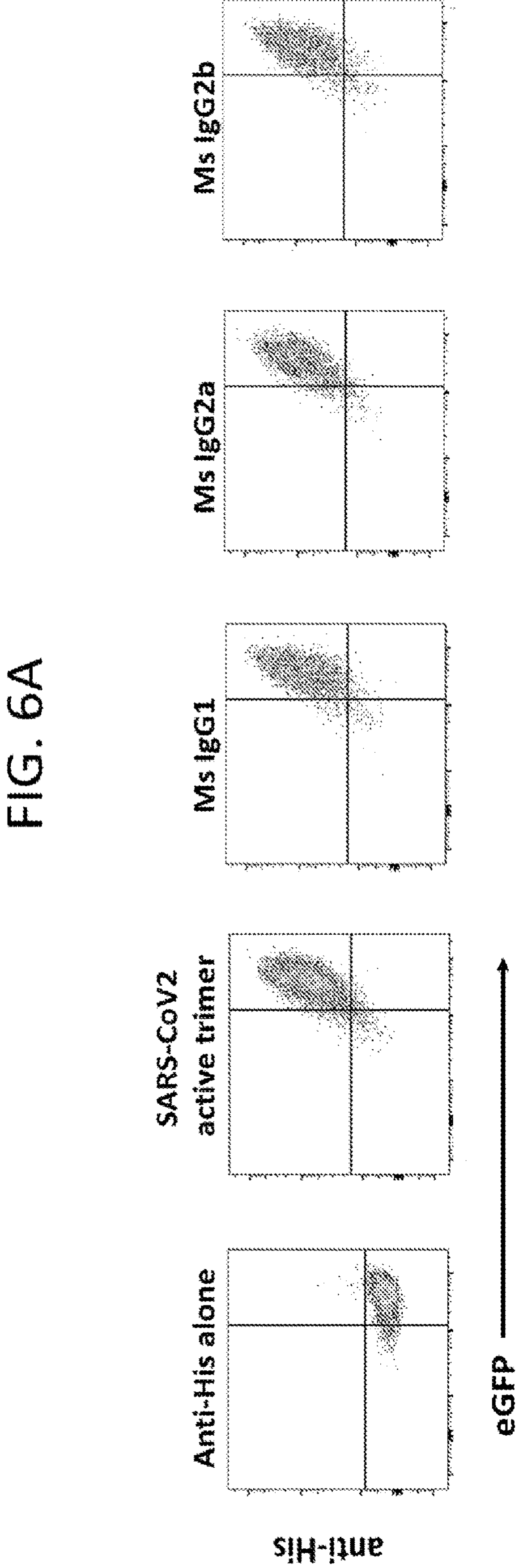
FIG. 6A-FIG. 6B show anti-SARS-CoV-2 antibodies block binding of trimeric SARS-CoV-2 spike protein to ACE-2. rSARS-CoV-2 homotrimeric spike protein was mixed and then incubated with PBS staining buffer, Mouse IgG1, IgG2a or IgG2b isotype control antibodies (FIG. 6A); or with anti-SARS-CoV-2 monoclonal antibodies from panels 10352XX, 10354XX, or 10357XX (FIG. 6B) to allow a complex to form. After incubation, the mixture was added to a single cell suspension of hACE-2 HEK/eGFP Tfx, followed by addition of a secondary anti-His antibody to assess viral antibody blocking. Flow cytometry gates were set on anti-His fluorescence of hACE-2 HEK/eGFP Tfx cells without SARS-CoV-2 trimeric spike protein.

Typically, the SARS-CoV-2 spike protein does not exist as a monomeric protein, but rather, as homotrimer that includes three 180-kDa monomers, each containing both $S_1$ and $S_2$ subunits (Walls et al. *Cell* 181, 281-292 e286 (2020)). Because the anti-SARS-CoV-2 monoclonal antibodies identified above could block the binding of recombinant $S_1$ monomers and $S_1$ RBD monomers to ACE-2, whether the antibodies would also be able to block the binding of recombinant homotrimeric SARS-CoV-2 spike protein to ACE-2 was also examined Recombinant his-tagged homotrimeric SARS-CoV-2 protein was titrated on hACE-2 HEK/eGFP Tfx cells, and binding was detected using an anti-His secondary antibody (FIG. 6A). Monoclonal antibodies from panels 10352XX, 10354XX, and 10357XX were individually incubated with homotrimeric SARS-CoV-2 protein to form a complex, and then the complex added to hACE-2 HEK/eGFP Tfx cells to determine if the antibodies blocked biding of the trimeric protein to ACE-2.

Figure 6B:
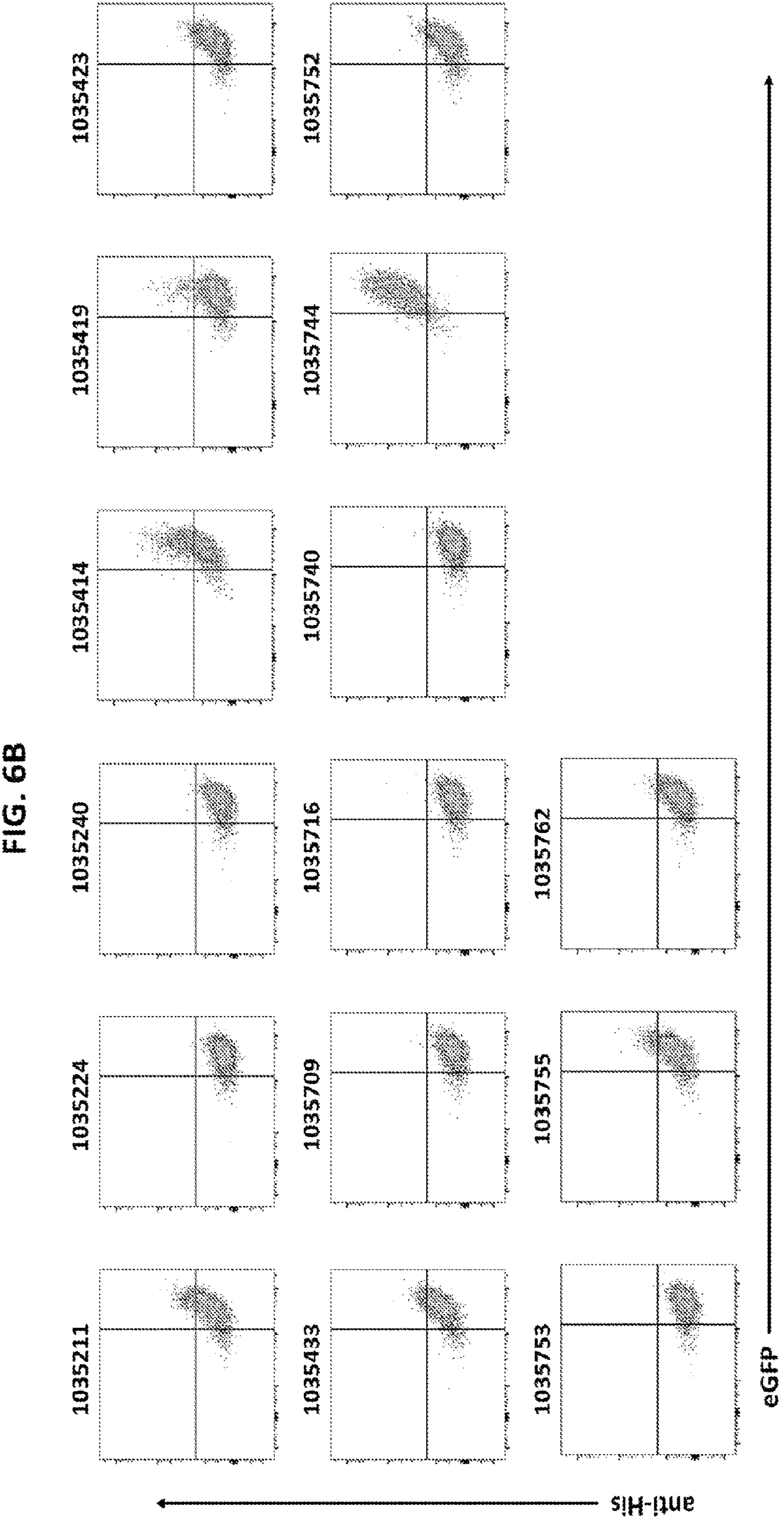

As shown in FIG. 6B and Table 3, with the exception of antibodies 1035744 and 1035414, each of the tested antibodies substantially inhibited the binding of the trimeric protein to ACE-2 compared to mouse irrelevant isotype control antibodies complexed with the homotrimeric SARS-CoV-2 protein (FIG. 6A). In many cases, greater than 90% inhibition was observed (see Table 3).

TABLE 3

Antibody blocking of a recombinant homotrimeric SARS-CoV-2 Spike protein-ACE-2 interaction

| Target | Antibody clone | SARS-CoV2 active trimer blocking |
|---|---|---|
| S1 | 1035211 | 78.6% |
| S1 | 1035224 | 96.6% |
| S1 | 1035240 | 96.1% |
| RBD | 1035414 | 51.4% |
| RBD | 1035419 | 89.0% |
| RBD | 1035423 | 91.6% |
| RBD | 1035433 | 82.5% |
| S1 | 1035709 | 96.5% |
| S1 | 1035716 | 96.5% |
| S1 | 1035740 | 96.5% |
| S1 | 1035744 | 1.4% |
| S1 | 1035752 | 91.8% |
| S1 | 1035753 | 96.6% |
| S1 | 1035755 | 84.6% |
| S1 | 1035762 | 93.0% |

Percent Blocking was calculated by subtracting the percent of anti-His positive cells in the presence of each monoclonal antibody from the percent of anti-His positive cells incubated with homotrimeric spike protein alone. 100% Blocking would indicate an antibody that completely prevented the binding of SARS-CoV-2 spike protein to ACE-2.

SARS-CoV-1 Monomeric $S_1$ and RBD Blocking by Anti-SARS-CoV-2 Monoclonal Antibodies The spike proteins for the coronavirus family members SARS-CoV-2 and SARS-CoV-1 share significant homology (Zhou et al. *Nature* 579, 270-273 (2020); Lan et al. *Nature* 581, 215-220 (2020); Ou et al. *Nat Commun* 11, 1620 (2020)) suggesting that antibodies specific for SARS-CoV-2 spike proteins might exhibit cross-reactivity with SARS-CoV-1 spike proteins. An antigen-down ELISA assay was performed to determine whether any of the monoclonal antibodies from panels 10352XX, 10354XX, or 10357XX would bind to decreasing concentrations of SARS-CoV-1 $S_1$ or SARS-CoV-1 $S_1$ RBD.

Figures 7E, 7F, 7G, 7H:
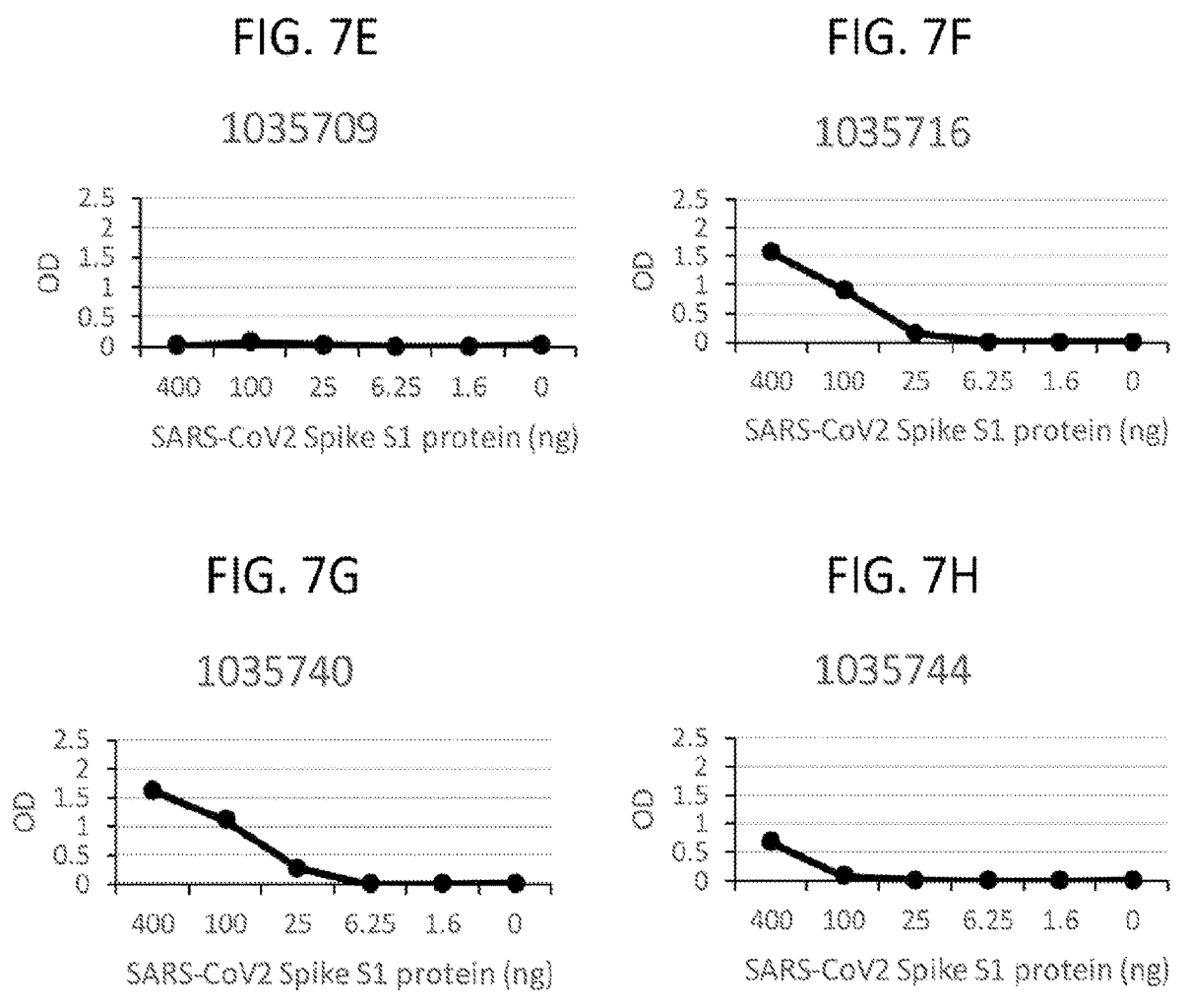
Figures 7I, 7J, 7K, 7L:
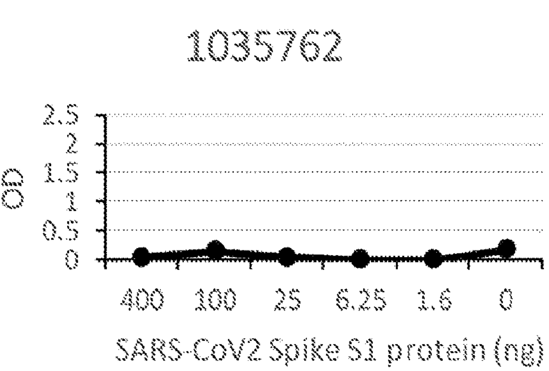
FIG. 7A-FIG. 7P show antibody binding of anti-SARS-CoV-2 antibodies to monomeric SARS-CoV-1 $S_1$. Wells of a 96-well microtiter plate were coated with recombinant monomeric SARS-CoV-1 $S_1$ protein diluted to 400 ng/mL, 100 ng/mL, 25 ng/mL, 6.25 ng/mL, and 1.56 ng/mL in 1×TBS Buffer. Control wells were coated in 1×TBS Buffer alone. Purified mouse anti-SARS-CoV-2 monoclonal antibodies 1035419 (FIG. 7A), 1035423 (FIG. 7B), 1035433 (FIG. 7C), 1035414 (FIG. 7D), 1035709 (FIG. 7E), 1035716 (FIG. 7F), 1035740 (FIG. 7G), 1035744 (FIG. 7H), 1035752 (FIG. 7I), 1035753 (FIG. 7J), 1035755 (FIG. 7K), 1035762 (FIG. 7L), 1035211 (FIG. 7M), 1035224 (FIG. 7N), and 1035240 (FIG. 7O) were subsequently added to wells containing monomeric SARS-CoV-1 $S_1$ at 1 μg/mL in Capture Buffer and incubated for either 30 minutes on a shaker table or for 1 hour without shaking. TMB buffer alone (with no antibody) is shown in FIG. 7P. Detection was performed by the addition of a goat anti-mouse/HRP-conjugated polyclonal secondary detection antibody in Capture Buffer followed by allowing a chromogenic reaction to proceed in TMB for 10 minutes.

As shown in FIG. 7, antibody candidates 1035419 (FIG. 7A), 1035414 (FIG. 7D), 1035716 (FIG. 7F), 1035740 (FIG. 7G), and to a lesser extent, 1035744 (FIG. 7H), bound to the highest concentration of recombinant SARS-CoV-1 $S_1$ and then showed decreased binding as protein concentration diminished.

Figures 8A, 8B, 8C, 8D:
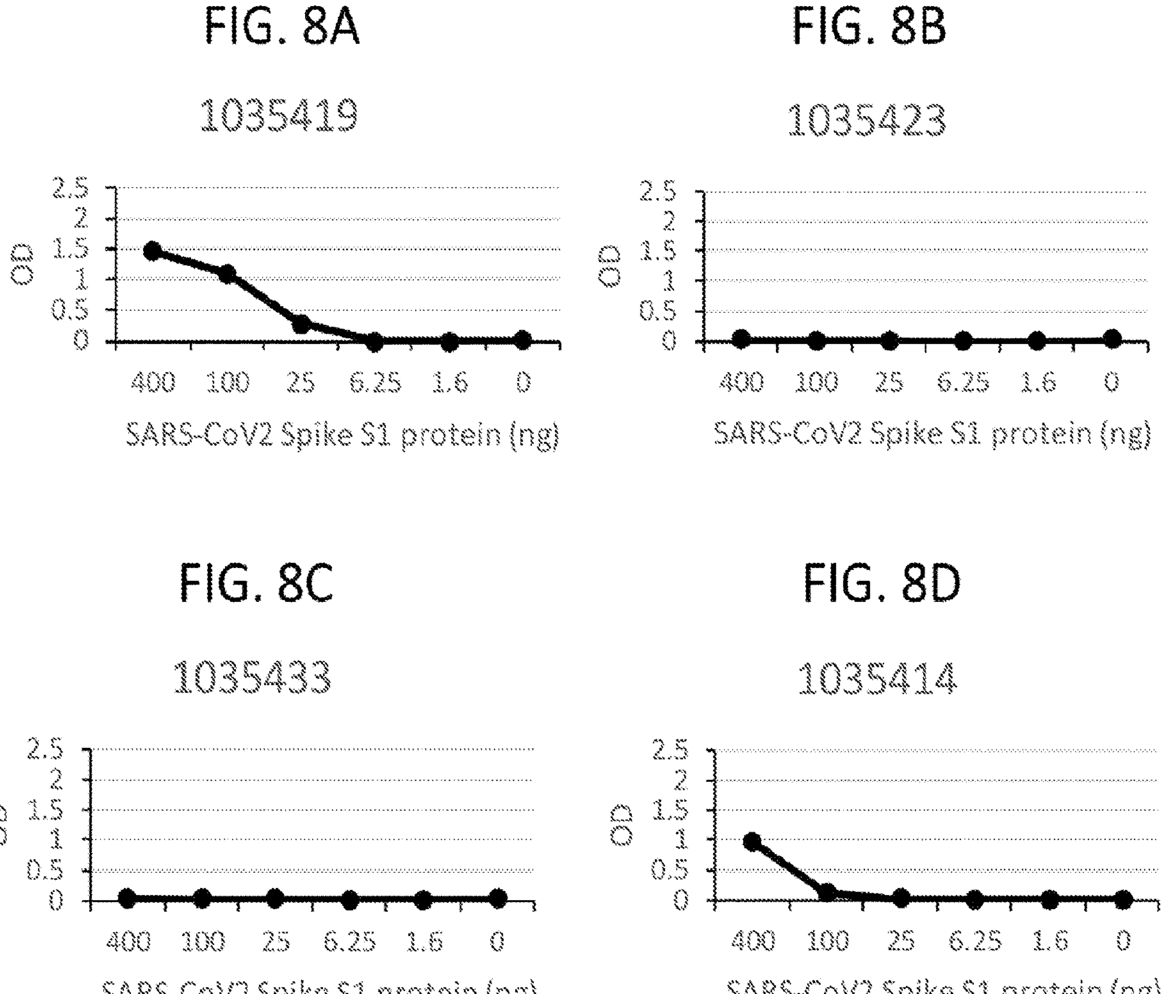
FIG. 8A-FIG. 8P show antibody binding of anti-SARS-CoV-2 antibodies to monomeric SARS-CoV-1 $S_1$ RBD. Wells of a 96-well microtiter plate were coated with recombinant monomeric SARS-CoV-1 $S_1$ RBD diluted to 400 ng/mL, 100 ng/mL, 25 ng/mL, 6.25 ng/mL, and 1.56 ng/mL in 1×TBS Buffer. Control wells were coated in 1×TBS Buffer alone. Purified mouse anti-SARS-CoV-2 monoclonal antibodies 1035419 (FIG. 8A), 1035423 (FIG. 8B), 1035433 (FIG. 8C), 1035414 (FIG. 8D), 1035709 (FIG. 8E), 1035716 (FIG. 8F), 1035740 (FIG. 8G), 1035744 (FIG. 8H), 1035752 (FIG. 8I), 1035753 (FIG. 8J), 1035755 (FIG. 8K), 1035762 (FIG. 8L), 1035211 (FIG. 8M), 1035224 (FIG. 8N), and 1035240 (FIG. 8O) were subsequently added to wells containing monomeric SARS-CoV-1 $S_1$ RBD at 1 μg/ml in Capture Buffer and incubated for either minutes on a shaker table or for 1 hour without shaking. TMB buffer alone (with no antibody) is shown in FIG. 8P. Detection was performed by the addition of a goat anti-mouse/HRP-conjugated polyclonal secondary detection antibody in Capture Buffer followed by allowing a chromogenic reaction to proceed in TMB for 10 minutes.
Figures 8E, 8F, 8G, 8H:
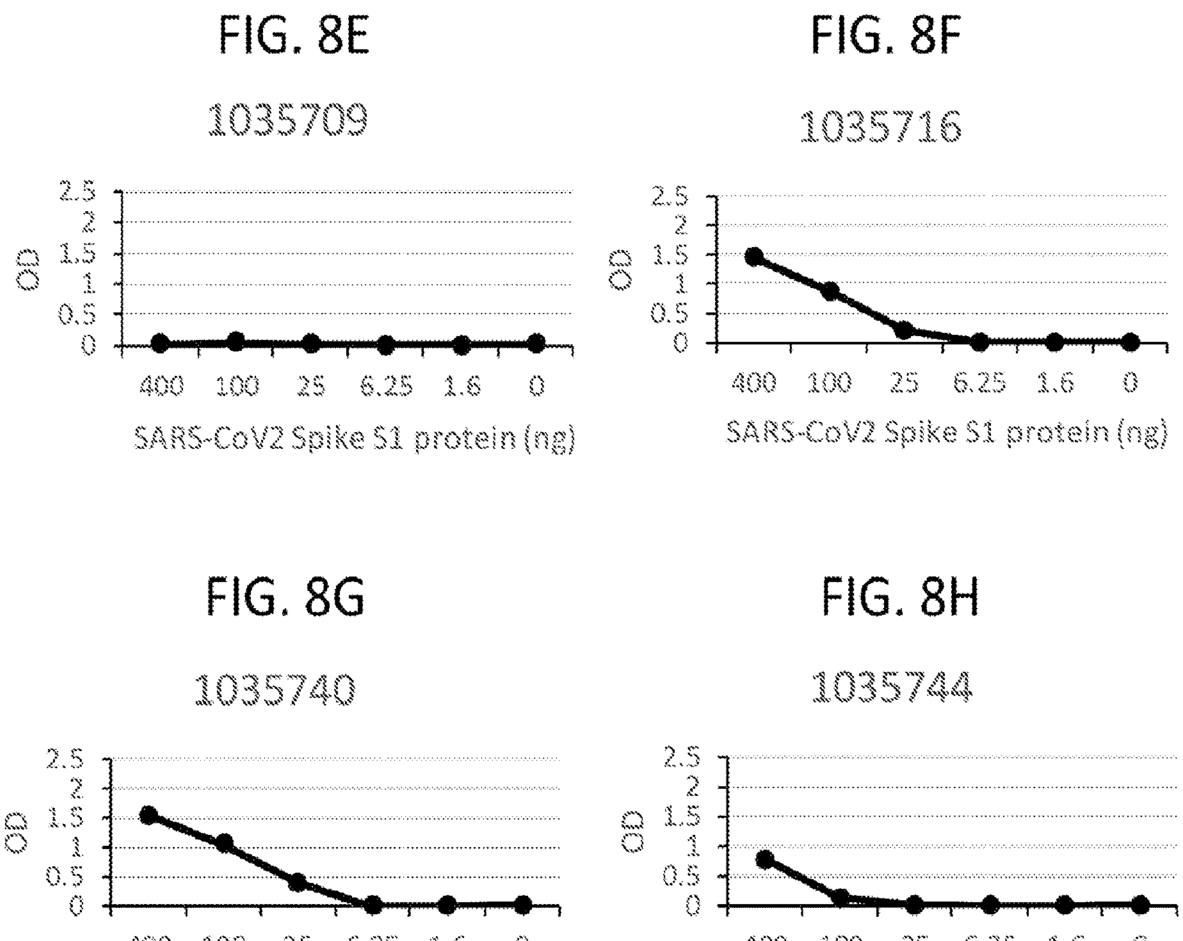
Figures 8I, 8J, 8K, 8L:
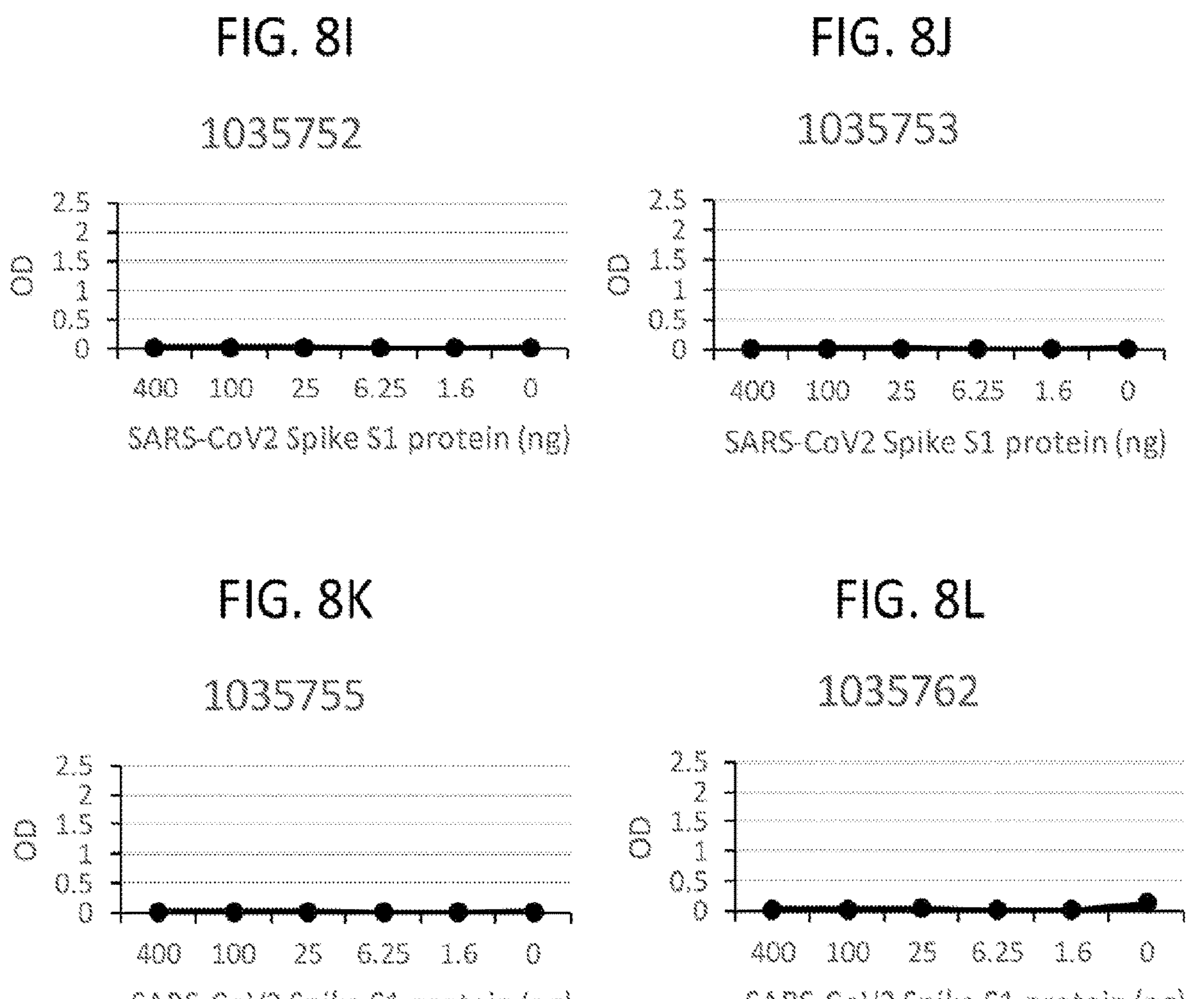

By comparison, most of the other antibodies in the three antibody fusion panels failed to bind recombinant SARS-CoV-1 $S_1$ at any concentration. When tested against SARS-CoV-1 $S_1$ RBD, these same five antibodies elicited some degree of binding; binding of monoclonal antibodies 1035419 (FIG. 8A), 1035716 (FIG. 8F), and 1035740 (FIG. 8G) showed the highest level of protein binding while the binding of antibodies 1035414 (FIG. 8D) and 1035744 (FIG. 8H) was reduced but was still significant compared the remaining antibodies in fusion panels 10352XX, 10354XX, and 10357XX. These results suggest that antibodies 1035414, 1035419, 1035716, 1035740, and 1035744 bind epitopes that are highly conserved between SARS-CoV-1 and SARS-CoV-2.

FIG. 9 shows the sequence alignments of the variable regions of these five antibodies: 1035414, 1035419, 1035716, 1035740, and 1036744. Annotation of the framework regions (FRs) and complementary domain regions (CDRs) was performed using the Kabat numbering scheme. Using this model, amino acid sequences of the variable region of the light (λ, κ) and heavy chain of antibodies, as well as the variable region of T cell receptors (α, β, γ, δ) were aligned and numbered. A high degree of homology (>70%) was seen in FR1, FR2, FR3, and FR4 regions between the five antibodies, indicating lower structural diversity in these framework regions. Framework regions determine the conformational space accessible to CDR regions. On the other hand, CDR1 showed significant homology between the five antibodies, but the similarity diminished in CDRs 2 and 3. Greatest diversity was observed in CDR-H3, a region that is important to specificity determination as well as antigen binding differences between the antibodies.

Figure 10A:
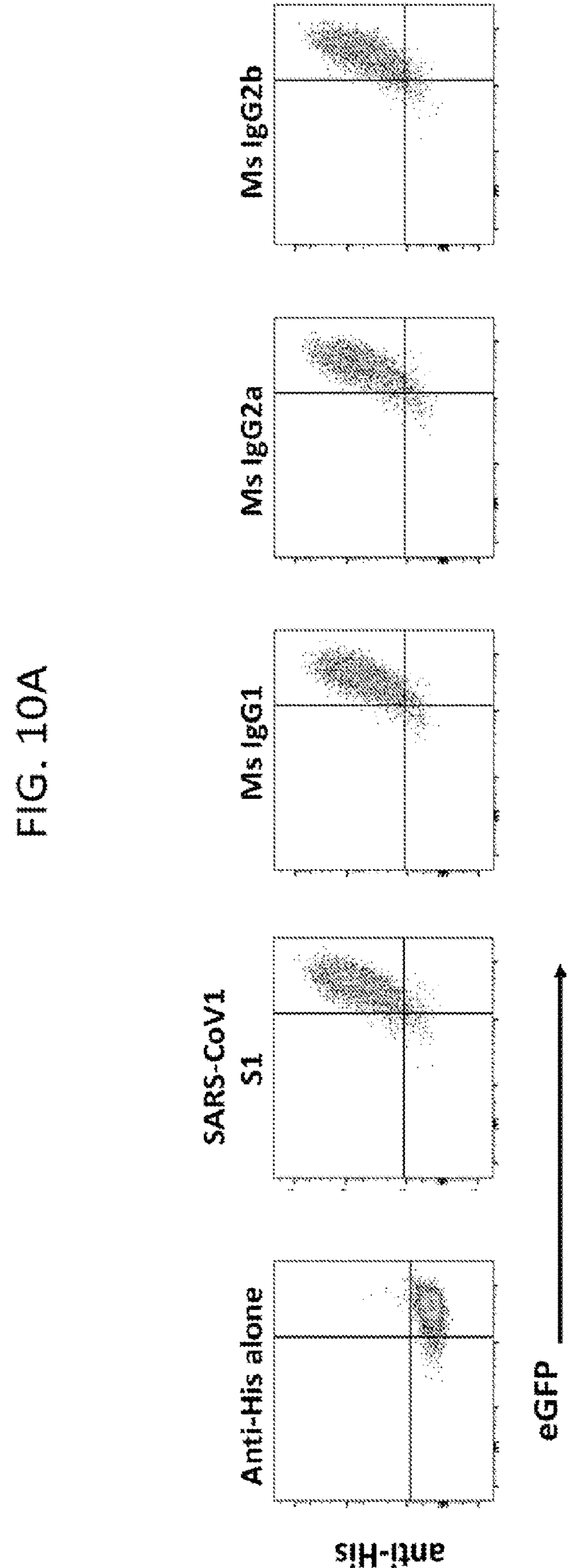
FIG. 10A-FIG. 10B show anti-SARS-CoV-2 antibody blocking of monomeric SARS-CoV-1 $S_1$ binding to ACE-2. Monomeric rSARS-CoV-1 $S_1$ was mixed and then incubated with staining buffer, mouse IgG1, IgG2a, or IgG2b isotype control antibodies (FIG. 10A) or anti-SARS-CoV-2 monoclonal antibodies from panels 10352XX, 10354XX, or 10357XX (FIG. 10B) to allow a complex to form. After incubation, the mixture was added to a single cell suspension of hACE-2 HEK/eGFP Tfx, followed by a secondary anti-His antibody to assess viral antibody blocking. Flow cytometry gates were set on anti-His fluorescence of hACE-2 HEK/eGFP Tfx cells without monomeric SARS-CoV-1 $S_1$.

To determine if anti-SARS-CoV-2 monoclonal antibodies from panels 10352XX, 10354XX, and 10357XX could prevent the binding of SARS-CoV-1 $S_1$ to ACE-2, SARS-CoV-1 $S_1$ was titrated on hACE-2 HEK/eGFP Tfx cells and binding was detected using an anti-His secondary antibody (FIG. 10A).

Figure 10B:
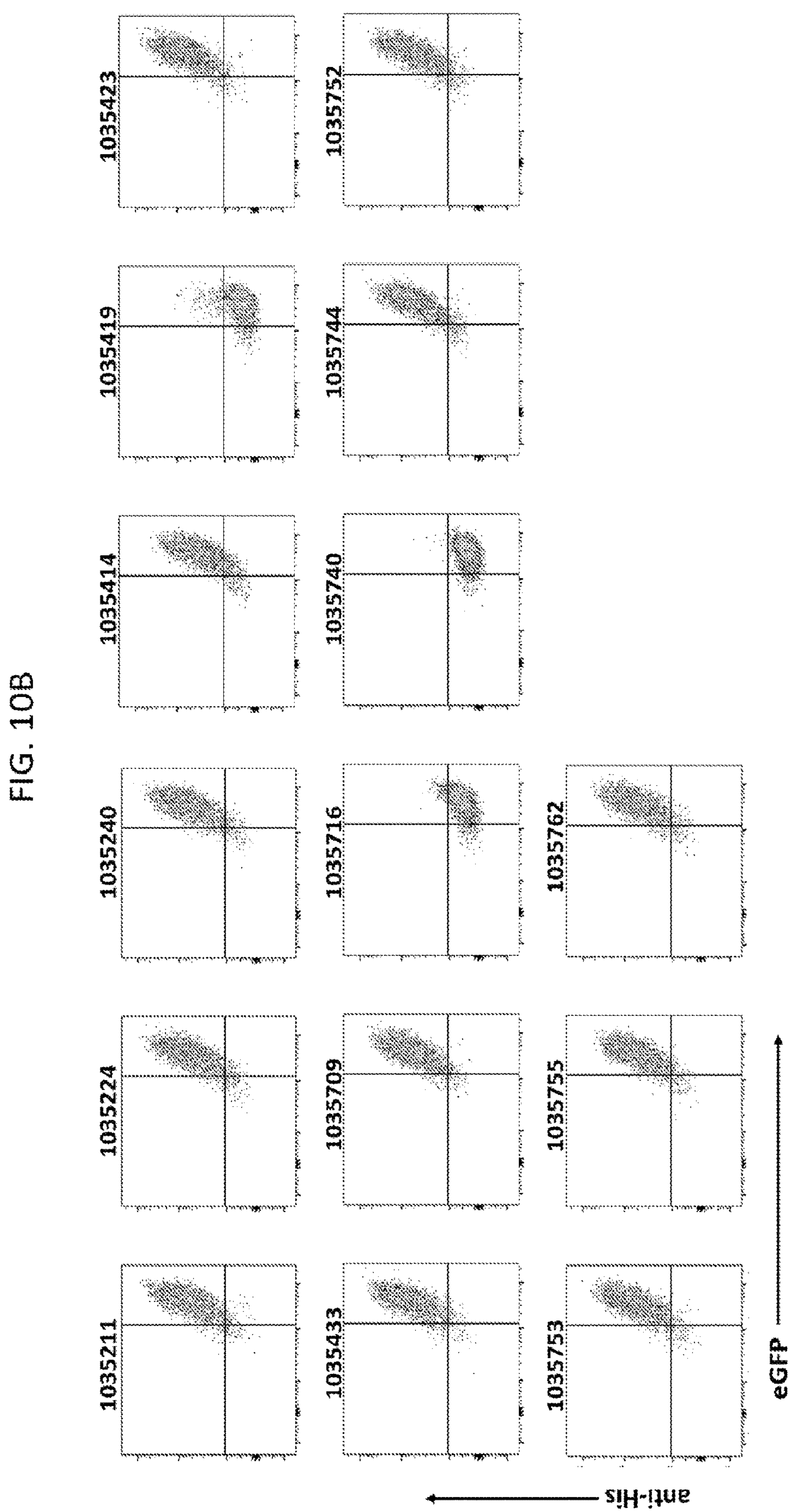

The monoclonal antibodies from panels 10352XX, 10354XX, and 10357XX were then individually incubated with recombinant monomeric SARS-CoV-1 $S_1$ protein for form a complex, and then the complex added to hACE-2 HEK/eGFP Tfx cells to determine if the antibodies could block binding of the monomeric $S_1$ protein to ACE-2. As shown in FIG. 10B, only three antibodies, 1035419, 1035716, and 1035740, showed an ability to cross-react and block SARS-CoV-1 $S_1$ binding to ACE-2 compared to mouse irrelevant isotype control antibodies complexed with the SARS-CoV-1 $S_1$ protein (FIG. 10A).

The ability of the monoclonal antibodies to block recombinant monomeric SARS-CoV-1 $S_1$ RBD binding to ACE-2 was also examined. The monoclonal antibodies from panels 10352XX, 10354XX, and 10357XX were individually incubated with recombinant monomeric SARS-CoV-1 $S_1$ RBD to form a complex, and then the complex added to hACE-2 HEK/eGFP Tfx cells to determine if the antibodies could block biding of the monomeric SARS-CoV-1 $S_1$ RBD to ACE-2.

Figure 11A:
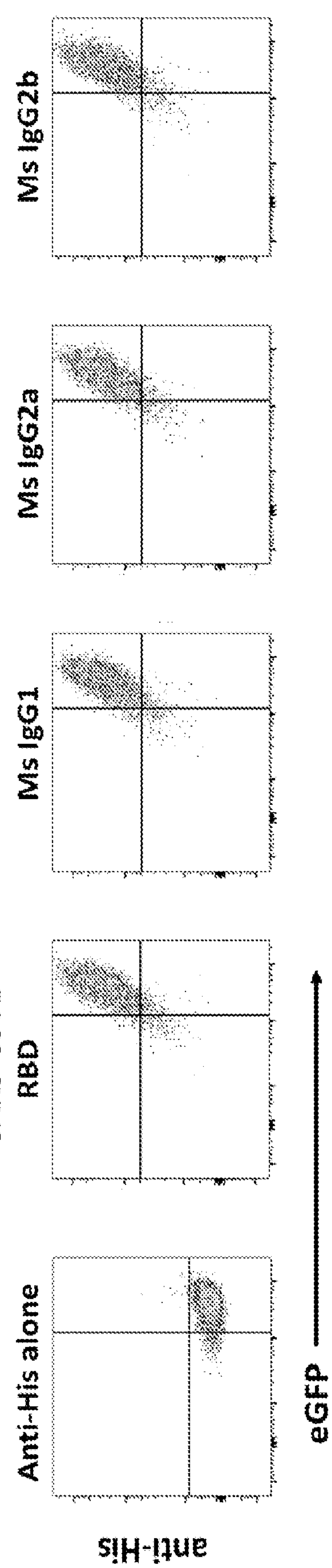
FIG. 11A-FIG. 11B show anti-SARS-CoV-2 antibody blocking of monomeric SARS-CoV-1 $S_1$ RBD to ACE-2. Monomeric rSARS-CoV-1 $S_1$ RBD was mixed and then incubated with PBS staining buffer, Mouse IgG1, IgG2a or IgG2b isotype control antibodies (FIG. 11A) or anti-SARS-CoV-2 monoclonal antibodies from panels 10352XX, 10354XX, or 10357XX (FIG. 11B) to allow a complex to form. After incubation, the mixture was added to a single cell suspension of hACE-2 HEK/eGFP Tfx, followed by a secondary anti-His antibody to assess viral antibody blocking. Flow cytometry gates were set on anti-His fluorescence of hACE-2 HEK/eGFP Tfx cells without monomeric SARS-CoV-1 $S_1$ RBD protein.
Figure 11B:
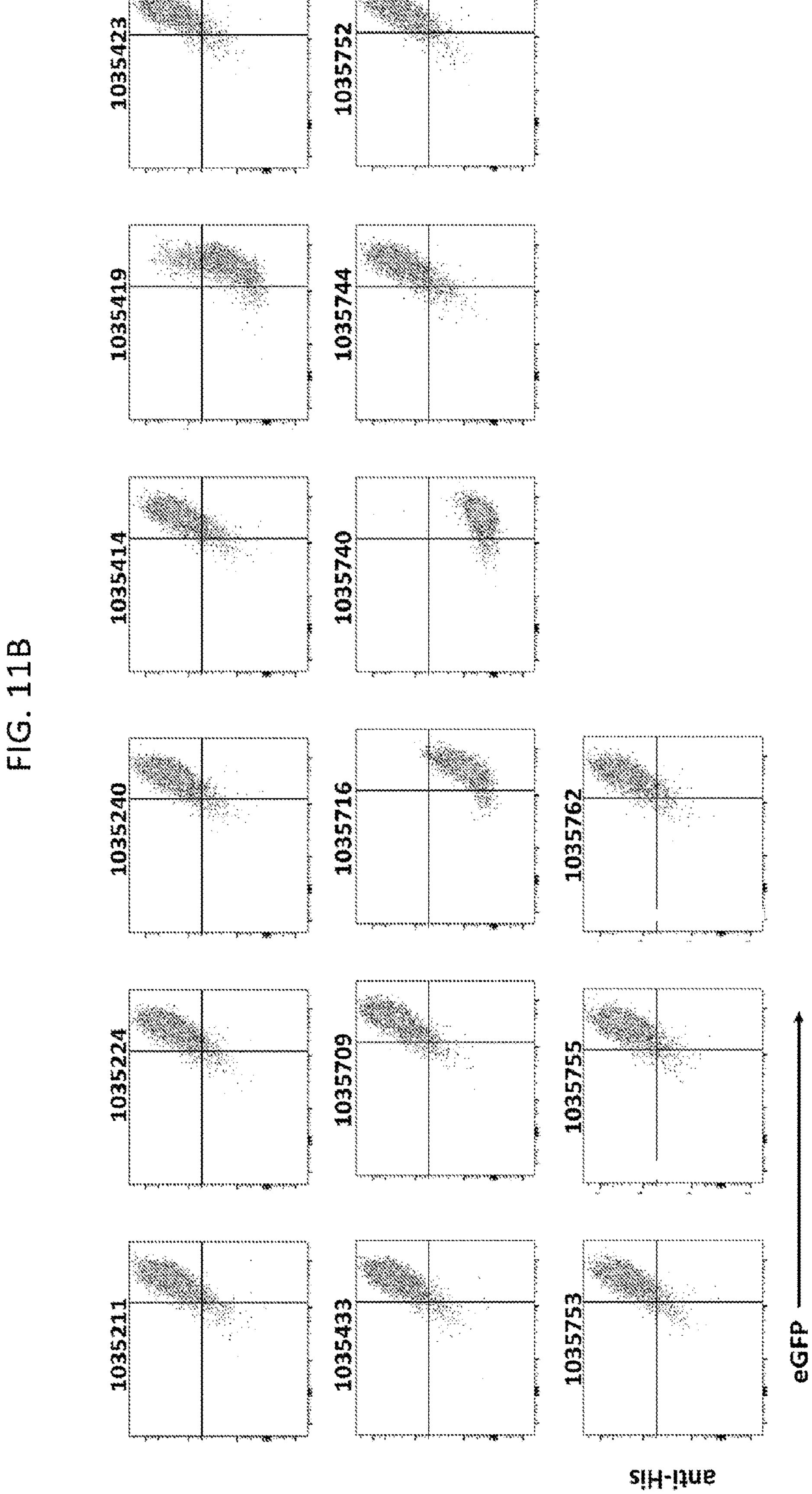

As shown in FIG. 11B, antibodies 1035716 and 1035740 blocked SARS-CoV-1 $S_1$ RBD binding to ACE-2 with the blocking by antibody 1035740 being nearly 100% (FIG. 11 and Table 4). Interestingly, antibody 1035740 showed greater that 90% blocking against all proteins used: monomeric SARS-CoV-2 $S_1$, monomeric SARS-CoV-2 $S_1$ RBD, trimeric SARS-CoV-2 spike protein, monomeric SARS-CoV-1 $S_1$, and SARS-CoV-1 $S_1$ RBD (see Table 2, Table 3, and Table 4).

TABLE 4

Antibody blocking of a recombinant SARS-CoV-1 $S_1$-ACE-2 interaction and a recombinant SARS-CoV-1 $S_1$ RBD-ACE-2 interaction.

| Target | Antibody clone | SARS-CoV S1 blocking | SARS-CoV RBD blocking |
|---|---|---|---|
| S1 | 1035211 | 0.0% | 0.1% |
| S1 | 1035224 | 0.0% | 0.0% |
| S1 | 1035240 | 0.0% | 0.0% |
| RBD | 1035414 | 12.0% | 0.4% |
| RBD | 1035419 | 88.5% | 44.1% |
| RBD | 1035423 | 0.0% | 0.0% |
| RBD | 1035433 | 0.0% | 0.0% |
| S1 | 1035709 | 0.0% | 0.0% |

TABLE 4-continued

Antibody blocking of a recombinant SARS-CoV-1 $S_1$-ACE-2 interaction and a recombinant SARS-CoV-1 $S_1$ RBD-ACE-2 interaction.

| Target | Antibody clone | SARS-CoV S1 blocking | SARS-CoV RBD blocking |
|---|---|---|---|
| S1 | 1035716 | 89.5% | 68.7% |
| S1 | 1035740 | 92.4% | 98.8% |
| S1 | 1035744 | 0.6% | 0.2% |
| S1 | 1035752 | 0.0% | 0.0% |
| S1 | 1035753 | 0.0% | 0.0% |
| S1 | 1035755 | 1.3% | 0.0% |
| S1 | 1035762 | 0.0% | 0.0% |

Percent Blocking was calculated by subtracting the percent of anti-His positive cells in the presence of each monoclonal antibody from the percent of anti-His positive cells incubated with either $S_1$ or $S_1$ RBD. 100% Blocking would indicate an antibody that completely prevented the binding SARS-CoV-1 $S_1$ or SARS-CoV-1 $S_1$ RBD to ACE-2.

MERS Monomeric $S_1$ and $S_1$ RBD Binding is not Blocked by Anti-SARS-CoV-2 Monoclonal Antibodies The spike proteins for MERS and SARS-CoV-2 share approximately 22% homology (Li et al. *iScience* 23, 101160 (2020)) suggesting that antibodies specific for SARS-CoV-2 spike proteins might exhibit cross-reactivity with MERS spike proteins.

To determine if anti-SARS-CoV-2 monoclonal antibodies from panels 10352XX, 10354XX, and 10357XXX could prevent the binding of MERS $S_1$ or MERS $S_1$ RBD, MERS $S_1$ and MERS $S_1$ RBD were titrated on hCD26 HEK/eGFP Tfx cells and binding was detected using an anti-Fc or anti-His secondary antibody. The monoclonal antibodies from panels 10352XX, 10354XX, and 10357XX were then individually incubated with recombinant monomeric MERS $S_1$ or MERS $S_1$ RBD to form a complex, and then the complex was added to hCD26 HEK/eGFP Tfx cells to determine if the antibodies could block binding of the monomeric MERS S1 or monomeric MERS S1 RBD protein to CD26. No blocking was observed (Table 5).

TABLE 5

Summary of anti-SARS-CoV-2 antibody blocking of recombinant SARS-CoV-2 $S_1$, SARS-CoV-2 $S_1$ RBD, trimeric SARS-CoV-2 spike protein, SARS-CoV-1 $S_1$, SARS-CoV-1 $S_1$ RBD, MERS S1, and MERS $S_1$ RBD.

| Target | Antibody clone | SARS-CoV2 S1 blocking | SARS-CoV2 RBD blocking | SARS-CoV2 active trimer blocking | SARS-CoV S1 blocking | SARS-CoV RBD blocking | MERS S1 blocking | MERS RBD blocking |
|---|---|---|---|---|---|---|---|---|
| S1 | 1035211 | 88.7% | 98.7% | 78.6% | 0.0% | 0.1% | 6.4% | 0.8% |
| S1 | 1035224 | 86.6% | 99.1% | 96.6% | 0.0% | 0.0% | 4.9% | 0.9% |
| S1 | 1035240 | 56.5% | 99.1% | 96.1% | 0.0% | 0.0% | 5.4% | 1.5% |
| RBD | 1035414 | 25.9%% | 85.2% | 51.4% | 12.0% | 0.4% | 5.4% | 0.5% |
| RBD | 1035419 | 70.1% | 90.2% | 89.0% | 88.5% | 44.1% | 5.8% | 1.9% |
| RBD | 1035423 | 19.7% | 94.1% | 91.6% | 0.0% | 0.0% | 5.4% | 0.9% |
| RBD | 1035433 | 9.3% | 93.7% | 82.5% | 0.0% | 0.0% | 6.0% | 1.1% |
| S1 | 1035709 | 93.6% | 94.7% | 96.5% | 0.0% | 0.0% | 4.1% | 0.9% |
| S1 | 1035716 | 93.8% | 94.6% | 96.5% | 89.5% | 68.7% | 6.0% | 0.9% |
| S1 | 1035740 | 93.4% | 94.6% | 96.5% | 92.4% | 98.8% | 7.4% | 1.5% |
| S1 | 1035744 | 84.2% | 85.4% | 1.4% | 0.6% | 0.2% | 6.7% | 0.8% |
| S1 | 1035752 | 93.3% | 94.5% | 91.8% | 0.0% | 0.0% | 6.6% | 1.1% |
| S1 | 1035753 | 94.0% | 94.7% | 96.6% | 0.0% | 0.0% | 6.4% | 0.9% |
| S1 | 1035755 | 93.3% | 94.1% | 84.6% | 1.3% | 0.0% | 6.3% | 1.3% |
| S1 | 1035762 | 93.2% | 94.1% | 93.0% | 0.0% | 0.0% | 6.0% | 0.7% |

Example 2

Figure 12B:
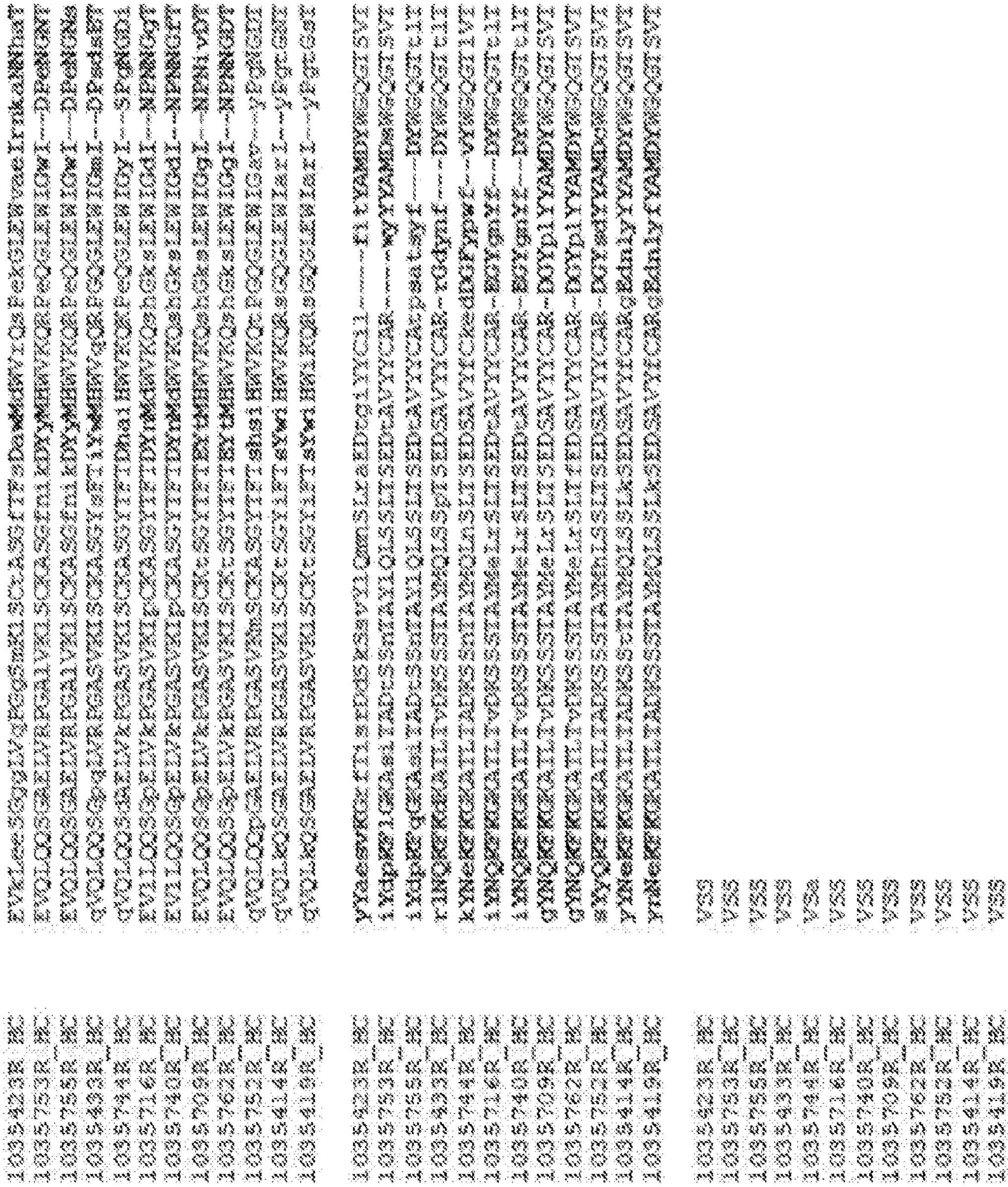

The antibodies described in Example 1 were sequenced. Results are shown in Tables 6-9. Sequence alignments of the various members of the antibody panel are shown in FIG. 9, FIG. 12A, and FIG. 12B. Multiple sequence alignment was performed using ClustalW, and annotation using the Kabat numbering scheme which included identification of loop and framework regions, as well as the canonical assignments of the CDR domains. Using this model, the three hypervariable regions (CDRs) in the V region are defined by number of different amino acids at a given position divided by the frequency of the most occurring amino acid at that position. Alignment is based upon the "Belvu Coloring Scheme" for coloring residues by conservation: Belvu light blue >3; light gray >0.2, and no shading if no conservation is calculated. The Belvu Scheme is an X-windows viewer constructed for multiple sequence alignments and uses the BLOSUM62 score system. Upper case letters indicate detection of conservation while lower case letters are a result of absence of any calculated conservation within the context of the multiple alignment.

TABLE 6

Annotated (Kabat numbering) variable light chain antibody sequences. CDR regions 1 thru 3 are bold and underlined; FR1 regions 1 thru 4 are in plain lettering.

| Antibody | Light Chain | SEQ ID NO: |
|---|---|---|
| 1035211 | DIKMTQSPSSMYASLGERVTITC**KASQDINSYLN**WFQQKPGKSPKTLIY**RANRLVD**<br>GVPSRFSGSGSGQDYSLTISSLEFEDMGIYYC**LQYDEFPYT**FGGGTKLEIK | 1 |
| 1035224 | QIVLTQSPAIMSASPGEKVTISC**SASSSVSYMY**WYQQKPGSSPKPWIY**RTSNLAS**<br>GVPARFSGSGSGTSYSLTISSMEAEDAATYYC**QQYHSYPYMYT**FGGGTKLEIK | 2 |
| 1035240 | DIKMTQSPSSMYASLGERVTITC**KASQDINSYLN**WFQQKPGKSPKTLIY**RANRLVD**<br>GVPSRFSGSGSGQDYSLTISSLEYEDMGIYYC**LQYDEFPYT**FGGGTKLEIK | 3 |
| 1035414 | NIVLTQSPASLAVSLGQRATISC**RASESVDSYGTSFMH**WYQQKPGQPPKLLIY**LASNLES**<br>GVPASFSGSGSRTDFTLTIDPVEADDAATYYC**QQNNEDPWT**FGGGTKLEIK | 4 |
| 1035419 | NIVLTQSPASLAVSLGQRATISC**RASESVDSYGASFMH**WCQQKPGQPPKLLIY**LASNLES**<br>GVPARFSGSGSRTDFTLTIDPVEADDAATYYC**QQNYEDPWT**FGGGTKLEIK | 5 |
| 1035423 | DIVLTQSQKFMSTSVGDRVSITC**KASQNVRTAVA**WYQQKPGQSPKALIY**LASNRHT**<br>GVPDRFTGSGSGTDFTLTISNVQSEDLADYFC**LQHWNYPLT**FGSGTKLELK | 6 |
| 1035433 | DIVMTQAAPSVPATPGESVSISC**RSSKSLLHSNGNTYLY**WFLQRPGQSPQLLIF**RMSNLAS**<br>GVPDRFSGSGSGTAFTLRISRVEAEDVGVYYC**MQHLEYPYT**FGGGTKLEIK | 7 |
| 1035709 | DIQMTQSPSSLSASLGERVSLTC**RASQEISGYLS**WLQQKPDGTIKRLIY**AASTLDS**<br>GVPKRFSGSRSGSDYSLTISSLESEDFADYYC**LQYASYPWT**FGGGTKLEIK | 8 |
| 1035716 | DILLTQSPAILSVSPGERVSFSC**RASQSIGTSIH**WYQQRTNGSPRLLIK**YASESIS**<br>GIPSRFSGSGSGTDYTLSINSVESEDIADYYC**QQSYSWPTT**FGAGTKLELK | 9 |
| 1035740 | DVLLTQSPAILSVSPGERVSFSC**RASQSIGTSLH**WYQQRTNGSPRLLIK**YVSESIS**<br>GIPSRFSGSGSGTDFTLSINSVESEDIADYYC**QQSSSWPTT**FGAGTKLELK | 10 |
| 1035744-1* | DIKMTQSPSSMYASLGERVTITC**KASQDINSYLS**WFQQKPGKSPKTLIY**RANRMVD**<br>GVPSRFSGSGSGQDYSLTISSLEYEDMGIYYC**LQYDEFPYT**FGGGTKLEIK | 11 |
| 1035744-2* | DVQITQSPSYLAASPGETITINC**RVSKSISKYLA**WYQEKPGKTDKLLIY**SGSTLQS**<br>GIPSRFSGSGSGQDYSLTISSLEYEDMGIYYC**LQYDEFPYT**FGGGTKLEIK | 12 |
| 1035752 | DIVMTQSQKFMSTSVGDRVSVTC**KASQNVGTNVA**WYQQKPGQSPKALIY**SASYRYS**<br>GVPDRFTGSGSGTDFTLTINNVQSEDLAEYFC**QQYNRYPWT**FGGGTKLEIK | 13 |
| 1035753 | DIQMTQTTSSLSASLGDRVTISC**SASQGISNYLNWY**QQKPDGTVKLLIY**YTSSLHS**<br>GVPSRFSGSGSGTDYSLTISNLEPEDIATYYC**QQYSKLPFT**FGGGTNLEMK | 14 |
| 1035755 | QIVLTQSPAIMSASPGEKVTISC**SASSSVSYMYWY**QQKPGSSPKPWIY**RTSNLAS**<br>GVPARFSGSGSGTSYSLTISSMEAEDAATYYC**QQYHSYPYMYT**FGGGTKLEIK | 15 |
| 1035762 | DIQMTQSPSSLSASLGERVSLTC**RASQEISGYLC**WLQQKPDGTIKRLIY**AASTLDS**<br>AVPKRFSGSRSGSDYSLTISSLESEDFADFYC**LQYASYPWT**FGGGTKLEIK | 16 |

*1035744.11 appears to be bi-clonal; that is, the clone produced antibodies with one heavy chain and two light chains in repeated rounds of sequencing

TABLE 7

Annotated (Kabat numbering) variable heavy chain antibody sequences. CDR regions 1 thru 3 are bold, underlined, and highlighted in yellow; FR1 regions 1 thru 4 are in plain black lettering.

| Antibody | Heavy Chain | SEQ ID NO: |
|---|---|---|
| 1035211 | QVQLQQSGAELARPGASVKMSCKASGYTFT**NYTMH**WVKQRPGQGLEWIG**YINPSSGYTNYNQKFKD** KATLTADKSSSTAYMQLSSLTSEDSAVYYCAR**RNPLYAMDY**WGQGTSVTVSS | 17 |
| 1035224 | EVQLQQSGAEFVRPGALVKLSCKASGFNIK**DDYMH**WVKQRPEQGLEWIG**WIDPENGNSIYDPKFQG** KASITADTSSNTAYLQLSSLTSEDTAVYYCAR**GEYFGSGSFAY**WGQGTLVTVSA | 18 |
| 1035240 | QVQLQQSGAELARPGASVKMSCKASGYTFT**TYTMH**WVKQRPGQGLEWIG**YINPSSGYTNYNQKFKD** KATLTADTSSSTAYMQLSSLTSEDSAVYYCAR**RNPLYAMDY**WGQGTSVTVSS | 19 |
| 1035414 | QVQLKQSGAELVRPGASVKLSCKTSGYIFT**SYWIH**WVKQRSGQGLEWIA**RIYPGTGNTYYNEKFKG** KATLTADKSSTTAYMQLSSLKSEDSAVYFCAR**GEDNLYYYAMDY**WGQGTSVTVSS | 20 |
| 1035419 | QVQLKQSGAELVRPGASVKLSCKTSGYIFT**SYWIH**WIKQRSGQGLEWIA**RIYPGTGSTYNNEKFKG** KATLTADKSSSTAYMQLSSLKSEDSAVYFCAR**GEDNLYFYAMDY**WGQGTSVTVSS | 21 |
| 1035423 | EVKLEESGGGLVQPGGSMKLSCTASGFTFS**DAWMD**WVRQSPEKGLEWVA**EIRNKANNHATYYAESVKG** RFTISRDDSKSSVYLQMNSLRAEDTGIYYCIL**FITYAMDY**WGQGTSVTVSS | 22 |
| 1035433 | QVQLQQSGPQLVRPGASVKISCKASGYSFT**IYWMH**WVQQRPGQGLEWIG**MIDPSDSETRLNQKFKD** KATLTVDKSSSTAYMQLSSPTSEDSAVYYCAR**RGDYNFDY**WGQGTTLTVSS | 23 |
| 1035709 | EVQLQQSGPELVKPGASVKISCKTSGYTFT**EYTMH**WVKQSHGKSLEWIG**GINPNIVDTGYNQKFKG** KATLTVDKSSSTAYMELRSLTSEDSAVYYCAR**DGYPLYYAMDY**WGQGTSVTVSS | 24 |
| 1035716 | EVLLQQSGPELVKPGASVKIPCKASGYTFT**DYNMD**WVKQSHGKSLEWIG**DINPNNGGTIYNQKFKG** KATLTVDKSSSTAYMELRSLTSEDTAVYYCAR**EGYGNYFDY**WGQGTTLTVSS | 25 |
| 1035740 | EVLLQQSGPELVKPGASVKIPCKASGYTFT**DYNMD**WVKQSHGKSLEWIG**DINPNNGFTIYNQKFKG** KATLTVDKSSSTAYMELRSLTSEDTAVYYCAR**EGYGNYFDY**WGQGTTLTVSS | 26 |
| 1035744 | QVQLQQSDAELVKPGASVKISCKASGYTFT**DHAIH**WVKQKPEQGLEWIG**YISPGNGDIKYNEKFKG** KATLTADKSSNTAYMQLNSLTSEDSAVYFCKE**DDGFYPWFVY**WGQGTLVTVSA | 27 |
| 1035752 | QVQLQQPGAELVRPGASVKMSCKASGYTFT**SHSIH**WVKQTPGQGLEWIG**AVYPGNGDTSYYQKFKG** KATLTADKSSSTAYMHLSSLTSEDSAVYYCAR**DGYSDYYAMDC**WGQGTSVTVSS | 28 |
| 1035753 | EVQLQQSGAELVRPGALVKLSCKASGFNIK**DYYMH**WVKQRPEQGLEWIG**WIDPENGNTIYDPKFLG** KASITADTSSNTAYLQLSSLTSEDTAVYYCAR**WYYYAMDS**WGQGTSVTVSS | 29 |
| 1035755 | EVQLQQSGAELVRPGALVKLSCKASGFNIK**DYYMH**WVKQRPEQGLEWIG**WIDPENGNSIYDPKFQG** KASITADTSSNTAYLQLSSLTSEDTAVYYCAT**PSATSYFDY**WGQGTTLTVSS | 30 |
| 1035762 | EVQLQQSGPELVKPGASVKISCKTSGYTFT**EYTMH**WVKQSHGKSLEWIG**GINPNNGDTGYNQKFKG** KATLTVDKSSSTAYMELRSLTFEDSAVYYCAR**DGYPLYYAMDY**WGQGTSVTVSS | 31 |

TABLE 8

CDR regions of light chains

| Antibody | | Light Chain | SEQ ID NO: |
|---|---|---|---|
| 1035211 | CDR 1 | KASQDINSYLN | 32 |
| | CDR 2 | RANRLVD | 33 |
| | CDR 3 | LQYDEFPYT | 34 |
| 1035224 | CDR 1 | SASSSVSYMY | 35 |
| | CDR 2 | RTSNLAS | 36 |
| | CDR 3 | QQYHSYPYMYT | 37 |
| 1035240 | CDR 1 | KASQDINSYLN | 32 |
| | CDR 2 | RANRLVD | 33 |
| | CDR 3 | LQYDEFPYT | 34 |
| 1035414 | CDR 1 | RASESVDSYGTSFMH | 47 |
| | CDR 2 | LASNLES | 39 |
| | CDR 3 | QQNNEDPWT | 48 |
| 1035419 | CDR 1 | RASESVDSYGASFMH | 38 |
| | CDR 2 | LASNLES | 39 |
| | CDR 3 | QQNYEDPWT | 40 |

TABLE 8-continued

CDR regions of light chains

| Antibody | | Light Chain | SEQ ID NO: |
|---|---|---|---|
| 1035423 | CDR 1 | KASQNVRTAVA | 41 |
| | CDR 2 | LASNRHT | 42 |
| | CDR 3 | LQHWNYPLT | 43 |
| 1035433 | CDR 1 | RSSKSLLHSNGNTYLY | 44 |
| | CDR 2 | RMSNLAS | 45 |
| | CDR 3 | MQHLEYPYT | 46 |
| 1035709 | CDR 1 | RASQEISGYLS | 49 |
| | CDR 2 | AASTLDS | 50 |
| | CDR 3 | LQYASYPWT | 51 |
| 1035716 | CDR 1 | RASQSIGTSIH | 52 |
| | CDR 2 | YASESIS | 53 |
| | CDR 3 | QQSYSWPTT | 54 |

TABLE 8-continued

CDR regions of light chains

| Antibody | | Light Chain | SEQ ID NO: |
|---|---|---|---|
| 1035740 | CDR 1 | RASQSIGTSLH | 55 |
| | CDR 2 | YVSESIS | 56 |
| | CDR 3 | QQSSSWPTT | 57 |
| 1035744-1 | CDR 1 | KASQDINSYLS | 58 |
| | CDR 2 | RANRMVD | 59 |
| | CDR 3 | LQYDEFPYT | 34 |
| 1035744-2 | CDR 1 | RVSKSISKYLA | 60 |
| | CDR 2 | SGSTLQS | 61 |
| | CDR 3 | LQYDEFPYT | 34 |
| 1035752 | CDR 1 | KASQNVGTNVA | 62 |
| | CDR 2 | SASYRYS | 63 |
| | CDR 3 | QQYNRYPWT | 64 |
| 1035753 | CDR 1 | SASQGISNYLN | 65 |
| | CDR 2 | YTSSLHS | 66 |
| | CDR 3 | QQYSKLPFT | 67 |
| 1035755 | CDR 1 | SASSSVSYMYWY | 35 |
| | CDR 2 | RTSNLAS | 36 |
| | CDR 3 | QQYHSYPYMYT | 37 |
| 1035762 | CDR 1 | RASQEISGYLC | 68 |
| | CDR 2 | AASTLDS | 50 |
| | CDR 3 | LQYASYPWT | 51 |

TABLE 9

CDR regions of heavy chains

| Antibody | | Heavy Chain | SEQ ID NO: |
|---|---|---|---|
| 1035211 | CDR 1 | NYTMH | 69 |
| | CDR 2 | YINPSSGYTNYNQKFKD | 70 |
| | CDR 3 | RNPLYAMDY | 71 |
| 1035224 | CDR 1 | DDYMH | 72 |
| | CDR 2 | WIDPENGNSIYDPKFQG | 73 |
| | CDR 3 | GEYFGSGSFAY | 74 |
| 1035240 | CDR 1 | TYTMH | 75 |
| | CDR 2 | YINPSSGYTNYNQKFKD | 70 |
| | CDR 3 | RNPLYAMDY | 71 |
| 1035414 | CDR 1 | SYWIH | 76 |
| | CDR 2 | RIYPGTGNTYYNEKFKG | 85 |
| | CDR 3 | GEDNLYYYAMDY | 86 |
| 1035419 | CDR 1 | SYWIH | 76 |
| | CDR 2 | RIYPGTGSTYNNEKFKG | 77 |
| | CDR 3 | GEDNLYFYAMDY | 78 |
| 1035423 | CDR 1 | DAWMD | 79 |
| | CDR 2 | EIRNKANNHATYYAESVKG | 80 |
| | CDR 3 | FITYAMDY | 81 |
| 1035433 | CDR 1 | IYWMH | 82 |
| | CDR 2 | MIDPSDSETRLNQKFKD | 83 |
| | CDR 3 | RGDYNFDY | 84 |
| 1035709 | CDR 1 | EYTMH | 87 |
| | CDR 2 | GINPNIVDTGYNQKFKG | 88 |
| | CDR 3 | DGYPLYYAMDY | 89 |
| 1035716 | CDR 1 | DYNMD | 90 |
| | CDR 2 | DINPNNGGTIYNQKFKG | 91 |
| | CDR 3 | EGYGNYFDY | 92 |

TABLE 9-continued

CDR regions of heavy chains

| Antibody | | Heavy Chain | SEQ ID NO: |
|---|---|---|---|
| 1035740 | CDR 1 | DYNMD | 90 |
| | CDR 2 | DINPNNGFTIYNQKFKG | 93 |
| | CDR 3 | EGYGNYFDY | 92 |
| 1035744 | CDR 1 | DHAIH | 94 |
| | CDR 2 | YISPGNGDIKYNEKFKG | 95 |
| | CDR 3 | DDGFYPWFVY | 96 |
| 1035752 | CDR 1 | SHSIH | 97 |
| | CDR 2 | AVYPGNGDTSYYQKFKG | 98 |
| | CDR 3 | DGYSDYYAMDC | 99 |
| 1035753 | CDR 1 | DYYMH | 100 |
| | CDR 2 | WIDPENGNTIYDPKFLG | 101 |
| | CDR 3 | WYYYAMDS | 102 |
| 1035755 | CDR 1 | DYYMH | 100 |
| | CDR 2 | WIDPENGNSIYDPKFQG | 73 |
| | CDR 3 | PSATSYFDY | 103 |
| 1035762 | CDR 1 | EYTMH | 87 |
| | CDR 2 | GINPNNGDTGYNQKFKG | 104 |
| | CDR 3 | DGYPLYYAMDY | 89 |

Significant homology was observed in FR-L3, L4, H1, and H3 regions among all the antibodies in this panel. A high degree of diversity was seen in the LC CDRs of all the antibodies. However, a closer analysis of CDR-H3 diversity indicated three distinct populations with diverse CDR H3 sequences representing structurally distinct possibilities for critical antigen engagements with a given epitope and binding modality.

Example 3

Use of the Lateral Flow Immunoassay to Characterize SARS-CoV-2 RBD-Specific Antibodies and Their Ability to React with the UK, SA, and BR P.1 Variant RBDs Identifying anti-spike antibodies that maintain strong neutralizing activity against current dominant circulating variants and antibodies that are escaped by these variants have important implications in the development of therapeutic and diagnostic solutions as well as in improving understanding of the humoral response to SARS-CoV-2 infection. With this example, seven anti-RBD monoclonal antibodies are characterized for binding activity, pairing capability, and neutralization activity to SARS-CoV-2 and three RBD variants (UK, SA, and BR P.1) via lateral flow immunoassays. From these studies, the antibodies were classified into three distinct epitope bins. Two antibodies had strong neutralizing activity against all four RBDs and one antibody was completely escaped by the SA and BR P.1 RBDs. The antibody escaped by the SA and BR P.1 RBDs retained binding to SA and BR P.1 RBDs but was unable to induce neutralization. Further, this example demonstrated that the lateral flow immunoassay can be a rapid and effective tool for antibody characterization and determining epitope bins and antibody neutralization kinetics. From these studies, the potential contributions of the mutations (N501Y, E484K and K417N/T) contained in these variant RBDs on their antibody pairing capability, neutralization activity and therapeutic antibody targeting strategy were discussed.

Introduction

The continued emergence of SARS-CoV-2 variants has raised concerns and challenges for the control, prevention, and management of the coronavirus disease (COVID-19) (Abdool Karim et al. *N Engl J Med* 384, 1866-1868 (2021)). Currently, the circulating variants of greatest concern include the United Kingdom variant (B.1.1.7 lineage, UK) (Santos et al. *bioRxiv,* 2020.2012.2029.424708 (2021)) (Rambaut et al. nCoV-2019 *Genomic Epidemiology—Virological*, (2020)) the South African variant (B.1.351 lineage, SA) (Villoutreix et al. *International Journal of Molecular Sciences* 22, 1695 (2021)), the Brazilian variant P.1 (B.1.1.28.1 lineage, BR P.1) (Faria et al. *Science* 372, 815-821 (2021)), the Brazilian variant P.2 (B.1.1.28.2 lineage, BR P.2) (Voloch et al. *Journal of Virology* 95, e00119-00121 (2021)), the Denmark mink variant (B.1.1.298 lineage, DM) (Bayarri-Olmos et al. *bioRxiv,* 2021.2001.2029.428834 (2021)), the California variants (B.1.429/427 lineage, CA) (Zhang et al. *JAMA* 325, 1324-1326 (2021)), the New York variants (B.1.526/525 lineage, NY) (Annavajhala et al. *medRxiv,* 2021.2002.2023.21252259 (2021)), and the more recent Indian variant (B.1.617 lineage, IN) (Cherian et al. *bioRxiv,* 2021.2004.2022.440932 (2021)). In the absence of an effective strategy to curb the spread of SARS-CoV-2 virus infection and more individuals harboring the virus, it is inevitable that more variants will emerge.

The SARS-CoV-2 virus infects mammalian cells by attaching transmembrane spike proteins (S protein) to angiotensin-converting enzyme 2 receptors (ACE-2) found on the surface of human target cells (Ou et al. *Nature Communications* 11, 1620 (2020)) (Shang et al. *Proceedings of the National Academy of Sciences* 117, 11727-11734 (2020)). Hence, inhibiting the binding of SARS-CoV-2 spike protein to ACE-2 has been the primary strategy behind most SARS-CoV-2 vaccines (Jackson et al. *N Engl J Med* 383, 1920-1931 (2020)) (Mulligan et al. *Nature* 590, E26-E26 (2021)), therapeutic antibodies (Food and Drug Administration. Letter to Regeneron Pharmaceuticals, Inc. (21 Nov. 2020)) (Food and Drug Administration. Letter to Eli Lilly and Company. (10 Nov. 2020)), and therapeutic soluble ACE-2 molecules (Zoufaly et al. *Lancet Respir Med* 8, 1154-1158 (2020)). It is evident that the receptor binding domain (RBD) of the viral spike protein plays a critical role in the binding of SARS-CoV-2 to ACE-2.

As of May 14, 2021, there are two therapeutic neutralizing antibody cocktails in use for the treatment of COVID-19 patients that have received Emergency Use Authorization from the FDA ((Food and Drug Administration, Letter to Regeneron Pharmaceuticals, Inc. (21 Nov. 2020)) (Food and Drug Administration. Letter to Eli Lilly and Company. (10 Nov. 2020)). Regeneron's REGN-COV2 is a combination of two anti-SARS-CoV-2 RBD monoclonal antibodies (REGN10933 and REGN10987), and Eli Lily's cocktail is a combination of two anti-SARS-CoV-2 RBD monoclonal antibodies (LY-CoV555 and LY-CoV016). Unfortunately, SARS-CoV-2 variants have rendered monoclonal antibody therapies and spike protein-based vaccines less effective (Xie et al. *Nature Medicine* 27, 620-621 (2021)) (Hansen et al. *Science* 369, 1010-1014 (2020)). In fact, the FDA recently revoked the Emergency Use Authorization for the monoclonal antibody (LY-CoV555) monotherapy due to the sustained increase in COVID-19 viral variants that are resistant to LY-CoV555 (FDA Revokes Emergency Use Authorization for Monoclonal Antibody Bamlanivimab, (2020)).

Viral variants contain numerous mutations and/or deletions along the viral spike protein, this analysis focuses on the key mutations in the RBD that have a direct impact on the RBD-ACE-2 interaction and the escape mechanism of virus from the neutralizing antibodies. FIG. 14 summarizes currently circulating SARS-CoV-2 variants and their respective mutations within the spike RBD, including: N501Y in the UK, SA, and BR-P.1 variants (Santos et al. *bioRxiv,* 2020.2012.2029.424708 (2021); Rambaut et al. *nCoV*-2019 *Genomic Epidemiology—Virological*, (2020)); E484K/Q in the SA, BR P.1, BR P.2, NY and IN variants (Rambaut et al. *nCoV*-2019 *Genomic Epidemiology—Virological*, (2020); Ou et al. *Nature Communications* 11, 1620 (2020)); K417N/T in the SA and BR P.1 variants (Faria et al. *Science* 372, 815-821 (2021); Voloch et al. *Journal of Virology* 95, e00119-00121 (2021)); L452R in the CA and IN variants (Zhang et al. *Jama* 325, 1324-1326 (2021); Cherian et al. *bioRxiv,* 2021.2004.2022.440932 (2021)); S477N in the NY variant (Annavajhala et al. *medRxiv,* 2021.2002.2023.21252259 (2021)); and Y453F in the Denmark mink variant (Bayarri-Olmos et al. *bioRxiv,* 2021.2001.2029.428834 (2021)). These mutations cause a higher rate of viral infectivity, enhanced disease severity, and escape the antibody neutralization action, resulting in reduced vaccine efficacy (Xie et al. *Nature Medicine* 27, 620-621 (2021)). Starr et. al. was able to demonstrate that the RBD containing the E484K mutation escapes LY-CoV555 antibody, and the RBD containing the K417N/T mutations escapes LY-CoV016 antibody by mapping the SARS-CoV-2 RBD mutations (Starr et al. *bioRxiv*, (2021)).

To better understand how mutations mediate escape of antibody neutralizing activity and to identify anti-RBD antibodies for potential diagnostic and therapeutic uses against SARS-CoV-2 variant infection, a straightforward lateral flow immunoassay was employed to characterize seven anti-RBD monoclonal antibodies for their binding activity, pairing capability and neutralizing activity to SARS-CoV-2 RBD and UK, SA, and BR P.1 variant RBDs. The objectives were three-fold: (1) to screen and identify variant-specific antibodies or escaped neutralizing antibodies for potential diagnostic applications, (2) to characterize and identify broadly potent neutralizing antibodies against SARS-CoV-2 and the variant RBDs for improved neutralization strategies, and (3) to explore the use of rapid lateral flow-based dipstick assay and cassette assay for such studies. It is reported in this example that two of the seven antibodies studied have broad, potent neutralizing activity against SARS-CoV-2 RBD and three variant RBDs and that one antibody has strong neutralizing activity against SARS-CoV-2 RBD and UK variant RBD but has lost the neutralizing activity against the SA and BR P.1 variant RBDs.

Materials and Methods

Anti-SARS-CoV-2 RBD Antibodies

Seven in-house generated anti-SARS-CoV-2 spike RBD murine monoclonal antibodies (Ab1-Ab7) were selected for this analysis. Ab1 (clone No. 1035709), Ab2 (clone No. 1035740), Ab3 (clone No. 1035753) and Ab4 (clone No. 1035762) were generated using the SF21-derived SARS-CoV-2 S1 subunit as the immunogen. Ab5 (clone No. 1035419) was generated using the HEK293-derived SARS-CoV-2 RBD (R319-F541) protein as the immunogen. Ab6 (clone No. 1035224) and Ab7 (clone No. 1035240) were generated using SARS-CoV-2 S1 subunit in a separate fusion. An anti-nucleocapsid monoclonal antibody (anti-NP, clone No. 1035138), generated in-house using the SARS-CoV-2 nucleocapsid full-length protein as immunogen, was used as negative control.

Recombinant SARS-CoV-2 and Variant RBDs

All recombinant RBD proteins were generated in-house (R&D Systems, Minneapolis, MN) corresponding to NCBI reference sequence using the HEK293 expression system, accession YP_009724390.1 (NCBI Reference Sequence). Recombinant RBD proteins include the SARS-CoV-2 RBD (R319-F541), the UK variant RBD (R319-F541 with N501Y), the SA variant RBD (R319-F541 with K417N, E484K, N501Y), and the BR P.1 variant RBD (R319-F541 with K417T, E484K, N501Y). Secreted recombinant proteins were purified from the conditioned media by nickel chelating chromatography, followed by size exclusion chromatography. All recombinant RBD constructs include a C-terminal 6-His tag.

Other Materials

Triton X-100, 30% bovine serum albumin (BSA) solution, 30% Brij-35 solution, 10× phosphate buffered saline (PBS), and other chemicals were from Millipore-Sigma (Burlington, MA). Casein solution (1%) in Tris buffer, pH 7.4, was from Thermo Fisher Scientific (Waltham, MA). Recombinant human ACE-2 protein, goat polyclonal anti-chicken IgY antibody and chicken IgY protein (cIgY) were from R&D Systems (Minneapolis, MN).

Preparation of Antibody-AuNP Conjugate

Anti-RBD antibodies were conjugated to 40 nm citrate protected gold nanoparticles (AuNP, nanoComposix, San Diego, CA) using a direct adsorption according to a procedure modified from the manufacture recommended protocol. Briefly, AuNP solution of 20 OD was combined with high purity water at 1:4 ratio (1 part of AuNP solution in 0.02 mM sodium citrate and 4 parts of water; volume/volume). Antibody solution in 1×PBS was added to the AuNP solution at 5% or less of the total reaction volume, with the antibody to AuNP ratio of 50 μg antibody per mL of 20 OD AuNP. Due to partial particle aggregation during the adsorption process, the amount of Ab7 was reduced to 20 μg per mL 20 OD AuNP solution. For the analysis on the discriminative binding characteristic of the Ab7-Ab4 pair to the four RBDs, Ab4 and Ab5 were adsorbed at 20 jig per mL 20 OD AuNP solution. After the AuNP and antibody mixture was incubated at ambient room temperature for 30 minutes, BSA was added to a final concentration of 5 mg/mL to block the remaining AuNP surface. After another 30-minute incubation period, the AuNP and antibody conjugate solution was centrifuged at 3800 RCF for 10 minutes to pellet the AuNP-antibody conjugate. The conjugate was washed twice with wash and storage buffer, then finally resuspended in wash and storage buffer, and stored at 4° C. until use. The optical density of the conjugate solution was confirmed by an absorbance reading at 525 nm using the NanoDrop 2000 spectrophotometer. The wash and storage buffer is composed of 0.05×PBS, pH 7.4, containing 0.5% (w/v) BSA and 0.05% (w/v) sodium azide.

Lateral Flow Dipstick and Assay Procedure for Antibody Pairing Capability and Epitope Binning Dipsticks were prepared using a 60 mm×300 mm FF120HP nitrocellulose membrane card (Cytiva, Marlborough, MA). The 20 mm wide adhesive with release liner was removed from the nitrocellulose card using a paper cutter. The 15 mm wide adhesive portion was attached with a 17 mm×300 mm cellulose fiber sample pad strip as the absorbent pad (Millipore-Sigma, Burlington MA) with ~2 mm overlapping the nitrocellulose membrane. The card assembly was cut to 40 mm wide dipsticks using a Matrix 2360 Programmable Shear. Therefore, each dipstick is composed of a plastic backing with 25 mm long nitrocellulose membrane and a 17 mm long absorbent pad.

Dipsticks were coated with a single row of nine-spot protein array, consisting of 7 spots for the anti-RBD antibodies, two spots for the anti-NP antibody and BSA, as negative controls. Each protein was diluted to 1 mg/mL in 1×PBS, pH 7.4 and the protein panel were manually pipetted onto the nitrocellulose membrane at 1 μL per spot. The coated dipsticks were dried at 37° C. oven with air constantly blowing for at least 30 minutes prior to use or kept in a plastic bag with desiccant.

To run the lateral flow dipstick assay for the epitope binning and pairing capability analysis, the dipstick with the protein array was placed in a reservoir, with the nitrocellulose end at the bottom, allowing the liquid to flow into the nitrocellulose membrane and then to the absorbent pad away from the point of origin where the sample was applied. Immediately prior to running an assay, a 300 μL sample mixture was prepared by mixing 150 μL 1 μg/mL RBD protein solution made in assay run buffer, 80 μL antibody-AuNP conjugate of 4 OD solution in wash and storage buffer, and 70 μL assay run buffer. The sample mixture was added to the reservoir and allowed to run for 12-15 minutes until the sample mixture ran out. A second liquid of 250 μL assay run buffer was added and run for another 12-15 minutes to rinse off the non-bound antibody-AuNP conjugates. Thus, each assay run took approximately 30 minutes from the addition of sample mixture to the finish of the assay rinse. The capture antibody-(RBD antigen)-antibody-AuNP complexes accumulate on the coated protein spots of the nitrocellulose membrane and form a red-colored crescent line or circular spot. The assay run buffer was made of 1×PBS, pH 7.4, with 1.5% (w/v) BSA, 0.25% (w/v) Tween-20, 0.2% (w/v) casein, and 0.025% (w/v) sodium azide. The dipsticks were imaged using an iPhone camera.

For evaluating the comparative binding characteristics to four RBD proteins, the assay procedure was modified for better assay sensitivity. All steps were the same as the above procedure for the epitope binning and pairing capability analysis, except (1) the 300 μL sample mixture was prepared by mixing 50 μL RBD protein solution made in the Brij-35 assay buffer, 404 antibody-AuNP conjugate of 4 OD in the wash and storage buffer, and 210 μL Brij-35 assay buffer; (2) 250 μL Brij-35 assay buffer was used as the assay chase buffer; (3) The Brij35 assay buffer was composed of 1×PBS, pH 7.4, containing 1% (w/v) BSA, 0.1% (v/v) TX-100, 0.3% (v/v) Brij-35 and 0.3% (w/v) casein and 0.05% (w/v) sodium azide.

Lateral Flow Cassette and Assay Procedure for the Neutralization Kinetics

The lateral flow neutralization test devices were developed and manufactured according to the procedures developed in-house. Briefly, recombinant human ACE-2 and goat polyclonal anti-chicken IgY antibody were striped in the "test zone" and the "control zone" as the capture agents, respectively, using an IsoFlow Reagent Dispenser. Recombinant RBD and cIgY were conjugated onto the 40 nm gold nanoparticles as the detectors for the test zone and the control zone, respectively. The AuNP-RBD and AuNP-cIgY conjugates were pooled in a drying down buffer containing salt, stabilizer and AuNP releasing agents and sprayed onto conjugate pad strips using an IsoFlow Reagent Dispenser. Sprayed conjugate pad strips were dried at 37° C. and stored in sealed foil pouches with desiccants until use. Four types of rapid neutralizing antibody test cassettes were prepared for SARS-CoV-2 RBD and UK, SA, and BR P.1 variant RBDs by alternating the AuNP-RBD conjugate while keeping other components the same.

The neutralization antibody test strip consists of a plastic backing card attached with a sample pad, a conjugate pad with dried gold conjugate detectors, a nitrocellulose membrane stripped with the capture antibodies, and an absorbent (wicking) pad. Each test strip is assembled into a plastic cassette and sealed in a foil pouch with desiccant, stored at ambient room temperature, with at least 3-month stability (longest time point tested so far). The dropper bottle used for introducing the neutralization assay buffer has a drop size of ~25 μL per drop. The neutralization assay buffer is composed of 1×PBS, pH 7.4, containing 3% (w/v) BSA, 0.5% (v/v) Tween-20 and (w/v) sodium azide.

To run a neutralization kinetic curve for a given antibody, the antibody was diluted in neutralization assay buffer, with the antibody concentrations at 10, 2, 0.5, and 0.1 μg/mL, respectively, and the zero-antibody control. The assays were run in stacking modes with each assay delaying for 30 seconds for up to 20 tests per run or delaying for 60 seconds for up to 10 tests per run. Each run took slightly more than 20 minutes, including 10 minutes of assay time and 10 minutes for reading the test cassettes using an LFA reader. For each cassette assay, an aliquot of 20 μL diluted antibody solution was added to the sample port of the test cassette to start the assay. After the antibody sample absorbing for ~25 seconds, three drops (~75 μL) of neutralization assay buffer was added to the sample port using a dropper bottle. The signal intensities of the test zone, the control zone, and a reference negative zone were measured at 10 minutes from the start of the assay using an RDS-2500 LFA reader. If the antibody has no neutralizing activity, the AuNP-RBD conjugate is captured by the immobilized ACE-2 at the test zone and a darker red colored test line is formed. If the antibody has neutralizing activity, then the antibody will bind to the AuNP-RBD and prevent it from being captured by the immobilized ACE-2, resulting in a lighter red or no red colored test line at all. The cIgY control zone serves to monitor that the added liquid to the sample port has properly flowed through the test strip and the biological reagents of the test strip are active. The reference negative zone is the entering area of the test view window of the cassette, that has no printed capture agent, but rather serves as a general flow control.

Each test will have three intensity values—for the control zone, the test zone, and the reference negative zone. For the comparison of the neutralizing activity against SARS-CoV-2 and three variant RBDs, four sets of data were collected for each antibody. Two or three replicates were run for each antibody concentration, except the zero-antibody control with 6-8 replicates per test condition.

Determination of the $NC_{50}$ for the Neutralization Kinetic Curve

The $NC_{50}$ in μg/mL is the concentration of antibody that yields a 50% inhibition or neutralization of the maximal RBD-ACE-2 binding capacity for a given neutralization cassette type. To calculate the $NC_{50}$ value per device type for each antibody, the mean signal intensity of the test zone was first calculated from the replicates of the zero-antibody concentration to represent the maximum RBD-ACE-2 binding activity (100% binding capacity or 0% neutralization). When an antibody has neutralizing activity, the binding capacity of AuNP-RBD conjugate to immobilized ACE-2 is reduced. Thus, the decreased portion of the binding activity from the maximum binding activity is the neutralization activity in percentage (% Neutralization).

The % Neutralization of each individual test was calculated from the signal intensity of the test zone using the conversion formula shown below:

$$\%\ \text{Neutralization of individual test} = [\text{Mean intensity}_{zero\text{-}Ab} - \text{Signal Intensity}_{individual\ test}) / \text{Mean Intensity}_{zero\text{-}Ab}].$$

Figure 15:
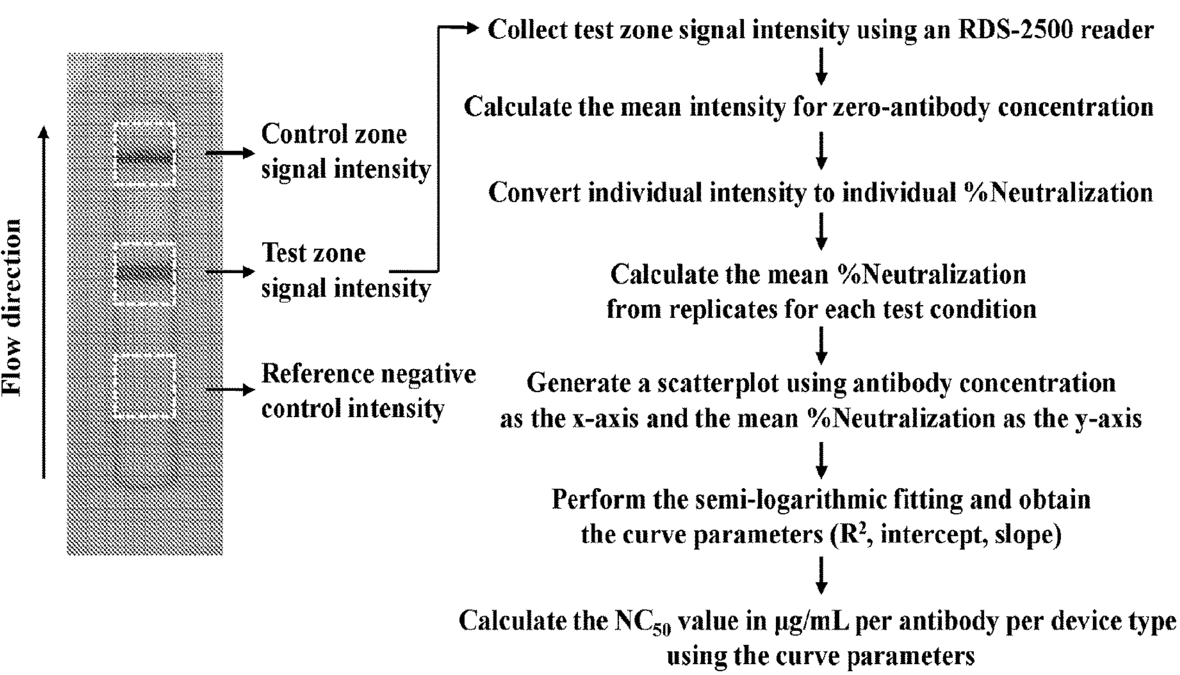
FIG. 15 shows a collection of signal intensities and flowchart for the calculation of the $NC_{50}$ from the signal intensity. On the left is an example of test cassette image recorded by the RDS-2500 reader with designated zones for collection of signal intensities. On the right is a flowchart for the calculation of the $NC_{50}$ value for each neutralization kinetic curve.

The averaged % Neutralization and the standard deviation were then calculated from the converted % Neutralization replicate values for each test condition. A scatterplot was generated using the antibody concentration as the x-axis and the averaged % Neutralization value as the y-axis. A semi-logarithmic curve fitting was performed and used for the determination of the $NC_{50}$ value of each antibody against all RBDs (FIG. 15).

Instrumentation and Statistics

The Nanodrop 2000 spectrophotometer was purchased from Thermo Fisher Scientific (Waltham, MA). The RDS-2500 LFA reader was purchased from Detekt Biomedical LLC (Austin, TX) with the default R/G/B of 0/1/0 settings. Matrix 2360 Programmable Shear was purchased from Kinematic Automation (Sonora, CA). IsoFlow reagent dispenser was purchased from Imagene Technology (Lebanon, NH).

Results

Antibody Pairing Capability and Epitope Binning Using the SARS-CoV-2 RBD

Figure 16:
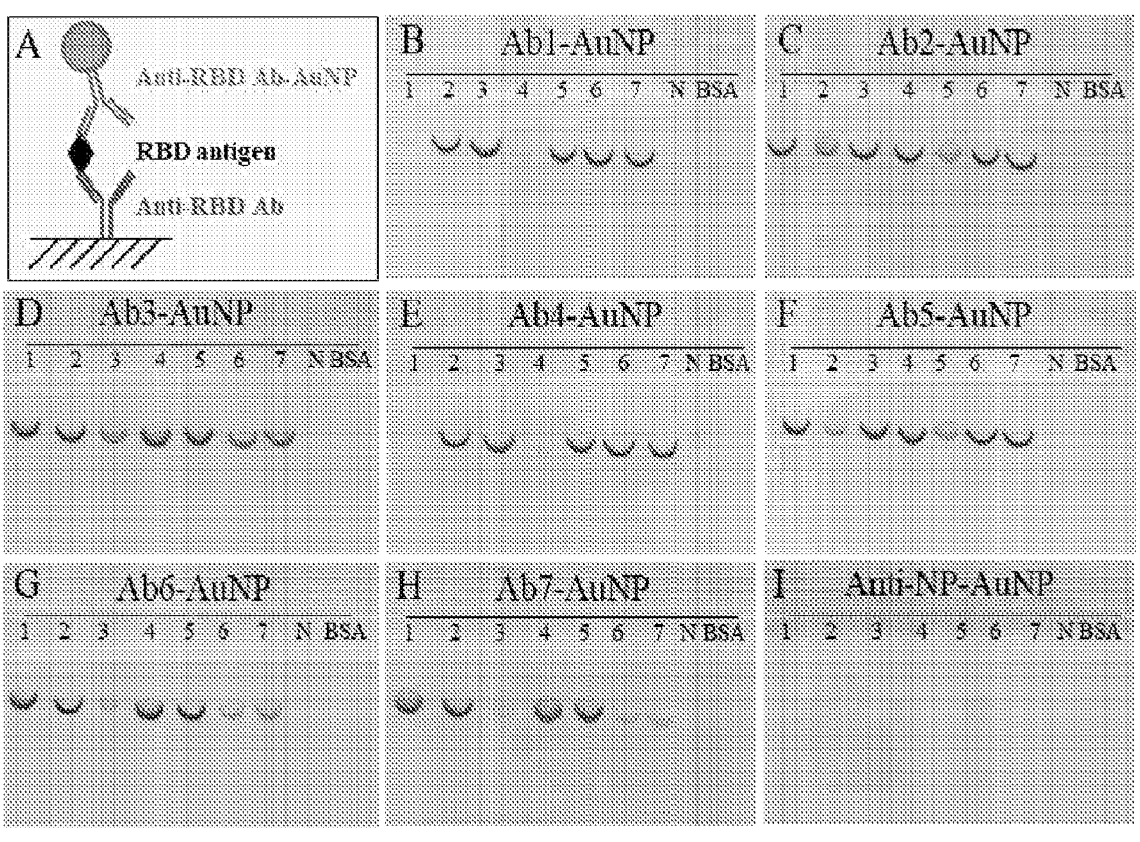
FIG. 16 shows antibody pairing capability and epitope binning, using the antibodies Ab1, Ab2, Ab3, Ab4, Ab5, Ab6, Ab7 as captures, paired with each anti-RBD-antibody conjugated gold nanoparticle as detector, for the detection SARS-CoV-2 RBD protein. Panel A is a schematic of the sandwich immunoassay test principle. Panels B-I are representative sets of photo images of lateral flow dipstick assays. Each dipstick has 9 spots: 7 spots for the antibodies of interest, and 2 negative control spots: anti-NP antibody and BSA. A dark crescent line or circular spot indicates strong binding activity, a light crescent line or circular spot indicates weak binding activity, and an empty spot indicates no binding activity. Ab1 is clone No. 1035709, Ab2 is clone No.

Seven anti-SARS-CoV-2 RBD antibodies were studied for their pairing capability and epitope binning using a lateral flow dipstick immunoassay. These antibodies were spotted to lateral flow nitrocellulose membranes as capture agents, and then reacted with SARS-CoV-2 RBD in the presence of one antibody-AuNP conjugate. A non-competing antibody will pair and forms a sandwich immunocomplex with the SARS-CoV-2 RBD, appearing as a dark red colored crescent line or spot on the nitro-cellulose membrane. A competing antibody will not form a sandwich immunocomplex, appearing as a light red colored spot or no spot at all. The sandwich immunoassay principle is shown in panel A of FIG. 16. The immunodetection results for each detector anti-RBD antibody-AuNP conjugate and the negative control anti-NP antibody-AuNP conjugate are presented in panels B-I of FIG. 16. Based on the binding pattern and pairing capability, these antibodies were grouped into three epitope bins: bin A antibodies Ab1 and Ab4, bin B antibodies Ab2 and Ab5, and bin C antibodies Ab3, Ab6 and Ab7 (Table 10). The fact that these seven monoclonal antibodies were generated through three distinct fusions along with the classification of these antibodies into three epitope bins, suggests that these epitopes constitute dominant antigenic domains of SARS-CoV-2 RBD and play a very important role in the natural immune response to SARS-CoV-2 infection and, presumably, vaccination.

TABLE 10

Epitope bin and pairing summary.

| | Epitope Bin A | Epitope Bin B | Epitope Bin C |
|---|---|---|---|
| Detector | Ab1 and Ab4 | Ab2 and Ab5 | Ab3, Ab6 and Ab7 |
| Capture | Ab2, Ab3, Ab5, Ab6 & Ab7 | Ab1, Ab3, Ab4, Ab6 & Ab7 | Ab1, Ab2, Ab4 & Ab5 |

Comparative Binding Characteristics to Three Variant RBDs Vs. SARS-CoV-2 RBD

To investigate whether the above antibody pairings could detect the UK, SA, and BR P.1 RBD variants, similar dipstick sandwich immunoassays were performed using the same capture antibody panel along with three representative epitope bin detectors, Ab4-AuNP, Ab5-AuNP, and Ab6-AuNP conjugates, respectively. The initial experiment showed that the Ab7-Ab4 (capture/detector) has a discriminative detection of the four RBDs, with the SARS-CoV-2 and UK RBDs strongly detected and the SA and BR P.1 RBDs weakly detected. All other pairing options tested showed no apparent difference in the detection of these four RBDs.

To verify these discriminative binding characteristics, dipstick immunoassays were carried out using serially diluted RBD solutions, ranging from 0.001 μg/mL to 1 μg/mL. Since Ab6 and Ab7 belong to the sample epitope bin, only the Ab4-AuNP and Ab5-AuNP detectors were used in this confirmatory analysis. As shown in FIG. 17A, with the Ab5-AuNP as detector and Ab1, Ab3, Ab4, Ab6 and Ab7, as capture agents, all pairing options strongly detected the four RBDs with a detection sensitivity of 0.001 μg/mL. Similarly, with the Ab4-AuNP as detector (FIG. 17B) and Ab2, Ab3, Ab5 and Ab6 as capture agents, all pairing options detected the four RBDs with a detection sensitivity of 0.01 μg/mL. It's noteworthy that, Ab5-AuNP appeared to have a better detection sensitivity than Ab4-AuNP.

Interestingly, when the Ab4-AuNP detector was paired with Ab7 as the capture agent, the SARS-CoV-2 and UK RBDs were strongly detected with a detection sensitivity of 0.01 μg/mL; however, the SA and BR P.1 RBDs were weakly detected with a detection sensitivity between 0.1-1.0 μg/mL. This discriminative binding behavior of the Ab7-Ab4 pair for the detection of SARS-CoV-2 RBD and the three variant RBDs was also observed when Ab7 was paired with Ab1 (another bin A epitope antibody). Given the fact that the Ab5-AuNP pairing with Ab7 capture strongly detected the SA and BR P.1 RBDs and that the Ab4-AuNP pairing with antibodies Ab2, Ab3, Ab5 and Ab6 also strongly detected the SA and BR P.1 RBDs, both AB7 and Ab4 appear to bind to the SA and BR P.1 RBDs well alone. Therefore, the weak binding activity of the Ab7-Ab4 pair (and Ab7-Ab1 pair) to the SA and BR P.1 RBDs, as compared to the SARS-CoV-2 and UK RBDs, indicates that the E484K and K417N/T mutations contained in the SA and BR P.1 RBDs most likely induced conformational changes near or within the epitopes of where these antibodies bind. The conformational change could result in steric interference between Ab7 and bin A epitope antibodies.

Neutralizing Kinetics of Individual Antibody and Combination of Antibodies

To investigate the neutralization kinetics of these antibodies with the three variant RBDs in comparison to the original SARS-CoV-2 RBD, lateral flow neutralization cassette assays were carried out using rapid neutralizing antibody test devices for the SARS-CoV-2, the UK, the SA, and the BR P.1 RBDs. The lateral flow neutralization test principle is illustrated in FIG. 18A. Essentially, AuNP-RBD conjugates are captured by immobilized ACE2 protein in the absence of a neutralizing antibody, forming a red-colored line at the test zone; but if a neutralizing antibody is present then it will bind to the AuNP-RBD and prevent the AuNP-RBD from being captured by the immobilized ACE2 protein. The signal intensity of the test zone is inversely correlated with the concentration of the neutralizing antibody. The signal intensity of the control zone is not affected by the neutralizing antibody. A representative set of lateral flow neutralizing antibody test cassettes is depicted in FIG. 18B.

The neutralization kinetics of each individual antibody against SARS-CoV-2 RBD and three variant RBDs was studied using serially diluted antibody solutions targeting antibody concentrations at 10, 2, 0.5, 0.1 and 0 μg/mL suspended in neutralization assay buffer (FIG. 19A-6G). The $NC_{50}$ value was determined from the signal intensity of the test zone as described in the method section and shown in FIG. 15B. Five antibodies (Ab1, Ab2, Ab4, Ab6 and Ab7) showed strong neutralizing activity against the SARS-CoV-2 RBD with an $NC_{50}$ values between 0.34 and 1.43 μg/mL and two antibodies (Ab3 and Ab5) showed a moderate neutralizing activity against SARS-CoV-2 RBD with an $NC_{50}$ value of 1.66 and 3.27 μg/mL, respectively, indicating that the epitopes of these seven antibodies are all near or in the RBD interface zone. The $NC_{50}$ values for all seven antibodies against the four RBDs were summarized in Table 11.

TABLE 11

| | $NC_{50}$ (μg/mL) | | | | | | | |
|---|---|---|---|---|---|---|---|---|
| Neutralization Target | Ab1 | Ab2 | Ab1 + Ab2 | Ab3 | Ab4 | Ab5 | Ab6 | Ab7 |
| SARS-CoV-2 RBD | 0.63 | 1.43 | 0.50 | $1.66^{m}$ | 0.69 | $3.27^{m}$ | 0.66 | 0.34 |
| UK variant RBD | 1.08 | 1.35 | 0.82 | $1.51^{m}$ | 0.95 | $27.63^{w}$ | $2.72^{m}$ | 0.86 |
| South African variant RBD | 0.91 | $1.83^{m}$ | 0.66 | $3.19^{m}$ | 0.70 | $24.03^{w}$ | 1.14 | ** |
| Brazilian P.1 variant RBD | 0.70 | 1.40 | 0.46 | $2.21^{m}$ | 0.69 | $44.79^{w}$ | 1.11 | ** |

$NC_{50}$ summary table. Semi-logarithmic curve fitting was used to extrapolate the $NC_{50}$ values. For antibody Ab5, the range of 0.5~10 μg/mL was used for curve fitting. For other six antibodies and the combined antibodies, the range of 0.1~10 μg/mL was used for curve fitting. Strong neutralizing activity: $NC_{50} < 1.5$ μg/mL; Moderate neutralizing activity (indicated by a superscript "m"): 1.5 μg/mL ≤ $NC_{50} < 15$ μg/mL Weak or no neutralizing activity indicated by a superscript "w"): $NC_{50} \geq 15$ μg/mL.
** Indicate that the $NC_{50}$ value was not calculated due to flat nature of the curve and the very weak neutralizing activity.

Two antibodies, Ab1 and Ab4 of bin A, maintained strong neutralizing activity against the three variant RBDs with an $NC_{50}$ value between 0.69 and 1.08 μg/mL, suggesting that these two antibodies target an epitope that is not affected by the mutations (N501Y, E484K and K417N/T) contained in the UK, SA, and BR P.1 variant RBDs. The remaining five monoclonal antibodies either partially or completely lost their neutralizing activity against at least one variant RBD. Ab7 showed strong neutralizing activity against the SARS-CoV-2 and UK RBDs with an $NC_{50}$ value of 0.34 and 0.86 μg/mL, respectively, but completely lost its neutralizing activity against the SA and BR P.1 RBDs with an $NC_{50}$ value at least greater than 45 mg/mL (not able to precisely calculate due the flat curve). This indicates that the Ab7 epitope is not affected by the N501Y mutation, but very likely is affected by the E484K and/or K417N/T mutations. Ab5 had reduced neutralizing activity against SARS-CoV-2 RBD with an $NC_{50}$ value of 3.27 μg/mL. This reduction in neutralizing activity was even greater for the three variant RBDs with an NC50 value between 24 and 45 mg/mL. This suggests that the Ab5 epitope is in the proximity of the N501Y mutation, which is the only mutation shared among the UK, SA, and BR P.1 RBDs.

The neutralization activity of an antibody cocktail, combining Ab1 of bin A and Ab2 of bin B (FIG. 19H) was then determined. A partial additive effect was observed in the neutralizing activity of this antibody cocktail to SARS-CoV-2 RBD and three variant RBDs yielding $NC_{50}$ values between 0.46 and 0.82 μg/mL, which are all less than their corresponding $NC_{50}$ values of Ab1 (between 0.63 and 1.08 μg/mL) or Ab2 (between 1.35 and 1.83 μg/mL) alone. These data indicate that a combination of two or three antibodies of different epitope bins could be used to enhance the neutralization capabilities for a therapeutic cocktail and that such an enhancement can be characterized by this lateral flow cassette assay.

Analysis and Functional Epitope Arrangement Map

Based on the binding characteristics and the neutralization activity against SARS-CoV-2 RBD and three variant RBDs, a functional arrangement map of these seven antibodies versus each RBD was generated. Five antibodies (Ab1, Ab2, Ab4, Ab6 and Ab7) showed strong neutralizing activity with an $NC_{50}$ value less than 1.5 μg/mL and two antibodies (Ab3 and Ab5) showed a moderate neutralizing activity with an $NC_{50}$ value between 1.5 and 15 tag/mL. Overall, these seven antibodies paired freely among the three epitope bins and showed moderate to strong neutralizing activities against the SARS-CoV-2 RBD (FIG. 20).

Similar to SARS-CoV-2 RBD, these seven antibodies paired freely among the three epitope bins for sandwich immunodetection of UK RBD (FIG. 20). However, their neutralizing activity differs significantly. Four antibodies (Ab1, Ab2, Ab4 and Ab7) showed strong neutralizing activity against UK RBD, with an $NC_{50}$ value less than 1.5 μg/mL, two antibodies (Ab3 and Ab6) had moderate neutralizing activity with an $NC_{50}$ value between 1.5 and 15 μg/mL, and one antibody (Ab5) had very weak neutralizing activity with an $NC_{50}$ value of 27.63 μg/mL. The reduced neutralizing activity of Ab5 against UK RBD is likely caused by the N501Y mutation—the only mutation contained in the UK RBD.

The SA and BR P.1 RBDs showed similar binding and neutralizing characteristics to these seven antibodies. Unlike the SARS-CoV-2 and UK RBDs, when Ab7 paired with Ab1 or Ab4 of bin A the detection of SA RBD or BR P.1 RBD in the sandwich assay format is reduced significantly (FIG. 20). Ab7 did not show neutralizing activity against the SA and BR P.1 RBDs, while retained strong neutralizing activity against the SARS-CoV-2 and UK RBDs. The E484K and/or K417N/T mutations contained in the SA and BR P.1 RBDs very likely caused Ab7 to lose neutralizing activity.

Discussion

SARS-CoV-2 spike protein is a critical component for SARS-CoV-2 to adhere to and enter mammalian cells (Ou et al. *Nature Communications* 11, 1620 (2020); Shang et al. *Proceedings of the National Academy of Sciences* 117, 11727-11734 (2020)). The spike protein and its RBD are highly antigenic and have been the primary target of numerous recently developed vaccines and therapeutics (Jackson et al. *N Engl J Med* 383, 1920-1931 (2020); Mulligan et al. *Nature* 590, E26-E26 (2021)) (Food and Drug Administration. Letter to Regeneron Pharmaceuticals, Inc. (21 Nov. 2020), Food and Drug Administration. Letter to Eli Lilly and Company. (10 Nov. 2020)). Given that these seven antibodies evaluated in this report were generated from three distinct fusions, the classification of these antibodies into three epitope bins by virtue of their binding and neutralization characteristics suggests that their corresponding target regions on the RBD protein belong to dominant antigenic epitopes, which could elicit protective humoral immune responses to the SARS-CoV-2 infection or vaccination. The two antibodies (Ab1 (clone No. 1035709) and Ab4 (clone No. 1035762) of bin A epitope, which exhibited broad and potent neutralization activity against all four RBDs, offer a useful alternative for the development of therapeutic antibody for emerging virus variants. These studies suggest that therapeutic antibodies targeting the epitopes similar to bin A are likely to provide better protection against the UK, SA, and BR P.1 variants, while therapeutic antibodies targeting the epitopes similar to bin B and bin C are more likely be escaped by these variants. Based on studies showing that three variants (UK, SA and BR P.1 RBD mutants) escaped the therapeutic LY-CoV555 antibody and two variants (SA and BR P.1 RBD mutants) escaped the LY-CoV016 antibody, Starr et al. suggested that both the SA and the BR P.1 variants may also escape the antibody cocktail of LY-CoV555 and LY-CoV016 (Starr et al. *bioRxiv*, (2021)). Thus, further elucidation of the exact nature of the epitopes recognized by our bin A antibodies (Ab1 and Ab4) could provide a useful framework and insight into the development of therapeutic cocktails against constantly emerging SARS-CoV-2 variants.

Although numerous factors can affect the binding of SARS-CoV-2 spike protein to the ACE-2 receptor (Chi et al. *Science* 369, 650-655 (2020)), the virus spike protein RBD plays a central role for this inter-action (Ou et al. *Nature Communications* 11, 1620 (2020); Shang et al. *Proceedings of the National Academy of Sciences* 117, 11727-11734 (2020)). The N501Y mutation was first found in the UK variant (Rambaut et al, *nCoV*-2019 *Genomic Epidemiology—Virological*, (2020)). Several reports demonstrated that the RBD with N501Y mutation showed a stronger interaction force with ACE-2 receptor, which is associated with increased infectivity of the UK variant (Santos et al. *bioRxiv,* 2020.2012.2029.424708 (2021); Zhang et al. *Jama* 325, 1324-1326 (2021); Gu et al. *Science* 369, 1603-1607 (2020)). In regard to the impact of N501Y mutation on the escape of neutralizing antibody, Supasa et al. (Supasa et al. *Cell* 184, 2201-2211.e2207 (2021)) reported that the UK variant is not neutralized as easily as SARS-CoV-2 by the convalescent, vaccine sera and some anti-RBD monoclonal antibodies, while Xie et al. (Xie et al. *Nature Medicine* 27, 620-621 (2021)) observed only a small reduction in neutralization activity against the UK variant by sera elicited by two doses of the Pfizer vaccine BNT162b2. The present results demonstrated that Ab5 had significantly reduced neutralizing activity ($NC_{50}$: >15 μg/mL) against the UK, SA and BR P.1 variant RBDs, suggesting that the N501Y mutation not only increases ACE-2-RBD interaction (Santos et al. *bioRxiv,* 2020.2012.2029.424708 (2021)), but also induces the escape phenomenon of neutralizing antibody. Together, this may contribute to the weakened efficacy of vaccines or therapeutic antibodies against these variants.

The E484K mutation was reported to be "associated with escape from neutralizing antibodies" which adversely affects the efficacy of spike protein dependent COVID-19 vaccines (Weisblum et al. *Elife* 9, (2020)). Several studies have demonstrated that spike-targeted vaccines or convalescent plasma from SARS-CoV-2 infected human subjects are less effective in neutralizing the South African variant (Hoffmann et al. *bioRxiv,* 2021.2002.2011.430787 (2021)). In fact, Moderna Inc recently initiated a clinical trial using a modified version of spike RNA vaccine to counter the South African and perhaps other known variants (NIH clinical trial evaluating Moderna COVID-19 variant vaccine begins, March 2021). The present results that both the SA and BR P.1 variants RBDs completely escaped Ab7 neutralization confirmed that the E484/K417 mutations may be directly involved with the escape mechanism. Further characterization of antibody Ab7 epitope could shed light on better understanding the humoral immune response and the escape mechanism of SARS-CoV-2 and offer a potential rapid test tool for clinical diagnostics and epidemiological studies for SARS-CoV-2 variant infection.

Antibody Ab7 of bin C pairing with antibody Ab4 (and Ab1) of bin A showed very weak binding activity to the SA and BR P.1 RBDs using the sandwich immunoassay format, however Ab7 pairing with Ab5 and Ab2 of bin B did not show any apparent difference in the binding activities to the four RBDs studied. This discriminative binding behavior suggests that the E484K and/or K417N/T mutations have likely induced conformational changes near the epitopes where these antibodies bind to in the SA and BR P.1 RBDs, thus resulting in steric interference between Ab7 and bin A antibodies, but no apparent steric interference between Ab7 and bin B antibodies. Furthermore, such a mutation-induced conformational change of the spike molecule could contribute to the escape phenomenon of antibody Ab7 by the SA and the BR P.1 variant RBDs. Since the neutralization activities of bin A antibodies (Ab1 and Ab4) are not affected by the three mutations contained in the UK, SA, and BR P.1 variant RBDs, further investigation on the mechanism by which the E484K and/or K417N/T alters the binding and neutralizing activities of these antibodies may help in the identification of a better therapeutic epitope target.

Lateral flow assays are commonly used for rapid clinical testing, such as COVID-19 serological tests, antigen tests, certain molecular tests, and the neutralizing antibody test (Wang et al. *Expert Rev Mol Diagn,* 1-8 (2021); Lake et al. *medRxiv,* 2020.2012.2015.20248264 (2020); Tan et al. *Nature Biotechnology* 38, 1073-1078 (2020))(United States FDA—In Vitro Diagnostics EUAs, Accessed April, 2021). Indeed, Wang et al. have reported the use of a lateral flow dipstick assay with wild-type and the South African spike $S_1$ protein for the characterization of the neutralizing activity of post-vaccination plasma samples (Wang et al. *Expert Rev Mol Diagn,* 1-8 (2021)). The present observation that the $NC_{50}$ values of five mouse monoclonal antibodies to the SARS-CoV-2 RBD are between the 0.3 and 1.5 μg/mL appears to be consistent with a reported IC50 of 1.402 μg/mL for a mouse monoclonal antibody using a dipstick assays (Wang et al. *Expert Rev Mol Diagn,* 1-8 (2021)).

This example demonstrates that (1) sandwich-based immunoassays, such as rapid lateral flow assays and dipstick immunoassays, offer an attractive and cost-effective alternative in characterizing the antibody binding properties, epitope binning, and the in vitro neutralizing kinetics of therapeutic antibodies and cocktails; (2) lateral flow based rapid neutralizing antibody tests could potentially be used to assess the neutralizing antibody activities against SARS-CoV-2 RBD and the UK, SA, and BR P.1 variant RBDs of human blood samples; (3) anti-RBD antibodies (Ab1 and Ab4 of epitope Bin A and Ab2 of epitope Bin B) have strong and broad neutralization/inhibition activity to the binding of SARS-CoV-2 RBDs (SARS-CoV-2 RBD, UK variant or B.1.1.7 RBD, SA variant or B.1.351 RBD and BR P.1 variant RBD) to its ACE2 receptor, which could be further characterized and developed for therapeutic use for treatment of severe SARS-CoV-2 infection; and (4) these antibodies could be used for the detection of SARS-CoV-2 spike protein for diagnostic application.

The information of Example 3 is included in the publication "Use of Lateral Flow Immunoassay to Characterize SARS-CoV-2 RBD-Specific Antibodies and Their Ability to React with the UK, SA and BR P.1 Variant RBDs" of Tan et al., *Diagnostics* (*Basel*); 2021 Jun. 30; 11(7):1190. doi: 10.3390/diagnostics11071190.

Example 4

A Dual Antibody Combination Targeting Opposite Epitopes Near the RBD Interface Broadly and Strongly Inhibits the Binding of SARS-CoV and SARS-CoV-2 Variant RBDs to ACE2

Amino acid mutations (K417N/T, L452R, T478K, E484K/Q, and N501Y) within the receptor binding domain (RBD) of current dominant SARS-CoV-2 (severe acute respiratory syndrome coronavirus 2) variants play an important role in altering the interaction dynamics between RBD and ACE2 (Angiotensin-converting enzyme 2), thus enhancing viral adhesion and infectivity and causing viral evasion from the post-infection and post-vaccination immune protection. Identification of broadly potent neutralizing antibodies against these dominant variants will help develop effective therapeutic antibodies and better understanding the humoral immune response to SARS-CoV-2 and the variants. By use of the lateral flow surrogate neutralizing antibody assay and the multiplexed antigen array dipstick assay, the neutralizing activity and binding activity of seven anti-RBD monoclonal antibodies against SARS-CoV (severe acute respiratory syndrome associated coronavirus) RBD and ten SARS-CoV-2 and variants RBDs (including alpha, beta, gamma, delta, kappa, and iota) were studied. The neutralization study results demonstrated three main things. First, three antibodies (Ab1, Ab2 and Ab4) had strong broad potent neutralizing activity against all SARS-CoV-2 variant RBDs including the delta variant RBD. Second, two antibodies effectively cross-neutralized the SARs-CoV RBD. Third, a dual anti-RBD antibody combination or cocktail targeting the opposite epitope regions near the RBD interface have strong neutralization activity against all variant RBDs studied. The antigenic stability and accessibility upon direct adsorption onto the nitrocellulose membrane by these mAbs and ACE2 were studied. These two antibodies could be further characterized and developed for therapeutic use in treatment of severe SARS-CoV-2 infection. The binding study results demonstrated that three antibodies were not able to detect the variant RBDs that contain E484K/Q, L452R or T478K mutations and two antibodies cross-detected the SARS-CoV RBD. For the adsorbed RBDs, ACE2 strongly bound to the UK, BR P.1 and the Delta variant RBDs and very weakly detected the K417E RBD and the SARS-CoV RBD. From these results, the epitopes on the RBD where these antibodies bind to were predicted and illustrated on a surface presentation of RBD protein. In addition, the use of these antibodies for the detection of SARS-CoV-2 spike antigen for potential diagnostic application and the strategy for variant specific spike antigen detection was explored.

Introduction

After over 18 months since the World Health Organization (WHO) declared COVID-19 a pandemic on Mar. 11, 2020 (Cucinotta et al. *Acta Blamed* 91, 157-160 (2020)), the spread of constantly emerging SARS-CoV-2 variants remains a global threat to the worldwide health and economy. As of Oct. 1, 2021, the WHO classify four variants (alpha, beta, gamma, and delta) as VOC (variants of concern), two variants (lambda and mu) as VOI (variants of interest), and eleven variants as VUM (variants under monitoring) (WHO website—Tracking SARS-CoV-2 variants). Each variant carries a specific set of mutations in their respective viral genome, particularly in the spike protein that is key to the virus adhesion to target cells. Since the RBD plays a central role in the binding of the spike protein and the viral particle to the ACE2 receptor, mutations in the RBD that result in changes of the epitope structure or conformations on the RBD, at the location where the neutralizing antibodies bind, will cause subsequent evasion of post-infection and/or post vaccination induced immune protection (Tao et al. *Nat Rev Genet,* 22, 757-773 (2021); Xie et al. *Nat Med* 27, 620-621 (2021)).

The SARS-CoV-2 RBD is a 220-amino acid fragment (Arg319-Phe541) in the S1 subunit of SARS-CoV-2 spike protein. The spike protein has two conformational states—the pre-fusion state (closed conformation) and the post-fusion state (open conformation) (Cai et al. *Science* 369, 1586-1592 (2020)), and the RBD portion fluctuates between the "up" and "down" conformations (Khare et al. *Front Artif Intell* 4, 630955 (2021)). The RBD consists of a twisted five-stranded antiparallel β sheet core with disulfide bonds and short connecting helices and loops outside as well as a looped-out extension from the β4 and β7 strands of the core (Lan et al. *Nature* 581, 215-220 (2020)). The looped-out extension, e.g., the receptor binding motif (RBM), forms the boat-shaped bowl structure that interacts with and holds the contacting arm of ACE2. Seventeen amino acid resides of the RBD contact their partners in ACE2. These contacting resides of the RBD include one residue from the non-RBM portion (K417) and 16 residues from the RBM portion (i.e., G446, Y449, Y453, L455, F456, A475, F486, N487, Y489, Q493, G496, Q498, T500, N501, G502, and Y505) (Lan et al. *Nature* 581, 215-220 (2020)). Five amino acid residues of the RBD are often mutated in currently dominant variants, including two ACE2 contacting residues (K417 and N501) and three residues near the ACE2 contacting residues (L452, T478, E484). These mutations have been shown to increase ACE2-RBD affinity, induce escape from monoclonal antibody or convalescent sera, and cause severe disease (Tao et al. *Nat Rev Genet* 22, 757-773 (2021); Xie et al. *Nat Med* 27, 620-621 (2021)).

Spike protein is highly antigenic glycosylated protein (Henderson et al. *bioRxiv*, (2020)). Numerous anti-spike antibodies, isolated from the sera post-infection patients, are able to neutralize the SARS-CoV-2 adhesion and reduces viral infection, alleviating the disease status (Huang et al. *Antib Ther* 3, 285-299 (2020); Zost et al. *Nature* 584, 443-449 (2020)). Most of these neutralizing antibodies belong to anti-RBD antibodies. Therefore, the identification of potent neutralizing antibodies has significant implication for the development of therapeutic antibodies and better understanding the humoral immune response to SARS-CoV-2 variants. In fact, two of the three FDA approved anti-SARS-CoV-2 monoclonal antibody products with Emergency Use Authorizations (EUAs) designation are anti-RBD antibodies. For example, the bamlanivimab (LY-CoV555) plus etesevimab (LY-CoV016) cocktail targets two different but non-overlapping epitopes on the RBD and the casirivimab (REGN10933) plus imdevimab (REGN10987) cocktail targets two nonoverlapping epitopes on the RBD. The third antibody product, sotrovimab, targets an epitope on the RBD that is conserved between SARS-CoV and SARS-CoV-2 (NIH website—Anti-SARS-CoV-2 Monoclonal Antibodies).

Several methods have been used to characterize the neutralizing activity of therapeutic molecules, convalescent and post-vaccination plasma, and therapeutic antibodies, i.e., the authentic virus based plaque reduction neutralization test (PRNT) assay or animal model assay (Jackson et al. *N Engl J Med* 383, 1920-1931 (2020)), the pseudo virus based neutralizing assay (Ou et al. *Nat Commun* 11, 1620 (2020)), the viral antigen based total antibody serological assay, and the protein-protein interaction based surrogate neutralizing antibody assay (Embregts et al. *One Health* 13, 100313 (2021); Fulford et al. *medRxiv,* 2021.2004.2012.21255368 (2021); Tan et al. *Nat Biotechnol* 38, 1073-1078 (2020)). The former two methods utilize the spike-protein induced viral adhesion and fusion. The antigen based total antibody test only estimate the humoral serological response, not necessarily representative of the neutralizing activity. The surrogate assay method takes advantage of the interaction of RBD (or spike) and ACE2. Several studies have demonstrated the RBD-ACE2 based surrogate neutralization assay can predict the neutralization capability of convalescent and post-vaccine blood samples, as well as used for determination of neutralization activity of monoclonal antibodies (Embregts et al. *One Health* 13, 100313 (2021); Fulford et al. *medRxiv,* 2021.2004.2012.21255368 (2021); Tan et al. *Nat Biotechnol* 38, 1073-1078 (2020)). For example, an RBD-ACE2 interaction based surrogate virus neutralization gave similar or improved accuracy for qualitative delineation of the SARS-CoV-2 neutralizing activity between positive and negative samples, when compared directly with eight SARS-CoV-2 IgG serology and two live-cell neutralization tests (Tan et al. *Nat Biotechnol* 38, 1073-1078 (2020); Johnson et al. *J Clin Virol* 130, 104572 (2020); Taylor et al. *J Clin Microbiol* 59, (2021)). In fact, FDA has authorized one protein based surrogate assays for use (FDA letter—cPass™ SARS-CoV-2 Neutralization Antibody Detection Kit package), to qualitatively test the neutralizing antibody activity to SARS-CoV-2 in human serum and plasma, in which a PRNT assay utilizing the SARS-CoV-2 virus (WA01/2020 isolate) was used a reference. Thus, in this analysis, the term "neutralizing activity" or "blocking activity" or "inhibitory activity' were interchangeably used.

In Example 3, lateral flow immunoassays were used for the characterization of anti-RBD monoclonal antibodies, including antibody pairing capability, epitope binning, and their neutralizing activity against SARS-CoV-2 and three variant RBDs (UK, SA, and BR.P.1). To address the current dominant delta variant and other variants, these on their neutralizing activity studies were expanded against six additional SARS-CoV-2 RBDs (P2, kappa, CA, delta variants; and K417E and T478K RBDs) and SARS-CoV RBD, using the rapid protein-protein interaction based surrogate neutralization assay. By use of these additional RBDs, covering 5 mutations commonly seen among current dominant SARS-CoV-2 variants, the epitope regions of the RBD where these antibodies bind to were predicted (estimated). In addition, it was shown that upon adsorption of these variant RBDs onto nitrocellulose membrane, they showed drastic difference in their detectability by these anti-RBD antibodies and ACE2. In addition, it was shown that a combination of two antibodies targeting opposite epitope regions near the RBD contact surface area showed broad and potent neutralizing activity against all the SARS-CoV-2 RBDs including the delta variant RBD and the SARS-CoV RBD.

Materials and Methods

Anti-SARS-CoV-2 Antibodies

Seven anti-SARS-CoV-2 spike RBD murine monoclonal antibodies (Ab1-Ab7), as described in more detail in Examples 1 and 2 were selected for this study (see also Tan et al. *Diagnostics* (*Basel*) 11, 1190 (2021)). All antibodies used were produced by Bio-Techne Corporation (Minneapolis, MN). These antibodies include Ab1 (clone No. 1035709), Ab2 (clone No. 1035740), Ab3 (clone No. 1035753) and Ab4 (clone No. 1035762), Ab5 (clone No. 1035419), Ab6 (clone No. 1035224), and Ab7 (clone No. 1035240).

Additionally, one anti-SARS-CoV-2 spike S2 subunit antibody, MAB10557 (clone No. 1034617), generated using recombinant SARS-CoV2 Spike S2 Subunit (Met697-Pro1213) as immunogen, was used a negative control. One anti-nucleocapsid antibody (AnAb4, clone No. 1035129) was generated using recombinant SARS-CoV-2 nucleocapsid protein.

Recombinant Receptor Binding Domain Proteins

All recombinant RBD proteins were generated by Bio-Techne Corporation (Minneapolis, MN, USA), using the HEK293 expression system as described in more detail in Example 3 (see also Tan et al. *Diagnostics* (*Basel*) 11, 1190 (2021)). In addition to these four recombinant SARS-CoV-2 RBDs (CoV-2 RBD and SA, UK, BR P.1 RBDs), six additional SARS-CoV-2 RBDs and the SARS-CoV RBD were tested in this study. These proteins include the BR P.2 variant RBD (R319-F541 with E484K), the K417E RBD (R319-F541 with K417E), the L452R RBD (R319-F541 with L452R), the IN v1 variant RBD (R319-F541 with L452R, E484Q), the IN v2 variant RBD (R319-F541 with L452R, T478K), and the T478K RBD (R319-F541 with T478K).

The SARS-CoV spike RBD (R306-F527, with a C-terminal 6-His tag; based on accession #NP_828851.1), was generated using the Chinese hamster ovary (CHO) cell expression system.

Other Materials

Triton X-100, 30% bovine serum albumin (BSA) solution, 30% Brij-35 solution, 10× phosphate buffered saline (PBS), 10× casein solution in PBS, and other chemicals were purchased from Millipore-Sigma (Burlington, MA). Casein solution (1%, w/v) in a Tris buffer with a pH of 7.4 was purchased from Thermo Fisher Scientific (Waltham, MA). Recombinant human ACE2 protein, goat polyclonal anti-chicken IgY antibody, biotinylated ACE2, and chicken IgY protein (cIgY) were acquired from Bio-Techne Corporation (Minneapolis, MN). Goat anti-mIgG (GAM) antibody conjugated 40 nm gold nanoparticle (GAM-AuNP) and streptavidin conjugated 40 nm AuNP (SA-AuNP) were purchased from Arista Biological (Allentown, PA). Anti-nucleocapsid antibody M9547 was purchased from Meridian Life Science (Memphis, TN).

Preparation of Lateral Flow NAb Test Cassette and Assay Procedure for Neutralization Kinetics Lateral flow neutralization test devices were manufactured according to the procedures described in more detail in Example 3 (see also Tan et al. *Diagnostics* (*Basel*) 11, 1190 (2021)). Briefly, recombinant human ACE2 was striped in the "test zone" and goat polyclonal anti-chicken IgY antibody was striped in the "control zone" as the capture agent on the nitrocellulose membrane card. Recombinant RBD and cIgY were conjugated to the 40 nm gold nanoparticles as the detectors for the test zone and the control zone, respectively. The AuNP-RBD and AuNP-cIgY conjugates were combined in a drying down buffer containing salt, stabilizer and AuNP releasing agents and sprayed onto conjugate pad strips. The antibody stripped card was assembled with a conjugate pad, sample pad and a wicking pad. The card assembly was then slitted into test strip that was then assembled into a plastic cassette and sealed in a foil pouch with desiccant, stored at ambient room temperature. As shown in FIG. 21, by alternating the AuNP-RBD conjugate while keeping other components the same, seven types of rapid neutralizing antibody test cassettes were prepared for the P.2 (E484K) RBD, the K417E RBD, the B.1.6171 RBD, the B.1.6172 RBD, the CA (L452R) RBD, the T478K RBD, and the SARS-CoV RBD. The dropper bottle used for introducing the neutralization as-say buffer has a drop size of ~25 μL per drop. The neutralization assay buffer consists of 1×PBS, pH 7.4, containing 3% (w/v) BSA, 0.5% (v/v) Tween-20 and 0.05% (w/v) sodium azide.

The strip design and neutralizing antibody test device assay principle is given in FIG. 21A and FIG. 21B. The assay protocol for neutralizing antibody kinetic curves, and the determination of $NC_{50}$ value were carried out according to the procedures described in more detail in Example 3 (see also Tan et al. *Diagnostics* (*Basel*) 11, 1190 (2021)). Briefly, a neutralization kinetic curve was generated for all seven antibodies and a dual antibody cocktail (Ab1 and Ab2) at different concentrations to determine the percent neutralization against seven RBDs. Each antibody was diluted in neutralization assay buffer targeting antibody concentrations at 10, 2, 0.5, and 0.1 μg/mL, and a zero-antibody control. The assays were run in stacking modes with each assay delaying for seconds for up to 20 tests per run or delaying for 60 seconds for up to 10 tests per run. For each cassette assay, an aliquot of 20 μL diluted antibody solution was added to the sample port of a test cassette to start the assay. After the antibody sample absorbed for ~25 s, three drops (~75 μL) of neutralization assay buffer were added to the sample port using a dropper bottle. The signal intensities of the test zone, the control zone, and a reference negative zone were measured at 10 minutes from the start of the assay using an RDS-2500 LFA reader.

For each data point a minimum of two replicates were performed. For the zero-analyte condition per test device type, a minimum of six replicates were performed to set up the baseline at 100% RBD-ACE2 binding activity and 0% neutralizing activity, which is used for the determination of the $NC_{50}$ value for each antibody or antibody combination vs each variant RBD. The $NC_{50}$ in μg/mL is the concentration of antibody that yields a 50% inhibition or neutralization of the maximal RBD-ACE2 binding capacity for a given neutralization cassette type.

Lateral Flow Dipstick Assay Using Spotted RBD Protein Panel

Preparation of Lateral Flow Dipsticks with the RBD Protein Panel

The lateral flow dipstick was prepared as described in more detail in Example 3 (see also Tan et al. *Diagnostics* (*Basel*) 11, 1190 (2021)). Each 60-mm wide dipstick consisted of a polystyrene card backing with a 25-mm long nitrocellulose membrane and attached a 17-mm or 20-mm long absorbent pad. The dipsticks were spotted with a thirteen-spot protein array: ten spots for the SARS-CoV-2 and variant RBDs, one spot for the SARS-CoV RBD, one spot for the positive control (i.e, anti-S2 antibody, used as mIgG), and one spot for the negative control (i.e., BSA). Each protein was diluted to 0.5 mg/mL in 1×PBS with a pH of 7.4 and manually pipetted onto the nitrocellulose membrane at 0.8 μL per spot. The coated dipsticks were dried in a 37° C. oven with circulating air for a minimum of 30 min prior to use; longer term storage occurred in a plastic bag with desiccant.

Lateral Flow Dipstick Assay Procedure for Antibody Reactivity

To study the binding of anti-RBD antibodies to the immobilized RBD antigens, a 60-mm wide dipstick with the spotted antigen panel was placed in a reservoir. Three assay solutions were sequentially added. First, an aliquot of 300 μL of 10 μg/mL primary antibody solution was added into the reservoir to start the assay. After the primary antibody solution is completed in 10~12 minutes. An aliquot of 300 μL secondary antibody-AuNP conjugate solution was added and allow to run another 10~12 minutes. In the end, 300 μL assay run buffer was added to rinse off the non-bound GAM-AuNP conjugate. All detection solutions are prepared in the Brij-35 assay buffer. The primary antibody solution contains 3 μg of anti-RBD antibody or control antibody (i.e., anti-S2 antibody). The secondary antibody solution contains 1:10 (1 part/9 parts, v/v) diluted GAM-AuNP conjugate in the same buffer. The Brij-35 assay run buffer is the same buffer as well. After all assay solutions were completed, the dipstick was examined, and an image was taken using an iPhone. The Brij-35 assay buffer consists of 1×PBS with a pH of 7.4, containing 1% (w/v) BSA, (v/v) TX-100, 0.3% (v/v) Brij-35, 0.3% (w/v) casein, and 0.05% (w/v) sodium azide.

The assayed dipsticks were photographed within 60 minutes using an iPhone camera after the assay was completed to document assay results.

Lateral Flow Dipstick Assay Procedure for ACE2 Reactivity

The binding activity of ACE2 to the immobilized RBD antigens was tested similarly as for the antibody binding. Each 60-mm wide dipstick with the RBD panel was sequentially reacted with three detection solutions. The three solutions are 300 μL biotinylated ACE2 solution (i.e, 10, 3.3, or 1 μg/mL), 300 μL 1:10 (1 part/9 parts, v/v) diluted SA-AuNP conjugate solution and 300 μL assay run buffer. The neutralization assay buffer was used for the dilutions and the assay run buffer.

The assayed dipsticks were photographed within 60 minutes using an iPhone camera after the assay was completed to document the assay results.

Evaluation of an S/N Dual Antigen Lateral Flow Assay for SARS-CoV-2 Detection

The S/N (spike and nucleocapsid proteins) dual antigen test cassettes were prepared similarly as the neutralizing antibody test cassettes, with the exceptions below. Anti-RBD monoclonal antibody (Ab2, clone No. 1035224) and anti-nucleocapsid (NP) monoclonal antibody (AnAb4, clone No. 1035129) were used as the capture agents for RBD and NP, respectively. These two antibodies were stripped onto the nitrocellulose membrane at 0.5 mg/mL in PBS and at a flow rate of 0.06 μL/mm using an ISOFlow dispenser, Anti-RBD monoclonal antibody Ab6 and anti-NP monoclonal antibody M9547 were adsorbed to 40-nm gold nanoparticles and used as the detectors for RBD and NP, respectively. The test strip assembly consists of an antibody stripped NCM with plastic banking, a sample pad, a conjugate pad, and a wick pad, was cut into 4.2 mm wide test strip and assembled into plastic cassette (Kinbio) and used in the same day or stored with descant in foil pouch.

For the assay, the RBD antigen was diluted into a PBS containing 3% BSA (w/v), 0.5% Tween-20 (v/v), 1× casein (Sigma brand), and 0.05% $NaN_3$, targeting concentrations of 1000, 100, 10, 1, 0.1 ng/mL and zero analyte condition. An aliquot of 75 μL samples was added into the sample port and the assay signal was read at 10 minutes after the sample was added using an RDS-2500 reader and the assayed cassette image was taken using an iPhone camera within 60 min after the assay was completed.

Instrumentation and Statistics

The Nanodrop 2000 spectrophotometer was purchased from Thermo Fisher Scientific (Waltham, MA, USA). The RDS-2500 lateral flow reader was purchased from Detekt Biomedical LLC (Austin, TX, USA).

Results

SARS-CoV-2 Variants and Key Mutations in their RBD

This example identifies potent neutralizing antibodies against current dominant SARS-CoV-2 variants and prediction of the epitope region on the RBD where these anti-RBD antibodies bind to. Current dominant SARS-CoV-2 variants contain five common amino acid mutations in their RBDs, i.e., K417N/T, L452R, T478K, E484K/Q, and N510Y. To characterize the impact of these single mutations on the neutralizing activity of these anti-RBD antibodies, a total of ten SARS-CoV-2 and variant RBDs were used. These include the epsilon variant RBD (B.1.427/9, with L452R only), the zeta variant RBD (P.2, with E484K only), the alpha variant RBD (B.1.1.7, with N501Y only), K417E RBD and T478K RBD. These RBDs with single amino acid mutation are important in the predication of the epitopes on the RBD where these antibodies bind to. SARS-CoV-2 variant RBDs with double or triple mutations include the beta variant RBD (B.1.351, with K417N, E484K, and N501Y), the gamma variant RBD (P.1, with K417T, E484K, and N501Y), the delta variant RBD (B.1.617.2, with L452R and T478K), the kappa variant (B1.617.1, with L452R and E484Q). SARS-CoV RBD was included to investigate if any of our seven mAbs bind to both SARS-CoV2 and SARS-CoV RBD as evidence of a conserved epitope between the two.

Neutralizing Activities of Anti-RBD Antibodies Against SARS-CoV and SARS-CoV-2 RBDs To investigate the neutralizing or inhibitory activity of these anti-RBD antibodies to the binding of RBDs of SARS-CoV, SARS-CoV-2, and current dominant variant strains to ACE2, the neutralization kinetics of each antibody and a dual antibody combination against these RBDs was studied using serially diluted antibody solutions targeting antibody concentrations at 10, 2, 0.5, 0.1, and 0 μg/mL suspended in a neutralization assay buffer (FIGS. 22A-22I). The $NC_{50}$ value was determined from the signal intensity of the test zone. The $NC_{50}$ values for the seven antibodies and the dual antibody cocktail against all RBDs tested are summarized in Table 12 below. For the comparison purpose, the neutralization data previously reported on the SARS-CoV-2 RBD, the alpha variant RBD (B.1.1.7, UK variant), the beta variant RBD (B.1.351, SA variant) and the gamma variant RBD (Brazilian P.1) were included in the data analysis along with the data generated from these seven RBDs.

TABLE 12

| | RBD name | | Mutations in RBD | | | | | $IC_{50}$ or $NC_{50}$ (μg/mL) | | | | | | | |
|---|---|---|---|---|---|---|---|---|---|---|---|---|---|---|---|
| | | | M-1 | M-2 | M-3 | M-4 | M-5 | Ab1 | Ab4 | Ab2 | Ab5 | Ab3 | Ab6 | Ab7 | Ab1 &Ab2 |
| SARS-CoV-2 RBD variants | * SARS-CoV-2 RBD | wildtype | | | | | | 0.63 | 0.69 | 1.43 | 3.27 | 1.66 | 0.66 | 0.34 | 0.50 |
| | * UK (B.1.1.7) RBD | Alpha | | | | | N501Y[a] | 1.08 | 0.95 | 1.35 | 27.63[a] | 1.51 | 2.72[a] | 0.86 | 0.82 |
| | * SA (B.1.351) RBD | Beta | K417N | | | E484K[b] | N501Y[a] | 0.91 | 0.70 | 1.83 | 24.03[a] | 3.19 | 1.14[a] | **[b] | 0.66 |
| | * P.1 (B.1.1.28.1) RBD | Gamma | K417T | | | E484K[b] | N501Y[a] | 0.70 | 0.69 | 1.40 | 44.79[a] | 2,21 | 1.11[a] | **[b] | 0.46 |
| | P.2 (B.1.1.28.2) RBD | Zeta/Eta | | | | E484K[b] | | 0.61 | 0.85 | 1.48 | 6.48 | 3.22 | 0.54 | **[b] | 0.39 |
| | B.1.617.1 RBD | Kappa | | L452R[c] | | E484K[b] | | 0.66 | 0.77 | 1.79 | 16.54[c] | **[c] | **[c] | **[bc] | 0.35 |
| | K417E RBD | n/a | K417E | | | | | 0.38 | 0.49 | 1.09 | 1.51 | 0.89 | 0.38 | 0,33 | 0.38 |
| | L452R RBD | Epsilon | | L452R[c] | | | | 0.92 | 0.73 | 1.17 | 20.58[c] | **[c] | **[c] | **[c] | 0.49 |
| | B.1.617.2 RBD | Delta | | L452R[c] | T478K[d] | | | 2.33[d] | 2.57[d] | 1.61 | 33.25[c] | **[c] | **[c] | **[c] | 0.68 |
| | T478K RBD | n/a | | | T478K[d] | | | 1.35[a] | 3.77[d] | 1.21 | 9.01 | 2.29 | 0.76 | 0.61 | 0.60 |
| | SARS-CoV RBD | willtype | | | | | | ** | ** | 0.84 | 2.86 | ** | ** | ** | 0.93 |

Antibody neutralization $NC_{50}$ summary table. The data for CoV-2, UK, SA, and BR P.1 RBDs are from Example 3 (see also Tan et al. *Diagnostics* (*Basel*) 11, 1190 (2021)) and all other data were newly generated. Semi-logarithmic curve fitting was used to extrapolate the $NC_{50}$ values. For antibodies Ab1, Ab6, Ab7, and the Ab1&Ab2 antibody cocktail, the range of 0.1~2 μg/mL was used for curve fitting. For antibodies Ab2, Ab3 and Ab5, the range of 0.5~10 μg/mL was used for curve fitting. For antibody Ab4, the range of 0.1~10 μg/mL was used. Neutralizing activity level designation: Strong neutralizing activity: NC50 < 1.5 μg/mL. Moderate neutralizing activity: 1.5 μg/mL ≤ $NC_{50}$ < 15 μg/mL Weak or no neutralizing activity: $NC_{50}$ ≥ 15 μg/mL.

* Indicates that the data of these four RBDs were from Example 3 and included here for side-by-side comparison purposes.

** indicates that the $NC_{50}$ value was not calculated due to the flat nature of the curve and the very weak neutralizing activity. The predicated correlation pattern between the mutations and the $NC_{50}$ values are designated with a superscripted "a", "b", "c", and "d" for mutations N501Y, E484K/Q, L452R and T478K, respectively.

For SARS-CoV-2 RBD, five antibodies (Ab1, Ab2, Ab4, Ab6, and Ab7) showed strong neutralizing activity, with NCH) values between 0.34 and 1.43 μg/mL, and two antibodies (Ab3 and Ab5) showed a moderate neutralizing activity with an $NC_{50}$ value of 1.66 and 3.27 μg/mL, respectively, indicating that the epitopes of these seven antibodies were all near or in the RBD interface zone.

Ab1 and Ab4 had similar neutralization activity profile. These two antibodies did not neutralize the binding of ACE2 to SARS-CoV RBD, moderately inhibited the binding of ACE2 to two T478-bearing variants RBDs (T478K RBD and Delta RBD with L452R and T478K), strongly neutralized the binding of ACE2 to SARS-CoV-2 RBD and seven variant RBDs. These results suggest that the epitope(s) of Ab1 and Ab4 is in a region near the T478 residue but not much affected by the T478K mutation and away from other four commonly mutated residues (K417, L452, E484, and N501).

Ab2 and Ab5 shared similar neutralization activity profile. These two antibodies strongly or moderately neutralized the binding of ACE2 to SARS-CoV RBD, with $NC_{50}$ of 0.84 and 2.86 μg/m, respectively. Ab2 strongly or moderately neutralized the binding of ACE2 to all SARS-CoV-2 variant RBDs, with $NC_{50}$ values between 1.09 and 1.83 μg/mL antibody. In contrast, Ab5 moderately neutralized the binding of ACE2 to four variant RBD (SARS-CoV-2 RBD, E484K RBD, K417E RBD, and T478K RBD), with $NC_{50}$ values between 1.51. and 9.01 μg/mL antibody, and weakly neutralized six variant RBDs that contain either the N501Y or the L452R mutation), with $NC_{50}$ values between 16.54 and 44.79 μg/mL. The loss of neutralizing activity of Ab5 with the variant RBDs containing N501Y or L452R, suggesting that the N501 and L452 residues are likely part of the of the Ab5 epitope. Given the facts that (a) Ab2 and Ab5 neutralize the binding of ACE2 SARS-CoV RBD, and (b) A2 and Ab5 compete in sandwich assay format for the detection of SARS-CoV-2 RBD (Example 3; Tan et al. *Diagnostics* (*Basel*) 11, 1190 (2021)), the Ab2 epitope partially overlaps with the Ab5 epitope.

Ab3 and Ab6 had similar neutralization activity profile. These two antibodies both inhibit the binding of ACE2 to SARS-CoV RBD. Ab3 and Ab6 did not inhibit the binding of ACE2 to variant RBDs (L452R, Kappa and Delta RBDs) that contain the L452R mutation. Ab3 showed strong neutralization against K417E RBD, with an $NC_{50}$ value of 0.89 μg/mL and moderately inhibited six remaining RBDs with $NC_{50}$ values between 1.51. and 3.22 μg/mL. In contrast, Ab6 strongly neutralized four RBDs (CoV-2 RBD, E484K RBD, K417E RBD and T478K RBD), with $NC_{50}$ values between 0.38 and 0.66 μg/mL and strongly neutralized other three RBDs (UK, SA, and BR P.1 RBDs) that contain the N510Y mutation, with $NC_{50}$ values between 1.11 and 2.72 μg/mL. These results suggest that Ab6 epitope is in the region near or at the L452 and N501 residues. As Ab3 and Ab6 antibodies compete when used as a pair for the detection of SARS-CoV-2 RBD (Example 3 and Tan et al., *Diagnostics* (*Basel*) 11, 1190 (2021)) and that Ab3 had slightly weaker neutralizing activity overall than that of Ab6, the Ab3 epitope overlaps the Ab6 epitope, but the Ab3 epitope is likely more outward of the RBD interface than the Ab6 epitope.

Ab7 did not inhibit the binding of ACE2 to SARS-CoV RBD, strongly inhibited the binding of ACE2 to four SARS-CoV-2 RBDs (wild-type, UK, K417E, and T478K), and failed to inhibit the binding of ACE2 to six other SARS-CoV-2 RBDs that contained E494K/Q and/or L452R mutations. These results suggest that the Ab7 epitope is located near the E484 and L452 amino acid residues.

Antibody Reactivity and ACE2 Binding to the Adsorbed RBD Proteins on the Nitrocellulose Membrane.

To investigate if the adsorbed variants RBDs differ in their reactivity with these seven anti-RBD antibodies and the ACE2, the RBDs were directly adsorbed onto the NCM at pH 7.4. Specifically, each RBD protein was diluted to a concentration of 0.5 mg/mL concentration in 1×PBS, spotted onto the FF120 lateral flow nitrocellulose membrane and dried. The adsorbed RBD protein arrays were reacted with anti-RBD monoclonal antibody and then detected by GAM-AuNP conjugate. The results are given in FIG. 23. Antibodies (Ab1 and Ab4) detected all adsorbed SARS-CoV-2 and variant RBDs strongly except they detected B.1.617.v2 RBD and T478K-RBD slightly weaker, suggesting that the epitope of Ab1 and Ab4 is in proximity of the T478 residue. Ab1 and Ab4 compete when used in sandwich immunoassay (Example 3; Tan et al. *Diagnostics* (Basel) 11, 1190 (2021)). Ab1 and Ab4 did not bind to SARS-CoV RBD. Antibodies (Ab2 and Ab5) strongly detected all SARS-CoV2 variant RBDs, suggesting that the Ab2/5 epitope is not impacted by the five mutations (K417, L452R, T478K, E484K.Q and N501Y) contained in these SARS-CoV-2 RBDs by the direct antibody binding. However, the neutralizing activity of Ab5 was largely affected by the N501Y and L452R mutations. This discrepancy between binding activity and neutralizing activity suggests that L452R and N501Y mutations is near the Ab2/Ab5 epitope, where Ab5 epitope is closer to the RBD interface than Ab2. A2 and Ab5 compete when used in sandwich immunoassay (Example 3; Tan et al. *Diagnostics* (Basel) 11, 1190 (2021)). Interestingly, Ab2 and Ab5 showed moderate reactivity to SARS-CoV RBD, which is consistent with the observation that both Ab2 and Ab5 showed strong or moderate neutralizing activity against SARS-CoV RBD. Antibodies (Ab3 and Ab6) had no reactivity to the adsorbed RBDs that have the L452R mutation (L452R-RBD, B1.617.v1, and B1.617.V1.v2), indicating that the epitope of these two antibodies is at or near the L452 residue. A3, Ab6 and Ab7 partially compete when used in sandwich immunoassay (Example 3; Tan et al. Diagnostics (Basel) 11, 1190 (2021)). Ab3 and Ab6 did not bind to SARS-CoV RBD. Antibody Ab7 showed no reactivity to four adsorbed SARS-CoV-2 variant RBDs that contain the E484K/Q and no reactivity to three adsorbed RBDs that contain the L452R mutation, suggesting that the epitope of Ab7 is near both E484 and L452 residues. Ab7 had no reactivity to SARS-CoV RBD.

RBD binds to ACE2 through their contact interface. Mutations in the RBD, especially the more accessible RBM, may alter the protein-surface interaction and the accessibility. To assess the reactivity of adsorbed RBDS by ACE2, the dipstick RBD protein array was reacted with biotinylated ACE2, then detected with SA-AuNP. If the ACE2 interface of the adsorbed RBD proteins is functional and accessible by biotinylated ACE2, then upon detection by SA-AuNP, a complex of RBD-ACE2-bt-SA-AuNP complex will be formed, forming a red-colored circular spot. As shown in FIG. 24, ACE2 concentration-dependently detected most adsorbed SARS-CoV-2 RBDs with moderate spot signal intensity, except that the K417E RBD spot was only weakly detected, with light spot color intensity. Based on the visual interpretation of the spot color intensity, the overall ranking of the binding activity of these adsorbed RBDs to ACE2 is as follows: strong binding (UK, P.1, and B.1.617.2 RBDs), moderate binding (CoV-2, SA, P2, B.1.617.1, L452R, T478K RBDs), weak binding (K417E RBD and SARS-CoV RBD). As all SARS-CoV-2 RBDs were detected by anti-RBD Ab5 similarly, the weak binding between ACE2 and the adsorbed K417E RBD is consistent with low affinity as reported. For example, Barton et al reported that RBD-K417N and RBD K417T have KD of 364 nM and 230 nM respectively, compared to wildtype SARS-CoV-2 RBD having a KD of 74.4 nM, as measured using Biacore T200 and ACE2-immobilized CMS sensor at 37° C. (Barton, et al. *eLife* 2021; 10:e70658). In addition, the weaker detection of SARS-CoV RBD by ACE2 than SARS-CoV-2 appears to agree with the common understanding that the binding of SARS-CoV-2 to ACE2 is stronger than SARS-CoV RBD.

Surface Presentation of SARS-CoV-2 RBD and the Predicted Epitopes on the RBD Surface In order to visualize and predict the epitopes of these seven antibodies, surface diagrams were created for the ACE2 contacting area and two side surfaces of the SARS-CoV-2 RBD. The surface diagrams, key residues and the predicted epitope areas are given in FIG. 25A-FIG. 25C. The ACE2-contacting surface includes 15 non-mutation contact residues, 2 mutated contact residues and three mutated but not contacting residues. First, the epitope of antibodies (Ab1 and Ab4) is near the T478 residues, not affected by other four mutations, suggesting that these two antibodies bind to the RBD interface contact region 1 (CR1). These two antibodies showed strong neutralization activity against all SARS-CoV-2 variants RBDs, which is only slightly affected by the T478K mutation and insensitive to all other four common RBD mutations. Ab1 and Ab4 do not neutralizing or bind to SARS-CoV RBD. Second, the epitope of antibodies (Ab2 and Ab5) is near N501 and L452 residues. These two antibodies neutralize the SARS-CoV RBD suggesting that they recognize an area that is conserved between SARS-CoV and SARS-CoV-2 RBDs. Ab2 showed moderate or strong neutralizing activities against all SARS-CoV-2 variant RBDs, and the neutralizing activity of Ab5 was largely reduced for SARS-CoV-2 variants RBDs that contain the N501Y and/or the L452R mutations and moderately reduced for the remaining four SARS-CoV-2 variant RBDs (CoV-2, P2, K417E RBD and T478K RBD). Thus, the epitope regions of these two antibodies overlap with the RBD interface contact region 3 (CR3). Third, the epitope of antibodies (Ab3 and Ab6) appears to overlap the L452 residues and may be near the N501 residues. These two antibodies neither neutralized the SARS-CoV RBD nor bind to the immobilized SARS-CoV RBD on the nitrocellulose membrane. Both Ab3 and Ab6 do not neutralize the SARS-CoV-2 RBDs that contain the L452R mutation. Ab3 strongly neutralized K417E RBD, while moderately neutralized other six SARS-CoV-2 RBDs. Ab6 strongly neutralized SARS-CoV-2 RBD and variant RBDs that contain single mutations (E484K, K417, or T478K), and moderately neutralized the RBDs that contain N510Y mutation. Fourth, the epitope of Ab7 appears to overlap the epitopes of Ab3 and Ab6, as they can pair with Ab7 with partial competition immunoassay (Example 3; Tan et al. *Diagnostics* (*Basel*) 11, 1190 (2021)). As previously demonstrated that Ab7 when pairing with Ab1/Ab4 strongly detect SARS-CoV-2 wildtype RBD and UK RBD while weakly detected the SA and BR P.1 RBD that contain E484K mutation. Therefore, the Ab7 epitope likely contains E484 and/or L452R and is in the RBD contact region 2 (CR2).

In summary, the five common mutations (K417N/T/E, L452R, T478K, E484K/Q, and N501Y) of recent SARS-CoV-2 variants differ in their impact on the neutralization and binding activities of the seven antibodies to the SARS-CoV-2 variant RBDs studied. The K417N/TIE mutation has no impact on the neutralization and binding activities of seven antibodies. The L452R mutation abolished the neutralization and binding activities of antibodies (Ab3, Ab6, and Ab7) and largely reduced the neutralizing activity of Ab5. The T478K mutation slightly reduced the neutralization and binding activities of Ab1 and Ab4. The E494K/Q abolished the neutralization and binding activities of Ab7. The N501Y mutation largely reduced the neutralization and binding activities of Ab5 and slightly reduced the neutralization and binding activities of Ab6.

Diagnostic Application of these Anti-RBD Monoclonal Antibodies and Construction of a Rapid S/N Dual Antigen Assay for SARS-CoV-2 Diagnostics To evaluate if these antibodies can be used in sandwich immunoassay for the detection of SARS-CoV-2 spike or RBD protein and nucleocapsid protein, a S/N (spike and nucleocapsid) dual antigen test strip was prepared. The anti-RBD Ab2 was used as the capture and the anti-RBD antibody Ab6 was conjugated to 40-nm AuNP as the detector. The use of the Ab2-Ab6 antibody pair was based on initial antibody pairing studies. At the time when the strip was prepared, knowledge on the neutralization/inhibition of these antibodies on the binding of 10 SARS-CoV-2 variant RBD to ACE2 was not yet available. The RBD was diluted in a PBS buffer containing BSA, Tween-20 and casein, targeting concentrations of 1000, 100, 10, 1, 0.1 ng/mL and zero analyte condition. An aliquot of 75 μL of each diluted sample was used for each assay, with no additional assay chase buffer added. As shown in FIG. 26A and FIG. 26B, the detection sensitivity of the S/N dual Ag strip for recombinant SARS-CoV-2 RBD in buffer system was around 0.1-1 ng/mL. In the presence of RBD, the NP zone was clean with no observable non-specific binding. The assay signal of the spike zone has a 2-log assay range, approximately from 0.1 ng/ml to 10 ng/mL for the current proof of concept design.

Discussion

According to the CDC's national SARS-CoV-2 genomic surveillance program report, since July of 2021 (CDC genomic data tracking variant) the Delta variant has become the super dominant variant circulating in the United States, constituting over 98% of all the weekly collected genomic sequences data. Several studies have reported that the Delta variant had reduced sensitivity to antibody neutralization and the post-infection and post-vaccination human plasma samples (Planas et al. *Nature* 596, 276-280 (2021)). Identification of broad potent antibodies that can neutralize the delta and other variants of SARS-CoV-2 has been one of recent research focuses. Wang et al. isolated two ultra-potent antibodies against 23 variants (Wang et al. *Science* 373, (2021)). Tortorici et al. described a human monoclonal antibody designated S2X259 (Tortorici et al. *Science* 370, 950-957 (2020)), which recognizes a highly conserved cryptic epitope of RBD and broadly neutralizes spike-mediated cell entry of SARS-CoV-2. The epitope A antibodies (Ab1 and Ab4) were found to resist the impact of the five common mutations and neutralize all 10 RBD variants investigated in this example. These two antibodies appear to share similar binding and neutralization behavior as the reported ultra-potent antibody (B1-182.1) (Wang et al. *Science* 373, (2021)). Moreover, the epitopes of our Ab1/Ab4 and the B1-182.1 antibody are likely located at the RBD interface contact region 1. Indeed, the FDA approved dual antibody cocktail targeting non-overlapping epitopes on the RBD has been confirmed to provide broader and more potent protection than another approved dual antibody cocktail that targets partially overlapping epitopes (Starr et al., Cell Reports Medicine. 2 (4): 100255.doi:10.1016/j.xcrm.2021.100255. PMC 8020059. PMID 33842902; Starr et al. Science 371, 850-854 (2021)).

The RBD interact with ACE2 through the RBM that forms a boat shaped bowl surface.

Most neutralizing antibodies interfere the RBD-ACE2 interaction by binding to the RBD and especially the area close to the RBD contact area. The ACE2 contacting area of the RBM is further described as three contact regions: the outer extended knob (CR1), the middle-concaved base (CR3, and the outer expanded tip (CR2) (Deshpande et al. *Front Immunol* 12, 691715 (2021); Pegu et al. *Science* 373, 1372-1377 (2021); Wang et al. *Proc Natl Acad Sci USA* 117, 13967-13974 (2020); Yang et al. *arXiv preprint arXiv:* 2103.06578, (2021)). One FDA approved therapeutic antibody cocktail target non-overlapping epitopes and the 2$^{nd}$ cocktail targets partially overlapped epitopes on RBD. The epitope A antibodies (Ab1 and Ab4) bind to the contact region 1 and the epitope B antibodies (Ab2 and Ab5) bind to the contact region 2 of the RBD interface area. Based on the neutralization study and the binding study, three anti-RBD antibodies were identified (i.e., Ab1 and Ab4 of epitope A and Ab2 of epitope B) that have strong or moderate neutralizing activity gains all SARS-CoV-2 variant RBDs, included in this study. As the epitope A is near the contact region 1 and the epitope B is near the contact region 2 and that both regions are on the outer surface with better accessibility, a dual antibody cocktail was designed by combining Ab1 and Ab2, targeting the opposite epitope regions near the RBD interface. This example demonstrated this dual antibody combo strongly neutralized the ACE2 binding to all SARS-CoV-1 variant RBDs studied, including alpha, beta, gamma, delta, kappa, and iota variants. In addition, this dual antibody combo also had strong neutralizing activity against SARS-CoV RBD. It reasonable to predict that the Ab4/Ab2 combination may achieve similar effect. These two antibodies maybe further optimized for development of an effective anti-COVID therapeutic antibody recipe. In fact, Nie et al. even used a combination of three epitope-distinct human antibodies from RenMab mice to effectively neutralize SARS-CoV-2 and cooperatively minimize the escape of mutants (Nie et al. *Cell Discov* 7, 53 (2021)).

In this Example, a spike and nucleocapsid dual antigen assay was constructed using anti-RBD antibody Ab2 (clone No. 1035740) and anti-nucleocapsid antibody (AnAb4 clone No. 1035129) as captures and anti-RBD antibody Ab6 (clone No. 1035224) and anti-nucleocapsid antibody M47 as detectors. The use of the recombinant SARS-CoV-2 RBD antigen demonstrated that this 10-min rapid S/N dual antigen test has a detection sensitivity of 0.1-1 ng/ml RBDs in buffer system. These studies indicate that these antibodies can be used for diagnostic sandwich immunoassay for the detection of SARS-CoV-2 spike protein. It is possible that a spike/nucleocapsid dual antigen assay can enhance the detection sensitivity of SARS-CoV-2.

Currently molecular and antigen tests are used to demonstrate the presence of viral particle in a patient specimen for SARS-CoV-2 infection. Molecular test is beyond the discussion of this study. Current SARS-CoV-2 rapid antigen tests mostly detect the viral nucleocapsid antigen. In fact, out of 36 FDA-approved EUA antigens assays, except one test for detection of the spike antigen and another test for the detection of spike and nucleocapsid antigens, all other tests detect the presence of nucleocapsid protein (FDA—In Vitro Diagnostics EUAs—Antigen Diagnostic Tests for SARS-CoV-2). However, the nucleocapsid assay cannot differentiate among the SARS-CoV-2 variants. In contrast, proper selection of anti-spike (RBD) antibody pair may provide a rapid tool to detect certain specific SARS-CoV-2 variant. This example demonstrates that pairing antibody Ab1 or Ab4 with antibody Ab2 will enable a test for broad detection of all variant spike proteins. Secondly, pairing Ab1 or Ab2 or Ab4 with an anti-S2 antibody will also help for the detection of all variants. The Ab2-Ab6 antibody pair used in our proof-of-concept study was initially selected without the knowledge of their reactivities with SARS-CoV-2 variant RBDs.

The multiplex RBD protein array used for the antibody and ACE2 binding studies may be further developed into a lateral flow based rapid multiplexed test for IgG, IgM, or IgG specific serological response to variant RBDs and a lateral flow based rapid multiplexed neutralizing antibody screening test based on the interaction of RBD and ACE2.

This example demonstrated (1) that a dual antibody cocktail (Ab1 and Ab2) broadly and strongly inhibits the binding of ten SARS-CoV-2 variant RBDs and SARS-CoV-2 RBD to ACE2. These two antibodies could be further developed for therapeutic use in treatment of COVID-19 disease; (2) these anti-RBD monoclonal antibodies can be used for preparation of diagnostics test kits for SARS-CoV-2 diagnostic use. Upon further characterization and development, these antibodies may be used for SARS-CoV-2 variant specific screening test; (3) a multiplex RBD panel dipstick assay can be used for variant-specific serological assays and variant specific neutralizing antibody assay.

Example 5

Select Anti-Severe Acute Respiratory Syndrome Coronavirus Antibodies Block SARS-CoV-2 Variant Protein Binding to ACE-2

With the global expansion of the COVID-19 pandemic, amino acid mutations within the spike and receptor binding domains of the SARS-CoV2 virus have given rise to local variants of the virus such as the Alpha, Beta, Gamma and Delta variants (Lauring and Malani. *JAMA* 326(9), 880 (2021)). The emergence of these "variants of concern" (Cherian et al. bioRxiv 2021.04.22.440932 (2021)) has had the medical and scientific communities racing to discover antibodies that recognize multiple SARS-CoV2 variants which can be used to diagnosis clinical disease and be used a post-exposure prophylactic therapies to combat an ever growing global health and humanitarian crisis. A select group of SARS-CoV2 viral antibodies that prevent the binding of SARS-CoV2 $S_1$ protein, SARS-CoV S1 protein and SARS-CoV $S_1$ RBD protein to human ACE-2, the human receptor for the SARS-CoV2 virus has been described here. Interestingly, when recombinant SARS-CoV2 S1 and RBD proteins that were derived from the original Wuhan virus were used, all 15 of the SARS-CoV2 viral antibodies described blocked the binding of SARS-CoV2 $S_1$ RBD to ACE-2, To further identify potential diagnostic and therapeutic antibodies that recognize multiple variants of the SARS-CoV2 virus, the ability of the antibodies to block SARS-CoV2:human ACE-2 binding was characterized using recombinant SARS-CoV2 51 and RBD proteins derived from five additional SARS-CoV2 variants: the SARS-CoV2 Alpha B.1.1.7 variant (UK/London variant; Davies et al. *Science* 372 (2021)), SARS-CoV2 N439 variant (Scotland variant; Thomson et al. Cell 184(5), 1171-1187 (2021)), the D614G variant (an offshoot of Scotland and London variants; Volz, et al. *Cell* 184, 64-75 (2021)), the Gamma P.1 variant (Brazilian variant; Hoffmann et al. *Cell* 184(9), 2384-2393 (2021)), and the Delta B.1.617.2 variant (Indian variant; Cherian et al. bioRxiv 2021.04.22.440932 (2021)). All 15 antibodies clones blocked the binding of SARS-CoV2 S1 RBD D614G to ACE-2, albeit to varying degrees. Notably, of the 15 SARS-CoV2 antibodies described, two of the 15 clones tested, clones 1035716 and 1035740, were found to have broad cross reactivity, and were able to block the binding of all 5 variant viral proteins to ACE-2.

Materials and Methods:

The blocking assays described herein used hACE-2 HEK/eGFP Tfx for the cell model; rSARS-CoV-2 C-His tagged variants (rSARS2 RBD aa319-541, N439K; rSARS2-S1 aa16-681, D614G; rSARS2-B.1.1.7 S aa16-1211 2×aa mut.; rSARS2-B.1.1.7 S aa16-1211 4×aa mut.; P.1 RBD aa319-541 3×aa mut.; rSARS2-B.1.617.2 RBD aa319-541 L452R T478K; rSARS2-B.1.617.2 S aa16-1211 10+4×aa mut.) as a protein; and an antibody including, for example, the antibodies produced by the anti-SARS-CoV-2 antibody panels 10352XX, 10354XX, and 10357XX Monoclonal antibodies were added at a concentration in a range of 10 ng/mL to 50 ng/mL. Proteins were added at a concentration in a range of 50 ng/mL to 500 ng/mL.

Viral proteins/antibodies were co-incubated to form a complex and then added to hACE-2 HEK/eGFP Tfx. Anti-His APC was added to the antibody/protein/Tfx samples for detection. The samples were then washed, a live/dead stain was added to exclude dead cells, and analysis was carried out on a BD LSRFortessa™.

Negative controls included hACE-2 HEK/eGFP Tfx alone; anti-His APC+(hACE-2 HEK/eGFP Tfx (FIG. 27A); and isotype controls (Ms IgG1, Ms IgG2a, or Ms IgG2b)+protein+(hACE-2 HEK/eGFP Tfx)+anti-His APC (FIG. 27A).

Each of the variant His-tagged proteins+anti-His APC served as a protein binding control for rSARS-CoV-2.

Anti-viral antibodies+viral proteins+(hACE-2 HEK/eGFP Tfx)+(anti-His APC) were used to assess viral antibody blocking of hACE-2 vs. SARS-CoV-2 proteins (FIG. 27B). The results of this example are shown in FIGS. 27-33.

FIG. 27A and FIG. 27B show select anti-SARS-CoV-2 antibodies block binding of the SARS-CoV-2 $S_1$ RBD N439K variant to ACE-2. rSARS2 RBD aa319-541 N439K protein was mixed and then incubated with flow cytometry staining buffer, Mouse IgG1, IgG2a or IgG2b isotype control antibodies (FIG. 27A); or with anti-SARS-CoV-2 monoclonal antibodies from panels 10352XX, 10354XX, or 10357XX (FIG. 27B) to allow a complex to form. After incubation, the mixture was added to a single cell suspension of hACE-2 HEK/eGFP Tfx, followed by addition of a secondary anti-His antibody to assess viral antibody blocking. Flow cytometry gates were set on anti-His fluorescence of hACE-2 HEK/eGFP Tfx cells without SARS-CoV-2 $S_1$ RBD N439K variant protein.

FIG. 28A and FIG. 28B show anti-SARS-CoV-2 antibodies block binding of the SARS-CoV-2 $S_1$ D614G variant to ACE-2. rSARS2-S1 aa16-681 D614G protein was mixed and then incubated with flow cytometry staining buffer, Mouse IgG1, IgG2a or IgG2b isotype control antibodies (FIG. 28A); or with anti-SARS-CoV-2 monoclonal antibodies from panels 10352XX, 10354XX, or 10357XX (FIG. 28B) to allow a complex to form. After incubation, the mixture was added to a single cell suspension of hACE-2 HEK/eGFP Tfx, followed by addition of a secondary anti-His antibody to assess viral antibody blocking. Flow cytometry gates were set on anti-His fluorescence of hACE-2 HEK/eGFP Tfx cells without SARS-CoV-2 $S_1$ D614G variant protein.

FIG. 29A and FIG. 29B show select anti-SARS-CoV-2 antibodies block binding of the SARS-CoV-2 S B.1.1.7 2× variant to ACE-2. rSARS2-B.1.1.7 S aa16-1211 2×aa mut. protein was mixed and then incubated with flow cytometry staining buffer, Mouse IgG1, IgG2a or IgG2b isotype control antibodies (FIG. 29A); or with anti-SARS-CoV-2 monoclonal antibodies from panels 10352XX, 10354XX, or 10357XX (FIG. 29B) to allow a complex to form. After incubation, the mixture was added to a single cell suspension of hACE-2 HEK/eGFP Tfx, followed by addition of a secondary anti-His antibody to assess viral antibody blocking. Flow cytometry gates were set on anti-His fluorescence of hACE-2 HEK/eGFP Tfx cells without SARS-CoV-2 S B.1.1.7 2× variant protein.

FIG. 30A and FIG. 30B show select anti-SARS-CoV-2 antibodies block binding of the SARS-CoV-2 S B.1.1.7 4× variant to ACE-2. rSARS2-B.1.1.7 S aa16-1211 4×aa mut. protein was mixed and then incubated with flow cytometry staining buffer, Mouse IgG1, IgG2a or IgG2b isotype control antibodies (FIG. 30A); or with anti-SARS-CoV-2 monoclonal antibodies from panels 10352XX, 10354XX, or 10357XX (FIG. 30B) to allow a complex to form. After incubation, the mixture was added to a single cell suspension of hACE-2 HEK/eGFP Tfx, followed by addition of a secondary anti-His antibody to assess viral antibody blocking. Flow cytometry gates were set on anti-His fluorescence of hACE-2 HEK/eGFP Tfx cells without SARS-CoV-2 S B.1.1.7 4× variant protein.

FIG. 31A and FIG. 31B show select anti-SARS-CoV-2 antibodies block binding of the SARS-CoV-2 $S_1$ RBD P.1 variant to ACE-2. rSARS2-P.1 RBD aa319-541 3×aa mut. protein was mixed and then incubated with flow cytometry staining buffer, Mouse IgG1, IgG2a or IgG2b isotype control antibodies (FIG. 31A); or with anti-SARS-CoV-2 monoclonal antibodies from panels 10352XX, 10354XX, or 10357XX (FIG. 31B) to allow a complex to form. After incubation, the mixture was added to a single cell suspension of hACE-2 HEK/eGFP Tfx, followed by addition of a secondary anti-His antibody to assess viral antibody blocking. Flow cytometry gates were set on anti-His fluorescence of hACE-2 HEK/eGFP Tfx cells without SARS-CoV-2 $S_1$ RBD P.1 variant protein.

FIG. 32A and FIG. 32B show select anti-SARS-CoV-2 antibodies block binding of the SARS-CoV-2 $S_1$ RBD B.1.617.2 variant to ACE-2. rSARS2-B.1.617.2 $S_1$RBD aa319-541 L452R T478K protein was mixed and then incubated with flow cytometry staining buffer, Mouse IgG1, IgG2a or IgG2b isotype control antibodies (FIG. 32A); or with anti-SARS-CoV-2 monoclonal antibodies from panels 10352XX, 10354XX, or 10357XX (FIG. 32B) to allow a complex to form. After incubation, the mixture was added to a single cell suspension of hACE-2 HEK/eGFP Tfx, followed by addition of a secondary anti-His antibody to assess viral antibody blocking. Flow cytometry gates were set on anti-His fluorescence of hACE-2 HEK/eGFP Tfx cells without SARS-CoV-2 $S_1$ RBD B.1.617.2 variant protein.

FIG. 33A and FIG. 33B show select anti-SARS-CoV-2 antibodies block binding of the SARS-CoV-2 S B.1.617.2 variant to ACE-2. rSARS2-B.1.617.2 S aa16-1211 10+4×aa mut. protein was mixed and then incubated with flow cytometry staining buffer, Mouse IgG1, IgG2a or IgG2b isotype control antibodies (FIG. 33A); or with anti-SARS-CoV-2 monoclonal antibodies from panels 10352XX, 10354XX, or 10357XX (FIG. 33B) to allow a complex to form. After incubation, the mixture was added to a single cell suspension of hACE-2 HEK/eGFP Tfx, followed by addition of a secondary anti-His antibody to assess viral antibody blocking. Flow cytometry gates were set on anti-His fluorescence of hACE-2 HEK/eGFP Tfx cells without SARS-CoV-2 $S_1$ S B.1.617.2 variant protein.

A summary of anti-SARS-CoV-2 antibody blocking of a recombinant SARS-CoV-2 $S_1$ RBD N439K, SARS-CoV-2 $S_1$D614G, SARS-CoV-2 S B.1.1.7 2×, SARS-CoV-2 S B.1.1.7 4×, SARS-CoV-2 $S_1$ RBD P.1, SARS-CoV-2 $S_1$ RBD B.1.617.2, and SARS-CoV-2 S RBD B.1.617.2 variant protein binding to ACE-2 is shown in Table 13 below.

TABLE 13

| Target | Antibody clone | SARS-CoV2 S1 RBD N439K | SARS-CoV2 S1 D614G | SARS-CoV2 S B.1.1.7 2x | SARS-CoV2 S B.1.1.7 4x | SARS-CoV2 S1 RBD P.1 | S1 RBD B.1.617.2 | SARS-CoV2 S B.1.617.2 |
|---|---|---|---|---|---|---|---|---|
| S1 | 1035211 | 18.1 | 86.6 | 76.3 | 72.4 | 0 | 1.7 | 0 |
| S1 | 1035224 | 96.1 | 86.7 | 33.9 | 74.1 | 88 | 0 | 0 |
| S1 | 1035240 | 49 | 86.8 | 91.2 | 78.6 | 0 | 0.7 | 0 |
| RBD | 1035423 | 34.6 | 86.6 | 71.1 | 75.9 | 22 | 81.4 | 89.5 |
| S1 | 1035709 | 90.8 | 86.7 | 92.1 | 80.7 | 90 | 5.3 | 58.8 |
| S1 | 1035716 | 96.2 | 86.7 | 94.4 | 81.5 | 95 | 96.5 | 89.3 |
| S1 | 1035740 | 96 | 86.8 | 94.3 | 82.1 | 95 | 96.5 | 89.6 |
| S1 | 1035752 | 53 | 86.7 | 81.4 | 74.4 | 77.2 | 0.8 | 0 |
| S1 | 1035753 | 96.2 | 86.7 | 93.6 | 81.2 | 90.4 | 0 | 0 |
| S1 | 1035755 | 25.2 | 86.6 | 12 | 35.8 | 14.9 | 0.9 | 0 |
| S1 | 1035762 | 42.7 | 86.6 | 75.7 | 75.2 | 40.5 | 1.5 | 18.7 |
| RBD | 1035414 | 43 | 78 | 17.8 | 4.8 | 0.4 | 37.4 | 73.5 |
| RBD | 1035419 | 69.3 | 85.8 | 21.8 | 33.3 | 8.7 | 72.5 | 78.5 |
| RBD | 1035433 | 0.9 | 81.4 | 82.0 | 23.5 | 0 | 18.4 | 93.8 |
| S1 | 1035744 | 36.5 | 67.7 | 6.2 | 0 | 0 | 32.6 | 14.1 |

Summary of anti-SARS-CoV-2 antibody blocking. Percent Blocking was calculated by subtracting the percent of anti-His positive cells in the presence of each monoclonal antibody from the percent of anti-His positive cells incubated with each of the rSARS-CoV-2 variant proteins.

As new mutations occur resulting in the emergence of novel variants of the SARS-CoV2 virus, broadly cross-reactive antibodies that can identify multiple SARS-CoV2 variants and prevent their binding to the human ACE-2 will be in high demand. Disclosed herein are 15 novel antibody clones that recognize the S1 and/or RBD proteins of the original Wuhan strain of the SARS-CoV2 virus and prevent the binding of these viral proteins in a human ACE2 over-expression system. Also described herein is the ability of these 15 clones to recognize S, S1 and/or RBD proteins from five prevalent SARS-CoV2 variants, the SARS-CoV2 Alpha B.1.1.7 variant (UK/London variant); the SARS-CoV2 N439 variant (Scotland variant); the D614G variant (an offshoot of Scotland and London variants); the Gamma P.1 variant (Brazilian variant); and the Delta B.1.617.2 variant (Indian variant) and prevent the binding of these viral proteins in the same human ACE-2 over-expression system.

Of the 15 SARS-CoV2 antibodies tested, two of the 15 clones tested, clones 1035716 and 1035740, were found to have the most broad cross reactivity, and were each able to block the binding of all 5 variant viral proteins to ACE-2: the SARS-CoV2 Alpha B. 1.1.7 UK/London variant (80-95% blocking); the SARS-CoV2 N439 Scotland variant (>95% blocking); the D614G Scotland/UK variant (>85% blocking); the Gamma P.1 Brazilian variant (95% blocking); and the Delta B.1.617.2 Indian variant (89%-95% blocking). Notably, while all clones failed to block MERS protein binding to its human receptor, CD26, most likely due to the low homology between the SARS and MERS viruses, clone 1035740 exhibited the highest percentage of blocking against all SARS-CoV and SARS-CoV2 $S_1$ and RBD proteins tested.

Two other clones, 103224 and 103753, showed modest to good blocking against four of the SARS-CoV2 variants, the SARS-CoV2 Alpha B.1.1.7 UK/London variant; the SARS-CoV2 N439 Scotland variant; the D614G Scotland/UK variant; the Gamma P.1 Brazilian variant (95% blocking), but completely failed to blocking binding of the Delta B.1.617.2 Indian variant proteins. Moreover, most of the clones (9 out of 15) showed relatively poor blocking against the Delta B.1.617.2 Indian variant proteins highlighting the unique nature of clones 1035716 and 1035740 which effectively blocked binding of Delta variant proteins. The noticeable lack of cross-reactivity of our 15 antibody clones with the Delta variant viral proteins may also offer a potential explanation as to why the Delta variant has been suggested to be more contagious than other SARS-CoV2 variants (Li et al. *medRxiv* 2021.07.07.21260122 (2021)) and how patients in two different studies that were infected with the Delta variant were more likely to be hospitalized than patients infected with Alpha or the original virus strains where pre-existing immunity to the original SARS-CoV2 virus may provide little protection (Fisman and Tuite. *medRxiv* 2021.07.05.21260050 (2021); Bernal et al. *N Engl J Med* 385:585-594 (2021); Mlcochova et al. *Nature* 599, 114-119 (2021)).

All 15 viral SARS-CoV2 antibodies blocked binding of SARS-CoV2 $S_1$ RBD D614G to ACE-2. 12 of the 15 clones blocked SARS-CoV2 51 RBD D614G by more than 85% while the remaining three clones blocked binding between 65% and 81%. In general, antibodies that were originally generated by immunizing with the full S1 protein of the original Wuhan SARS-CoV2 virus displayed greater overall cross reactivity with the five SARS-CoV2 variants whether the variant protein being blocked were the S, full length S1 protein or the shorter RBD protein. For example, 14 or the 15 clones reduced binding of the N439K variant RBD protein. Antibody clones generated by immunizing with the full $S_1$ protein of the original Wuhan SARS-CoV2 virus reduced the binding of the SARS-CoV2 N439K variant RBD protein an average of 64%. By comparison, antibody clones generated by immunizing with the shorter RBD protein of the original Wuhan SARS-CoV2 virus reduced the binding of the SARS-CoV2 N439K variant RBD protein only by an average of 37%.

A similar trend was seen when using the Brazilian P.1 variant; however, only 10 of the 15 clones reduced viral protein binding. In this scenario, antibody clones generated against the full Wuhan SARS-CoV2 $S_1$ protein reduced the binding of the SARS-CoV2 P.1 variant RBD protein an average of 54%. By comparison, antibody clones generated against the shorter RBD protein of the original Wuhan virus reduced the binding of the SARS-CoV2 P.1 variant RBD protein only by an average of 8%.

Interestingly, this trend was reversed when the blocking of Delta variant S and RBD proteins was assayed. Both recombinant S and RBD proteins were available only for the Delta variant at the time these assays were performed. For the N439K, D614G, and P.1 variants, either recombinant S1 or RBD proteins were used, but not both. When S1 Wuhan strain antibodies were assayed for blocking against recombinant S Delta variant protein, only five clones were able to reduce Delta S1 binding, resulting in an average blocking of only 25%. Similarly, only three of the S1 clones were able to block recombinant RBD Delta variant protein, resulting in an average blocking of only 21%. However, when the RBD Wuhan strain antibodies were assays for blocking, they performed much better. All four RBD clones were able to reduce recombinant Delta variant RBD protein binding by an average of 52 percent and this improved dramatically when assayed against recombinant Delta variant S protein where the same four clones reduced Delta variant S1 protein binding by an average of 83%. This again likely highlights the unique nature of, and the challenges posed by, the SARS-CoV2 Delta variant virus.

While the overall trend was reversed when the blocking of Delta variant S and RBD proteins was assayed, it is worth noting that the two antibody clones that were found to have the most broad cross reactivity were generated by immunizing against the full length Wuhan strain $S_1$ protein and showed potent blocking against both Delta variant S (clone 1035716=89.3% blocking; clone 1035740=89.6% blocking) and RBD proteins (clone 1035716=96.5% blocking; clone 1035740=96.5% blocking).

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

SEQUENCE FREE LISTING

SEQ ID NO: 1 Amino acid sequence light chain 1035211 antibody

SEQ ID NO: 2 Amino acid sequence light chain 1035224 antibody

SEQ ID NO: 3 Amino acid sequence light chain 1035240 antibody

SEQ ID NO: 4 Amino acid sequence light chain 1035414 antibody

SEQ ID NO: 5 Amino acid sequence light chain 1035419 antibody

SEQ ID NO: 6 Amino acid sequence light chain 1035423 antibody

SEQ ID NO: 7 Amino acid sequence light chain 1035433 antibody

SEQ ID NO: 8 Amino acid sequence light chain 1035709 antibody

SEQ ID NO: 9 Amino acid sequence light chain 1035716 antibody

SEQ ID NO: 10 Amino acid sequence light chain 1035740 antibody

SEQ ID NO: 11 Amino acid sequence light chain 1035744-1 antibody

SEQ ID NO: 12 Amino acid sequence light chain 1035744-2 antibody
SEQ ID NO: 13 Amino acid sequence light chain 1035752 antibody
SEQ ID NO: 14 Amino acid sequence light chain 1035753 antibody
SEQ ID NO: 15 Amino acid sequence light chain 1035755 antibody
SEQ ID NO: 16 Amino acid sequence light chain 1035762 antibody
SEQ ID NO: 17 Amino acid sequence heavy chain 1035211 antibody
SEQ ID NO: 18 Amino acid sequence heavy chain 1035224 antibody
SEQ ID NO: 19 Amino acid sequence heavy chain 1035240 antibody
SEQ ID NO: 20 Amino acid sequence heavy chain 1035414 antibody
SEQ ID NO: 21 Amino acid sequence heavy chain 1035419 antibody
SEQ ID NO: 22 Amino acid sequence heavy chain 1035423 antibody
SEQ ID NO: 23 Amino acid sequence heavy chain 1035433 antibody
SEQ ID NO: 24 Amino acid sequence heavy chain 1035709 antibody
SEQ ID NO: 25 Amino acid sequence heavy chain 1035716 antibody
SEQ ID NO: 26 Amino acid sequence heavy chain 1035740 antibody
SEQ ID NO: 27 Amino acid sequence heavy chain 1035744 antibody
SEQ ID NO: 28 Amino acid sequence heavy chain 1035752 antibody
SEQ ID NO: 29 Amino acid sequence heavy chain 1035753 antibody
SEQ ID NO: 30 Amino acid sequence heavy chain 1035755 antibody
SEQ ID NO: 31 Amino acid sequence heavy chain 1035762 antibody
SEQ ID NO: 32 Amino acid sequence light chain CDR 1 of 1035211 and 1035240 antibodies
SEQ ID NO: 33 Amino acid sequence light chain CDR 2 of 1035211 and 1035240 antibodies
SEQ ID NO: 34 Amino acid sequence light chain CDR 3 of 1035211, 1035240, 1035744-1, and 1035744-2 antibodies
SEQ ID NO: 35 Amino acid sequence light chain CDR 1 of 1035224 and 1035755 antibodies
SEQ ID NO: 36 Amino acid sequence light chain CDR 2 of 1035224 and 1035755 antibodies
SEQ ID NO: 37 Amino acid sequence light chain CDR 3 of 1035224 and 1035755 antibodies
SEQ ID NO: 38 Amino acid sequence light chain CDR 1 of 1035419 antibody
SEQ ID NO: 39 Amino acid sequence light chain CDR 2 of 1035419 and 1035414 antibodies
SEQ ID NO: 40 Amino acid sequence light chain CDR 3 of 1035419 antibody
SEQ ID NO: 41 Amino acid sequence light chain CDR 1 of 1035423 antibody
SEQ ID NO: 42 Amino acid sequence light chain CDR 2 of 1035423 antibody
SEQ ID NO: 43 Amino acid sequence light chain CDR 3 of 1035423 antibody
SEQ ID NO: 44 Amino acid sequence light chain CDR 1 of 1035433 antibody
SEQ ID NO: 45 Amino acid sequence light chain CDR 2 of 1035433 antibody
SEQ ID NO: 46 Amino acid sequence light chain CDR 3 of 1035433 antibody
SEQ ID NO: 47 Amino acid sequence light chain CDR 1 of 1035414 antibody
SEQ ID NO: 48 Amino acid sequence light chain CDR 3 of 1035414 antibody
SEQ ID NO: 49 Amino acid sequence light chain CDR 1 of 1035709 antibody
SEQ ID NO: 50 Amino acid sequence light chain CDR 2 of 1035709 and 1035762 antibodies
SEQ ID NO: 51 Amino acid sequence light chain CDR 3 of 1035709 and 1035762 antibodies
SEQ ID NO: 52 Amino acid sequence light chain CDR 1 of 1035716 antibody
SEQ ID NO: 53 Amino acid sequence light chain CDR 2 of 1035716 antibody
SEQ ID NO: 54 Amino acid sequence light chain CDR 3 of 1035716 antibody
SEQ ID NO: 55 Amino acid sequence light chain CDR 1 of 1035740 antibody
SEQ ID NO: 56 Amino acid sequence light chain CDR 2 of 1035740 antibody
SEQ ID NO: 57 Amino acid sequence light chain CDR 3 of 1035740 antibody
SEQ ID NO: 58 Amino acid sequence light chain CDR 1 of 1035744-1 antibody
SEQ ID NO: 59 Amino acid sequence light chain CDR 2 of 1035744-1 antibody
SEQ ID NO: 60 Amino acid sequence light chain CDR 1 of 1035744-2 antibody
SEQ ID NO: 61 Amino acid sequence light chain CDR 2 of 1035744-2 antibody
SEQ ID NO: 62 Amino acid sequence light chain CDR 1 of 1035752 antibody
SEQ ID NO: 63 Amino acid sequence light chain CDR 2 of 1035752 antibody
SEQ ID NO: 64 Amino acid sequence light chain CDR 3 of 1035752 antibody
SEQ ID NO: 65 Amino acid sequence light chain CDR 1 of 1035753 antibody
SEQ ID NO: 66 Amino acid sequence light chain CDR 2 of 1035753 antibody
SEQ ID NO: 67 Amino acid sequence light chain CDR 3 of 1035753 antibody
SEQ ID NO: 68 Amino acid sequence light chain CDR 1 of 1035762 antibody
SEQ ID NO: 69 Amino acid sequence heavy chain CDR 1 of 1035211 antibody
SEQ ID NO: 70 Amino acid sequence heavy chain CDR 2 of 1035211 and 1035240 antibodies
SEQ ID NO: 71 Amino acid sequence heavy chain CDR 3 of 1035211 and 1035240 antibodies
SEQ ID NO: 72 Amino acid sequence heavy chain CDR 1 of 1035224 antibody
SEQ ID NO: 73 Amino acid sequence heavy chain CDR 2 of 1035224 and 1035755 antibodies
SEQ ID NO: 74 Amino acid sequence heavy chain CDR 3 of 1035224 antibody
SEQ ID NO: 75 Amino acid sequence heavy chain CDR 1 of 1035240 antibody
SEQ ID NO: 76 Amino acid sequence heavy chain CDR 1 of 1035414 and 1035419 antibodies
SEQ ID NO: 77 Amino acid sequence heavy chain CDR 2 of 1035419 antibody SEQ ID NO: 78 Amino acid sequence heavy chain CDR 3 of 1035419 antibody
SEQ ID NO: 79 Amino acid sequence heavy chain CDR 1 of 1035423 antibody
SEQ ID NO: 80 Amino acid sequence heavy chain CDR 2 of 1035423 antibody
SEQ ID NO: 81 Amino acid sequence heavy chain CDR 3 of 1035423 antibody
SEQ ID NO: 82 Amino acid sequence heavy chain CDR 1 of 1035433 antibody
SEQ ID NO: 83 Amino acid sequence heavy chain CDR 2 of 1035433 antibody
SEQ ID NO: 84 Amino acid sequence heavy chain CDR 3 of 1035433 antibody
SEQ ID NO: 85 Amino acid sequence heavy chain CDR 2 of 1035414 antibody
SEQ ID NO: 86 Amino acid sequence heavy chain CDR 3 of 1035414 antibody
SEQ ID NO: 87 Amino acid sequence heavy chain CDR 1 of 1035709 and 1035762 antibodies
SEQ ID NO: 88 Amino acid sequence heavy chain CDR 2 of 1035709 antibody
SEQ ID NO: 89 Amino acid sequence heavy chain CDR 3 of 1035709 and 1035762 antibodies
SEQ ID NO: 90 Amino acid sequence heavy chain CDR 1 of 1035716 and 1035740 antibodies
SEQ ID NO: 91 Amino acid sequence heavy chain CDR 2 of 1035716 antibody
SEQ ID NO: 92 Amino acid sequence heavy chain CDR 3 of 1035716 and 1035740 antibodies
SEQ ID NO: 93 Amino acid sequence heavy chain CDR 2 of 1035740 antibody
SEQ ID NO: 94 Amino acid sequence heavy chain CDR 1 of 1035744 antibody
SEQ ID NO: 95 Amino acid sequence heavy chain CDR 2 of 1035744 antibody
SEQ ID NO: 96 Amino acid sequence heavy chain CDR 3 of 1035744 antibody
SEQ ID NO: 97 Amino acid sequence heavy chain CDR 1 of 1035752 antibody
SEQ ID NO: 98 Amino acid sequence heavy chain CDR 2 of 1035752 antibody
SEQ ID NO: 99 Amino acid sequence heavy chain CDR 3 of 1035752 antibody
SEQ ID NO: 100 Amino acid sequence heavy chain CDR 1 of 1035753 and 1035755 antibodies
SEQ ID NO: 101 Amino acid sequence heavy chain CDR 2 of 1035753 antibody
SEQ ID NO: 102 Amino acid sequence heavy chain CDR 3 of 1035753 antibody
SEQ ID NO: 103 Amino acid sequence heavy chain CDR 3 of 1035755 antibody
SEQ ID NO: 104 Amino acid sequence heavy chain CDR 2 of 1035762 antibody

What is claimed is:

1. An anti-SARS-CoV antibody or antigen binding fragment thereof, wherein the anti-SARS-CoV antibody or antigen binding fragment thereof comprises:

a light chain variable region comprising a CDR1 comprising SEQ ID NO: 32, a CDR2 comprising SEQ ID NO: 33, and a CDR3 comprising SEQ ID NO: 34 and a heavy chain variable region comprising a CDR1 comprising SEQ ID NO: 69, a CDR2 comprising SEQ ID NO: 70, and a CDR3 comprising SEQ ID NO: 71; or a light chain variable region comprising a CDR1 comprising SEQ ID NO: 35, a CDR2 comprising SEQ ID NO: 36, and a CDR3 comprising SEQ ID NO: 37 and a heavy chain variable region comprising a CDR1 comprising SEQ ID NO: 72, a CDR2 comprising SEQ ID NO: 73, and a CDR3 comprising SEQ ID NO: 74; or a light chain variable region comprising a CDR1 comprising SEQ ID NO: 32, a CDR2 comprising SEQ ID NO: 33, and a CDR3 comprising SEQ ID NO: 34 and a heavy chain variable region comprising a CDR1 comprising SEQ ID NO: 75, a CDR2 comprising SEQ ID NO: 70, and a CDR3 comprising SEQ ID NO: 71; or a light chain variable region comprising a CDR1 comprising SEQ ID NO: 47, a CDR2 comprising SEQ ID NO: 39, and a CDR3 comprising SEQ ID NO: 48 and a heavy chain variable region comprising a CDR1 comprising SEQ ID NO: 76, a CDR2 comprising SEQ ID NO: 85, and a CDR3 comprising SEQ ID NO: 86; or a light chain variable region comprising a CDR1 comprising SEQ ID NO: 38, a CDR2 comprising SEQ ID NO: 39, and a CDR3 comprising SEQ ID NO: 40 and a heavy chain variable region comprising a CDR1 comprising SEQ ID NO: 76, a CDR2 comprising SEQ ID NO: 77 and a CDR3 comprising SEQ ID NO: 78; or a light chain variable region comprising a CDR1 comprising SEQ ID NO: 41, a CDR2 comprising SEQ ID NO: 42, and a CDR3 comprising SEQ ID NO: 43 and a heavy chain variable region comprising a CDR1 comprising SEQ ID NO: 79, a CDR2 comprising SEQ ID NO: 80, and a CDR3 comprising SEQ ID NO: 81; or a light chain variable region comprising a CDR1 comprising SEQ ID NO: 44, a CDR2 comprising SEQ ID NO: 45, and a CDR3 comprising SEQ ID NO: 46 and a heavy chain variable region comprising a CDR1 comprising SEQ ID NO: 82, a CDR2 comprising SEQ ID NO: 83, and a CDR3 comprising SEQ ID NO: 84; or a light chain variable region comprising a CDR1 comprising SEQ ID NO: 49, a CDR2 comprising SEQ ID NO: 50, and a CDR3 comprising SEQ ID NO: 51 and a heavy chain variable region comprising a CDR1 comprising SEQ ID NO: 87, a CDR2 comprising SEQ ID NO: 88, and a CDR3 comprising SEQ ID NO: 89; or a light chain variable region comprising a CDR1 comprising SEQ ID NO: 52, a CDR2 comprising SEQ ID NO: 53, and a CDR3 comprising SEQ ID NO: 54 and a heavy chain variable region comprising a CDR1 comprising SEQ ID NO: 90, a CDR2 comprising SEQ ID NO: 91, and a CDR3 comprising SEQ ID NO: 92; or a light chain variable region comprising a CDR1 comprising SEQ ID NO: 55, a CDR2 comprising SEQ ID NO: 56, and a CDR3 comprising SEQ ID NO: 57 and a heavy chain variable region comprising a CDR1 comprising SEQ ID NO: 90, a CDR2 comprising SEQ ID NO: 93, and a CDR3 comprising SEQ ID NO: 92; or a light chain variable region comprising a CDR1 comprising SEQ ID NO: 58, a CDR2 comprising SEQ ID NO: 59, and a CDR3 comprising SEQ ID NO: 34 and a heavy chain variable region comprising a CDR1 comprising SEQ ID NO: 94, a CDR2 comprising SEQ ID NO: 95, and a CDR3 comprising SEQ ID NO: 96; or a light chain variable region comprising a CDR1 comprising SEQ ID NO: 60, a CDR2 comprising SEQ ID NO: 61, and a CDR3 comprising SEQ ID NO: 34 and a heavy chain variable region comprising a CDR1 comprising SEQ ID NO: 94, a CDR2 comprising SEQ ID NO: 95 and a CDR3 comprising SEQ ID NO: 96; or a light chain variable region comprising a CDR1 comprising SEQ ID NO: 62, a CDR2 comprising SEQ ID NO: 63, and a CDR3 comprising SEQ ID NO: 64 and a heavy chain variable region comprising a CDR1 comprising SEQ ID NO:97, a CDR2 comprising SEQ ID NO: 98, and a CDR3 comprising SEQ ID NO: 99; or a light chain variable region comprising a CDR1 comprising SEQ ID NO: 65, a CDR2 comprising SEQ ID NO: 66, and a CDR3 comprising SEQ ID NO: 67 and a heavy chain variable region comprising a CDR1 comprising SEQ ID NO: 100, a CDR2 comprising SEQ ID NO: 101, and a CDR3 comprising SEQ ID NO: 102; or a light chain variable region comprising a CDR1 comprising SEQ ID NO: 35, a CDR2 comprising SEQ ID NO: 36, and a CDR3 comprising SEQ ID NO: 37 and a heavy chain variable region comprising a CDR1 comprising SEQ ID NO: 100, a CDR2 comprising SEQ ID NO: 73, and a CDR3 comprising SEQ ID NO: 103; or a light chain variable region comprising a CDR1 comprising SEQ ID NO: 68, a CDR2 comprising SEQ ID NO: 50, and a CDR3 comprising SEQ ID NO: 51 and a heavy chain variable region comprising a CDR1 comprising SEQ ID NO: 87, a CDR2 comprising SEQ ID NO: 104, and a CDR3 comprising SEQ ID NO: 89.

2. An anti-SARS-CoV antibody or antigen binding fragment thereof of claim 1, wherein the anti-SARS-CoV antibody or antigen binding fragment thereof comprises:

a heavy chain variable region (VH) with an amino acid sequence selected from SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO:28, SEQ ID NO: 29, SEQ ID NO: 30, and SEQ ID NO: 31; or a light chain variable region (VL) with an amino acid sequence selected from SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16; or a VH with amino acid sequence SEQ ID NO: 17 and a VL with amino acid sequence SEQ ID NO: 1, or a VH with amino acid sequence SEQ ID NO: 18 and a VL with amino acid sequence SEQ ID NO: 2, or
a VH with amino acid sequence SEQ ID NO: 19 and a VL with amino acid sequence SEQ ID NO: 3, or
a VH with amino acid sequence SEQ ID NO: 20 and a VL with amino acid sequence SEQ ID NO: 4, or
a VH with amino acid sequence SEQ ID NO: 21 and a VL with amino acid sequence SEQ ID NO: 5, or
a VH with amino acid sequence SEQ ID NO: 22 and a VL with amino acid sequence SEQ ID NO: 6, or
a VH with amino acid sequence SEQ ID NO: 23 and a VL with amino acid sequence SEQ ID NO: 7, or
a VH with amino acid sequence SEQ ID NO: 24 and a VL with amino acid sequence SEQ ID NO: 8, or
a VH with amino acid sequence SEQ ID NO: 25 and a VL with amino acid sequence SEQ ID NO: 9, or
a VH with amino acid sequence SEQ ID NO: 26 and a VL with amino acid sequence SEQ ID NO: 10, or
a VH with amino acid sequence SEQ ID NO:27 and a VL with amino acid sequence SEQ ID NO: 11, or
a VH with amino acid sequence SEQ ID NO: 27 and a VL with amino acid sequence SEQ ID NO: 12, or
a VH with amino acid sequence SEQ ID NO: 28 and a VL with amino acid sequence SEQ ID NO: 13, or
a VH with amino acid sequence SEQ ID NO: 29 and a VL with amino acid sequence SEQ ID NO: 14, or
a VH with amino acid sequence SEQ ID NO: 30 and a VL with amino acid sequence SEQ ID NO: 15, or
a VH with amino acid sequence SEQ ID NO: 31 and a VL with amino acid sequence SEQ ID NO: 16.

3. The anti-SARS-CoV antibody of claim 1, wherein the anti-SARS-CoV antibody specifically binds to the receptor binding domain (RBD) of the SARS-CoV spike(S) protein.

4. The anti-SARS-CoV antibody of claim 1, wherein the anti-SARS-CoV antibody decreases binding of SARS-CoV-1 or SARS-CoV-2 or both SARS-CoV-1 and SARS-CoV-2 to ACE-2 by at least 10 percent (%), at least 15%, at least 20%, at least 25%, at least 30%, at least 40%, at least 50%, at least 60%, at least 70%, at least 80%, at least 90%, at least 95%, or at least 98%.

5. The anti-SARS-CoV antibody of claim 1, wherein the anti-SARS-CoV antibody specifically binds SARS-CoV-2.

6. The anti-SARS-CoV antibody of claim 1, wherein the anti-SARS-CoV antibody specifically binds SARS-CoV-1.

7. The anti-SARS-CoV antibody of claim 1, wherein the anti-SARS-CoV antibody specifically binds to a SARS-CoV-2 variant selected from:
the alpha variant (the United Kingdom variant (UK), B.1.1.7 lineage, RBD with N501Y);
the beta variant (South African variant (SA), B.1.3512 lineage, RBD with K417N, E484K, and N501Y);
the gamma variant (Brazilian variant P.1 (BR P.1), B.1.1.28.1 lineage, RBD with K417T, E484K, and N501Y);
the delta variant (Indian variant 2 (IN v2), B.1.617.2 lineage, RBD with L452R and T478K);
the epsilon variant (California variant (CA), B.1.427/9 lineage, RBD with L452R);
the kappa variant (Indian variant 1 (IN v1), B.1.617.1 lineage, RBD with L452R and E484Q);
the zeta variant (Brazilian variant P.2 (BR P.2), B.1.1.28.2 lineage, RBD with E484K);
the K417E RBD (R319-F541 with K417E);
the T478K RBD (R319-F541 with T478K);
the iota variant (New York variant (NY), B.1.526 lineage, RBD with a single mutation E484K);
the eta variant (Nigeria variant, B.1.525 lineage);
the lambda variant (Peru variant, C.37 lineage, RBD with L452Q and F490S);
the theta variant (Philippine variant, P.3 lineage, RBD with E484K and N501Y); and/or
the Denmark mink variant (B.1.1.298 lineage, DM, RBD with Y453).

8. The anti-SARS-CoV antibody of claim 1, wherein the anti-SARS-CoV antibody has an $NC_{50}$ of about 0.3 μg/ul to about 1.5 μg/ul, and wherein $NC_{50}$ is the concentration of antibody in μg/mL that yields a 50% inhibition of the maximal binding capacity of recombinant RBD and recombinant ACE2 as measured by lateral flow immunoassay.

9. The anti-SARS-CoV antibody of claim 1, wherein the anti-SARS-CoV antibody comprises a humanized antibody.

10. The anti-SARS-CoV antibody of claim 1, wherein the anti-SARS-CoV antibody is labeled with one or more detectable markers.

11. A composition comprising the anti-SARS-CoV antibody of claim 1.

12. The composition of claim 11 further comprising one or more additional anti-SARS-CoV antibodies.

13. A composition comprising two or more anti-SARS-CoV antibodies of claim 1.

14. The composition of claim 13, wherein one anti-SARS-CoV antibody binds to a bin A epitope of RBD and one anti-SARS-CoV antibody binds to a bin B epitope of RBD:
wherein an anti-SARS-CoV antibody binding to a bin A epitope of RBD comprises:
an antibody comprising a light chain variable region comprising a CDR1 comprising SEQ ID NO: 49, a CDR2 comprising SEQ ID NO: 50, and a CDR3 comprising SEQ ID NO: 51 and a heavy chain variable region comprising a CDR1 comprising SEQ ID NO: 87, a CDR2 comprising SEQ ID NO: 88, and a CDR3 comprising SEQ ID NO: 89, or
an antibody comprising a light chain variable region comprising a CDR1 comprising SEQ ID NO: 68, a CDR2 comprising SEQ ID NO: 50, and a CDR3 comprising SEQ ID NO: 51 and a heavy chain variable region comprising a CDR1 comprising SEQ ID NO: 87, a CDR2 comprising SEQ ID NO: 104, and a CDR3 comprising SEQ ID NO: 89; and
wherein an anti-SARS-CoV antibody binding to a bin B epitope of RBD comprises:
an antibody comprising a light chain variable region comprising a CDR1 comprising SEQ ID NO: 55, a CDR2 comprising SEQ ID NO: 56, and a CDR3 comprising SEQ ID NO: 57 and a heavy chain variable region comprising a CDR1 comprising SEQ ID NO: 90, a CDR2 comprising SEQ ID NO: 93, and a CDR3 comprising SEQ ID NO: 92, or
an antibody comprising a light chain variable region comprising a CDR1 comprising SEQ ID NO: 38, a CDR2 comprising SEQ ID NO: 39, and a CDR3 comprising SEQ ID NO: 40 and a heavy chain variable region comprising a CDR1 comprising SEQ ID NO: 76, a CDR2 comprising SEQ ID NO: 77, and a CDR3 comprising SEQ ID NO: 78.

15. A method comprising administering the anti-SARS-CoV antibody of claim 1 to a subject.

16. The method of claim 15, wherein the subject is suspected of having, has been diagnosed with, or has been exposed to a SARS-CoV-2 variant selected from:
the alpha variant (the United Kingdom variant (UK), B.1.1.7 lineage, RBD with N501Y);
the beta variant (South African variant (SA), B.1.3512 lineage, RBD with K417N, E484K, and N501Y);

the gamma variant (Brazilian variant P.1 (BR P.1), B.1.1.28.1 lineage, RBD with K417T, E484K, and N501Y);

the delta variant (Indian variant 2 (IN v2), B.1.617.2 lineage, RBD with L452R and T478K);

the epsilon variant (California variant (CA), B.1.427/9 lineage, RBD with L452R);

the kappa variant (Indian variant 1 (IN v1), B.1.617.1 lineage, RBD with L452R and E484Q);

the zeta variant (Brazilian variant P.2 (BR P.2), B.1.1.28.2 lineage, RBD with E484K);

the K417E RBD (R319-F541 with K417E);

the T478K RBD (R319-F541 with T478K);

the iota variant (New York variant (NY), B.1.526 lineage, RBD with a single mutation E484K);

the eta variant (Nigeria variant, B.1.525 lineage);

the lambda variant (Peru variant, C.37 lineage, RBD with L452Q and F490S);

the theta variant (Philippine variant, P.3 lineage, RBD with E484K and N501Y); and/or the Denmark mink variant (B.1.1.298 lineage, DM, RBD with Y453).

17. An immunoassay device, the immunoassay device comprising one or more of the anti-SARS-CoV antibodies of claim 1.

18. A lateral flow immunoassay device, the lateral flow immunoassay device comprising one or more of the anti-SARS-CoV antibodies of claim 1.

19. A method of identifying a SARS-CoV-2 receptor binding domain (RBD) variant in a sample, the method comprising contacting the biosample with an antibody of claim 1.

20. The method of claim 15, wherein the subject is suspected of having, has been diagnosed with, or has been exposed to a SARS-CoV-2 to SARS-CoV-1 or SARS-CoV-2.

21. A method comprising administering the composition of claim 13 to a subject, wherein the subject is suspected of having, has been diagnosed with, or has been exposed to SARS-CoV-1 or SARS-CoV-2.

22. A method comprising administering the composition of claim 14 to a subject, wherein the subject is suspected of having, has been diagnosed with, or has been exposed to SARS-CoV-1 or SARS-CoV-2.

23. The composition of claim 13, wherein one anti-SARS-CoV antibody binds to a bin A epitope of RBD and one anti-SARS-CoV antibody binds to a bin C epitope of RBD;

wherein an anti-SARS-CoV antibody binding to a bin A epitope of RBD comprises:

an antibody comprising a light chain variable region comprising a CDR1 comprising SEQ ID NO: 49, a CDR2 comprising SEQ ID NO: 50, and a CDR3 comprising SEQ ID NO: 51 and a heavy chain variable region comprising a CDR1 comprising SEQ ID NO: 87, a CDR2 comprising SEQ ID NO: 88, and a CDR3 comprising SEQ ID NO: 89, or an antibody comprising a light chain variable region comprising a CDR1 comprising SEQ ID NO: 68, a CDR2 comprising SEQ ID NO: 50, and a CDR3 comprising SEQ ID NO: 51 and a heavy chain variable region comprising a CDR1 comprising SEQ ID NO: 87, a CDR2 comprising SEQ ID NO: 104, and a CDR3 comprising SEQ ID NO: 89; and wherein an anti-SARS-CoV antibody binding to a bin C epitope of RBD comprises:

a light chain variable region comprising a CDR1 comprising SEQ ID NO: 65, a CDR2 comprising SEQ ID NO: 66, and a CDR3 comprising SEQ ID NO: 67 and a heavy chain variable region comprising a CDR1 comprising SEQ ID NO: 100, a CDR2 comprising SEQ ID NO: 101, and a CDR3 comprising SEQ ID NO: 102, or a light chain variable region comprising a CDR1 comprising SEQ ID NO: 35, a CDR2 comprising SEQ ID NO: 36, and a CDR3 comprising SEQ ID NO: 37 and a heavy chain variable region comprising a CDR1 comprising SEQ ID NO: 72, a CDR2 comprising SEQ ID NO: 73, and a CDR3 comprising SEQ ID NO: 74, or a light chain variable region comprising a CDR1 comprising SEQ ID NO: 32, a CDR2 comprising SEQ ID NO: 33, and a CDR3 comprising SEQ ID NO: 34 and a heavy chain variable region comprising a CDR1 comprising SEQ ID NO: 75, a CDR2 comprising SEQ ID NO: 70, and a CDR3 comprising SEQ ID NO: 71.

24. The composition of claim 13, wherein one anti-SARS-CoV antibody binds to a bin B epitope of RBD and one anti-SARS-CoV antibody binds to a bin C epitope of RBD;

wherein an anti-SARS-CoV antibody binding to a bin B epitope of RBD comprises:

an antibody comprising a light chain variable region comprising a CDR1 comprising SEQ ID NO: 55, a CDR2 comprising SEQ ID NO: 56, and a CDR3 comprising SEQ ID NO: 57 and a heavy chain variable region comprising a CDR1 comprising SEQ ID NO: 90, a CDR2 comprising SEQ ID NO: 93, and a CDR3 comprising SEQ ID NO: 92, or an antibody comprising a light chain variable region comprising a CDR1 comprising SEQ ID NO: 38, a CDR2 comprising SEQ ID NO: 39, and a CDR3 comprising SEQ ID NO: 40 and a heavy chain variable region comprising a CDR1 comprising SEQ ID NO: 76, a CDR2 comprising SEQ ID NO: 77, and a CDR3 comprising SEQ ID NO: 78, and wherein an anti-SARS-CoV antibody binding to a bin C epitope of RBD comprises:

a light chain variable region comprising a CDR1 comprising SEQ ID NO: 65, a CDR2 comprising SEQ ID NO: 66, and a CDR3 comprising SEQ ID NO: 67 and a heavy chain variable region comprising a CDR1 comprising SEQ ID NO: 100, a CDR2 comprising SEQ ID NO: 101, and a CDR3 comprising SEQ ID NO: 102, or a light chain variable region comprising a CDR1 comprising SEQ ID NO: 35, a CDR2 comprising SEQ ID NO: 36, and a CDR3 comprising SEQ ID NO: 37 and a heavy chain variable region comprising a CDR1 comprising SEQ ID NO: 72, a CDR2 comprising SEQ ID NO: 73, and a CDR3 comprising SEQ ID NO: 74, or a light chain variable region comprising a CDR1 comprising SEQ ID NO: 32, a CDR2 comprising SEQ ID NO: 33, and a CDR3 comprising SEQ ID NO: 34 and a heavy chain variable region comprising a CDR1 comprising SEQ ID NO: 75, a CDR2 comprising SEQ ID NO: 70, and a CDR3 comprising SEQ ID NO: 71.

25. A method of diagnosing a subject with SARS-CoV-1 or SARS-CoV-2, the method comprising contacting a biosample from the subject with an antibody of claim 1.

* * * * *